(12) United States Patent
Champion et al.

(10) Patent No.: US 9,481,875 B2
(45) Date of Patent: Nov. 1, 2016

(54) PCSK9 VACCINE

(71) Applicants: Brian Robert Champion, Abingdon (GB); Leonard Gabriel Contillo, Jr., Groton, CT (US); Michael Dale Eisenbraun, San Diego, CA (US); James Downey Fraser, San Diego, CA (US); Julie Jia Li Hawkins, Old Lyme, CT (US); James Richard Merson, Sandwich (GB); Brian Gregory Pierce, Marblehead, MA (US); Xiayang Qiu, Mystic, CT (US); Jakir Hussain Ullah, Sandwich (GB); David Michael Wyatt, Sandwich (GB)

(72) Inventors: Brian Robert Champion, Abingdon (GB); Leonard Gabriel Contillo, Jr., Groton, CT (US); Michael Dale Eisenbraun, San Diego, CA (US); James Downey Fraser, San Diego, CA (US); Julie Jia Li Hawkins, Old Lyme, CT (US); James Richard Merson, Sandwich (GB); Brian Gregory Pierce, Marblehead, MA (US); Xiayang Qiu, Mystic, CT (US); Jakir Hussain Ullah, Sandwich (GB); David Michael Wyatt, Sandwich (GB)

(73) Assignee: Pfizer Vaccines LLC, New York, NY (US)

(*) Notice: Subject to any disclaimer, the term of this patent is extended or adjusted under 35 U.S.C. 154(b) by 0 days.

(21) Appl. No.: 14/508,977

(22) Filed: Oct. 7, 2014

(65) Prior Publication Data
US 2015/0098957 A1    Apr. 9, 2015

Related U.S. Application Data

(62) Division of application No. 12/872,645, filed on Aug. 31, 2010, now Pat. No. 8,889,144.

(60) Provisional application No. 61/239,541, filed on Sep. 3, 2009.

(51) Int. Cl.
*C12N 9/64* (2006.01)
*A61K 39/00* (2006.01)

(52) U.S. Cl.
CPC ......... *C12N 9/6424* (2013.01); *A61K 39/0005* (2013.01); *C12Y 304/21061* (2013.01)

(58) Field of Classification Search
None
See application file for complete search history.

(56) References Cited

U.S. PATENT DOCUMENTS

| | | | |
|---|---|---|---|
| 4,709,017 A | 11/1987 | Collier et al. | |
| 4,950,740 A | 8/1990 | Greenfield et al. | |
| 5,843,711 A | 12/1998 | Collier et al. | |
| 5,917,017 A | 6/1999 | Collier et al. | |
| 6,455,673 B1 | 9/2002 | Collier | |
| 8,263,353 B2 | 9/2012 | Sitlani et al. | |
| 2002/0141989 A1 | 10/2002 | Kricek et al. | |
| 2004/0076611 A1 | 4/2004 | Bachmann et al. | |
| 2004/0091496 A1 | 5/2004 | Mettens et al. | |
| 2006/0034839 A1 | 2/2006 | Barker et al. | |
| 2009/0232795 A1 | 9/2009 | Condra et al. | |
| 2009/0326202 A1 | 12/2009 | Jackson et al. | |
| 2010/0068199 A1 | 3/2010 | Liang et al. | |
| 2011/0212122 A1 | 9/2011 | Bachmann et al. | |

FOREIGN PATENT DOCUMENTS

| | | |
|---|---|---|
| EP | 0 378 881 | 12/1989 |
| EP | 0 421 635 | 9/1990 |
| EP | 0 427 347 | 11/1990 |
| EP | 0 471 177 | 7/1991 |
| WO | WO 91/01146 | 2/1991 |
| WO | WO 91/18926 | 12/1991 |
| WO | WO 92/11291 | 7/1992 |
| WO | WO 92/17712 | 10/1992 |
| WO | WO 94/03208 | 2/1994 |
| WO | WO 96/30523 | 10/1996 |
| WO | WO 98/58668 | 12/1998 |
| WO | WO 00/37105 | 6/2000 |
| WO | WO 00/61761 | 10/2000 |
| WO | WO 01/72337 | 10/2001 |
| WO | WO 01/98334 | 12/2001 |
| WO | WO 02/056905 | 7/2002 |
| WO | WO 02/091998 | 11/2002 |
| WO | WO 03/024481 | 3/2003 |
| WO | WO 03/031466 | 4/2003 |
| WO | WO 03/054007 | 7/2003 |
| WO | WO 2004/007538 | 1/2004 |
| WO | WO 2004/081515 | 9/2004 |
| WO | WO 2004/097047 | 11/2004 |
| WO | WO 2006/032499 | 3/2006 |
| WO | WO 2007/128121 | 11/2007 |
| WO | WO 2008/105797 | 9/2008 |
| WO | WO 2008/125623 | 10/2008 |
| WO | WO 2009/000826 | 12/2008 |
| WO | WO 2009/026558 | 2/2009 |
| WO | WO 2009/055783 | 4/2009 |
| WO | WO 2009/100297 | 8/2009 |
| WO | WO 2010/057242 | 5/2010 |

OTHER PUBLICATIONS

Dartmouth 2015 "Cholesterol disorders" accessed from dartmouth-hitchcock.org.*
FierceBiotech 2014 "updated:regeneron, sanofi, and amgen shares suffer on fda's frets about pcsk9 class" accessed from fiercebiotech.com.*

(Continued)

*Primary Examiner* — Adam M Weidner
(74) *Attorney, Agent, or Firm* — Austin W. Zhang

(57) ABSTRACT

The present invention relates to the provision of immunogens comprising an antigenic PCSK9 peptide linked to an immunogenic carrier for the prevention, treatment or alleviation of PCSK9-mediated disorders. The invention further relates to methods for production of these medicaments, immunogenic compositions and pharmaceutical compositing thereof and their use in medicine.

30 Claims, 19 Drawing Sheets

(56) References Cited

OTHER PUBLICATIONS

Healthline 2012 "familial hypercholesterolemia" accessed from healthline.com.*
Shibita 2005 "no genetic association between psck9 polymorphisms and alzheimer's disease and plasma cholesterol level in japanese patients" Psy Genetics 15:239.*
Song 2010 "primary and secondary hypocholesterolemia" Beijing Da xue xue bao 42(5):612-5 (abstract only).*
Baraldo, K., et al., "N19 Polyepitope as a Carrier for Enhanced Immunogenicity and Protective Efficacy of Meningococcal Conjugate Vaccines", Infection and Immunity, 2004, vol. 72, No. 8, 4884-4887.
Chan, J., et al., "A proprotein convertase subtilisinldexin type 9 neutralizing antibody reduces serum cholesterol in mice and non-human primates," PNAS, 2009, vol. 106/24: 9820-9825.
Cohen, J., et al., "Sequence Variations in PCSK9, Low LDL, and Protection against Coronary Heart Disease", The New England Journal of Medicine, 2006, vol. 354, 1264-1272.
Cunningham, D., et al., "Structural and Biophysical Studies of PCSK9 and its Mutants Linked to Familial Hypercholesterolemia", Nature Structural & Molecular Biology, 2007, vol. 14, No. 5, 413-419.
Duff, J., et al., "Antibody-mediated disruption of the interaction between PCSK9 and the low-density lipoprotein receptor," Biochemical Journal, 2009, vol. 419: 577-584.
Falugi, F., et al., "Rationally designed strings of promiscuous CD4+ T cell epitopes provide help to Haemophilus influenzae type b oligosaccharide: a model for new conjugate vaccines," Eur. J. Immunology, 2001, vol. 31, 3816-3824.
Frank-Kamenetsky, M., et al., "Therapeutic RNAi targeting PCSK9 acutely lowers plasma cholesterol in rodents and LDL cholesterol in nonhuman primates", PNAS, 2008, vol. 105, No. 33, 11915-11920.
Galactionov V.G. Immunologija, 3-e isd., Academia, Moskva, 1998, pp. 38-46 (Russian Language).
English Translation of the Relevant Part from Galactionov V.G. Immunologija, 3-e isd., ACADEMIA, Moskva, 1998, pp. 38-46 (Russian Language).
Horton, J., et al., "Molecular biology of PCSK9: its role in LDL metabolism," Trends in Biochemical Sciences, vol. 32, No. 2, 71-7, 2007.
Jiang, X., et al., "Norwalk Virus Genome Cloning And Characterization," Science, 1990, vol. 250, 1580-1583.
Jones, L., et al., "Active Immunization with a Glycolipid Transition State Analogue Protects against Endotoxic Shock", Anqew. Chem. Int. Ed., 2002, vol. 41, No. 22, 4122-4242.
Kim, J., et al., "Overexpression of Low-Density Lipoprotein Receptor in the Brain Markedly Inhibits Amyloid Deposition and Increases Extracellular Aβ Clearance," Neuron, 2009, vol. 64, 632-644.
Kozlovska, T., et al., "RNA Phage Qβ Coat Protein As A Carrier For Foreign Epitopes," Intervirology, 1996, vol. 39, 9-15.
Krieg, A., et al., "CpG Motifs in Bacterial DNA Trigger Direct B-cell Activation," Nature, 1995, vol. 374, pp. 546-549.
Kuo, J., et al., "Characterization of a Recombinant Pneumolysin and Its Use as a Protein Carrier for Pneumococcal Type 18C Conjugate Vaccines," Infection and Immunity, 1995, vol. 63, No. 7, 2706-2713.
Kwon, H., et al., "Molecular basis for LDL receptor recognition by PCSK9," PNAS, 2008, vol. 105, No. 6, 1820-1825.
Liu, M., et al., "PCSK9 is not involved in the degradation of LDL receptors and BACE1 in the adult mouse brain," Journal of Lipid Research, 2010, vol. 51, 2611-2618.
Lopez, D., et al., "Inhibition of PCSK9 as a Novel Strategy for the Treatment of Hypercholesterolemia," Drug News Perspect, 2008, 323-330, vol. 21, No. 6.
Matsui, S., et al., "The Isolation And Characterization Of A Norwalk Virus-specific cDNA," The American Journal Of Clinical Investigation, 1991, vol. 87, 1456-1461.
McNutt, M., et al., "Antagonism of Secreted PCSK9 Increases Low Density Lipoprotein Receptor Expression in HepG2 Cells," The Journal of Biological Chemistry, 2009, 10561-10570, vol. 284, No. 16.
Neirynck, S., et al., "A Universal Influenza a Vaccine Based on the Extracellular Domain of the M2 Protein," Nature Medicine, 1999, vol. 5, No. 10, 1157-1163.
Pumpens, P., et al., "HBV Core Particles As A Carrier for B Cell/T Cell Epitopes," Intervirology, 2001, vol. 44, 98-114.
Sasnauskas, K., et al. Generation Of Recombinant Virus-Like Particles Of Human And Non-Human Polyomaviruses In Yeast *Saccharomyces cerevisiae*, Intervirology, 2002, vol. 45, 308-317.
Sasnauskas, K., et al., "Yeast Cells Allow High-level Expression And Formation Of Polyomavirus-like Particles," Biological Chemistry, 1999, vol. 380, 381-386.
Seidah, N., et al., "The secretory proprotein convertase neural apoptosis-regulated convertase 1 (NARC-1 ):Liver regeneration and neuronal differentiation," PNAS, 2003,vol. 100, No. 3, 928-933.
Soutar, A., et al., "Mechanisms of Disease: genetic causes of familial hypercholesterolemia," Nature Clinical Practice, 2007, vol. 4, No. 4, 214-225.
Spath, J., et al., "Stabilization of a β-Hairpin Conformation in a Cyclic Peptide Using the Templating Effect of a Heterochiral Diproline Unit", Helvetica Chimica Acta, 1998, vol. 81, 1726-1738.
Stacey, K., et al., "Macrophages Ingest and are Activated by Bacterial DNA," the Journal of Immunology, 1996, vol. 157, 2116-2122.
Twomey, T., et al., "Structure And Immunogenicity Of Experimental Foot-and-mouth Disease And Poliomyelitis Vaccines," Vaccine, 1995, vol. 13, No. 16, 1603-1610.
Uchida, T., et al., "Diphtheria Toxin and Related Proteins," The Journal of Biological Chemistry, 1973, vol. 248, No. 11, 3838-3844.
Ulrich, R., et al., "Core Particles Of Hepatitis B Virus As Carrier For Foreign Epitopes," Advances in Virus Research, 1998. vol. 50, 141-182.
Van Regenmortel, Marc H.V., "What is a B-Cell Epitope?", Ulrich Reineke and Mike Schutkowski (eds.), Chapter 1, D Methods in Molecular Biology, Epitope Mapping Protocols, vol. 524, 2009.
Warnes, A., "Expression Of The Measles Virus Nucleoprotein Gene In *Escherichia coli* And Assembly Of Nucleocapsid-like Structures," Gene, 1995, vol. 160, 173-178.
Weiss, G., et al, "Rapid mapping of protein functional epitopes by combinatorial alanine scanning", PNAS, Aug. 1, 2000, vol. 97, No. 16, pp. 8950-8954.
Winsauer, G., et al., "A Peptide Vaccine Targeting the Interaction of PCSK9 and LDLR," PCSK9 conference. From Gene To Therapeutics. Nantes, France. Mar. 11-13, 2010.
Current Protocols in Immunology, 2004, Supplement 60. B Cell Epitope Mapping Using Synthetic Peptides, Chapter 9, Unit 9.4.

* cited by examiner

Peptide 1:
371-380: ASSDCSTCFV

Peptide 2:
213-223: GTRFHRQASKC

Peptide 3:
191-200: SDHREIEGRV

Peptide 4:
235-245: SGRDAGVAKGA

Peptide 5:
153-163: SIPWNLERITP

Treatment groups n=8. Each spot represents the reciprocal Ab titre for one mouse. Mean +/- SE are represented by lines Complex of PCSK9 (ribbons) and EGF-A (space fill). Potential regions of PCSK9 that may interact with domains of LDLR other than EGF-A are indicated by the elipse.

Complex of PCSK9 (ribbons) and EGF-A (space fill) with the amino acids corresponding to peptides VR_13/14 (A) and VR_15/16 (B) and VR_9.5 (C) are displayed.

Complex of PCSK9 (ribbons) and EGF-A (space fill) with the amino acids corresponding to peptides VR_9.25 / VR_9.27 (A*), VR_9.29 (B), VR_9.31 (C), VR_9.33 (D), VR_9.35 (E), and VR_9.23 (F) are displayed.

*VR_9.25 and VR_9.27 are in an unresolved N-term region of PCSK9; highlighted residue is closest in sequence (aa Thr61).

PCSK9 VACCINE

CROSS-REFERENCE TO RELATED APPLICATIONS

This application is a division of U.S. application Ser. No. 12/872,645 filed on Aug. 31, 2010, now U.S. Pat. No. 8,889,144, which claims benefit of U.S. Provisional Application No. 61/239,541 filed on Sep. 3, 2009. Both application Ser. No. 12/872,645 and U.S. Provisional Application No. 61/239,541 are incorporated herein by reference in their entirety.

REFERENCE TO SEQUENCE LISTING

This application is being filed electronically via EFS-Web and includes an electronically submitted sequence listing in .txt format. The .txt file contains a sequence entitled "PC33896B_UpdatedSequenceListing_ST25.txt" created on Jun. 6, 2016 and having a size of 121 KB. The sequence listing contained in this .txt file is part of the specification and is herein incorporated by reference in its entirety.

FIELD OF THE INVENTION

The present invention relates to the provision of novel immunogens comprising an antigenic PCSK9 peptide preferably linked to an immunogenic carrier for the prevention, treatment or alleviation of PCSK9-related disorders. The invention further relates to methods for production of these medicaments, immunogenic compositions and pharmaceutical composition thereof and their use in medicine.

BACKGROUND

Proprotein convertase subtilisin-kexin type 9 (hereinafter called "PCSK9"), also known as neural apoptosis-regulated convertase 1 ("NARC-I"), is a proteinase K-like subtilase identified as the 9th member of the mammalian PCSK family; see Seidah et al, 2003 PNAS 100:928-933. The gene for PCSK9 localizes to human chromosome 1p33-p34.3. PCSK9 is expressed in cells capable of proliferation and differentiation including, for example, hepatocytes, kidney mesenchymal cells, intestinal ileum, and colon epithelia as well as embryonic brain telencephalon neurons.

Original synthesis of PCSK9 is in the form of an inactive enzyme precursor, or zymogen, of ~72-kDa which undergoes autocatalytic, intramolecular processing in the endoplasmic reticulum ("ER") to activate its functionality. The gene sequence for human PCSK9, which is ~22-kb long with 12 exons encoding a 692 amino acid protein, can be found, for example, at Deposit No. NP_777596.2. Human, mouse and rat PCSK9 nucleic acid sequences have been deposited; see, e.g., GenBank Accession Nos.: AX127530 (also AX207686), AX207688, and AX207690, respectively.

Human PCSK9 is a secreted protein expressed primarily in the kidneys, liver and intestines. It has three domains: an inhibitory pro-domain (amino acids 1-152; including a signal sequence at amino acids 1-30), a catalytic domain (amino acids 153-448), and a C-terminal domain 210 residues in length (amino acids 449-692), which is rich in cysteine residues. PCSK9 is synthesized as a zymogen that undergoes autocatalytic cleavage between the pro-domain and catalytic domain in the endoplasmic reticulum. The pro-domain remains bound to the mature protein after cleavage, and the complex is secreted. The cysteine-rich domain may play a role analogous to the P-(processing) domains of other Furin/Kexin/Subtilisin-like serine proteases, which appear to be essential for folding and regulation of the activated protease. Mutations in PCSK9 are associated with abnormal levels of low density lipoprotein cholesterol (LDL-c) in the blood plasma (Horton et al., 2006 Trends. Biochem. Sci. 32(2):71-77).

PCSK9 has been ascribed a role in the differentiation of hepatic and neuronal cells (Seidah et al, supra), is highly expressed in embryonic liver, and has been strongly implicated in cholesterol homeostasis.

The identification of compounds and/or agents effective in the treatment of cardiovascular affliction is highly desirable. Reductions in LDL cholesterol levels have already demonstrated in clinical trials to be directly related to the rate of coronary events; Law et al, 2003 BMJ 326: 1423-1427. More, recently moderate lifelong reduction in plasma LDL cholesterol levels has been shown to be substantially correlated with a substantial reduction in the incidence of coronary events; Cohen et al, supra. This was found to be the case even in populations with a high prevalence of non-lipid-related cardiovascular risk factors; supra.

Accordingly, it is of great importance to identify therapeutic agent permitting the control of LDL cholesterol levels.

Accordingly, it would be of great importance to produce a medicament that inhibits or antagonizes the activity of PCSK9 and the corresponding role PCSK9 plays in various therapeutic conditions.

Expression or upregulation of PCSK9 is associated with increased plasma levels of LDL cholesterol, and inhibition or the lack of expression of PCSK9 is associated with low LDL cholesterol plasma levels. Significantly, lower levels of LDL cholesterol associated with sequence variations in PCSK9 have conferred protection against coronary heart disease; Cohen, 2006 N. Engl. J. Med. 354: 1264-1272.

SUMMARY OF THE INVENTION

The present invention relates to an immunogen comprising an antigenic PCSK9 peptide and optionally an immunogenic carrier.

The invention also relates to methods for producing such antigenic PCSK9 peptide optionally linked to an immunogenic carrier.

The invention also relates to immunogenic compositions comprising such antigenic PCSK9 peptide optionally linked to an immunogenic carrier, optionally comprising one or several adjuvants, preferably one or two adjuvants.

Another aspect of the invention relates to pharmaceutical compositions comprising an antigenic PCSK9 peptide according to the invention, or an immunogenic composition thereof, as well as to medical uses of such compositions.

In particular, the invention relates to an antigenic PCSK9 peptide of the invention, or an immunogenic or pharmaceutical composition thereof, for use as a medicament, preferably in treatment, alleviation or prophylaxis of PCSK9-related disorders.

In particular, the invention relates to an antigenic PCSK9 peptide of the invention, or an immunogenic or pharmaceutical composition thereof, for use as a medicament preferably in treatment, alleviation or prophylaxis of diseases associated with an elevated level of cholesterol.

The antigenic PCSK9 peptides of the invention are particularly suitable for treating human patients having, or at risk for, elevated LDL-cholesterol or a condition associated with elevated LDL-cholesterol, e.g., a lipid disorder (e.g., hyperlipidemia, type I, type II, type III, type IV, or type V hyperlipidemia, secondary hypertriglyceridemia, hypercholesterolemia, familial hypercholesterolemia, xanthomatosis, cholesterol acetyltransferase deficiency). Antigenic PCSK9 peptide of the invention are also suitable for treating human patients having arteriosclerotic conditions (e.g., atherosclerosis), coronary artery disease, cardiovascular disease, and patients at risk for these disorders, e.g., due to the presence of one or more risk factors (e.g., hypertension, cigarette smoking, diabetes, obesity, or hyperhomocysteinemia).

In yet another aspect, the present invention provides the use of an antigenic PCSK9 peptide of the invention or of an immunogenic composition or a pharmaceutical composition thereof, in the manufacture of a medicament for the treatment of Alzheimer's disease.

In one embodiment, the antigenic PCSK9 peptide or an immunogenic composition or a pharmaceutical composition thereof is administered together with another agent.

DETAILED DESCRIPTION OF THE INVENTION

Antigenic PCSK9 Peptide of the Invention

Figure 1:
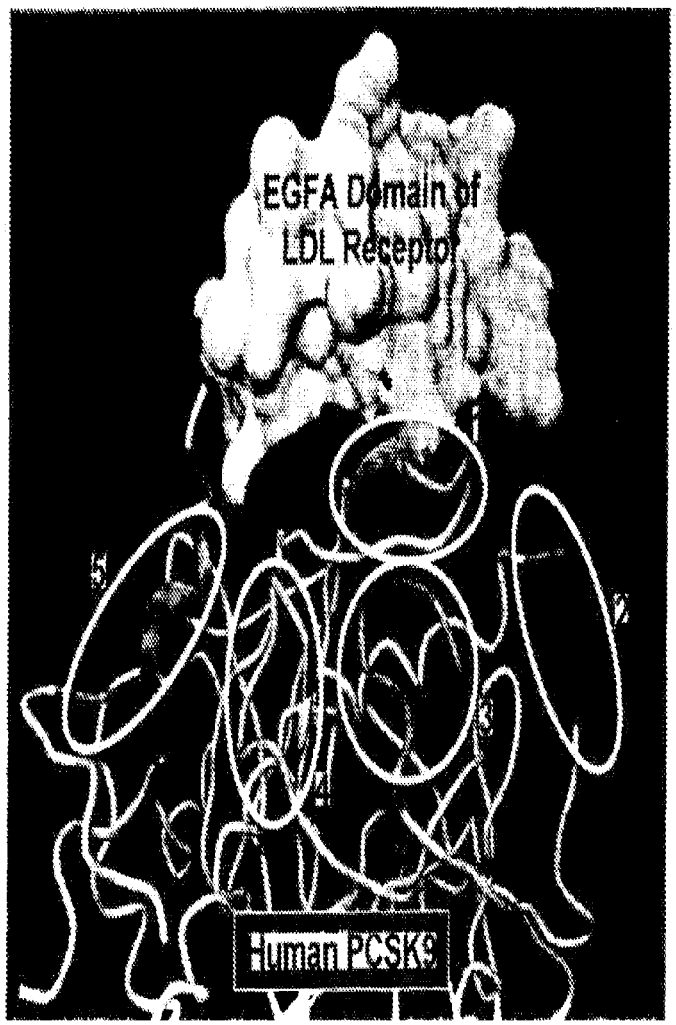
FIG. 1: The PDB structure of human PCSK9 bound to the EGF-A domain of the LDL-R (3BPS) showing 5 peptide sequences in PCSK9 (Peptides 1-5) chosen as being involved in the interaction between these two proteins. The amino acid sequence of each of these peptides is set forth below:
Peptide 1: ASSDCSTCFV (SEQ ID NO:19);
Peptide 2: GTRFHRQASKC (SEQ ID NO:62);
Peptide 3: SDHREIEGRV (SEQ ID NO:121);
Peptide 4: SGRDAGVAKGA (SEQ ID NO:153);
Peptide 5: SIPWNLERITP (SEQ ID NO:184).

The present invention relates to an immunogen comprising an antigenic PCSK9 peptide optionally linked to an immunogenic carrier.

In one embodiment, the antigenic PCSK9 peptide is a portion of PCSK9 comprising between 4 to 20 amino acids and, when administered to a subject, is able to lower the LDL-cholesterol level in blood of said subject. Preferably, said subject is a mammal, preferably a human. Preferably, said antigenic PCSK9 peptide is able to lower the LDL-cholesterol level by at least 2%, 5%, 10%, 20%, 30% or 50%.

In one embodiment, the antigenic PCSK9 peptide is a portion of PCSK9 which participates in the interaction of PCSK9 with the LDL receptor.

In one embodiment, the antigenic PCSK9 peptide is a portion of PCSK9 which participates in the interaction of PCSK9 with the LDL receptor, comprising between 4 and 20 amino acids and, when administered to a subject is able to lower the LDL-cholesterol level in blood of said subject. Preferably, said subject is a mammal, preferably a human. Preferably, said antigenic PCSK9 peptide is able to lower the LDL-cholesterol level by at least 2%, 5%, 10%, 20%, 30% or 50%.

In one embodiment, the antigenic PCSK9 peptide is selected from the group consisting of SEQ ID Nos 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587 and 588.

In one embodiment, the antigenic PCSK9 peptide is selected from the group consisting of SEQ ID Nos 1 to 312, 330 to 398, 421, 423, 424, 426 and 428 to 588.

In one embodiment, the antigenic PCSK9 peptide is selected from the group consisting of SEQ ID Nos 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397 and 398.

In one embodiment, the antigenic PCSK9 peptide is a portion of PCSK9 which may participate in the interaction with the domain EGF-A of the LDL receptor. Examples of such portions are represented on FIG. 1.

In one embodiment, the antigenic PCSK9 peptide is a portion of PCSK9 which may participate in the interaction with the domain EGF-A of the LDL receptor, comprising between 4 and 20 amino acids and, when administered to a subject, is able to lower the LDL-cholesterol level in blood of said subject. Preferably, said subject is a mammal, preferably a human. Preferably, said antigenic PCSK9 peptide is able to lower the LDL-cholesterol level by at least 2%, 5%, 10%, 20%, 30% or 50%.

In one embodiment, the antigenic PCSK9 peptide is a peptide comprising 5 to 13, preferably 6 to 8, consecutive amino acids of the PCSK9 fragment of SEQ ID No 1.

In one embodiment, the antigenic PCSK9 peptide is selected from the group consisting of SEQ ID Nos 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 and 45.

In one embodiment, the antigenic PCSK9 peptide is a peptide comprising 5 to 15, preferably 6 to 8, consecutive amino acids of the PCSK9 fragment of SEQ ID No 46.

In one embodiment, the antigenic PCSK9 peptide is selected from the group consisting of SEQ ID Nos 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 and 101.

In one embodiment, the antigenic PCSK9 peptide is a peptide comprising 5 to 14, preferably 6 to 8, consecutive amino acids of the PCSK9 fragment of SEQ ID No 102.

In one embodiment, the antigenic PCSK9 peptide is selected from the group consisting of SEQ ID Nos 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145 and 146.

In one embodiment, the antigenic PCSK9 peptide is a peptide comprising 5 to 13, preferably 6 to 8, consecutive amino acids of the PCSK9 fragment of SEQ ID No 147.

In one embodiment, the antigenic PCSK9 peptide is selected from the group consisting of SEQ ID Nos 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180 and 181.

In one embodiment, the antigenic PCSK9 peptide is a peptide comprising 5 to 13, preferably 6 to 8, consecutive amino acids of the PCSK9 fragment of SEQ ID No 182.

In one embodiment, the antigenic PCSK9 peptide is selected from the group consisting of SEQ ID Nos 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225 and 226.

In one embodiment, the antigenic PCSK9 peptide is a peptide comprising 5 to 13, preferably 6 to 8, consecutive amino acids of the PCSK9 fragment of SEQ ID No 330.

In one embodiment, the antigenic PCSK9 peptide is selected from the group consisting of SEQ ID Nos 330, 331, 332, 333, 334, 335, 336, 337, 338, 339, 340, 341, 342, 343, 344, 345, 346, 347, 348, 349, 350, 351, 352, 353, 354, 355, 356, 357, 358 and 359.

In a preferred embodiment, the antigenic PCSK9 peptide is selected from the group consisting of SEQ ID Nos 19, 56, 63, 109, 153, 165, 184, 186, 187, 188, 332 and 424.

In a preferred embodiment, the antigenic PCSK9 peptide is selected from the group consisting of SEQ ID Nos 19, 56, 63, 109, 153 and 184.

In a preferred embodiment, the antigenic PCSK9 peptide is selected from the group consisting of SEQ ID Nos 56, 184, 186, 187, 188 and 332.

In a most preferred embodiment, the antigenic PCSK9 peptide is a peptide of sequence SEQ ID No 56.

In a more preferred embodiment, the antigenic PCSK9 peptide is a peptide of sequence SEQ ID No 184 or 187.

In a most preferred embodiment, the antigenic PCSK9 peptide is a peptide of sequence SEQ ID No 184.

In a most preferred embodiment, the antigenic PCSK9 peptide is a peptide of sequence SEQ ID No 332.

Figure 7:
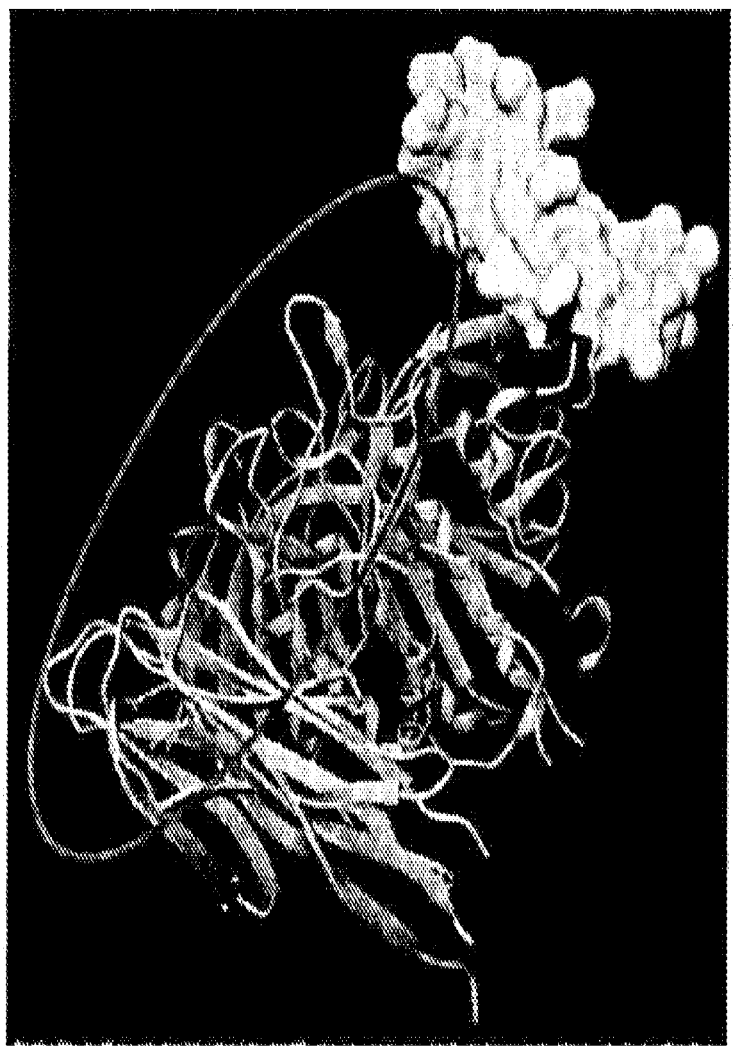
FIG. 7: Complex of PCSK9 (ribbons) and EGF-A (space fill) from PDB:3BPS. Potential regions of PCSK9 that may interact with domains of LDLR other than EGF-A are indicated by the ellipse.

In one embodiment, the antigenic PCSK9 peptide is selected in a region of PCSK9 which may participate in the interaction with a region of the LDL receptor other than the EGF-A domain. Examples of such portions are represented on FIGS. 7 and 8.

In one embodiment, the antigenic PCSK9 peptide is a portion of PCSK9 which may participate in the interaction with a region of the LDL receptor other than the EGF-A domain, comprising between 4 and 20 amino acids and, when administered to a subject, is able to lower the LDL-cholesterol level in blood of said subject. Preferably, said subject is a mammal, preferably a human. Preferably, said antigenic PCSK9 peptide is able to lower the LDL-cholesterol level by at least 2%, 5%, 10%, 20%, 30% or 50%.

In one embodiment, the antigenic PCSK9 peptide is a peptide comprising 5 to 12, preferably 6 to 8, consecutive amino acids of the PCSK9 fragment of SEQ ID No 227.

In one embodiment, the antigenic PCSK9 peptide is selected from the group consisting of SEQ ID Nos 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261 and 262.

In one embodiment, the antigenic PCSK9 peptide is a peptide comprising 5 to 13, preferably 6 to 8, consecutive amino acids of the PCSK9 fragment of SEQ ID No 263.

In one embodiment, the antigenic PCSK9 peptide is selected from the group consisting of SEQ ID Nos 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306 and 307.

In one embodiment, the antigenic PCSK9 peptide is a peptide comprising 5 to 13, preferably 6 to 8, consecutive amino acids of the PCSK9 fragment of SEQ ID No 360.

In one embodiment, the antigenic PCSK9 peptide is selected from the group consisting of SEQ ID Nos 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397 and 398.

In an embodiment, the antigenic PCSK9 peptide is selected in a region of PCSK9 pro-domain (SEQ ID No 329).

In one embodiment, the antigenic PCSK9 peptide is a portion of PCSK9 pro-domain, comprising between 4 and 20 amino acids and, when administered to a subject, is able to lower the LDL-cholesterol level in blood of said subject. Preferably, said subject is a mammal, preferably a human. Preferably, said antigenic PCSK9 peptide is able to lower the LDL-cholesterol level by at least 2%, 5%, 10%, 20%, 30% or 50%.

In one embodiment, the antigenic PCSK9 peptide is selected from the group consisting of SEQ ID Nos 308, 309, 310, 311 and 312.

In one embodiment, the antigenic PCSK9 peptide is a peptide comprising 5 to 12, preferably 6 to 8, consecutive amino acids of the PCSK9 fragment of SEQ ID No 309.

In one embodiment, the antigenic PCSK9 peptide is selected from the group consisting of SEQ ID Nos 309, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462 and 463.

In one embodiment, the antigenic PCSK9 peptide is a peptide comprising 5 to 12, preferably 6 to 8, consecutive amino acids of the PCSK9 fragment of SEQ ID No 508.

In one embodiment, the antigenic PCSK9 peptide is selected from the group consisting of SEQ ID Nos 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542 and 543.

In one embodiment, the antigenic PCSK9 peptide is a peptide comprising 5 to 13, preferably 6 to 8, consecutive amino acids of the PCSK9 fragment of SEQ ID No 310.

In one embodiment, the antigenic PCSK9 peptide is selected from the group consisting of SEQ ID Nos 310, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506 and 507.

In one embodiment, the antigenic PCSK9 peptide is a peptide comprising 5 to 13, preferably 6 to 8, consecutive amino acids of the PCSK9 fragment of SEQ ID No 544.

In one embodiment, the antigenic PCSK9 peptide is selected from the group consisting of SEQ ID Nos 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, and 588.

In a preferred embodiment, the antigenic PCSK9 peptide is selected from the group consisting of SEQ ID Nos 312, 421, 422, 423, 426, 427, 428, 445, 482, 525, and 563.

In a more preferred embodiment, the antigenic PCSK9 peptide is selected from the group consisting of SEQ ID Nos 445, 482, 525, and 563.

In a most preferred embodiment, the antigenic PCSK9 peptide is a peptide of sequence SEQ ID No 445.

Such antigenic PCSK9 peptides may be used alone or in combination, preferably when conjugated to an immunogenic carrier, to induce auto anti-PCSK9 antibodies in a subject in order to treat, prevent or ameliorate PCSK9-related disorders.

It will be apparent to the man skilled in the art which techniques may be used to confirm whether a specific construct falls within the scope of the present invention. Such techniques include, but are not restricted to, the techniques described in the Example section of the present application, and also to the following.

The ability of the antigenic PCSK9 peptide of the invention to induce auto anti-PCSK9 antibodies may be measured in mice, using the test disclosed in example 3 of the present application. The ability of auto-antibodies induced by the antigenic PCSK9 peptide of the invention to decrease the level of circulating plasma cholesterol may be measured in mice, using the test disclosed in example 3. The ability of auto-antibodies induced by the antigenic PCSK9 peptide of the invention to inhibit the interaction between PCSK9 and LDL receptors may be measured directly using the test disclosed in example 3 (FRET assay) or indirectly by measuring the upregulation of cell surface LDL receptors which is a consequence of blocking PCSK9-mediated down-regulation (as well described in the relevant literature, either using cell lines in vitro or by measuring LDL receptor levels in liver biopsies of antibody expressing animals (e.g. by Western blotting)).

The term "antigenic PCSK9 peptide biological activity", when used herein, refers to the ability of the antigenic PCSK9 peptides of the invention to induce auto anti-PCSK9 antibodies in a patient.

Preferably said antigenic PCSK9 peptide, when administered to a subject, is able to lower the LDL-cholesterol level in blood of said subject. Preferably, said subject is a mammal, preferably a human. Preferably, said antigenic PCSK9 peptide is able to lower the LDL-cholesterol level by at least 2%, 5%, 10%, 20%, 30% or 50%.

In an embodiment the antigenic PCSK9 peptides of the present invention are of a size such that they mimic a region selected from the whole PCSK9 domain in which the native epitope is found. In a particular embodiment, the antigenic PCSK9 peptides of the invention are less than 100 amino acids in length, preferably shorter than 75 amino acids, more preferably less than 50 amino acids, even more preferably less than 40 amino acids. The antigenic PCSK9 peptides of the invention are typically 4, 5, 6, 7, 8, 9, 10, 11, 12, 13, 14, 15, 16, 17, 18, 19, 20, 21, 22, 23, 24, 25, 26, 27, 28, 29 or 30 amino acids in length, preferably from 4 to 20 amino acids, for example 6 to 12, 6 to 8 or 9 to 12 amino acids.

Specific examples of antigenic PCSK9 peptides of the invention are provided in the sequence listing and include peptides ranging from 5 to 17 amino acids in length.

The antigenic peptides of the invention include an amino acid sequence derived from a portion of a mammalian PCSK9, preferably a human PCSK9 (SEQ ID No 399) or mouse PCSK9 (SEQ ID Nos 400), more preferably human PCSK9, such derived portion of PCSK9 either corresponding to the amino acid sequence of naturally occurring PCSK9 or corresponding to variant PCSK9, i.e. the amino acid sequence of naturally occurring PCSK9 in which a small number of amino acids have been substituted, added or deleted but which retains essentially the same immunological properties. In addition, such derived PCSK9 portion can be further modified by amino acids, especially at the N- and C-terminal ends to allow the antigenic PCSK9 peptide to be conformationally constrained and/or to allow coupling of the antigenic PCSK9 peptide to an immunogenic carrier after appropriate chemistry has been carried out.

The antigenic PCSK9 peptides disclosed herein encompass functionally active variant peptides derived from the amino acid sequence of PCSK9 in which amino acids have been deleted, inserted or substituted without essentially detracting from the immunological properties thereof, i.e. such functionally active variant peptides retain a substantial antigenic PCSK9 peptide biological activity. Typically, such functionally variant peptides have an amino acid sequence homologous, preferably highly homologous, to an amino acid sequence selected from the group consisting of SEQ ID Nos: 1 to 312, 330 to 398 and 420 to 588.

In one embodiment, such functionally active variant peptides exhibit at least 60%, 65%, 70%, 75%, 80%, 85%, 90% or 95% identity to an amino acid sequence selected from the group consisting of SEQ ID Nos: 1 to 312, 330 to 398 and 420 to 588.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson, *Methods Enzymol.* 183:63-98 (1990); Pearson, *Methods Mol. Biol.* 132:185-219 (2000)). An alternative algorithm when comparing a sequence of the invention to a database containing a large number of sequences from different organisms is the computer program BLAST, especially blastp or tblastn, using default parameters. See, e.g., Altschul et al., *J. Mol. Biol.* 215:403-410 (1990); Altschul et al., *Nucleic Acids Res.* 25:3389-402 (1997).

Functionally active variants comprise naturally occurring functionally active variants such as allelic variants and species variants and non-naturally occurring functionally active variants that can be produced by, for example, mutagenesis techniques or by direct synthesis.

A functionally active variant differs by about, for example, 1, 2, 3, 4 or 5 amino acid residues from any of the peptide shown at SEQ ID Nos: 1 to 312, 330 to 398 and 420 to 588, and yet retain an antigenic PCSK9 biological activity. Where this comparison requires alignment the sequences are aligned for maximum homology. The site of variation can occur anywhere in the peptide, as long as the biological activity is substantially similar to a peptide shown in SEQ ID Nos: 1 to 312, 330 to 398 and 420 to 588.

Guidance concerning how to make phenotypically silent amino acid substitutions is provided in Bowie et al., Science, 247: 1306-1310 (1990), which teaches that there are two main strategies for studying the tolerance of an amino acid sequence to change.

The first strategy exploits the tolerance of amino acid substitutions by natural selection during the process of evolution. By comparing amino acid sequences in different species, the amino acid positions which have been conserved between species can be identified. These conserved amino acids are likely important for protein function. In contrast, the amino acid positions in which substitutions have been tolerated by natural selection indicate positions which are not critical for protein function. Thus, positions tolerating amino acid substitution can be modified while still maintaining specific immunogenic activity of the modified peptide.

The second strategy uses genetic engineering to introduce amino acid changes at specific positions of a cloned gene to identify regions critical for protein function. For example, site-directed mutagenesis or alanine-scanning mutagenesis can be used (Cunningham et al., Science, 244: 1081-1085 (1989)). The resulting variant peptides can then be tested for specific antigenic PCSK9 biological activity.

According to Bowie et al., these two strategies have revealed that proteins are surprisingly tolerant of amino acid substitutions. The authors further indicate which amino acid changes are likely to be permissive at certain amino acid positions in the protein. For example, the most buried or interior (within the tertiary structure of the protein) amino acid residues require nonpolar side chains, whereas few features of surface or exterior side chains are generally conserved.

Methods of introducing a mutation into amino acids of a protein is well known to those skilled in the art. See, e. g., Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N. Y. (1989)).

Mutations can also be introduced using commercially available kits such as "QuikChange™ Site-Directed Mutagenesis Kit" (Stratagene) or directly by peptide synthesis. The generation of a functionally active variant to an antigenic PCSK9 peptide by replacing an amino acid which does not significantly influence the function of said antigenic PCSK9 peptide can be accomplished by one skilled in the art.

A type of amino acid substitution that may be made in one of the peptides according to the invention is a conservative amino acid substitution. A "conservative amino acid substitution" is one in which an amino acid residue is substituted by another amino acid residue having a side chain R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See e.g. Pearson, *Methods Mol. Biol.* 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., Science 256:1443-45 (1992). A "moderately conservative" replacement is any change having a nonnegative value in the PAM250 log-likelihood matrix.

A functionally active variant peptide can also be isolated using a hybridization technique. Briefly, DNA having a high homology to the whole or part of a nucleic acid sequence encoding the peptide of interest, e.g. SEQ ID Nos: 1 to 312, 330 to 398 and 420 to 588, is used to prepare a functionally active peptide. Therefore, an antigenic PCSK9 peptide of the invention also includes peptides which are functionally equivalent to one or more of the peptide of SEQ ID Nos: 1 to 312, 330 to 398, and 420 to 588 and which are encoded by a nucleic acid molecule which hybridizes with a nucleic acid encoding any one of SEQ ID Nos: 1 to 312, 330 to 398 and 420 to 588, or a complement thereof. One of skill in the art can easily determine nucleic acid sequences that encode peptides of the invention using readily available codon tables. As such, these nucleic acid sequences are not presented herein.

The stringency of hybridization for a nucleic acid encoding a peptide, polypeptide or protein that is a functionally active variant is, for example, 10% formamide, 5×SSPE, 1× Denhart's solution, and 1× salmon sperm DNA (low stringency conditions). More preferable conditions are, 25% formamide, 5×SSPE, 1× Denhart's solution, and 1× salmon sperm DNA (moderate stringency conditions), and even more preferable conditions are, 50% formamide, 5×SSPE, 1× Denhart's solution, and 1× salmon sperm DNA (high stringency conditions). However, several factors influence the stringency of hybridization other than the above-described formamide concentration, and one skilled in the art can suitably select these factors to accomplish a similar stringency.

Nucleic acid molecules encoding a functionally active variant can also be isolated by a gene amplification method such as PCR using a portion of a nucleic acid molecule DNA encoding a peptide, polypeptide or protein of interest, e.g. any one of the peptides shown SEQ ID Nos: 1 to 312, 330 to 398 and 420 to 588, as the probe.

In one embodiment of the invention, a peptide of the invention is derived from a natural source and isolated from a mammal, such as a human, a primate, a cat, a dog, a horse, a mouse, or a rat, preferably from a human source. A peptide of the invention can thus be isolated from cells or tissue sources using standard protein purification techniques. Alternatively, peptides of the invention can be synthesized chemically or produced using recombinant DNA techniques.

For example, a peptide of the invention can be synthesized by solid phase procedures well known in the art. Suitable syntheses may be performed by utilising "T-boc" or "F-moc" procedures. Cyclic peptides can be synthesised by the solid phase procedure employing the well-known "F-moc" procedure and polyamide resin in the fully automated apparatus. Alternatively, those skilled in the art will know the necessary laboratory procedures to perform the process manually. Techniques and procedures for solid phase synthesis are described in 'Solid Phase Peptide Synthesis: A Practical Approach' by E. Atherton and R. C. Sheppard, published by IRL at Oxford University Press (1989) and 'Methods in Molecular Biology, Vol. 35: Peptide Synthesis Protocols (ed. M. W. Pennington and B. M. Dunn), chapter 7, pp 91-171 by D. Andreau et al.

Alternatively, a polynucleotide encoding a peptide of the invention can be introduced into an expression vector that can be expressed in a suitable expression system using techniques well known in the art, followed by isolation or purification of the expressed peptide, polypeptide, or protein of interest. A variety of bacterial, yeast, plant, mammalian, and insect expression systems are available in the art and any such expression system can be used. Optionally, a polynucleotide encoding a peptide of the invention can be translated in a cell-free translation system.

Antigenic PCSK9 peptides of the invention can also comprise those that arise as a result of the existence of multiple genes, alternative transcription events, alternative RNA splicing events, and alternative translational and postranslational events. A peptide can be expressed in systems, e.g. cultured cells, which result in substantially the same postranslational modifications present as when the peptide is expressed in a native cell, or in systems that result in the alteration or omission of postranslational modifications, e.g. glycosylation or cleavage, present when expressed in a native cell.

An antigenic PCSK9 peptide of the invention can be produced as a fusion protein that contains other non-PCSK9 or non-PCSK9-derived amino acid sequences, such as amino acid linkers or signal sequences or immunogenic carriers as defined herein, as well as ligands useful in protein purification, such as glutathione-S-transferase, histidine tag, and staphylococcal protein A. More than one antigenic PCSK9 peptide of the invention can be present in a fusion protein. The heterologous polypeptide can be fused, for example, to the N-terminus or C-terminus of the peptide of the invention. A peptide of the invention can also be produced as fusion proteins comprising homologous amino acid sequences, i. e., other PCSK9 or PCSK9-derived sequences.

The antigenic PCSK9 peptides of the invention might be linear or conformationally constrained. As used herein in reference to a peptide, the term "conformationally constrained" means a peptide, in which the three-dimensional structure is maintained substantially in one spatial arrangement over time. Conformationally constrained molecules can have improved properties such as increased affinity, metabolic stability, membrane permeability or solubility.

In addition, such conformationally constrained peptides are expected to present the antigenic PCSK9 epitope in a conformation similar to their native loop conformation, thereby inducing anti-PCSK9 antibodies more susceptible to recognize intact, native self PCSK9 molecules or with an increased affinity to recognize self PCSK9 molecules.

Methods of conformational constraint are well known in the art and include, without limitation, bridging and cyclization.

There are several approaches known in the prior art to introduce conformational constraints into a linear peptide. For example, bridging between two neighbouring amino acids in a peptide leads to a local conformational modification, the flexibility of which is limited in comparison with that of regular peptides. Some possibilities for forming such bridges include incorporation of lactams and piperazinones (for review see Giannis and Kolter, Angew. Chem. Int. Ed., 1993, 32: 1244).

As used herein in reference to a peptide, the term "cyclic" refers to a structure including an intramolecular bond between two non-adjacent amino acids or amino acid analogs.

The cyclization can be effected through a covalent or non-covalent bond. Intramolecular bonds include, but are not limited to, backbone to backbone, side-chain to backbone, side-chain to side-chain, side chain to end-group, end-to-end bonds. Methods of cyclization include, without limitation, formation of an amide bond between the N-term residue and the C-term residue of a peptide, formation of a disulfide bond between the side-chains of non-adjacent amino acids or amino acid analogs; formation of an amide bond between the side-chains of Lys and Asp/Glu residues; formation of an ester bond between serine residues and Asp/Glu residues; formation of a lactam bond, for example, between a side-chain group of one amino acid or analog thereof to the N-terminal amine of the amino-terminal residue; and formation of lysinonorleucine and dityrosine bonds. Carbon versions of a disulfide linkage, for example an ethenyl or ethyl linkage, could also be used (*J. Peptide Sc.*, 2008, 14, 898-902) as well as alkylation reactions with an appropriately polysubstituted electrophilic reagent such as a di-, tri- or tetrahaloalkane (*PNAS*, 2008, 105(40), 15293-15298; *ChemBioChem*, 2005, 6, 821-824). Various modified proline analogs can also be used to incorporate conformational constraints into peptides (Zhang et al., J. Med Chem., 1996, 39: 2738-2744; Pfeifer and Robinson, Chem. Comm., 1998, 1977-1978). Chemistries that may be used to cyclise peptides of the invention result in peptides cyclised with a bond including, but not limiting to the following: lactam, hydrazone, oxime, thiazolidine, thioether or sulfonium bonds.

Yet another approach in the design of conformationally constrained peptides, which is described in U.S. Ser. No. 10/114,918, is to attach a short amino acid sequence of interest to a template, to generate a cyclic constrained peptide. Such cyclic peptides are not only structurally stabilized by their templates, and thereby offer three-dimensional conformations that may imitate conformational epitopes on native proteins such as on viruses and parasites or on self proteins (autologous mammalian proteins such as PCSK9), but they are also more resistant than linear peptides to proteolytic degradation in serum. U.S. Ser. No. 10/114,918 further discloses the synthesis of conformationally constrained cross-linked peptides by preparation of synthetic amino acids for backbone coupling to appropriately positioned amino acids in order to stabilize the supersecondary structure of peptides. Cross-linking can be achieved by amide coupling of the primary amino group of an orthogonally protected (2S, 3R)-3-aminoproline residue to a suitably positioned side chain carboxyl group of glutamate. This approach has been followed in the preparation of conformationally constrained tetrapeptide repeats of the CS protein wherein at least one proline has been replaced by 2S, 3R)-3-aminoproline and, in order to introduce a side chain carboxyl group, glutamate has been incorporated as a replacement for alanine.

Cross-linking strategies also include the application of the Grubbs ring-closing metathesis reaction to form 'stapled' peptides designed to mimic alpha-helical conformations (*Angew. Int. Ed. Engl.*, 1998, 37, 3281 *JACS*, 2000, 122, 5891); use of poly-functionalised saccharides use of a tryptathionine linkage (*Chemistry Eu. J.*, 2008, 24, 3404-3409); use of 'click' reaction of azides and alkynes which could be incorporated as either a side chain amino acid residues or located within the backbone of the peptide sequence (*Drug Disc. Today*, 2003, 8(24), 1128-1137). It is also known in the literature that metal ions can stabilise constrained conformations of linear peptides through sequestering specific residues e.g. histidine, which co-ordinate to metal cations (*Angew. Int. Ed. Engl.*, 2003, 42, 421). Similarly, functionalising a linear peptide sequence with non-natural acid and amine functionality, or polyamine and polyacid functionality can be used to allow access to cyclised structures following activation and amide bond formation.

According to one embodiment, the antigenic PCSK9 peptide is conformationally constrained by intramolecular covalent bonding of two non-adjacent amino acids of the antigenic PCSK9 peptide to each other, e.g. the N- and C-terminal amino acids.

According to another embodiment, the antigenic PCSK9 peptide of the invention is conformationally constrained by covalent binding to a scaffold molecule. According to a further embodiment, the antigenic PCSK9 peptide is simply constrained, i.e. coupled either at one end, (C or N terminus) or through another amino acid not located at either end, to the scaffold molecule. According to another embodiment, the antigenic PCSK9 peptide is doubly constrained, i.e. coupled at both C and N termini to the scaffold molecule. According to another embodiment, the antigenic peptide is constrained by cyclising via the templating effect of a heterochiral Diproline unit (D-Pro-L-Pro) (Spath et al, 1998, Helvetica Chimica Acta 81, p 1726-1738).

The scaffold (also called 'platform') can be any molecule which is capable of reducing, through covalent bonding, the number of conformations which the antigenic PCSK9 peptide can assume. Examples of conformation-constraining scaffolds include proteins and peptides, for example lipocalin-related molecules such as beta-barrel containing thioredoxin and thioredoxin-like proteins, nucleases (e.g. RNaseA), proteases (e.g. trypsin), protease inhibitors (e.g. eglin C), antibodies or structurally-rigid fragments thereof, fluorescent proteins such as GFP or YFP, conotoxins, loop regions of fibronectin type III domain, CTL-A4, and virus-like particles (VLPs).

Other suitable platform molecules include carbohydrates such as sepharose. The platform may be a linear or circular molecule, for example, closed to form a loop. The platform is generally heterologous with respect to the antigenic PCSK9 peptide. Such conformationally constrained peptides linked to a platform are thought to be more resistant to proteolytic degradation than linear peptide.

According to a preferred embodiment, the scaffold is an immunogenic carrier as defined in the present application. In a further embodiment, the antigenic PCSK9 peptide is simply constrained onto the immunogenic carrier. In another further embodiment, the antigenic PCSK9 peptide is doubly constrained onto the immunogenic carrier. In this manner, the antigenic PCSK9 peptide forms a conformationally constrained loop structure which has proven to be a particularly suitable structure as an intracellular recognition molecule.

The antigenic PCSK9 peptides of the invention may be modified for the ease of conjugation to a platform, for example by the addition of a terminal cysteine at one or both ends and/or by the addition of a linker sequence, such a double glycine head or tail plus a terminal cysteine, a linker terminating with a lysine residue or any other linker known to those skilled in the art to perform such function. Details of such linkers are disclosed hereafter. Bioorthogonal chemistry (such as the click reaction described above) to couple the full peptide sequence to the carrier, thus avoiding any regiochemical and chemoselectivity issues, might also be used. Rigidified linkers such as the one described in Jones et al. Angew. Chem. Int. Ed. 2002, 41:4241-4244 are known to elicit an improved immunological response and might also be used.

Figure 19:
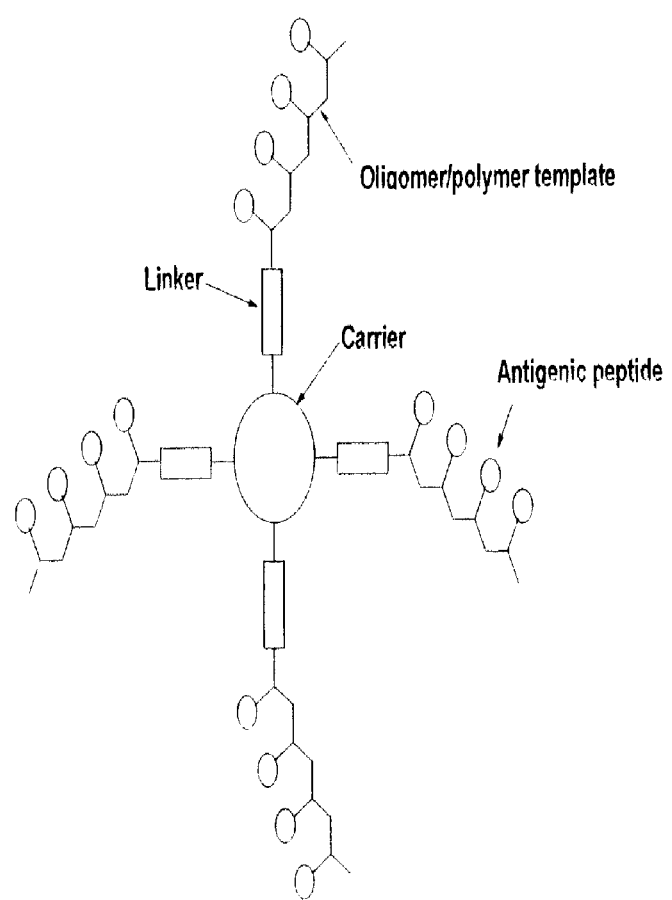
FIG. 19: Diagram illustrating linkage of an antigenic peptide to a carrier.

In a further embodiment, the antigenic PCSK9 peptide is attached to a multivalent template, which itself is coupled to the carrier, thus increasing the density of the antigen (see below). The multivalent template could be an appropriately functionalised polymer or oligomer such as (but not limited to) oligoglutamate or oligochitosan (see FIG. 19).

Immunogenic Carrier of the Invention

In an embodiment of the present invention, the antigenic PCSK9 peptide of the invention is linked to an immunogenic carrier molecule to form immunogens for vaccination protocols, preferably wherein the carrier molecule is not related to the native PCSK9 molecule.

The term "immunogenic carrier" herein includes those materials which have the property of independently eliciting an immunogenic response in a host animal and which can be covalently coupled to a peptide, polypeptide or protein either directly via formation of peptide or ester bonds between free carboxyl, amino or hydroxyl groups in the peptide, polypeptide or protein and corresponding groups on the immunogenic carrier material, or alternatively by bonding through a conventional bifunctional linking group, or as a fusion protein.

The types of carriers used in the immunogens of the present invention will be readily known to the person skilled in the art. Examples of such immunogenic carriers are: serum albumins such as bovine serum albumin (BSA); globulins; thyroglobulins; hemoglobins; hemocyanins (particularly Keyhole Limpet Hemocyanin [KLH]); polylysin; polyglutamic acid; lysine-glutamic acid copolymers; copolymers containing lysine or ornithine; liposome carriers; the purified protein derivative of tuberculin (PPD); inactivated bacterial toxins or toxoids such as tetanus or diptheria toxins (TT and DT) or fragment C of TT, CRM197 (a nontoxic but antigenically identical variant of diphtheria toxin) other DT point mutants, such as CRM176, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843,711, pneumococcal pneumolysin (Kuo et al (1995) Infect Immun 63; 2706-13) including ply detoxified in some fashion for example dPLY-GMBS (WO 04081515, PCT/EP2005/010258) or dPLY-formol, PhtX, including PhtA, PhtB, PhtD, PhtE (sequences of PhtA, PhtB, PhtD or PhtE are disclosed in WO 00/37105 or WO 00/39299) and fusions of Pht proteins for example PhtDE fusions, PhtBE fusions, Pht A-E (WO 01/98334, WO 03/54007, WO2009/000826), OMPC (meningococcal outer membrane protein—usually extracted from *N. meningitidis* serogroup B—EP0372501), PorB (from *N. meningitidis*), PD (*Haemophilus influenzae* protein D—see, e.g., EP 0 594 610 B), or immunologically functional equivalents thereof, synthetic peptides (EP0378881, EP0427347), heat shock proteins (WO 93/17712, WO 94/03208), pertussis proteins (WO 98/58668, EP0471 177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of *C. difficile* (WO 00/61761).

In a preferred embodiment, the immunogenic carrier of the invention is CRM197.

In another embodiment, the immunogenic carrier is a virus-like particle (VLPs), preferably a recombinant virus-like particle.

As used herein, the term "virus-like particle" refers to a structure resembling a virus particle but which has been demonstrated to be non pathogenic. In general, virus-like particles lack at least part of the viral genome. Also, virus-like particles can often be produced in large quantities by heterologous expression and can be easily purified. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, or RNA-phage.

As used herein, the term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition should, however, also encompass virus-like particles of bacteriophages, in which the aforementioned gene or genes are still present but inactive, and, therefore, also leading to non-replicative and noninfectious virus-like particles of a bacteriophage. The capsid structure formed from the self-assembly of 180 subunits of RNA phage coat protein and optionally containing host RNA is herein referred to as a "VLP of RNA phage coat protein". Specific examples are the VLP of Qbeta, MS2, PP7 or AP205 coat proteins. In the specific case of Qbeta coat protein, for example, the VLP may either be assembled exclusively from Qbeta CP subunits (generated by expression of a Qbeta CP gene containing, for example, a TAA stop codon precluding any expression of the longer A1 protein through suppression, see Kozlovska, T. M., et al., Intervirology 39: 9-15 (1996)), or additionally contain A1 protein subunits in the capsid assembly. Generally, the percentage of Qbeta A1 protein relative to Qbeta CP in the capsid assembly will be limited, in order to ensure capsid formation.

Examples of VLPs suitable as immunogenic carriers in the context of the present invention include, but are not limited to, VLPs of Qbeta, MS2, PP7, AP205 and other bacteriophage coat proteins, the capsid and core proteins of Hepatitis B virus (Ulrich, et al., Virus Res. 50: 141-182 (1998)), measles virus (Warnes, et al., Gene 160: 173-178 (1995)), Sindbis virus, rotavirus (U.S. Pat. Nos. 5,071,651 and 5,374,426), foot-and-mouth-disease virus (Twomey, et al., Vaccine 13: 1603-1610, (1995)), Norwalk virus (Jiang, X., et al., Science 250: 1580-1583 (1990); Matsui, S. M., et al., J Clin. Invest. 87: 1456-1461 (1991)), the retroviral GAG protein (PCT Patent Appl. No. WO 96/30523), the retrotransposon Ty protein pl, the surface protein of Hepatitis B virus (WO 92/11291), human papilloma virus (WO 98/15631), human polyoma virus (Sasnauskas K., et al., Biol. Chem. 380 (3): 381-386 (1999); Sasnauskas K., et al., Generation of recombinant virus-like particles of different polyomaviruses in yeast. 3rd Interational Workshop "Virus-like particles as vaccines." Berlin, September 26-29 (2001)), RNA phages, Ty, frphage, GA-phage, AP 205-phage and, in particular, Qbeta-phage, Cowpea chlorotic mottle virus, cowpea mosaic virus, human papilloma viruses (HPV), bovine papilloma viruses, porcine parvovirus, parvoviruses such as B19, porcine (PPV) and canine (CPV) parvovirues, caliciviruses (e.g. Norwalk virus, rabbit hemorrhagic disease virus [RHDV]), animal hepadnavirus core Antigen VLPs, filamentous/rod-shaped plant viruses, including but not limited to Tobacco Mosaic Virus (TMV), Potato Virus X (PVX), Papaya Mosaic Virus (PapMV), Alfalfa Mosaic Virus (AIMV), and Johnson Grass Mosaic Virus (JGMV), insect viruses such as flock house virus (FHV) and tetraviruses, polyomaviruses such as Murine Polyomavirus (MPyV), Murine Pneumotropic Virus (MPtV), BK virus (BKV), and JC virus (JCV).

As will be readily apparent to those skilled in the art, the VLP to be used as an immunogenic carrier of the invention is not limited to any specific form. The particle can be synthesized chemically or through a biological process, which can be natural or nonnatural. By way of example, this type of embodiment includes a virus-like particle or a recombinant form thereof. In a more specific embodiment, the VLP can comprise, or alternatively consist of, recombinant polypeptides of any of the virus known to form a VLP. The virus-like particle can further comprise, or alternatively consist of, one or more fragments of such polypeptides, as well as variants of such polypeptides. Variants of polypeptides can share, for example, at least 80%, 85%, 90%, 95%, 97%, or 99% identity at the amino acid level with their wild-type counterparts. Variant VLPs suitable for use in the present invention can be derived from any organism so long as they are able to form a "virus-like particle" and can be used as an "immunogenic carrier" as defined herein.

Preferred VLPs according to the invention include the capsid protein or surface antigen of HBV (HBcAg and HBsAg respectively) or recombinant proteins or fragments thereof, and the coat proteins of RNA-phages or recombinant proteins or fragments thereof, more preferably the coat protein of Qbeta or recombinant proteins or fragments thereof. In one embodiment, the immunogic carrier used in combination with an antigenic PCSK9 peptide of the invention is an HBcAg protein. Examples of HBcAg proteins that can be used in the context of the present invention can be readily determined by one skilled in the art. Examples include, but are limited to, HBV core proteins described in Yuan et al., (J. Virol. 73: 10122-10128 (1999)), and in WO00/198333, WO 00/177158, WO 00/214478, WO WO00/32227, WO01/85208, WO02/056905, WO03/024480, and WO03/024481. HBcAgs suitable for use in the present invention can be derived from any organism so long as they are able to form a "virus-like particle" and can be used as an "immunogenic carrier" as defined herein.

HBcAg variants of particular interest that could be used in the context of the present invention are those variants in which one or more naturally resident cysteine residues have been either deleted or substituted. It is well known in the art that free cysteine residues can be involved in a number of chemical side reactions including disulfide exchanges, reaction with chemical substances or metabolites that are, for example, injected or formed in a combination therapy with other substances, or direct oxidation and reaction with nucleotides upon exposure to UV light. Toxic adducts could thus be generated, especially considering the fact that HBcAgs have a strong tendency to bind nucleic acids. The toxic adducts would thus be distributed between a multiplicity of species, which individually may each be present at low concentration, but reach toxic levels when together. In view of the above, one advantage to the use of HBcAgs in vaccine compositions which have been modified to remove naturally resident cysteine residues is that sites to which toxic species can bind when antigens or antigenic determinants are attached would be reduced in number or eliminated altogether.

In addition, the processed form of HBcAg lacking the N-terminal leader sequence of the Hepatitis B core antigen precursor protein can also be used in the context of the invention, especially when HBcAg is produced under conditions where processing will not occur (e.g. expression in bacterial systems).

Other HBcAg variants according to the invention include i) polypeptide sequence having at least 80%, 85%, 90%, 95%, 97% or 99% identical to one of the wild-type HBcAg amino acid sequences, or a subportion thereof, using conventionally using known computer programs, ii) C-terminal truncation mutants including mutants where 1, 5, 10, 15, 20, 25, 30, 34 or 35, amino acids have been removed from the C-terminus, ii) N-terminal truncation mutants including mutants where 1, 2, 5, 7, 9, 10, 12, 14, 15, or 17 amino acids have been removed from the N-terminus, iii) mutants truncated in both N-terminal and C-terminal include HBcAgs where 1, 2, 5, 7, 9, 10, 12, 14, 15 or 17 amino acids have been removed from the N-terminus and 1, 5, 10, 15, 20, 25, 30, 34 or 35 amino acids have been removed from the C-terminus.

Still other HBcAg variant proteins within the scope of the invention are those variants modified in order to enhance immunogenic presentation of a foreign epitope wherein one or more of the four arginine repeats has been deleted, but in which the C-terminal cysteine is retained (see e.g. WO01/98333), and chimeric C-terminally truncated HBcAg such as those described in WO02/14478, WO03/102165 and WO04/053091.

In another embodiment, the immunogic carrier used in combination with an antigenic PCSK9 peptide of the invention is an HBsAg protein. HBsAg proteins that could be used in the context of the present invention can be readily determined by one skilled in the art. Examples include, but are not limited to, HBV surface proteins described in U.S. Pat. No. 5,792,463, WO02/10416, and WO08/020331. HBsAgs suitable for use in the present invention can be derived from any organism so long as they are able to form a "virus-like particle" and can be used as an "immunogenic carrier" as defined herein.

In still another embodiment, the immunogic carrier used in combination with an antigenic PCSK9 peptide or polypeptide of the invention is a Qbeta coat protein.

Qbeta coat protein was found to self-assemble into capsids when expressed in *E. coli* (Kozlovska™. et al., GENE 137: 133-137 (1993)). The obtained capsids or virus-like particles showed an icosahedral phage-like capsid structure with a diameter of 25 nm and T=3 quasi symmetry. Further, the crystal structure of phage Qss has been solved. The capsid contains 180 copies of the coat protein, which are linked in covalent pentamers and hexamers by disulfide bridges (Golmohammadi, R. et al., Structure 4: 5435554 (1996)) leading to a remarkable stability of the capsid of Qbeta coat protein. Qbeta capsid protein also shows unusual resistance to organic solvents and denaturing agents. The high stability of the capsid of Qbeta coat protein is an advantageous feature, in particular, for its use in immunization and vaccination of mammals and humans in accordance of the present invention.

Examples of Qbeta coat proteins that can be used in the context of the present invention can be readily determined by one skilled in the art. Examples have been extensively described in WO02/056905, WO03/024480, WO03/024481 (incorporated by reference in their entirety) and include, but are not limited to, amino acid sequences disclosed in PIR database, accession No. VCBPQbeta referring to Qbeta CP; Accession No. AAA16663 referring to Qbeta A1 protein; and variants thereof including variants proteins in which the N-terminal methionine is cleaved; C-terminal truncated forms of Qbeta A1 missing as much as 100, 150 or 180 amino acids; variant proteins which have been modified by the removal of a lysine residue by deletion or substitution or by the addition of a lysine residue by substitution or insertion (see for example Qbeta-240, Qbeta-243, Qbeta-250, Qbeta-251 and Qbeta-259 disclosed in WO03/024481, incorporated by reference in its entirety), and variants exhibiting at least 80%, 85%, 90%, 95%, 97%, or 99% identity to any of the Qbeta core proteins described above. Variant Qbeta coat proteins suitable for use in the present invention can be derived from any organism so long as they are able to form a "virus-like particle" and can be used as "immunogenic carriers" as defined herein.

The antigenic PCSK9 peptides of the invention may be coupled to immunogenic carriers via chemical conjugation or by expression of genetically engineered fusion partners. The coupling does not necessarily need to be direct, but can occur through linker sequences. More generally, in the case that antigenic peptides either fused, conjugated or otherwise attached to an immunogenic carrier, spacer or linker sequences are typically added at one or both ends of the antigenic peptides. Such linker sequences generally comprise sequences recognized by the proteasome, proteases of the endosomes or other vesicular compartment of the cell.

In one embodiment, the peptides of the present invention are expressed as fusion proteins with the immunogenic carrier. Fusion of the peptide can be effected by insertion into the immunogenic carrier primary sequence, or by fusion to either the N- or C-terminus of the immunogenic carrier. Hereinafter, when referring to fusion proteins of a peptide to an immunogenic carrier, the fusion to either ends of the subunit sequence or internal insertion of the peptide within the carrier sequence are encompassed. Fusion, as referred to hereinafter, may be effected by insertion of the antigenic peptide into the sequence of carrier, by substitution of part of the sequence of the carrier with the antigenic peptide, or by a combination of deletion, substitution or insertions.

When the immunogenic carrier is a VLP, the chimeric antigenic peptide-VLP subunit will be in general capable of self-assembly into a VLP. VLP displaying epitopes fused to their subunits are also herein referred to as chimeric VLPs. For example, EP 0 421 635 B describes the use of chimaeric hepadnavirus core antigen particles to present foreign peptide sequences in a virus-like particle.

Flanking amino acid residues may be added to either end of the sequence of the antigenic peptide to be fused to either end of the sequence of the subunit of a VLP, or for internal insertion of such peptidic sequence into the sequence of the subunit of a VLP. Glycine and serine residues are particularly favored amino acids to be used in the flanking sequences added to the peptide to be fused. Glycine residues confer additional flexibility, which may diminish the potentially destabilizing effect of fusing a foreign sequence into the sequence of a VLP subunit.

In a specific embodiment of the invention, the immunogenic carrier is a HBcAg VLP. Fusion proteins of the antigenic peptide to either the N-terminus of a HBcAg (Neyrinck, S. et al., Nature Med. 5: 11571163 (1999)) or insertions in the so called major immunodominant region (MIR) have been described (Pumpens, P. and Grens, E., Intervirology 44: 98114 (2001)), WO 01/98333), and are specific embodiments of the invention. Naturally occurring variants of HBcAg with deletions in the MIR have also been described (Pumpens, P. and Grens, E., Intervirology 44: 98-114 (2001)), and fusions to the N- or C-terminus, as well as insertions at the position of the MIR corresponding to the site of deletion as compared to a wt HBcAg are further embodiments of the invention. Fusions to the C-terminus have also been described (Pumpens, P. and Grens, E., Intervirology 44: 98-114 (2001)). One skilled in the art will easily find guidance on how to construct fusion proteins using classical molecular biology techniques. Vectors and plasmids encoding HBcAg and HBcAg fusion proteins and useful for the expression of a HBcAg and HBcAg fusion proteins have been described (Pumpens, P. and #38; Grens, E. Intervirology 44: 98-114 (2001), Neyrinck, S. et al., Nature Med. 5: 1157-1163 (1999)) and can be used in the practice of the invention. An important factor for the optimization of the efficiency of self-assembly and of the display of the epitope to be inserted in the MIR of HBcAg is the choice of the insertion site, as well as the number of amino acids to be deleted from the HBcAg sequence within the MIR (Pumpens, P. and Grens, E., Intervirology 44: 98-114 (2001); EP 0 421 635; U.S. Pat. No. 6,231,864) upon insertion, or in other words, which amino acids form HBcAg are to be substituted with the new epitope. For example, substitution of HBcAg amino acids 76-80, 79-81, 79-80, 75-85 or 80-81 with foreign epitopes has been described (Pumpens, P. and Grens, E., Intervirology 44: 98-114 (2001); EP0421635; U.S. Pat. No. 6,231,864, WO00/26385). HBcAg contains a long arginine tail (Pumpens, P. and Grens, E., Intervirology 44: 98-114 (2001)) which is dispensable for capsid assembly and capable of binding nucleic acids (Pumpens, P. and Grens, E., Intervirology 44: 98-114 (2001)). HBcAg either comprising or lacking this arginine tail are both embodiments of the invention.

In another specific embodiment of the invention, the immunogenic carrier is a VLP of a RNA phage, preferably Qbeta. The major coat proteins of RNA phages spontaneously assemble into VLPs upon expression in bacteria, and in particular in E. coli. Fusion protein constructs wherein antigenic peptides have been fused to the C-terminus of a truncated form of the A1 protein of Qbeta, or inserted within the A1 protein have been described (Kozlovska, T. M., et al., Intervirology, 39: 9-15 (1996)). The A1 protein is generated by suppression at the UGA stop codon and has a length of 329 aa, or 328 aa, if the cleavage of the N-terminal methionine is taken into account. Cleavage of the N-terminal methionine before an alanine (the second amino acid encoded by the Qbeta CP gene) usually takes place in E. coli, and such is the case for N-termini of the Qbeta coat proteins. The part of the A1 gene, 3' of the UGA amber codon encodes the CP extension, which has a length of 195 amino acids. Insertion of the antigenic peptide between position 72 and 73 of the CP extension leads to further embodiments of the invention (Kozlovska, T. M., et al., Intervirology 39: 9-15 (1996)). Fusion of an antigenic peptide at the C-terminus of a C-terminally truncated Qbeta A1 protein leads to further preferred embodiments of the invention. For example, Kozlovska et al., (Intervirology, 39: 9-15 (1996)) describe Qbeta A1 protein fusions where the epitope is fused at the C-terminus of the Qbeta CP extension truncated at position 19.

As described by Kozlovska et al. (Intervirology, 39: 9-15 (1996)), assembly of the particles displaying the fused epitopes typically requires the presence of both the A1 protein-antigen fusion and the wt CP to form a mosaic particle. However, embodiments comprising virus-like particles, and hereby in particular the VLPs of the RNA phage Qbeta coat protein, which are exclusively composed of VLP subunits having an antigenic peptide fused thereto, are also within the scope of the present invention.

The production of mosaic particles may be effected in a number of ways. Kozlovska et al., Intervirology, 39: 9-15 (1996), describe three methods, which all can be used in the practice of the invention. In the first approach, efficient display of the fused epitope on the VLPs is mediated by the expression of the plasmid encoding the Qbeta A11 protein fusion having a UGA stop codon between CP and CP extension in a E. coli strain harboring a plasmid encoding a cloned UGA suppressor tRNA which leads to translation of the UGA codon into Trp (pISM3001 plasmid (Smiley B. K., et al., Gene 134: 33-40 (1993))). In another approach, the CP gene stop codon is modified into UAA, and a second plasmid expressing the A1 protein-antigen fusion is cotransformed. The second plasmid encodes a different antibiotic resistance and the origin of replication is compatible with the first plasmid. In a third approach, CP and the A1 protein-antigen fusion are encoded in a bicistronic manner, operatively linked to a promoter such as the Trp promoter, as described in FIG. 1 of Kozlovska et al., Intervirology, 39: 9-15 (1996). Further VLPs suitable for fusion of antigens or antigenic determinants are described in WO03/024481 and include bacteriophage fr, RNA phase MS-2, capsid protein of papillomavirus, retrotransposon Ty, yeast and also Retrovirus-like-particles, HIV2 Gag, Cowpea Mosaic Virus, parvovirus VP2 VLP, HBsAg (U.S. Pat. No. 4,722,840, EP0020416B1). Examples of chimeric VLPs suitable for the practice of the invention are also those described in Intervirology 39: 1 (1996). Further examples of VLPs contemplated for use in the invention are: HPV-1, HPV-6, HPV-11, HPV-16, HPV-18, HPV-33, HPV-45, CRPV, COPV, HIV GAG, Tobacco Mosaic Virus. Virus-like particles of SV-40, Polyomavirus, Adenovirus, Herpes Simplex Virus, Rotavirus and Norwalk virus.

For any recombinantly expressed antigenic PCSK9 peptide according to the invention coupled or not to an immunogenic carrier, the nucleic acid which encodes said peptide or protein also forms an aspect of the present invention, as does an expression vector comprising the nucleic acid, and a host cell containing the expression vector (autonomously or chromosomally inserted). A method of recombinantly producing the peptide or protein by expressing it in the above host cell and isolating the immunogen therefrom is a further aspect of the invention. The full-length native PCSK9 molecule or the full-length native DNA sequence encoding it are not covered by the present invention.

In another embodiment, the peptide of the invention is chemically coupled to an immunogenic carrier, using techniques well known in the art. Conjugation can occur to allow free movement of peptides via single point conjugation (e.g. either N-terminal or C-terminal point) or as locked down structure where both ends of peptides are conjugated to either a immunogenic carrier protein or to a scaffold structure such as a VLP. Conjugation occurs via conjugation chemistry known to those skilled in the art such as via cysteine residues, lysine residues or other carboxy moiety's commonly known as conjugation points such as glutamic acid or aspartic acid. Thus, for example, for direct covalent coupling it is possible to utilise a carbodiimide, glutaraldehyde or (N-[y-malcimidobutyryloxy] succinimide ester, utilising common commercially available heterobifunctional linkers such as CDAP and SPDP (using manufacturers instructions). Examples of conjugation of peptides, particularly cyclised peptides, to a protein carrier via acylhydrazine peptide derivatives are described in WO03/092714. After the coupling reaction, the immunogen can easily be isolated and purified by means of a dialysis method, a gel filtration method, a fractionation method etc. Peptides terminating with a cysteine residue (preferably with a linker outside the cyclised region) may be conveniently conjugated to a carrier protein via maleimide chemistry.

When the immunogenic carrier is a VLP, several antigenic peptide, either having an identical amino acid sequence or a different amino acid sequence, may be coupled to a single VLP molecule, leading preferably to a repetitive and ordered structure presenting several antigenic determinants in an oriented manner as described in WO00/32227, WO03/024481, WO02/056905 and WO04/007538.

In a preferred embodiment, the antigenic PCSK9 peptide is bound to the VLP by way of chemical cross-linking, typically and preferably by using a heterobifunctional cross-linker. Several hetero-bifunctional cross-linkers are known to the art. In some embodiments, the hetero-bifunctional crosslinker contains a functional group which can react with first attachment sites, i. e. with the side-chain amino group of lysine residues of the VLP or VLP subunit, and a further functional group which can react with a preferred second attachment site, i. e. a cysteine residue fused to the antigenic peptide and optionally also made available for reaction by reduction. The first step of the procedure, typically called the derivatization, is the reaction of the VLP with the cross-linker. The product of this reaction is an activated VLP, also called activated carrier. In the second step, unreacted cross-linker is removed using usual methods such as gel filtration or dialysis. In the third step, the antigenic peptide is reacted with the activated VLP, and this step is typically called the coupling step. Unreacted antigenic peptide may be optionally removed in a fourth step, for example by dialysis. Several hetero-bifunctional crosslinkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company (Rockford, Ill., USA), and having one functional group reactive towards amino groups and one functional group reactive towards cysteine residues. The above mentioned cross-linkers all lead to formation of a thioether linkage.

Another class of cross-linkers suitable in the practice of the invention is characterized by the introduction of a disulfide linkage between the antigenic peptide and the VLP upon coupling. Preferred cross-linkers belonging to this class include for example SPDP and Sulfo-LC-SPDP (Pierce). The extent of derivatization of the VLP with cross-linker can be influenced by varying experimental conditions such as the concentration of each of the reaction partners, the excess of one reagent over the other, the pH, the temperature and the ionic strength. The degree of coupling, i. e. the amount of antigenic peptide per subunits of the VLP can be adjusted by varying the experimental conditions described above to match the requirements of the vaccine.

Another method of binding of antigenic peptides to the VLP, is the linking of a lysine residue on the surface of the VLP with a cysteine residue on the antigenic peptide. In some embodiments, fusion of an amino acid linker containing a cysteine residue, as a second attachment site or as a part thereof, to the antigenic peptide for coupling to the VLP may be required. In general, flexible amino acid linkers are favored. Examples of the amino acid linker are selected from the group consisting of: (a) CGG; (b) N-terminal gamma 1-linker; (c) N-terminal gamma 3-linker; (d) Ig hinge regions; (e) N-terminal glycine linkers; (f) (G) kC (G) n with n=0-12 and k=0-5; (g) N-terminal glycine-serine linkers; (h) (G) kC (G) m (S) i (GGGGS) n with n=0-3, k=0-5, m=0-10, i=0-2; (i) GGC; (k) GGC-NH2; (l) C-terminal gamma 1-linker; (m) C-terminal gamma 3-linker; (n) C-terminal glycine linkers; (o) (G) nC (G) k with n=0-12 and k=0-5; (p) C-terminal glycine-serine linkers; (q) (G) m (S) t (GGGGS) n (G) oC (G) k with n=0-3, k=0-5, m=0-10, 1=0-2, and o=0-8. Further examples of amino acid linkers are the hinge region of immunoglobulins, glycine serine linkers (GGGGS) n, and glycine linkers (G) n all further containing a cysteine residue as second attachment site and optionally further glycine residues. Typically preferred examples of said amino acid linkers are N-terminal gamma 1: CGDK-THTSPP (SEQ ID NO:608); C-terminal gamma 1: DKTHTSPPCG (SEQ ID NO:609); N-terminal gamma 3: CGGPKPSTPPGSSGGAP (SEQ ID NO:610); C-terminal gamma 3: PKPSTPPGSSGGAPGGCG (SEQ ID NO:611); N-terminal glycine linker: GCGGGG (SEQ ID NO:612) and C-terminal glycine linker: GGGGCG (SEQ ID NO:613). Other amino acid linkers particularly suitable in the practice of the invention, when a hydrophobic antigenic peptide is bound to a VLP, are CGKKGG (SEQ ID NO:614), or CGDEGG (SEQ ID NO:615) for N-terminal linkers, or GGKKGC (SEQ ID NO:616 and GGEDGC (SEQ ID NO:617), for the C-terminal linkers. For the C-terminal linkers, the terminal cysteine is optionally C-terminally amidated.

In some embodiments of the present invention, GGCG (SEQ ID NO:618), GGC or GGC-NH2 ("NH2" stands for amidation) linkers at the C-terminus of the peptide or CGG at its N-terminus are preferred as amino acid linkers. In general, glycine residues will be inserted between bulky amino acids and the cysteine to be used as second attachment site, to avoid potential steric hindrance of the bulkier amino acid in the coupling reaction. In a further embodiment of the invention, the amino acid linker GGC-NH2 is fused to the C-terminus of the antigenic peptide.

The cysteine residue present on the antigenic peptide has to be in its reduced state to react with the hetero-bifunctional cross-linker on the activated VLP, that is a free cysteine or a cysteine residue with a free sulfhydryl group has to be available. In the instance where the cysteine residue to function as binding site is in an oxidized form, for example if it is forming a disulfide bridge, reduction of this disulfide bridge with e. g. DTT, TCEP or p-mercaptoethanol is required. Low concentrations of reducing agent are compatible with coupling as described in WO 02/05690, higher concentrations inhibit the coupling reaction, as a skilled artisan would know, in which case the reductant has to be removed or its concentration decreased prior to coupling, e. g. by dialysis, gel filtration or reverse phase HPLC.

Binding of the antigenic peptide to the VLP by using a hetero-bifunctional cross-linker according to the methods described above, allows coupling of the antigenic peptide to the VLP in an oriented fashion. Other methods of binding the antigenic peptide to the VLP include methods wherein the antigenic peptide is cross-linked to the VLP using the carbodiimide EDC, and NHS.

In other methods, the antigenic peptide is attached to the VLP using a homo-bifunctional cross-linker such as glutaraldehyde, DSGBM [PEO] 4, BS3, (Pierce Chemical Company, Rockford, Ill., USA) or other known homo-bifunctional cross-linkers with functional groups reactive towards amine groups or carboxyl groups of the VLP. Other methods of binding the VLP to an antigenic peptide include methods where the VLP is biotinylated, and the antigenic peptide expressed as a streptavidin-fusion protein, or methods wherein both the antigenic peptide and the VLP are biotinylated, for example as described in WO 00/23955. In this case, the antigenic peptide may be first bound to streptavidin or avidin by adjusting the ratio of antigenic peptide to streptavidin such that free binding sites are still available for binding of the VLP, which is added in the next step. Alternatively, all components may be mixed in a "one pot" reaction. Other ligand-receptor pairs, where a soluble form of the receptor and of the ligand is available, and are capable of being cross-linked to the VLP or the antigenic peptide, may be used as binding agents for binding antigenic peptide to the VLP. Alternatively, either the ligand or the receptor may be fused to the antigenic peptide, and so mediate binding to the VLP chemically bound or fused either to the receptor, or the ligand respectively. Fusion may also be effected by insertion or substitution.

One or several antigen molecules can be attached to one subunit of the capsid or VLP of RNA phages coat proteins, preferably through the exposed lysine residues of the VLP of RNA phages, if sterically allowable. A specific feature of the VLP of the coat protein of RNA phages and in particular of the Qβ coat protein VLP is thus the possibility to couple several antigens per subunit. This allows for the generation of a dense antigen array. VLPs or capsids of Q coat protein display a defined number of lysine residues on their surface, with a defined topology with three lysine residues pointing towards the interior of the capsid and interacting with the RNA, and four other lysine residues exposed to the exterior of the capsid. These defined properties favor the attachment of antigens to the exterior of the particle, rather than to the interior of the particle where the lysine residues interact with RNA. VLPs of other RNA phage coat proteins also have a defined number of lysine residues on their surface and a defined topology of these lysine residues.

In a further embodiment of the present invention, the first attachment site is a lysine residue and/or the second attachment comprises sulfhydryl group or a cysteine residue. In an even further embodiment of the present invention, the first attachment site is a lysine residue and the second attachment is a cysteine residue. In further embodiments of the invention, the antigen or antigenic determinant is bound via a cysteine residue, to lysine residues of the VLP of RNA phage coat protein, and in particular to the VLP of Qbeta coat protein.

Another advantage of the VLPs derived from RNA phages is their high expression yield in bacteria that allows production of large quantities of material at affordable cost. Moreover, the use of the VLPs as carriers allow the formation of robust antigen arrays and conjugates, respectively, with variable antigen density. In particular, the use of VLPs of RNA phages, and hereby in particular the use of the VLP of RNA phage Qbeta coat protein allows a very high epitope density to be achieved.

According to an embodiment of the present invention the antigenic PCSK9 peptide disclosed herein are linked, preferably chemically cross linked, to CRM197, either directly or via one of the peptide linker disclosed herein, to generate an immunogen. In an embodiment, the antigenic PCSK9 peptide disclosed herein is linked to CRM197, by way of chemical cross-linking as described herein and preferably by using a heterobifunctional cross-linker, as disclosed above.

Preferred heterobifunctional cross-linkers for use with CRM197 are BAANS (bromoacetic acid N-hydroxysuccinimide ester), SMPH (Succinimidyl-6-[β-maleimidopropionamido]hexanoate), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company (Rockford, Ill., USA). In a preferred embodiment of the present invention, the heterobifunctional crosslinker is BAANS or SMPH.

Alternatively, cross-linkers suitable allowing the introduction of a disulfide linkage between the antigenic peptide and CRM197 could also be used in the context of the invention. Preferred cross-linkers belonging to this class include for example SPDP and Sulfo-LC-SPDP (Pierce).

In a particular embodiment, when the sequence of the antigenic PCSK9 peptide disclosed herein comprises a cysteine, said antigenic PCSK9 peptide may be covalently linked to CRM197 directly via said cysteine.

In some embodiments of the invention, immunogenic compositions of the invention may comprise mixtures of immunogenic conjugates, i.e. immunogenic carriers coupled to one or several antigenic PCSK9 peptides of the invention. Thus, these immunogenic compositions may be composed of immunogenic carriers which differ in amino acid sequence. For example, vaccine compositions could be prepared comprising a "wild-type" VLP and a modified VLP protein in which one or more amino acid residues have been altered (e. g., deleted, inserted or substituted). Alternatively, the same immunogenic carrier might be used but coupled to antigenic PCSK9 peptides of different amino acid sequences.

The invention therefore also relates to method for producing an immunogen according to the invention comprising i) providing an antigenic PCSK9 peptide according to the invention, ii) providing an immunogenic carrier according to the invention, preferably a VLP, and iii) combining said antigenic PCSK9 peptide and said immunogenic carrier. In one embodiment, said combining step occurs through chemical cross-linking, preferably through an heterobifunctional cross-linker.

In an embodiment of the present invention, the antigenic PCSK9 peptide disclosed herein is linked to an immunogenic carrier molecule. In an embodiment said immunogenic carrier is selected from the group consisting of any of the immunogenic carrier described herein. In another embodiment said immunogenic carrier is selected from the group consisting of: serum albumins such as bovine serum albumin (BSA); globulins; thyroglobulins; hemoglobins; hemocyanins (particularly Keyhole Limpet Hemocyanin [KLH]) and virus-like particle (VLPs). In a preferred embodiment said immunogenic carrier is Diphtheria Toxoid, CRM197 mutant of diphtheria toxin, Tetanus Toxoid, Keyhole Limpet Hemocyanin or virus-like particle (VLPs). In an even preferred embodiment, said immunogenic carrier is DT, CRM197 or a VLP selected from the group consisting of HBcAg VLP, HBsAg VLP, Qbeta VLP, PP7 VLP, PPV VLP, Norwalk Virus VLP or any variant disclosed herein. In an even preferred embodiment, said immunogenic carrier is a bacteriophage VLP such as Qbeta VLP selected from the group consisting of Qbeta CP; Qbeta A1, Qbeta-240, Qbeta-243, Qbeta-250, Qbeta-251 and Qbeta-259 (disclosed in WO03/024481) or PP7.

In another preferred embodiment, said immunogenic carrier is CRM197.

In an embodiment, said immunogenic carrier is covalently linked to the antigenic PCSK9 peptide disclosed herein either directly or via a linker. In an embodiment, said immunogenic carrier is linked to the antigenic PCSK9 peptide disclosed herein by expression of a fusion protein as described herein. In another embodiment, the antigenic PCSK9 peptide disclosed herein is linked to the immunogenic carrier, preferably a VLP, by way of chemical cross-linking as described herein and preferably by using a heterobifunctional cross-linker. Several hetero-bifunctional cross-linkers are known to the art. In some embodiments, the hetero-bifunctional crosslinker contains a functional group which can react with first attachment sites, i.e. with the side-chain amino group of lysine residues of the VLP or VLP subunit, and a further functional group which can react with a preferred second attachment site, i.e. a cysteine residue fused to the antigenic peptide made available for reaction by reduction.

Antigenic PCSK9 Peptide of the Invention Comprising a Linker

In an embodiment of the present invention the antigenic PCSK9 peptide disclosed herein further comprise either at its N-terminus, or at its C-terminus or at both the N-terminus and C-terminus a linker which is able to react with an attachment site of the immunogenic carrier in a chemical cross-linking reaction. In an embodiment, the antigenic PCSK9 peptide disclosed herein further comprise at its C-terminus a linker having the formula $(G)_nC$, $(G)_nSC$ or $(G)_nK$, preferably $(G)_nC$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n is 0 or 1 (where n is equal to 0 said formula represents a cysteine). Preferably the antigenic PCSK9 peptide disclosed herein further comprise at its C-terminus a linker having the formula GGGC (SEQ ID NO:619), GGC, GC or C. In another embodiment of the present invention the antigenic PCSK9 peptide disclosed herein further comprise at its N-terminus a linker having the formula $C(G)_n$, $CS(G)_n$ or $K(G)_n$, preferably $C(G)_n$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n is 0 or 1 (where n is equal to 0, the formula represents a cysteine). Preferably the antigenic PCSK9 peptide disclosed herein further comprise at its N-terminus a linker having the formula CGGG (SEQ ID NO:620), CGG, CG or C.

In another embodiment the antigenic PCSK9 peptide disclosed herein further comprise at its C-terminus a linker having the formula $(G)_nC$, $(G)_nSC$ or $(G)_nK$, preferably $(G)_nC$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n 0 or 1 (where n is equal to 0 said formula represents a cysteine) and at its N-terminus a linker having the formula $C(G)_n$, $CS(G)_n$ or $K(G)_n$, preferably $C(G)_n$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n is 0 or 1 (where n is equal to 0, the formula represents a cysteine). Preferably the antigenic PCSK9 peptide disclosed herein further comprise at its N-terminus a linker having the formula CGGG (SEQ ID NO:620), CGG, CG or C and at its C-terminus a linker having the formula GGGC (SEQ ID NO:619), GGC, GC or C. Preferably, the antigenic PCSK9 peptide disclosed herein further comprises at its N-terminus a cysteine and at its C-terminus a cysteine.

Representative of said antigenic PCSK9 peptides further comprising such a linker are disclosed at SEQ ID NO 313, 314, 315, 316, 317, 322, 323, 324, 325, 326, 327, 328, 401, 402, 403, 404, 405, 406, 407, 408, 409, 410, 411, 412, 413, 414, 415, 416, 417, 418 and 419.

Representative of said antigenic PCSK9 peptides further comprising such a linker are disclosed at SEQ ID NO 313, 314, 315, 316, 317, 322, 323, 324, 325, 326, 327 and 328. Preferred antigenic PCSK9 peptides comprising a linker are disclosed at SEQ ID Nos 317, 322, 323, 324, 401, 402, 403, 413, 414, 415 and 416.

Preferred antigenic PCSK9 peptides comprising a linker are disclosed at SEQ ID Nos 317, 322, 323 and 324.

Most preferred antigenic PCSK9 peptides comprising a linker are disclosed at SEQ ID Nos 317, 322, 402 and 413.

In one embodiment, the antigenic PCSK9 peptide is cyclised. In one embodiment, the cyclised antigenic PCSK9 peptide is attached to an immunogenic carrier. In one embodiment, said cyclised antigenic PCSK9 peptide is attached to an immunogenic carrier by covalent binding. In one embodiment, said cyclised antigenic PCSK9 peptide is attached to an immunogenic carrier by covalent binding of one of the side chain of its amino acids to the carrier. In one embodiment, a cysteine, a GC or a CC fragment comprising a variable number of glycine residues and one cysteine residue is added to the cyclised PCSK9 peptides to enable the covalent binding to the immunogenic carrier through the added cysteine.

In one embodiment, the antigenic PCSK9 peptide is cyclised and comprises a cysteine, a $(G)_nC$ or a $C(G)_n$ fragment wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n is 0 or 1 (where n is equal to 0, the formula represents a cysteine).

Non limitative examples of such conformationally constrained antigenic PCSK9 peptide are the peptides of SEQ ID Nos 318, 319, 320 and 321. A preferred cyclised peptide is the peptide of SEQ ID Nos 318.

Examples of conjugations of antigenic PCSK9 peptides with carrier or scaffolds described above, all within the scope of the present invention and constituting various embodiments, using various linkers are provided below: Peptide-GGGGGC (SEQ ID NO:621)-scaffold, peptide-GGGGC (SEQ ID NO:622)-scaffold, peptide-GGGC (SEQ ID NO:619)-scaffold, peptide-GGC-scaffold, peptide-GC-scaffold, peptide-C-scaffold, peptide-GGGGGK (SEQ ID NO:624)-scaffold, peptide-GGGGK (SEQ ID NO:625)-scaffold, Peptide-GGGK (SEQ ID NO:626)-scaffold, Peptide-GGK-scaffold, Peptide-GK-scaffold, Peptide-K-scaffold, Peptide-GGGGSC (SEQ ID NO:627)-scaffold, Peptide-GGGSC (SEQ ID NO:628)-scaffold, Peptide-GGSC (SEQ ID NO:629)-scaffold, Peptide-GSC-scaffold, Peptide-SC-scaffold, Scaffold-CSGGGG (SEQ ID NO:630)-Peptide, Scaffold-CSGGG (SEQ ID NO:631)-Peptide, Scaffold-CSGG (SEQ ID NO:632)-Peptide, Scaffold-CSG-Peptide, Scaffold-CS-Peptide, Scaffold-KGGGG (SEQ ID NO:633)-Peptide, Scaffold-KGGG (SEQ ID NO:634)-Peptide, Scaffold-KGG-Peptide, Scaffold-KG-Peptide, Scaffold-K-Peptide.

In an embodiment, the peptide consists of any of the antigenic PCSK9 peptide disclosed herein and the scaffold consists of any of the immunogenic carrier disclosed herein, preferably a VLP.

Exemplary combinations of conjugations using various linkers and doubly constrained peptides are provided below, where the carrier can be the identical monomer of a carrier or a differential monomer of a carrier. (In the example below, the GC linker can be substituted by any of the GK linker or GSC linker exemplified above or any other known to those skilled in the art):

Carrier-CGGGGG (SEQ ID NO:635)-Peptide-GGGGGC (SEQ ID NO:621)-carrier, Carrier-CGGGG (SEQ ID NO:636)-Peptide-GGGGC (SEQ ID NO:622)-carrier, Carrier-CGGGG (SEQ ID NO:6326-Peptide-GGGGC (SEQ ID NO:622)-carrier, Carrier-CGGG (SEQ ID NO:620)-Peptide-GGGC (SEQ ID NO:619)-carrier, Carrier-CG-Peptide-GC-carrier, Carrier-CG-Peptide-C-carrier, Carrier-C-Peptide-C-carrier.

In an embodiment, the peptide consists of any of the antigenic PCSK9 peptide disclosed herein and the carrier consists of any of the immunogenic carrier disclosed herein, preferably a VLP.

In an embodiment, the invention relates to an immunogen comprising an antigenic PCSK9 peptide consisting of, or consisting essentially of, an amino acid sequence selected from the group consisting of SEQ ID Nos: 1 to 312, 330 to 398 and 420 to 588, wherein said antigenic antigenic PCSK9 peptide further comprises at its C-terminus or at its N-terminus a cysteine which is chemically cross linked to an immunogenic carrier via a thioether linkage. In a preferred embodiment, said immunogenic carrier is selected from the group consisting of DT (Diphtheria toxin), TT (tetanus toxid) or fragment C of TT, PD (*Haemophilus influenzae* protein D), CRM197, other DT point mutants, such as CRM176, CRM228, CRM 45, CRM 9, CRM102, CRM 103 and CRM107. Preferably said immunogenic carrier is CRM197.

In an embodiment, the invention relates to an immunogen comprising an antigenic PCSK9 peptide consisting of, or consisting essentially of, an amino acid sequence selected from the group consisting of 1 to 312, 330 to 398 and 420 to 588, wherein said antigenic antigenic PCSK9 peptide further comprises at its C-terminus or at its N-terminus a cysteine which is chemically cross linked to an immunogenic carrier via a thioether linkage using SMPH (Succinimidyl-6-[β-maleimidopropionamido]hexanoate) or BAANS (bromoacetic acid N-hydroxysuccinimide ester) as cross linker. In a preferred embodiment, said immunogenic carrier is selected from the group consisting of DT (Diphtheria toxin), TT (tetanus toxid) or fragment C of TT, PD (*Haemophilus influenzae* protein D, CRM197, other DT point mutants, such as CRM176, CRM228, CRM 45, CRM 9, CRM102, CRM 103 and CRM107. Preferably said immunogenic carrier is CRM197. In an embodiment, the invention relates to an immunogen comprising an antigenic PCSK9 peptide consisting of, or consisting essentially of, an amino acid sequence selected from the group consisting of SEQ ID Nos: 1 to 312, 330 to 398 and 420 to 588, wherein said antigenic antigenic PCSK9 peptide further comprises at its C-terminus a cysteine which is chemically cross linked to an immunogenic carrier via a thioether linkage using SMPH (Succinimidyl-6-[β-maleimidopropionamido]hexanoate) or BAANS (bromoacetic acid N-hydroxysuccinimide ester) as cross linker, said linkage being between a lysine residue of CRM197 and the cysteine residue of said antigenic peptide.

Compositions Comprising an Antigenic PCSK9 Peptide of the Invention

The present invention further relates to compositions, particularly immunogenic compositions also referred to as "subject immunogenic compositions", comprising an antigenic PCSK9 peptide of the invention, preferably linked to an immunogenic carrier, and optionally at least one adjuvant. Such immunogenic compositions, particularly when formulated as pharmaceutical compositions, are deemed useful to prevent, treat or alleviate PCSK9-related disorders.

In some embodiments, a subject immunogenic composition according to the invention comprises an antigenic PCSK9 peptide, optionally comprising a linker, comprising an amino acid sequence selected from SEQ ID Nos 1 to 328, 330 to 398, and 401 to 588 and functionally active variants thereof. In some embodiment, said antigenic PCSK9 peptide is linked to an immunogenic carrier, preferably a DT, CRM197 or a VLP, more preferably to a HBcAg, HBsAg, Qbeta, PP7, PPV or Norwalk Virus VLP.

In a preferred embodiment, a subject immunogenic composition according to the invention comprises an antigenic PCSK9 peptide, optionally comprising a linker, comprising an amino acid sequence selected from SEQ ID Nos 1 to 328, 330 to 398 and 401 to 588, and functionally active variants thereof linked to a VLP, preferably a Qbeta VLP.

In a preferred embodiment, a subject immunogenic composition according to the invention comprises an antigenic PCSK9 peptide optionally comprising a linker, comprising an amino acid sequence selected from SEQ ID Nos 1 to 328, 330 to 398, and 401 to 588 and functionally active variants thereof linked to CRM197.

A subject immunogenic composition comprising an antigenic PCSK9 peptide according to the invention can be formulated in a number of ways, as described in more detail below.

In some embodiments, a subject immunogenic composition comprises single species of antigenic PCSK9 peptide, e.g., the immunogenic composition comprises a population of antigenic PCSK9 peptides, substantially all of which have the same amino acid sequence. In other embodiments, a subject immunogenic composition comprises two or more different antigenic PCSK9 peptides, e.g., the immunogenic composition comprises a population of antigenic PCSK9 peptides, the members of which population can differ in amino acid sequence. A subject immunogenic composition can comprise from two to about 20 different antigenic PCSK9 peptides, e.g., a subject immunogenic composition can comprise 2, 3, 4, 5, 6, 7, 8, 9, 10, 11-15, or 15-20 different antigenic PCSK9 peptides, each having an amino acid sequence that differs from the amino acid sequences of the other antigenic PCSK9 peptides.

In other embodiments, a subject immunogenic composition comprises a multimerized antigenic PCSK9 polypeptide, as described above. As used herein, the terms "immunogenic composition comprising an antigenic PCSK9 peptide" or "immunogenic composition of the invention" or "subject immunogenic composition" refers to an immunogenic composition comprising either single species (multimerized or not) or multiple species of antigenic PCSK9 peptide(s) coupled or not to an immunogenic carrier. Where two or more peptides are used coupled to a carrier, the peptide may be coupled to the same carrier molecule or individually coupled to carrier molecules and then combined to produce an immunogenic composition.

Another aspect of the invention relates to methods for producing an immunogen according to the invention, said method comprising coupling an antigenic PCSK9 peptide to an immunogenic carrier. In one embodiment, said coupling is chemical.

Adjuvants

In some embodiments, a subject immunogenic composition comprises at least one adjuvant. Suitable adjuvants include those suitable for use in mammals, preferably in humans. Examples of known suitable adjuvants that can be used in humans include, but are not necessarily limited to, alum, aluminum phosphate, aluminum hydroxide, MF59 (4.3% w/v squalene, 0.5% w/v polysorbate 80 (Tween 80), 0.5% w/v sorbitan trioleate (Span 85)), CpG-containing nucleic acid (where the cytosine is unmethylated), QS21 (saponin adjuvant), MPL (Monophosphoryl Lipid A), 3DMPL (3-O-deacylated MPL), extracts from Aquilla, ISCOMS (see, e.g., Sjölander et al. (1998) *J. Leukocyte Biol.* 64:713; WO90/03184, WO96/11711, WO 00/48630, WO98/36772, WO00/41720, WO06/134423 and WO07/026190), LT/CT mutants, poly(D,L-lactide-co-glycolide) (PLG) microparticles, Quil A, TiterMax classic, TiterMax Gold, interleukins, and the like. For veterinary applications including but not limited to animal experimentation, one can use Freund's adjuvant, N-acetyl-muramyl-L-threonyl-D-isoglu-tamine (thr-MDP), N-acetyl-nor-muramyl-L-alanyl-D-iso-glutamine (CGP 11637, referred to as nor-MDP), N-acetyl-muramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in *Vaccine design: the subunit and adjuvant approach*, eds. Powell & Newman, Plenum Press 1995), containing 5% Squalene, 0.5% Tween 80 (polyoxyethylene sorbitan mono-oleate), and 0.5% Span 85 (sorbitan trioleate) (optionally containing muramyl tri-peptide covalently linked to dipalmitoyl phosphatidylethanolamine (MTP-PE)) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21, STIMULON™ (Cambridge Bioscience, Worcester, Mass.), Abisco® (Isconova, Sweden), or Iscomatrix® (Commonwealth Serum Laboratories, Australia), may be used or particles generated therefrom such as ISCOMs (immunostimulating complexes), which ISCOMS may be devoid of additional detergent e.g. WO00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs [Krieg *Vaccine* 2000, 19, 618-622; Krieg *Curr opin Mol Ther* 2001 3:15-24; Roman et al., *Nat. Med.*, 1997, 3, 849-854; Weiner et al., *PNAS USA*, 1997, 94, 10833-10837; Davis et al, *J. Immunol*, 1998, 160, 870-876; Chu et al., *J. Exp. Med*, 1997, 186, 1623-1631; Lipford et al, *Ear. J. Immunol.*, 1997, 27, 2340-2344; Moldoveami et al., *Vaccine*, 1988, 16, 1216-1224, Krieg et al., *Nature*, 1995, 374, 546-549; Klinman et al., *PNAS USA*, 1996, 93, 2879-2883; Ballas et al, *J. Immunol*, 1996, 157, 1840-1845; Cowdery et al., *J. Immunol*, 1996, 156, 4570-4575; Halpern et al, *Cell Immunol*, 1996, 167, 72-78; Yamamoto et al, *Jpn. J. Cancer Res.*, 1988, 79, 866-873; Stacey et al, *J. Immunol.*, 1996, 157, 2116-2122; Messina et al, *J. Immunol*, 1991, 147, 1759-1764; Yi et al, *J. Immunol*, 1996, 157, 4918-4925; Yi et al, *J. Immunol*, 1996, 157, 5394-5402; Yi et al, *J. Immunol*, 1998, 160, 4755-4761; and Yi et al, *J. Immunol*, 1998, 160, 5898-5906; International patent applications WO96/02555, WO98/16247, WO98/18810, WO98/40100, WO98/55495, WO98/37919 and WO98/52581] i.e. containing at least one CG dinucleotide, where the cytosine is unmethylated; (8) a polyoxyethylene ether or a polyoxyethylene ester e.g. WO99/52549; (9) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (10) a saponin and an immunostimulatory oligonucleotide (e.g. a CpG oligonucleotide) (WO00/62800); (11) an immunostimulant and a particle of metal salt e.g. WO00/23105; (12) a saponin and an oil-in-water emulsion e.g. WO99/11241; (13) a saponin (e.g. QS21)+3dMPL+IM2 (optionally+a sterol) e.g. WO98/57659; (14) other substances that act as immunostimulating agents to enhance the efficacy of the composition, such as Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), (15) ligands for toll-like receptors (TLR), natural or synthesized (e.g. as described in Kanzler et al 2007, Nature Medicine 13, p 1552-9), including TLR3 ligands such as polyI:C and similar compounds such as Hiltonol and Ampligen.

In a particular embodiment, said adjuvant is an immunostimulatory oligonucleotide and more preferably a CpG oligonucleotide. A CpG oligonucleotide as used herein refers to an immunostimulatory CpG oligodeoxynucleotide (CpG ODN), and accordingly these terms are used interchangeably unless otherwise indicated. Immunostimulatory CpG oligodeoxynucleotides contain one or more immunostimulatory CpG motifs that are unmethylated cytosine-guanine dinucleotides, optionally within certain preferred base contexts. The methylation status of the CpG immunostimulatory motif generally refers to the cytosine residue in the dinucleotide. An immunostimulatory oligonucleotide containing at least one unmethylated CpG dinucleotide is an oligonucleotide which contains a 5' unmethylated cytosine linked by a phosphate bond to a 3' guanine, and which activates the immune system through binding to Toll-like receptor 9 (TLR-9). In another embodiment the immunostimulatory oligonucleotide may contain one or more methylated CpG dinucleotides, which will activate the immune system through TLR9 but not as strongly as if the CpG motif(s) was/were unmethylated. CpG immunostimulatory oligonucleotides may comprise one or more palindromes that in turn may encompass the CpG dinucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068.

Different classes of CpG immunostimulatory oligonucleotides have been identified. These are referred to as A, B, C and P class, and are described in greater detail below. Methods of the invention embrace the use of these different classes of CpG immunostimulatory oligonucleotides.

Any of the classes may be subjugated to an E modification which enhances its potency. An E modification may be a halogen substitution for the 5' terminal nucleotide; examples of such substitutions include but are not limited to bromo-uridine or iodo-uridine substitutions. An E modification can also include an ethyl-uridine substitution for the 5' terminal nucleotide.

The "A class" CpG immunostimulatory oligonucleotides are characterized functionally by the ability to induce high levels of interferon-alpha (IFN-α) from plasmacytoid dendritic cells (pDC) and inducing NK cell activation while having minimal effects on B cell activation. Structurally, this class typically has stabilized poly-G sequences at 5' and 3' ends. It also has a palindromic phosphodiester CpG dinucleotide-containing sequence of at least 6 nucleotides, for example but not necessarily, it contains one of the following hexamer palindromes: GACGTC, AGCGCT, or AACGTT described by Yamamoto and colleagues. Yamamoto S et al. J. Immunol 148:4072-6 (1992). A class CpG immunostimulatory oligonucleotides and exemplary sequences of this class have been described in U.S. Non-Provisional patent application Ser. No. 09/672,126 and published PCT application PCT/USOO/26527 (WO 01/22990), both filed on Sep. 27, 2000.

In an embodiment, the "A class" CpG oligonucleotide of the invention has the following nucleic acid sequence: 5' GGGGACGACGTCGTGGGGGGG 3' (SEQ ID NO:637) Some non-limiting examples of A-Class oligonucleotides include: 5' G*G*G_G_A_C_G_A_C_G_T_C_G_T_G_G*G*G*G* G*G 3' (SEQ ID NO:637); wherein * refers to a phosphorothioate bond and _ refers to a phosphodiester bond.

The B class CpG oligonucleotide sequences of the invention are those broadly described above as well as disclosed in published PCT Patent Applications PCT/US95/01570 and PCT/US97/19791, and in U.S. Pat. Nos. 6,194,388, 6,207,646, 6,214,806, 6,218,371, 6,239,116 and 6,339,068. Exemplary sequences include but are not limited to those disclosed in these latter applications and patents.

In an embodiment, the "B class" CpG oligonucleotide of the invention has the following nucleic acid sequence:

```
                                    (SEQ ID No 589)
5' TCGTCGTTTTTCGGTGCTTTT 3',
or
                                    (SEQ ID No 590)
5' TCGTCGTTTTTCGGTCGTTTT 3'
or
                                    (SEQ ID No 591)
5' TCGTCGTTTTGTCGTTTTGTCGTT 3'
or
                                    (SEQ ID No 592)
5' TCGTCGTTTCGTCGTTTTGTCGTT 3',
or
                                    (SEQ ID No 593)
5' TCGTCGTTTTGTCGTTTTTTCGA 3'.
```

In any of these sequences, all of the linkages may be all phosphorothioate bonds. In another embodiment, in any of these sequences, one or more of the linkages may be phosphodiester, preferably between the "C" and the "G" of the CpG motif making a semi-soft CpG oligonucleotide. In any of these sequences, an ethyl-uridine or a halogen may substitute for the 5' T; examples of halogen substitutions include but are not limited to bromo-uridine or iodo-uridine substitutions.

Some non-limiting examples of B-Class oligonucleotides include:

```
                                    (SEQ ID NO: 589)
5' T*C*G*T*C*G*T*T*T*T*T*C*G*G*T*G*C*T*T*T*T 3',
or
                                    (SEQ ID NO: 590)
5' T*C*G*T*C*G*T*T*T*T*T*C*G*G*T*C*G*T*T*T*T 3'
or
                                    (SEQ ID NO: 591)
5' T*C*G*T*C*G*T*T*T*T*G*T*C*G*T*T*T*T*G*T*C*G*T*
T 3',
or
                                    (SEQ ID NO: 592)
5' T*C*G*T*C*G*T*T*T*C*G*T*C*G*T*T*T*T*G*T*C*G*T*
T 3',
or
                                    (SEQ ID NO: 593)
5' T*C*G*T*C*G*T*T*T*T*G*T*C*G*T*T*T*T*T*T*C*G*
A 3'.
``` wherein * refers to a phosphorothioate bond.

The "C class" of CpG immunostimulatory oligonucleotides is characterized functionally by the ability to activate B cells and NK cells and induce IFN-α. Structurally, this class typically includes a region with one or more B class-type immunostimulatory CpG motifs, and a GC-rich palindrome or near-palindrome region that allows the molecules to form secondary (e.g., stem-loop) or tertiary (e.g., dimer) type structures. Some of these oligonucleotides have both a traditional "stimulatory" CpG sequence and a "GC-rich" or "B-cell neutralizing" motif. These combination motif oligonucleotides have immune stimulating effects that fall somewhere between the effects associated with traditional B class CpG oligonucleotides (i.e., strong induction of B cell activation and dendritic cell (DC) activation), and the effects associated with A class CpG ODN (i.e., strong induction of IFN-α and NK cell activation but relatively poor induction of B cell and DC activation). Krieg A M et al. (1995) Nature 374:546-9; Ballas Z K et al. (1996) J Immunol 157:1840-5; Yamamoto S et al. (1992) J Immunol 148:4072-6.

The C class of combination motif immune stimulatory oligonucleotides may have either completely stabilized, (e.g., all phosphorothioate), chimeric (phosphodiester central region), or semi-soft (e.g., phosphodiester within CpG motif) backbones. This class has been described in U.S. patent application U.S. Ser. No. 10/224,523 filed on Aug. 19, 2002. One stimulatory domain or motif of the C class CpG oligonucleotide is defined by the formula: 5' $X_1DCGHX_2$ 3'. D is a nucleotide other than C. C is cytosine. G is guanine. H is a nucleotide other than G. $X_1$ and $X_2$ are any nucleic acid sequence 0 to 10 nucleotides long. $X_1$ may include a CG, in which case there is preferably a T immediately preceding this CG. In some embodiments, DCG is TCG. $X_1$ is preferably from 0 to 6 nucleotides in length. In some embodiments, $X_2$ does not contain any poly G or poly A motifs. In other embodiments, the immunostimulatory oligonucleotide has a poly-T sequence at the 5' end or at the 3' end. As used herein, "poly-A" or "poly-T" shall refer to a stretch of four or more consecutive A's or T's respectively, e.g., 5' AAAA 3' or 5' TTTT 3'. As used herein, "poly-G end" shall refer to a stretch of four or more consecutive G's, e.g., 5' GGGG 3', occurring at the 5' end or the 3' end of a nucleic acid. As used herein, "poly-G oligonucleotide" shall refer to an oligonucleotide having the formula 5' $X_1X_2GGGX_3X_4$ 3' wherein $X_1$, $X_2$, $X_3$, and $X_4$ are nucleotides and preferably at least one of $X_3$ and $X_4$ is a G. Some preferred designs for the B cell stimulatory domain under this formula comprise TTTTTCG, TCG, TTCG, TTTCG, TTTTCG, TCGT, TTCGT, TTTCGT, TCGTCGT.

The second motif of the C class CpG oligonucleotide is referred to as either P or N and is positioned immediately 5' to $X_1$ or immediately 3' to $X_2$.

N is a B cell neutralizing sequence that begins with a CGG trinucleotide and is at least 10 nucleotides long. A B cell neutralizing motif includes at least one CpG sequence in which the CG is preceded by a C or followed by a G (Krieg A M et al. (1998) Proc Natl Acad Sd USA 95:12631-12636) or is a CG containing DNA sequence in which the C of the CG is methylated. Neutralizing motifs or sequences have some degree of immunostimulatory capability when present in an otherwise non-stimulatory motif, but when present in the context of other immunostimulatory motifs serve to reduce the immunostimulatory potential of the other motifs.

P is a GC-rich palindrome containing sequence at least 10 nucleotides long.

As used herein, "palindrome" and equivalently "palindromic sequence" shall refer to an inverted repeat, i.e., a sequence such as ABCDEE'D'C'B'A' in which A and A', B and B', etc., are bases capable of forming the usual Watson-Crick base pairs.

As used herein, "GC-rich palindrome" shall refer to a palindrome having a base composition of at least two-thirds G's and Cs. In some embodiments the GC-rich domain is preferably 3' to the "B cell stimulatory domain". In the case of a 10-base long GC-rich palindrome, the palindrome thus contains at least 8 G's and Cs. In the case of a 12-base long GC-rich palindrome, the palindrome also contains at least 8 G's and Cs. In the case of a 14-mer GC-rich palindrome, at least ten bases of the palindrome are G's and Cs. In some embodiments the GC-rich palindrome is made up exclusively of G's and Cs.

In some embodiments the GC-rich palindrome has a base composition of at least 81% G's and Cs. In the case of such a 10-base long GC-rich palindrome, the palindrome thus is made exclusively of G's and Cs. In the case of such a 12-base long GC-rich palindrome, it is preferred that at least ten bases (83%) of the palindrome are G's and Cs. In some preferred embodiments, a 12-base long GC-rich palindrome is made exclusively of G's and Cs. In the case of a 14-mer GC-rich palindrome, at least twelve bases (86%) of the palindrome are G's and Cs. In some preferred embodiments, a 14-base long GC-rich palindrome is made exclusively of G's and Cs. The Cs of a GC-rich palindrome can be unmethylated or they can be methylated.

In general this domain has at least 3 Cs and Gs, more preferably 4 of each, and most preferably 5 or more of each. The number of Cs and Gs in this domain need not be identical. It is preferred that the Cs and Gs are arranged so that they are able to form a self-complementary duplex, or palindrome, such as CCGCGCGG. This may be interrupted by As or Ts, but it is preferred that the self-complementarity is at least partially preserved as for example in the motifs CGACGTTCGTCG (SEQ ID NO:639) or CGGCGCCGTGCCG (SEQ ID NO:640). When complementarity is not preserved, it is preferred that the non-complementary base pairs be TG. In a preferred embodiment there are no more than 3 consecutive bases that are not part of the palindrome, preferably no more than 2, and most preferably only 1. In some embodiments, the GC-rich palindrome includes at least one CGG trimer, at least one CCG trimer, or at least one CGCG tetramer. In other embodiments, the GC-rich palindrome is not CCCCCCGGGGGG (SEQ ID NO:641) or GGGGGGCCCCCC (SEQ ID NO:642), CCCCCGGGGG (SEQ ID NO:643) or GGGGGCCCCC (SEQ ID NO:644).

At least one of the G's of the GC rich region may be substituted with an inosine (I). In some embodiments, P includes more than one I.

In certain embodiments, the immunostimulatory oligonucleotide has one of the following formulas 5' $NX_1DCGHX_2$ 3', 5' $X_1DCGHX_2N$ 3', 5' $PX_1DCGHX_2$ 3', 5' $X_1DCGHX_2P$ 3', 5' $X_1DCGHX_2PX_3$ 3', 5' $X_1DCGHPX_3$ 3', 5' $DCGHX_2PX_3$ 3', 5' $TCGHX_2PX3$ 3', 5' $DCGHPX_3$ 3' or 5'DCGHP 3'.

The invention provides other immune stimulatory oligonucleotides defined by a formula 5' $N_1PyGN_2P$ 3'. $N_1$ is any sequence 1 to 6 nucleotides long. Py is a pyrimidine. G is guanine. $N_2$ is any sequence 0 to 30 nucleotides long. P is a GC-rich palindrome containing a sequence at least 10 nucleotides long.

$N_1$ and $N_2$ may contain more than 50% pyrimidines, and more preferably more than 50% T. $N_1$ may include a CG, in which case there is preferably a T immediately preceding this CG. In some embodiments, N1PyG is TCG, and most preferably a $TCGN_2$, where $N_2$ is not G.

$N_1PyGN_2P$ may include one or more inosine (I) nucleotides. Either the C or the G in $N_1$ may be replaced by inosine, but the CpI is preferred to the IpG. For inosine substitutions such as IpG, the optimal activity may be achieved with the use of a "semi-soft" or chimeric backbone, where the linkage between the IG or the CI is phosphodiester. N1 may include at least one CI, TCI, IG or TIG motif.

In certain embodiments $N_1PyGN_2$ is a sequence selected from the group consisting of TTTTTCG, TCG, TTCG, TTTCG, TTTTCG, TCGT, TTCGT, TTTCGT, and TCGTCGT.

In an embodiment, the "C class" CpG oligonucleotide of the invention has the following nucleic acid sequence:

```
                                           (SEQ ID No 594)
5' TCGCGTCGTTCGGCGCGCGCCG 3',
or
                                           (SEQ ID No 595)
5' TCGTCGACGTTCGGCGCGCGCCG 3',
or
                                           (SEQ ID No 596)
5' TCGGACGTTCGGCGCGCGCCG 3',
or
                                           (SEQ ID No 597)
5' TCGGACGTTCGGCGCGCCG 3',
or
                                           (SEQ ID No 598)
5' TCGCGTCGTTCGGCGCGCCG 3',
or
                                           (SEQ ID No 599)
5' TCGACGTTCGGCGCGCGCCG 3',
or
                                           (SEQ ID No 600)
5' TCGACGTTCGGCGCGCCG 3',
or
```

```
                                                (SEQ ID No 601)
5' TCGCGTCGTTCGGCGCCG 3',
or
                                                (SEQ ID No 602)
5' TCGCGACGTTCGGCGCGCGCCG 3',
or
                                                (SEQ ID No 603)
5' TCGTCGTTTTCGGCGCGCGCCG 3',
or
                                                (SEQ ID No 604)
5' TCGTCGTTTTCGGCGGCCGCCG 3',
or
                                                (SEQ ID No 605)
5' TCGTCGTTTTACGGCGCCGTGCCG 3',
or
                                                (SEQ ID No 606)
5' TCGTCGTTTTCGGCGCGCGCCGT 3'.
```

In any of these sequences, all of the linkages may be all phosphorothioate bonds. In another embodiment, in any of these sequences, one or more of the linkages may be phosphodiester, preferably between the "C" and the "G" of the CpG motif making a semi-soft CpG oligonucleotide.

Some non-limiting examples of C-Class oligonucleotides include:

```
                                                (SEQ ID NO: 594)
5' T*C_G*C_G*T*C_G*T*T*C_G*G*C*G*C_G*C*G*C*C*G 3',
or
                                                (SEQ ID NO: 595)
5' T*C_G*T*C_G*A*C_G*T*T*C_G*G*C*G*C_G*C*G*C*C*G 3',
or
                                                (SEQ ID NO: 596)
5' T*C_G*G*A*C_G*T*T*C_G*G*C*G*C_G*C*G*C*C*G 3',
or
                                                (SEQ ID NO: 597)
5' T*C_G*G*A*C_G*T*T*C_G*G*C*G*C*G*C*C*G 3',
or
                                                (SEQ ID NO: 598)
5' T*C_G*C_G*T*C_G*T*T*C_G*G*C*G*C*G*C*C*G 3',
or
                                                (SEQ ID NO: 599)
5' T*C_G*A*C_G*T*T*C_G*G*C*G*C_G*C*G*C*C*G 3',
or
                                                (SEQ ID NO: 600)
5' T*C_G*A*C_G*T*T*C_G*G*C*G*C*G*C*C*G 3',
or
                                                (SEQ ID NO: 601)
5' T*C_G*C_G*T*C_G*T*T*C_G*G*C*G*C*C*G 3',
or
                                                (SEQ ID NO: 602)
5' T*C_G*C_G*A*C_G*T*T*C_G*G*C*G*C_G*C*G*C*C*G 3',
or
                                                (SEQ ID NO: 603)
5' T*C*G*T*C*G*T*T*T*T*C*G*G*C*G*C*G*C*G*C*C*G 3',
or
                                                (SEQ ID NO: 604)
5' T*C*G*T*C*G*T*T*T*T*C*G*G*C*G*G*C*C*G*C*C*G 3',
or
                                                (SEQ ID NO: 605)
5' T*C*G*T*C_G*T*T*T*T*A*C_G*G*C*G*C*C_G*T*G*C*C*G 3',
or
                                                (SEQ ID NO: 606)
5' T*C_G*T*C*G*T*T*T*T*C*G*G*C*G*C*G*C*G*C*C*G*T 3'
``` wherein * refers to a phosphorothioate bond and _ refers to a phosphodiester bond.

In any of these sequences, an ethyl-uridine or a halogen may substitute for the 5' T; examples of halogen substitutions include but are not limited to bromo-uridine or iodo-uridine substitutions.

The "P class" CpG immunostimulatory oligonucleotides have been described in WO2007/095316 and are characterized by the fact that they contain duplex forming regions such as, for example, perfect or imperfect palindromes at or near both the 5' and 3' ends, giving them the potential to form higher ordered structures such as concatamers. These oligonucleotides referred to as P-Class oligonucleotides have the ability to induce much high levels of IFN-α secretion than the C-Class. The P-Class oligonucleotides have the ability to spontaneously self-assemble into concatamers either in vitro and/or in vivo. Without being bound by any particular theory for the method of action of these molecules, one potential hypothesis is that this property endows the P-Class oligonucleotides with the ability to more highly crosslink TLR9 inside certain immune cells, inducing a distinct pattern of immune activation compared to the previously described classes of CpG oligonucleotides.

In an embodiment, the CpG oligonucleotide for use in the present invention is a P class CpG oligonucleotide containing a 5' TLR activation domain and at least two palindromic regions, one palindromic region being a 5' palindromic region of at least 6 nucleotides in length and connected to a 3' palindromic region of at least 8 nucleotides in length either directly or through a spacer, wherein the oligonucleotide includes at least one YpR dinucleotide. In an embodiment, said oligonucleotide is not T*C_G*T*C_G*A*C_G*T*T*C_G*G*C*G*C_G*C*G*C*C*G (SEQ ID NO:595). In one embodiment the P class CpG oligonucleotide includes at least one unmethylated CpG dinucleotide. In another embodiment the TLR activation domain is TCG, TTCG, TTTCG, TYpR, TTYpR, TTTYpR, UCG, UUCG, UUUCG, TTT, or TTTT. In yet another embodiment the TLR activation domain is within the 5' palindromic region. In another embodiment the TLR activation domain is immediately 5' to the 5' palindromic region. In still another embodiment the 5' palindromic region is at least 8 nucleotides in length. In another embodiment the 3' palindromic region is at least 10 nucleotides in length. In another embodiment the 5' palindromic region is at least 10 nucleotides in length. In yet another embodiment the 3' palindromic region includes an unmethylated CpG dinucleotide. In another embodiment the 3' palindromic region includes two unmethylated CpG dinucleotides. In another embodiment the 5' palindromic region includes an unmethylated CpG dinucleotide. In yet another embodiment the 5' palindromic region includes two unmethylated CpG dinucleotides. In another embodiment the 5' and 3' palindromic regions have a duplex stability value of at least 25. In another embodiment the 5' and 3' palindromic regions have a duplex stability value of at least 30. In another embodiment the 5' and 3' palindromic regions have a duplex stability value of at least 35. In another embodiment the 5' and 3' palindromic regions have a duplex stability value of at least 40. In another embodiment the 5' and 3' palindromic regions have a duplex stability value of at least 45. In another embodiment the 5' and 3' palindromic regions have a duplex stability value of at least 50. In another embodiment the 5' and 3' palindromic regions have a duplex stability value of at least 55. In another embodiment the 5' and 3' palindromic regions have a duplex stability value of at least 60. In another embodiment the 5' and 3' palindromic regions have a duplex stability value of at least 65.

In one embodiment the two palindromic regions are connected directly. In another embodiment the two palindromic regions are connected via a 3'-3' linkage. In another embodiment the two palindromic regions overlap by one nucleotide. In yet another embodiment the two palindromic regions overlap by two nucleotides. In another embodiment the two palindromic regions do not overlap. In another embodiment the two palindromic regions are connected by a spacer. In one embodiment the spacer is a nucleic acid having a length of 1-50 nucleotides. In another embodiment the spacer is a nucleic acid having a length of 1 nucleotide. In another embodiment the spacer is a non-nucleotide spacer. In one embodiment the non-nucleotide spacer is a D-spacer. In another embodiment the non-nucleotide spacer is a linker. In one embodiment the oligonucleotide has the formula 5' $XP_1SP_2T$ 3', wherein X is the TLR activation domain, $P_1$ is a palindrome, S is a spacer, $P_2$ is a palindrome, and T is a 3' tail of 0-100 nucleotides in length. In one embodiment X is TCG, TTCG, or TTTCG. In another embodiment T is 5-50 nucleotides in length. In yet another embodiment T is 5-10 nucleotides in length. In one embodiment S is a nucleic acid having a length of 1-50 nucleotides. In another embodiment S is a nucleic acid having a length of 1 nucleotide. In another embodiment S is a non-nucleotide spacer. In one embodiment the non-nucleotide spacer is a D-spacer. In another embodiment the non-nucleotide spacer is a linker. In another embodiment the oligonucleotide is not an antisense oligonucleotide or a ribozyme. In one embodiment $P_1$ is A and T rich. In another embodiment $P_1$ includes at least 4 Ts. In another embodiment $P_2$ is a perfect palindrome. In another embodiment P2 is G-C rich. In still another embodiment $P_2$ is $CGGCGCX_1GCGCCG$, where $X_1$ is T or nothing.

In one embodiment the oligonucleotide includes at least one phosphorothioate linkage. In another embodiment all internucleotide linkages of the oligonucleotide are phosphorothioate linkages. In another embodiment the oligonucleotide includes at least one phosphodiester-like linkage. In another embodiment the phosphodiester-like linkage is a phosphodiester linkage. In another embodiment a lipophilic group is conjugated to the oligonucleotide. In one embodiment the lipophilic group is cholesterol.

In an embodiment, the TLR-9 agonist for use in the present invention is a P class CpG oligonucleotide with a 5' TLR activation domain and at least two complementarity-containing regions, a 5' and a 3' complementarity-containing region, each complementarity-containing region being at least 8 nucleotides in length and connected to one another either directly or through a spacer, wherein the oligonucleotide includes at least one pyrimidine-purine (YpR) dinucleotide, and wherein at least one of the complementarity-containing regions is not a perfect palindrome. In one embodiment the oligonucleotide includes at least one unmethylated CpG dinucleotide. In another embodiment the TLR activation domain is TCG, TTCG, TTTCG, TYpR, TTYpR, TTTYpR, UCG, UUCG, UUUCG, TTT, or TTTT.

In another embodiment the TLR activation domain is within the 5' complementarity-containing region. In another embodiment the TLR activation domain is immediately 5' to the 5' complementarity-containing region. In another embodiment the 3' complementarity-containing region is at least 10 nucleotides in length. In yet another embodiment the 5' complementarity-containing region is at least 10 nucleotides in length. In one embodiment the 3' complementarity-containing region includes an unmethylated CpG dinucleotide. In another embodiment the 3' complementarity-containing region includes two unmethylated CpG dinucleotides. In yet another embodiment the 5' complementarity-containing region includes an unmethylated CpG dinucleotide. In another embodiment the 5' complementarity-containing region includes two unmethylated CpG dinucleotides. In another embodiment the complementarity-containing regions include at least one nucleotide analog. In another embodiment the complementarity-containing regions form an intramolecular duplex. In one embodiment the intramolecular duplex includes at least one non-Watson Crick base pair. In another embodiment the non-Watson Crick base pair is G-T, G-A, G-G, or C-A. In one embodiment the complementarity-containing regions form intermolecular duplexes. In another embodiment at least one of the intermolecular duplexes includes at least one non-Watson Crick base pair. In another embodiment the non-Watson Crick base pair is G-T, G-A, G-G, or C-A. In yet another embodiment the complementarity-containing regions contain a mismatch. In still another embodiment the complementarity-containing regions contain two mismatches. In another embodiment the complementarity-containing regions contain an intervening nucleotide. In another embodiment the complementarity-containing regions contain two intervening nucleotides.

In one embodiment the 5' and 3' complementarity-containing regions have a duplex stability value of at least 25. In another embodiment the 5' and 3' complementarity-containing regions have a duplex stability value of at least 30. In another embodiment the 5' and 3' complementarity-containing regions have a duplex stability value of at least 35. In another embodiment the complementarity-containing regions have a duplex stability value of at least 40. In another embodiment the complementarity-containing regions have a duplex stability value of at least 45. In another embodiment the complementarity-containing regions have a duplex stability value of at least 50. In another embodiment the complementarity-containing regions have a duplex stability value of at least 55. In another embodiment the complementarity-containing regions have a duplex stability value of at least 60. In another embodiment the complementarity-containing regions have a duplex stability value of at least 65.

In another embodiment the two complementarity-containing regions are connected directly. In another embodiment the two palindromic regions are connected via a 3'-3' linkage. In yet another embodiment the two complementarity-containing regions overlap by one nucleotide. In another embodiment the two complementarity-containing regions overlap by two nucleotides. In another embodiment the two complementarity-containing regions do not overlap. In another embodiment the two complementarity-containing regions are connected by a spacer. In another embodiment the spacer is a nucleic acid having a length of 1-50 nucleotides. In another embodiment the spacer is a nucleic acid having a length of 1 nucleotide. In one embodiment the spacer is a non-nucleotide spacer. In another embodiment the non-nucleotide spacer is a D-spacer. In yet another embodiment the non-nucleotide spacer is a linker.

In one embodiment the P-class oligonucleotide has the formula 5' XNSPT 3', wherein X is the TLR activation domain, N is a non-perfect palindrome, P is a palindrome, S is a spacer, and T is a 3' tail of 0-100 nucleotides in length. In another embodiment X is TCG, TTCG, or TTTCG. In another embodiment T is 5-50 nucleotides in length. In another embodiment T is 5-10 nucleotides in length. In another embodiment S is a nucleic acid having a length of 1-50 nucleotides. In another embodiment S is a nucleic acid having a length of 1 nucleotide. In another embodiment S is a non-nucleotide spacer. In another embodiment the non-nucleotide spacer is a D-spacer. In another embodiment the non-nucleotide spacer is a linker. In another embodiment the oligonucleotide is not an antisense oligonucleotide or a ribozyme. In another embodiment N is A and T rich. In another embodiment N is includes at least 4 Ts. In another embodiment P is a perfect palindrome. In another embodiment P is G-C rich. In another embodiment P is CGGCGCX$_1$GCGCCG, wherein X$_1$ is T or nothing. In another embodiment the oligonucleotide includes at least one phosphorothioate linkage. In another embodiment all interaucleotide linkages of the oligonucleotide are phosphorothioate linkages. In another embodiment the oligonucleotide includes at least one phosphodiester-like linkage. In another embodiment the phosphodiester-like linkage is a phosphodiester linkage. In another embodiment a lipophilic group is conjugated to the oligonucleotide. In one embodiment the lipophilic group is cholesterol.

In an embodiment, the "P class" CpG oligonucleotides of the invention has the following nucleic acid sequence: 5' TCGTCGACGATCGGCGCGCGCCG 3' (SEQ ID No 607).

In said sequences, all of the linkages may be all phosphorothioate bonds. In another embodiment, one or more of the linkages may be phosphodiester, preferably between the "C" and the "G" of the CpG motif making a semi-soft CpG oligonucleotide. In any of these sequences, an ethyl-uridine or a halogen may substitute for the 5' T; examples of halogen substitutions include but are not limited to bromo-uridine or iodo-uridine substitutions.

A non-limiting example of P-Class oligonucleotides include:

(SEQ ID NO: 607)
5' T*C_G*T*C_G*A*C_G*A*T*C_G*G*C*G*C_G*C*G*C*C*G 3' wherein * refers to a phosphorothioate bond and _ refers to a phosphodiester bond.

In an embodiment, all the internucleotide linkage of the CpG oligonucleotides disclosed herein are phosphodiester bonds ("soft" oligonucleotides, as described in the PCT application WO2007/026190). In another embodiment, CpG oligonucleotides of the invention are rendered resistant to degradation (e.g., are stabilized). A "stabilized oligonucleotide" refers to an oligonucleotide that is relatively resistant to in vivo degradation (e.g. via an exo- or endo-nuclease). Nucleic acid stabilization can be accomplished via backbone modifications. Oligonucleotides having phosphorothioate linkages provide maximal activity and protect the oligonucleotide from degradation by intracellular exo- and endo-nucleases.

The immunostimulatory oligonucleotides may have a chimeric backbone, which have combinations of phosphodiester and phosphorothioate linkages. For purposes of the instant invention, a chimeric backbone refers to a partially stabilized backbone, wherein at least one internucleotide linkage is phosphodiester or phosphodiester-like, and wherein at least one other internucleotide linkage is a stabilized internucleotide linkage, wherein the at least one phosphodiester or phosphodiester-like linkage and the at least one stabilized linkage are different. When the phosphodiester linkage is preferentially located within the CpG motif such molecules are called "semi-soft" as described in the PCT application WO2007/026190.

Other modified oligonucleotides include combinations of phosphodiester, phosphorothioate, methylphosphonate, methylphosphorothioate, phosphorodithioate, and/or p-ethoxy linkages.

Since boranophosphonate linkages have been reported to be stabilized relative to phosphodiester linkages, for purposes of the chimeric nature of the backbone, boranophosphonate linkages can be classified either as phosphodiester-like or as stabilized, depending on the context. For example, a chimeric backbone according to the instant invention could, in some embodiments, includes at least one phosphodiester (phosphodiester or phosphodiester-like) linkage and at least one boranophosphonate (stabilized) linkage. In other embodiments, a chimeric backbone according to the instant invention could include boranophosphonate (phosphodiester or phosphodiester-like) and phosphorothioate (stabilized) linkages. A "stabilized internucleotide linkage" shall mean an internucleotide linkage that is relatively resistant to in vivo degradation (e.g., via an exo- or endo-nuclease), compared to a phosphodiester internucleotide linkage. Preferred stabilized internucleotide linkages include, without limitation, phosphorothioate, phosphorodithioate, methylphosphonate, and methylphosphorothioate. Other stabilized internucleotide linkages include, without limitation, peptide, alkyl, dephospho, and others as described above.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described. Uhlmann E et al. (1990) Chem Rev 90:544; Goodchild J (1990) Bioconjugate Chem 1:165. Methods for preparing chimeric oligonucleotides are also known. For instance patents issued to Uhlmann et al have described such techniques.

Mixed backbone modified ODN may be synthesized as described in the PCT application WO2007/026190.

The oligonucleotides of the invention can also include other modifications. These include nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

The size of the CpG oligonucleotide (i.e., the number of nucleotide residues along the length of the oligonucleotide) also may contribute to the stimulatory activity of the oligonucleotide. For facilitating uptake into cells, CpG oligonucleotide of the invention preferably have a minimum length of 6 nucleotide residues. Oligonucleotides of any size greater than 6 nucleotides (even many kb long) are capable of inducing an immune response if sufficient immunostimulatory motifs are present, because larger oligonucleotides are degraded inside cells. In certain embodiments, the CpG oligonucleotides are 6 to 100 nucleotides long, preferentially 8 to 30 nucleotides long. In important embodiments, nucleic acids and oligonucleotides of the invention are not plasmids or expression vectors.

In an embodiment, the CpG oligonucleotide disclosed herein comprise substitutions or modifications, such as in the bases and/or sugars as described at paragraph 134 to 147 of WO2007/026190.

In an embodiment, the CpG oligonucleotide of the present invention is chemically modified. Examples of chemical modifications are known to the skilled person and are described, for example in Uhlmann E. et al. (1990), Chem. Rev. 90:543, S. Agrawal, Ed., Humana Press, Totowa, USA 1993; Crooke, S. T. et al. (1996) Annu. Rev. Pharmacol. Toxicol. 36:107-129; and Hunziker J. et al., (1995), Mod. Synth. Methods 7:331-417. An oligonucleotide according to the invention may have one or more modifications, wherein each modification is located at a particular phosphodiester internucleoside bridge and/or at a particular β-D-ribose unit and/or at a particular natural nucleoside base position in comparison to an oligonucleotide of the same sequence which is composed of natural DNA or RNA.

In some embodiments of the invention, CpG-containing nucleic acids might be simply mixed with immunogenic carriers according to methods known to those skilled in the art (see, e.g. WO03/024480).

In a particular embodiment of the present invention, any of the vaccine disclosed herein comprises from 20 µg to 20 mg of CpG oligonucleotide, preferably from 0.1 mg to 10 mg CpG oligonucleotide, preferably from 0.2 mg to 5 mg CpG oligonucleotide, preferably from 0.3 mg to 3 mg CpG oligonucleotide, even preferably from 0.4 to 2 mg CpG oligonucleotide, even preferably from 0.5 to 1.5 mg CpG oligonucleotide. In a preferred embodiment, any of the vaccine disclosed herein comprises approximately 0.5 to 1 mg CpG oligonucleotide.

Preferred adjuvants for use in the present invention are alum, QS21, CpG ODN, alum in combination with CpG ODN, Iscomatrix and Iscomatrix in combination with CpG ODN.

PHARMACEUTICAL COMPOSITIONS OF THE INVENTION

The invention also provides pharmaceutical compositions comprising an antigenic PCSK9 peptide of the invention or an immunogenic composition thereof, in a formulation in association with one or more pharmaceutically acceptable excipient(s) and optionally combined with one or more adjuvants (as adjuvant described above). The term 'excipient' is used herein to describe any ingredient other than the active ingredient, i.e. the antigenic PCSK9 peptide of the invention eventually coupled to an immunogenic carrier and optionally combined with one or more adjuvants. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the active ingredient.

Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, or proteins accepted in the art may suitably be employed for the peptides or proteins of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Preferred embodiments include the intravenous, subcutaneous, intradermal and intramuscular routes, even more preferred embodiments are the intramuscular or the subcutaneous routes.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, microparticles, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the anti-PCSK9 peptide, preferably coupled to an immunogenic carrier, optionally in combination with one or more adjuvants, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An exemplary, non-limiting pharmaceutical composition of the invention is a formulation as a sterile aqueous solution having a pH that ranges from about 5.0 to about 6.5 and comprising from about 0.1 mg/mL to about 20 mg/mL of a peptide of the invention, from about 1 millimolar to about 100 millimolar of histidine buffer, from about 0.01 mg/mL to about 10 mg/mL of polysorbate 80, from about 100 millimolar to about 400 millimolar of trehalose, and from about 0.01 millimolar to about 1.0 millimolar of disodium EDTA dihydrate.

The antigenic PCSK9 peptides of the invention can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurised container, pump, spray, atomiser (preferably an atomiser using electrohydrodynamics to produce a fine mist), or nebuliser, with or without the use of a suitable propellant, or as nasal drops.

The pressurised container, pump, spray, atomizer, or nebuliser generally contains a solution or suspension of an antibody of the invention comprising, for example, a suitable agent for dispersing, solubilising, or extending release of the active, a propellant(s) as solvent.

Prior to use in a dry powder or suspension formulation, the drug product is generally micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules, blisters and cartridges for use in an inhaler or insufflator may be formulated to contain a powder mix of the compound of the invention, a suitable powder base and a performance modifier.

A suitable solution formulation for use in an atomiser using electrohydrodynamics to produce a fine mist may contain a suitable dose of the antigenic PCSK9 peptide of the invention per actuation and the actuation volume may for example vary from 1 µL to 100 µL.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of an antibody of the invention. The overall daily dose will typically be administered in a single dose or, more usually, as divided doses throughout the day.

A pharmaceutical composition comprising an antigenic PCSK9 peptide may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compositions of the invention can be used to treat, alleviate or prevent PCSK9-mediated disorders or symptoms in a subject at risk or suffering from such disorder or symptom by stimulating an immune response in said subject by immunotherapy. Immunotherapy can comprise an initial immunization followed by additional, e. g. one, two, three, or more boosters.

An "immunologically effective amount" of an antigenic PCSK9 peptide of the invention, or composition thereof, is an amount that is delivered to a mammalian subject, either in a single dose or as part of a series, which is effective for inducing an immune response against PCSK9 in said subject. This amount varies depending upon the health and physical condition of the individual to be treated, the taxonomic group of individual to be treated, the capacity of the individual's immune system to synthesize antibodies, the formulation of the vaccine, and other relevant factors. It is expected that the amount will fall in a relatively broad range that can be determined through routine trials.

A "pharmaceutically effective dose" or "therapeutically effective dose" is that dose required to treat or prevent, or alleviate one or more PCSK9-related disorder or symptom in a subject. The pharmaceutically effective dose depends on inter alia the specific compound to administer, the severity of the symptoms, the susceptibility of the subject to side effects, the type of disease, the composition used, the route of administration, the type of mammal being treated, the physical characteristics of the specific mammal under consideration such as health and physical condition, concurrent medication, the capacity of the individual's immune system to synthesize antibodies, the degree of protection desired, and other factors that those skilled in the medical arts will recognize. For prophylaxis purposes, the amount of peptide in each dose is selected as an amount which induces an immunoprotective response without significant adverse side effects in typical vaccines. Following an initial vaccination, subjects may receive one or several booster immunisations adequately spaced.

It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy.

For example, antigenic PCSK9 peptides or pharmaceutical composition of the invention can be administered to a subject at a dose of about 0.1 μg to about 5 mg, e.g., from about 0.1 μg to about 5 μg, from about 5 μg to about 10 μg, from about 10 μg to about 25 μg, from about 25 μg to about 50 μg, from about 50 μg to about 100 μg, from about 100 μg to about 500 μg, from about 500 μg to about 1 mg, from about 1 mg to about 2 mg, with optional boosters given at, for example, 1 week, 2 weeks, 3 weeks, 4 weeks, two months, three months, 6 months and/or a year later.

In some embodiments, a single dose of an antigenic PCSK9 peptide or pharmaceutical composition according to the invention is administered. In other embodiments, multiple doses of an antigenic PCSK9 peptide or pharmaceutical composition according to the invention are administered. The frequency of administration can vary depending on any of a variety of factors, e.g., severity of the symptoms, degree of immunoprotection desired, whether the composition is used for prophylactic or curative purposes, etc. For example, in some embodiments, an antigenic PCSK9 peptide or pharmaceutical composition according to the invention is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). When the composition of the invention is used for prophylaxis purposes, they will be generally administered for both priming and boosting doses. It is expected that the boosting doses will be adequately spaced, or preferably given yearly or at such times where the levels of circulating antibody fall below a desired level. Boosting doses may consist of the antigenic PCSK9 peptide in the absence of the original immunogenic carrier molecule. Such booster constructs may comprise an alternative immunogenic carrier or may be in the absence of any carrier. Such booster compositions may be formulated either with or without adjuvant.

The duration of administration of an antigenic PCSK9 peptide according to the invention, e.g., the period of time over which an antigenic PCSK9 peptide is administered, can vary, depending on any of a variety of factors, e.g., patient response, etc. For example, an antigenic PCSK9 peptide can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

A variety of treatment methods are also contemplated by the present disclosure, which methods comprise administering an antigenic PCSK9 peptide according to the invention. Subject treatment methods include methods of inducing an immune response in an individual to self-PCSK9, and methods of preventing, alleviating or treating a PCSK9-related disorder or symptom in an individual.

In one aspect, the present invention provides a method for treating, preventing or alleviating a PCSK9-related disorder or symptom in a subject, comprising administering a therapeutically effective amount of an antigenic PCSK9 peptide of the invention, or immunogenic or pharmaceutical composition thereof, to said subject.

In another aspect, the present invention provides a method for inducing an immune response against self-PCSK9 in a subject, comprising administering a therapeutically or immunogenically effective amount of an antigenic PCSK9 peptide of the invention, or immunogenic or pharmaceutical composition thereof, to said subject.

A PCSK9 related disease or a PCSK9 mediated disease is, for example, a disease where the inhibition of PCSK9 activity or the inhibition of the interaction of PCSK9 with the LDL receptor could be beneficial.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment. Said subject is preferably human, and may be either male or female, of any age.

Other aspects of the invention relate to an antigenic PCSK9 peptide according to the invention or of an immunogenic composition or a pharmaceutical composition thereof, for use as a medicament, preferably in treatment, alleviation or prophylaxis of PCSK9-related disorders.

In yet another aspect, the present invention provides the use of an antigenic PCSK9 peptide of the invention or of an immunogenic composition or a pharmaceutical composition thereof, in the manufacture of a medicament, preferably for treating a PCSK9-related disorder.

In particular, the invention relates to an antigenic PCSK9 peptide of the invention, or an immunogenic or pharmaceutical composition thereof, for use as a medicament preferably in treatment, alleviation or prophylaxis of diseases associated with an elevated level of cholesterol.

In yet another aspect, the present invention provides the use of an antigenic PCSK9 peptide of the invention or of an immunogenic composition or a pharmaceutical composition thereof, in the manufacture of a medicament, preferably for lowering the LDL-cholesterol level in blood in a subject in need thereof.

In some aspects of the uses or methods of the invention, said PCSK9-related disorder is selected from the group consisting of elevated cholesterol, a condition associated with elevated LDL-cholesterol, e.g., a lipid disorder (e.g., hyperlipidemia, type I, type II, type III, type IV, or type V hyperlipidemia, secondary hypertriglyceridemia, hypercholesterolemia, familial hypercholesterolemia, xanthomatosis, cholesterol acetyltransferase deficiency), arteriosclerotic conditions (e.g., atherosclerosis), coronary artery disease, and cardiovascular disease.

In yet another aspect, the present invention provides the use of an antigenic PCSK9 peptide of the invention or of an immunogenic composition or a pharmaceutical composition thereof, in the manufacture of a medicament for treating or alleviating diseases where an up-regulation of the LDL receptor or an inhibition of the interaction between PCSK9 and the LDL receptor is beneficial.

In yet another aspect, the present invention provides the use of an antigenic PCSK9 peptide of the invention or of an immunogenic composition or a pharmaceutical composition thereof, in the manufacture of a medicament for the treatment of Alzheimer's disease.

In other aspects of the uses or methods of the invention, said subject is a mammal, preferably a human subject.

In still other aspects of the uses or methods of the invention, said subject suffers from said PSCK9-related disorder. Alternatively, said subject is at risk of suffering from said PCSK9-related disorder, e.g., due to the presence of one or more risk factors (e.g., hypertension, cigarette smoking, diabetes, obesity, or hyperhomocysteinemia).

The antigenic PCSK9 peptide of the invention or an immunogenic composition or a pharmaceutical composition thereof are useful for subjects who are intolerant to therapy with another cholesterol-reducing agent, or for whom therapy with another cholesterol-reducing agent has produced inadequate results (e.g., subjects who experience insufficient LDL-c reduction on statin therapy). The antigenic PCSK9 peptide of the invention described herein can be administered to a subject with elevated LDL-cholesterol.

Preferably a subject with elevated cholesterol is a human subject with total plasma cholesterol levels of 200 mg/dl or greater. Preferably a subject with elevated cholesterol is a human subject with LDL-cholesterol levels of 160 mg/dl or greater.

Total plasma cholesterol levels and LDL-cholesterol levels are measured using standard methods on blood samples obtained after an appropriate fast. Protocols to measure total plasma cholesterol levels and LDL-cholesterol levels are well-known to the man skilled in the art.

In one embodiment the antigenic PCSK9 peptide or an immunogenic composition or a pharmaceutical composition thereof is administered together with another agent, the two can be administered sequentially in either order or simultaneously. In some embodiments, an antigenic PCSK9 peptide or an immunogenic composition or a pharmaceutical composition thereof is administered to a subject who is also receiving therapy with a second agent (e.g., a second cholesterol-reducing agent). Cholesterol reducing agents include statins, bile acid sequestrants, niacin, fibric acid derivatives, and long chain alpha, omego-dicarboxylic acids. Statins inhibit cholesterol synthesis by blocking HMGCoA, a key enzyme in cholesterol biosynthesis. Examples of statins are lovastatin, pravastatin, atorvastatin, cerivastatin, fluvastatin, and simvastatin. Bile acid sequestrants interrupt the recycling of bile acids from the intestine to the liver. Examples of these agents are cholestyramine and colestipol hydrochloride. Examples of fibric acid derivatives are clofibrate and gemfibrozil. Long chain alpha, omego-dicarboxylic acids are described, e.g., by Bisgaier et al., 1998, J. Lipid Res. 39:17-30; WO 98/30530; U.S. Pat. No. 4,689,344; WO 99/001 16; U.S. Pat. No. 5,756,344; U.S. Pat. No. 3,773,946; U.S. Pat. No. 4,689,344; U.S. Pat. No. 4,689,344; U.S. Pat. No. 4,689,344; and U.S. Pat. No. 3,930,024); ethers (see, e.g., U.S. Pat. No. 4,711,896; U.S. Pat. No. 5,756,544; U.S. Pat. No. 6,506,799). Phosphates of dolichol (U.S. Pat. No. 4,613,593), and azolidinedione derivatives (U.S. Pat. No. 4,287,200) can also be used to reduce cholesterol levels. A combination therapy regimen may be additive, or it may produce synergistic results (e.g., reductions in cholesterol greater than expected for the combined use of the two agents). In some embodiments, combination therapy with an antigenic PCSK9 peptide or an immunogenic composition or a pharmaceutical composition thereof and a statin produces synergistic results (e.g., synergistic reductions in cholesterol). In some subjects, this can allow reduction in statin dosage to achieve the desired cholesterol levels.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Selection of Antigenic PCSK9 Peptides at the PCSK9-EGF-A Domain of the LDL Receptor Interface The structure of human PCSK9 binding to the EGF-A domain of the LDL receptor has been solved and published (Kwon et al, PNAS 105, 1820-1825, 2008). This structural information (PDB: 3BPS) was used together with information from the structure of free PCSK9, PDB: 2P4E (Cunningham et al, Nature Structural & Molecular Biology, 14, 413-419, 2007) to design the following peptides which would correspond to areas of importance for the PCSK9-LDL receptor interaction (see FIG. 1).

| Peptide 1. | ASSDCSTCFV | (SEQ ID No: 19) |
| Peptide 2. | GTRFHRQASK | (SEQ ID No: 63) |
| Peptide 3. | IQSDHREIEGRV | (SEQ ID No: 109) |

-continued

| Peptide 4. | SGRDAGVAKGA | (SEQ ID No: 153) |
| Peptide 5. | SIPWNLERITP | (SEQ ID No: 184) |

Since peptides 1-4 represent loops in the PCSK9 structure, the respective sequences (SEQ ID Nos 19, 63, 109 and 153) were made with added Cys, Cys-Gly or Lys linkers to allow coupling via both ends to the VLP carrier to provide a conformational mimetic of the natural loop structure (VR_9.1 to VR_9.4 in Table 1). In addition, cyclised versions of peptides 2-4 were also made (VR_9.6 to VR_9.9 in Table 1) which provided a Cys residue for coupling to VLPs. Peptide 1 was made with a Lys-Gly-Gly N-terminal linker for coupling purposes so that the two Cys residues were free to disulphide bond as they do in the native PCSK9 structure. Peptide 5 represents the N-terminal of the mature processed form of human PCSK9 and was coupled via a C-terminally added cysteine residue to allow the N-terminus to be free for antibody recognition (VR_9.5 in Table 1). The following table (Table 1) describes 9 peptides generated for evaluation as vaccine candidates.

TABLE 1

Peptide Sequences

| Peptide | Sequence | SEQ ID No |
|---|---|---|
| VR_9.1 | KGGASSDCSTCFV | 313 |
| VR_9.2 | CGGTRFHRQASKC | 314 |
| VR_9.3 | CGIQSDHREIEGRVC | 315 |
| VR_9.4 | CSGRDAGVAKGAC | 316 |
| VR_9.5 | SIPWNLERITPC | 317 |
| VR_9.6 | ASK-Cys(H)-GDGTRFHRQ | 318 |
| VR_9.7 | AG-Cys-(H)-GTRFHRQ | 319 |
| VR_9.8 | GRV-Cys(H)-IQSDHREIE | 320 |
| VR_9.9 | AGVAKGAG-Cvs(H)-SGRD | 321 |

Underscore indicates cysteine residues assed for conjugation purposes and double underscore indicates a GC or KGG linker.

Example 2

Preparation of Peptide-VLP Conjugates for Evaluation as Vaccine Candidates

The peptides were synthesised using a standard Fmoc protocol on CLEAR amide resin. The amino acid coupling reactions were carried out using 5 fold excess of Fmoc-protected amino acid activated with 1 eq of HBTU (2-(1H-Benzotriazole-1-yl)-1,1,3,3-tetramethyluronium hexafluorophosphate) in the presence of HOBt (hydroxybenzotriazole) and NMM (N-methylmorpholine). The deprotection of Fmoc group was achieved with 20% piperidine/DMF. Resin-bound peptide was then cleaved and side chain protecting groups removed simultaneously with Reagent D (TFA/H2O/DODT: 89/3/8). The peptide was made with a free N-terminus and amidated C-terminus. The crude peptide was purified to homogeneity by HPLC using a BEH 130 C18 column and a water/acetonitrile gradient in the presence of 0.1% TFA. The purified peptide was vacuum-dried using a lyophilizer. The peptide was analyzed using mass-spectrometry (LC-MS) and gave satisfactory data.

The Qβ VLP used in this study was produced by bacterial *E. Coli* fermentation in a BL21 (DE3) strain incorporating a pET28 plasmid encoding the 14 kD monomer protein: MAKLETVTLGNIGKDGKQTLVLN-PRGVNPTNGVASLSQAGAVPALEKRVTVSVSQPSR NRKNYKVQVKIQNPTACTANGSCDPSVTRQAYAD-VTFSFTQYSTDEERAFVRTELAAL LASPLLIDAIDQL-NPAY (SEQ ID NO:638) (Genbank ID: M99039). The fermentation is induced at an OD600 of 0.8 with IPTG and allowed to proceed overnight in terrific broth (TB) with kanamycin. The VLP, which self-assembles in the host cell, was then purified from the fermentation cell pellet using the method described in the patent application EP1736538 with the following differences: after cell disruption, the clarified homogenate was treated with ammonium sulphate at 50% saturation and the cell pellet recovered by centrifugation. Then, the pellet was redissolved in HEPES buffer and dialysed against HEPES buffer before proceeding to the first column step in the published method. After the ion-exchange column and hydroxylapatite column steps, the material was purified using a further anion-exchange column step and sterile filtered to make the final VLP bulk material, which was analysed by size-exclusion chromatography, SDS-PAGE and electron microscopy with acceptable results.

Conjugation of Peptides Through Cysteine Residues:

The Qβ VLP was activated using either N-gamma-maleimido-butyryloxy-succinimide ester (GMBS) or the longer Succinimidyl-6-[β-maleimidopropionamido]hexanoate linking reagent. The procedure for the usage of both these reagents was similar: Solid reagent was dissolved in dimethyl sulphoxide (DMSO) and added to the VLP solution at ≥10-fold molar excess. The activation reaction was allowed to proceed for ≥90 minutes and the solution was then desalted using a NAP-25 desalting column into Dulbeccos Phosphate Buffered Saline (DPBS) with 5 mM EDTA or Dulbeccos Phosphate Buffered Saline (DPBS) that had been modified by the addition of solid NaCl (14.6 g/L). If necessary, the protein solution was concentrated slightly using 10 kD spin microconcentrators prior to the next conjugation reaction.

Prior to the conjugation reaction, the peptides were dissolved in an aliquot of pH 7.4 DPBS, with 5 mM EDTA as an additive. The concentration of the peptide in solution was 10 mg/ml. The solubilised peptide was added to an aliquot of TCEP immobilised reducing agent (Pierce Chemical) which had been washed in DPBS containing 5 mM EDTA. The aliquot of peptides was incubated with mixing in the presence of the TCEP gel for approximately 1 hour, after which time the aliquot was spun down in a microfuge and the solid pellet discarded. The reduced peptide-containing supernatant was added directly to the activated VLP which had been prepared earlier. One alternative to this procedure however is the addition of solid peptide directly to the sample of activated Qβ VLP. Both methods work equally well for the generation of peptide-VLP conjugates.

The reaction between the VLPs and the reduced peptides was allowed to proceed for at least thirty minutes with very gentle mixing. At the end of the reaction time each sample was desalted into Dulbeccos PBS (DPBS) using NAP-10 or NAP-25 desalting columns (GE Healthcare). The desalted conjugated peptides were analysed for protein content using the Bradford (Coomassie Brilliant Blue, Pierce Chemical Co) assay or BCA protein assay (bicinchoninic acid) (Pierce Chemical Co) as well as by SDS-PAGE and size-exclusion chromatography. The conjugate products were sterile filtered using a 0.22 μm filter and stored at 2-8° C. until use.

Careful attention was paid to these samples during storage to prevent freezing or exposure to extremes in temperature.

The conjugation of the PCSK9 peptide to CRM197 was performed by using BAANS (Bromoacetic acid N-hydroxysuccinimide ester, Sigma B8271). CRM197 was first activated by reacting with BAANS in 0.1 M sodium carbonate pH 8.3 with a molar ratio of 100 in a cold room for 90 minutes. The reaction mixture was passed through a Zeba desalting column, and the flow-through was collected. The PCSK9 peptide at 10 mg/ml was incubated with an equal volume of immobilized TCEP reducing gel (Thermo Scientific) at room temperature for 1 hour, and collected after centrifugation through a 0.2 μm filter. The activated CRM197 was then mixed with the treated peptide in the cold room overnight, followed by an extensive dialysis in PBS buffer. The conjugate was recovered, concentrated, and sterilized through a 0.22 μm filter. The protein concentration was determined using Coomassie blue assay (Thermo Scientific).

Conjugation of Peptides Via Amines

For the conjugation of peptides to Qβ via amine residues, specifically peptide VR_9.1, the following procedure was followed. Qβ was initially derivatised by the addition of solid succinic anhydride at a ≥10-fold molar excess relative to the VLP monomer. The succinic anhydride was allowed to dissolve and the derivatisation reaction was allowed proceed for at least 30 mins. After this time, the sample was then desalted using a NAP-25 desalting column into Dulbeccos Phosphate Buffered Saline (DPBS) with 5 mM EDTA. Then, the following reagents were added in the order listed at a ≥10-fold molar excess relative to the VLP monomer: Solid peptide, N-hydroxysulfosuccinimide and finally 1-Ethyl-3-(3-dimethylaminopropyl)carbodiimide. Following the addition of reagents in the order listed above, the sample was incubated at room temperature and the reaction was allowed proceed for at least 30 mins, after which time the VLP-peptide conjugate was desalted using NAP-25 desalting columns into Dulbeccos Phosphate Buffered Saline (DPBS).

The extent of the conjugation for the VLP-peptide samples was measured using SDS-PAGE, and a molecular weight increase was observed for all samples which is consistent with the addition of the peptide to the VLP protein monomer. In addition, samples were tested in the HPLC size-exclusion chromatography assay (using a Tosoh PWXL5000 HPLC column) and found to contain assembled VLP when compared to unconjugated samples of VLP. VLP-peptide conjugation features are summarized in Table 2.

TABLE 2

VLP-Peptide Conjugates

| Peptide | Activated VLP added | Amount of peptide added | Percentage yield of input VLP | Approximate substitution (ug peptide per mg of VLP monomer) |
| --- | --- | --- | --- | --- |
| VR_9.1 | 4 mg | 5 mg | 40-60% | 25 ug |
| VR_9.2 | 3 mg | 5 mg | 40-60% | 125 ug |
| VR_9.3 | 3 mg | 5 mg | 40-60% | 125 ug |
| VR_9.4 | 3 mg | 5 mg | 40-60% | 125 ug |
| VR_9.5 | 3 mg | 5 mg | 40-60% | 50 ug |
| VR_9.6 | 3 mg | 5 mg | 40-60% | 125 ug |
| VR_9.7 | 3 mg | 5 mg | 40-60% | 125 ug |
| VR_9.8 | 3 mg | 5 mg | 40-60% | 125 ug |
| VR_9.9 | 3 mg | 5 mg | 40-60% | 125 ug |
| VR_9.10 | 3 mg | 5 mg | 40-60% | 125 ug |

TABLE 2-continued

VLP-Peptide Conjugates

| Peptide | Activated VLP added | Amount of peptide added | Percentage yield of input VLP | Approximate substitution (ug peptide per mg of VLP monomer) |
| --- | --- | --- | --- | --- |
| VR_9.11 | 3 mg | 2 mg | 40-60% | 125 ug |
| VR_9.12 | 3 mg | 2 mg | 40-60% | 125 ug |
| VR_9.13 | 3 mg | 2 mg | 40-60% | 125 ug |
| VR_9.14 | 3 mg | 2 mg | 40-60% | 125 ug |
| VR_9.15 | 3 mg | 2 mg | 40-60% | 125 ug |
| VR_9.16 | 3 mg | 2 mg | 40-60% | 125 ug |
| VR_9.17 | 10 mg | 9.5 mg | 95% | 82 ug |
| VR_9.18 | 10 mg | 8.7 mg | 90% | 74 ug |
| VR_9.19 | 10 mg | 7.6 mg | 80% | 58 ug |
| VR_9.20 | 10 mg | 8.7 mg | 95% | 86 ug |
| VR_9.21 | 10 mg | 8.8 mg | 95% | 92 ug |
| VR_9.22 | 10 mg | 6.6 mg | 85% | 62 ug |
| VR_9.23 | 10 mg | 10.0 mg | 90% | 85 ug |
| VR_9.24 | 10 mg | 10.5 mg | 75% | 64 ug |
| VR_9.25 | 10 mg | 5.1 mg | 40% | 1 ug |
| VR_9.26 | 10 mg | 10.0 mg | 60% | 123 ug |
| VR_9.27 | 10 mg | 9.6 mg | 60% | 136 ug |
| VR_9.28 | 10 mg | 9.4 mg | 65% | 153 ug |
| VR_9.29 | 10 mg | 4.2 mg | 75% | 19 ug |
| VR_9.30 | 10 mg | 4.4 mg | 63% | 15 ug |
| VR_9.31 | 10 mg | 4.4 mg | 70% | 13 ug |
| VR_9.32 | 10 mg | 4.4 mg | 63% | 15 ug |
| VR_9.33 | 10 mg | 7.4 mg | 40% | 18 ug |
| VR_9.34 | 10 mg | 7.3 mg | 50% | 23 ug |
| VR_9.35 | 7.5 mg | 4.3 mg | 61% | 16 ug |

*As determined by SDS-PAGE and densitometry calculations

Example 3

PCSK9 Peptide Immunogenicity

This study aimed to evaluate how efficacious peptides conjugated to a Qbeta VLP (as detailed in Example 2 above) were in inducing an antibody response that can bind to human and mouse PCSK9. Female Balb/c (6-8 weeks) were injected by the intramuscular route (50 microliter volume injected into each Tibialis anterior muscle) on days 0, 21 and 42 with VLP-peptide conjugates formulated in Alum with CpG of formula 5' TCGTCGTTTTTCGGTGCTTTT 3' (SEQ ID NO:589). One group of control mice was immunized with VLP coupled to a control (non-PCSK9) peptide following the same protocol and a second control group was left unimmunised. Necropsy took place on day 49. At necropsy 400-600 microliter blood was sampled from euthanised mice by cardiac puncture using an anti-coagulant. Blood was centrifuged to separate the plasma, which was stored frozen until testing.

IgG antibody responses to full length human recombinant PCSK9 protein were measured using a colorimetric ELISA method. Serial dilutions were prepared from sera samples and tested in the assay.

Human PCSK9 ELISA Method 1:

384-well high bind assay plates (Corning International Cat #3700) were coated with 25 μL/well of human PCSK9 protein stock diluted to 1 μg/mL with 0.01 M PBS pH 7.4 and incubated on a shaker at RT for 3 hours. After washing ×2 with PBS pH 7.4, plates were blocked using 80 μL/well of 0.01M PBS/1% BSA, incubated at RT for 1 hour before a final wash ×3 with 0.01M PBS pH 7.4/0.05% Tween 20. The following day, an 8 point ½ log serial dilution of each sample was prepared starting at 1:25 dilution (PBS/1% BSA diluent), 25 μL/well of the serial dilution transferred in duplicate into the human PCSK9 coated plate then incubated shaking at RT for 1.5 hours. After washing ×3 with 0.01 M PBS pH 7.4/0.05% Tween 20, 25 μL/well of Total IgG detection antibody (Rabbit anti-mu IgG-Fc, Cat# A90-130A Bethyl Laboratories) at a 1:6000 dilution with 0.01M PBS pH 7.4/1% BSA was added, then incubated shaking at RT for 1 hour. After washing ×5 with 0.01M PBS pH 7.4/0.05% Tween 20, added 25 μL/well Bio-Rad kit goat anti-rabbit horseradish peroxidase conjugate (Bio-Rad Cat #172-1019) 1:3000 with 0.01M PBS pH 7.4/0.05% Tween 20 pH 7.4, then incubated shaking at RT for 1 hour. After washing ×4 with 0.01M PBS pH 7.4/0.05% Tween 20 and then ×1 with 0.01M PBS pH 7.4 only, 25 μL/well Mouse Typer HRP Substrate (Bio-Rad Cat #172-1064) were added and the plates were incubated at RT for 30 mins. 25 μL/well 2% oxalic acid were added and the absorbance then read at Abs 405 nm.

Mouse PCSK9 ELISA Method 1:

Thermo Immunolon 4HBX 96-well ELISA plates were coated with 100 μl of 1 μg/ml recombinant mouse PCSK9 in PBS overnight at 4° C. After washing, plates were blocked with 300 ml PBS/0.5% BSA (Sigma A7030) for 1 hr, washed 4× with 300 μl PBS/0.01% Tween-20 and 100 μl of serial dilutions of plasma samples (in PBS/0.5% BSA) added. After incubation with gentle shaking for 1 hour at room temperature, plates were washed 4× with 300 μl PBS/0.01% Tween-20 and 100 μl of a 1:5000 dilution of goat anti-mouse IgG-HRP (horse radish peroxidase; Pierce 31430) added to each well. The plates were incubated at room temperature with gentle shaking for 45 minutes and then washed ×7 with 300 μl PBS/0.01% Tween-20. 100 μl TMB substrate (Sigma T-4444) was then added, the colorimetric reaction stopped after 4 minutes by addition of 2N sulphuric acid and the absorbance read at 450 nm.

Data Analysis:

Titration curves were plotted for each test sample (sample dilution vs absorbance). The sample titer (subsequently transformed into reciprocal titer) was then taken as the serum dilution achieving a cut-off optical density (O.D.) values of 1.0 or 0.5.

Measurement of Plasma/Serum Cholesterol Level

Cholesterol levels in plasma and serum samples were measured using a WAKO Cholesterol E Assay kit (Cat #439-17501) following the manufacturers' instructions. Dilutions of cholesterol standard or test plasma/serum samples (4 μl volume) were added to wells of a 96-well plate and 196 μl of prepared cholesterol reagent added. The plate was incubated for 5 minutes at 37° C. and the absorbance of the developed colour read at 600 nm within 30 minutes.

Measurement of Interaction Between PCSK9 and the Extracellular Domain of the LDL Receptor Interruption of LDLR and PCSK9 binding by mouse plasma was determined with TR-FRET assay (time-resolved fluorescence resonance energy transfer assay) using fluorophor-labeled LDLR extracellular domain (LDLR-ECD) and full length wild type PCSK9 protein. LDLR-ECD (R&D system, cat #2148-LD/CF)) was labeled with europium (GE healthcare, Cat#PA99148) according to manufacturer's instruction (at a Eu:LDLR molar ratio 6:1). PCSK9 was biotinylated with Biotin-XX-SSE (Pierce, cat #21237) at a Biotin:PCSK9 molar ratio of 8. The TR-FRET assay was conducted with 5 nM LDLR-Eu+3, 30 nM PCSK9-biotin and 50 nM Alexa Fluor 647 conjugated streptavidin (SA647, Invitrogen, cat# S21374) in 20 ul of assay buffer (20 mM Hepes, pH7.0, 150 mM NaCl, 0.1 mM CaCl2 and 0.05% (w/v) BSA) in 384-well black plates (Corning, Cat #3676). Serial dilution of mouse plasma were pre-incubated with PCSK9-biotin at RT for 30 minutes in humidified chamber, followed by mixing with LDLR and streptavidin-SA647. After an additional 60 minute incubation at RT in a humidified atmosphere in dark, the plates were read on a Perkin Elmer Victor2 plate reader using a 50 μs delay time and a 400 ρs window. Data are reported as the ratio of the signals at (665 nm/615 nM)×1000.

Figure 2:
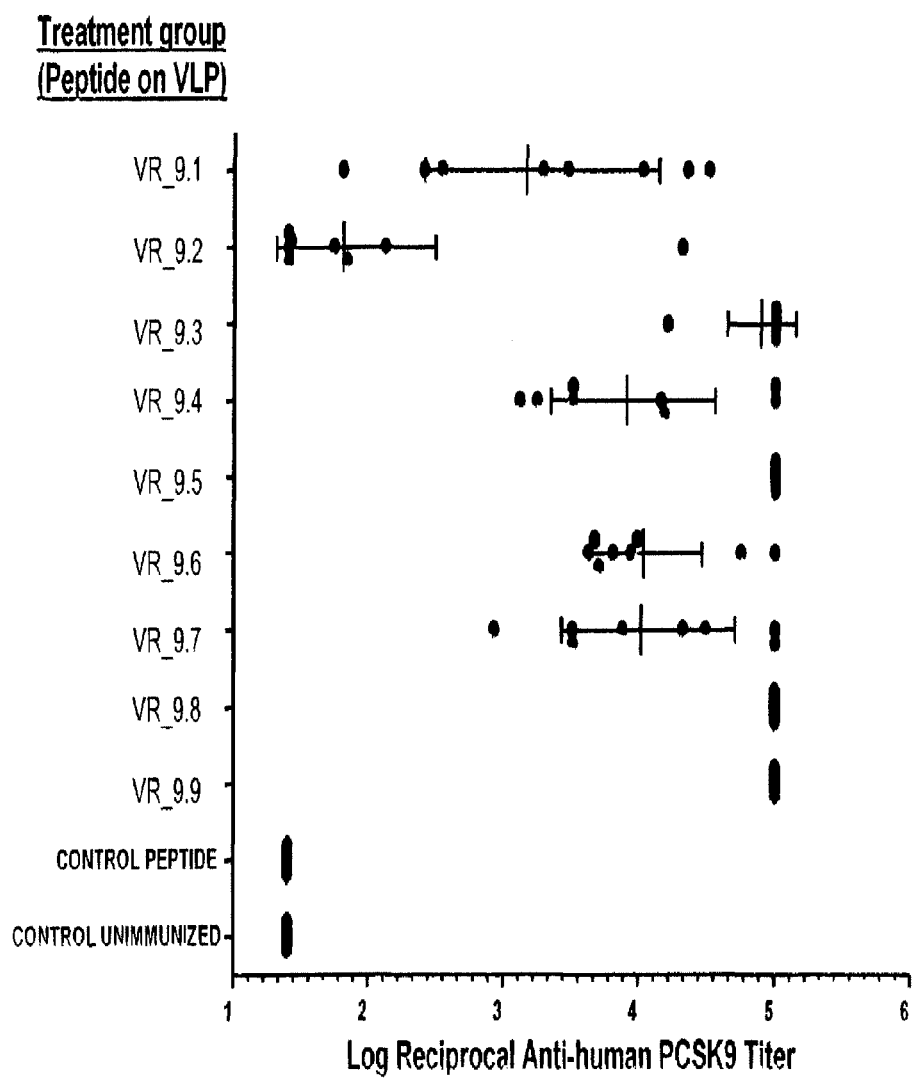
FIG. 2: Mice were immunized with peptides VR_9.1 to VR_9.9 conjugated to VLPs, using Alum plus CpG as adjuvant and antibody responses to full-length recombinant human PCSK9 were measured by titrating sera in an ELISA assay. Results are shown as reciprocal titres for each of 6 mice per group, with the reciprocal titre measured as the dilution of serum giving an optical density reading of 0.5.
Figure 3:
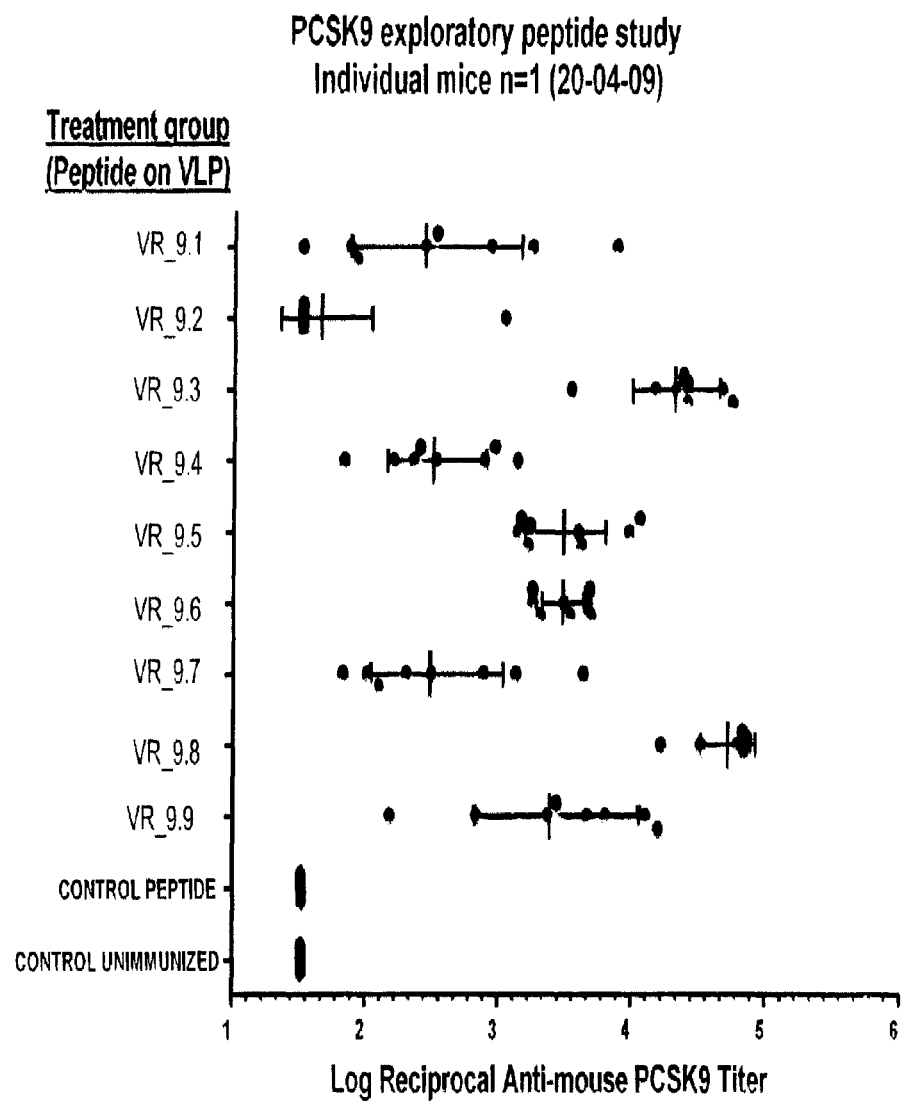
FIG. 3: Antibody responses to full-length recombinant mouse PCSK9 protein as described in FIG. 2.
Figure 4:
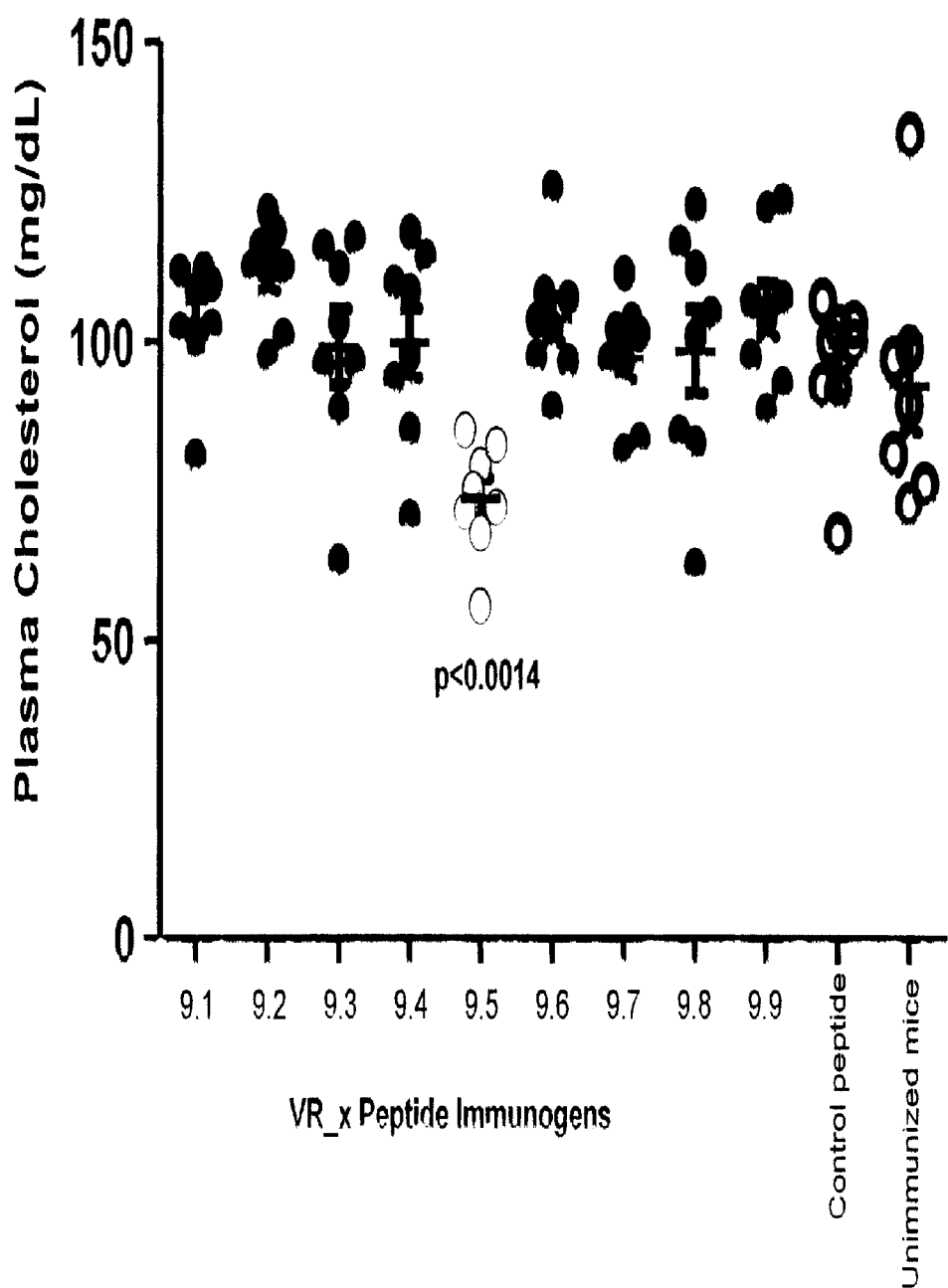
FIG. 4: Plasma cholesterol levels measured in the sera of vaccinated mice (same samples as used for antibody assays in FIGS. 2 and 3).
Figure 5:
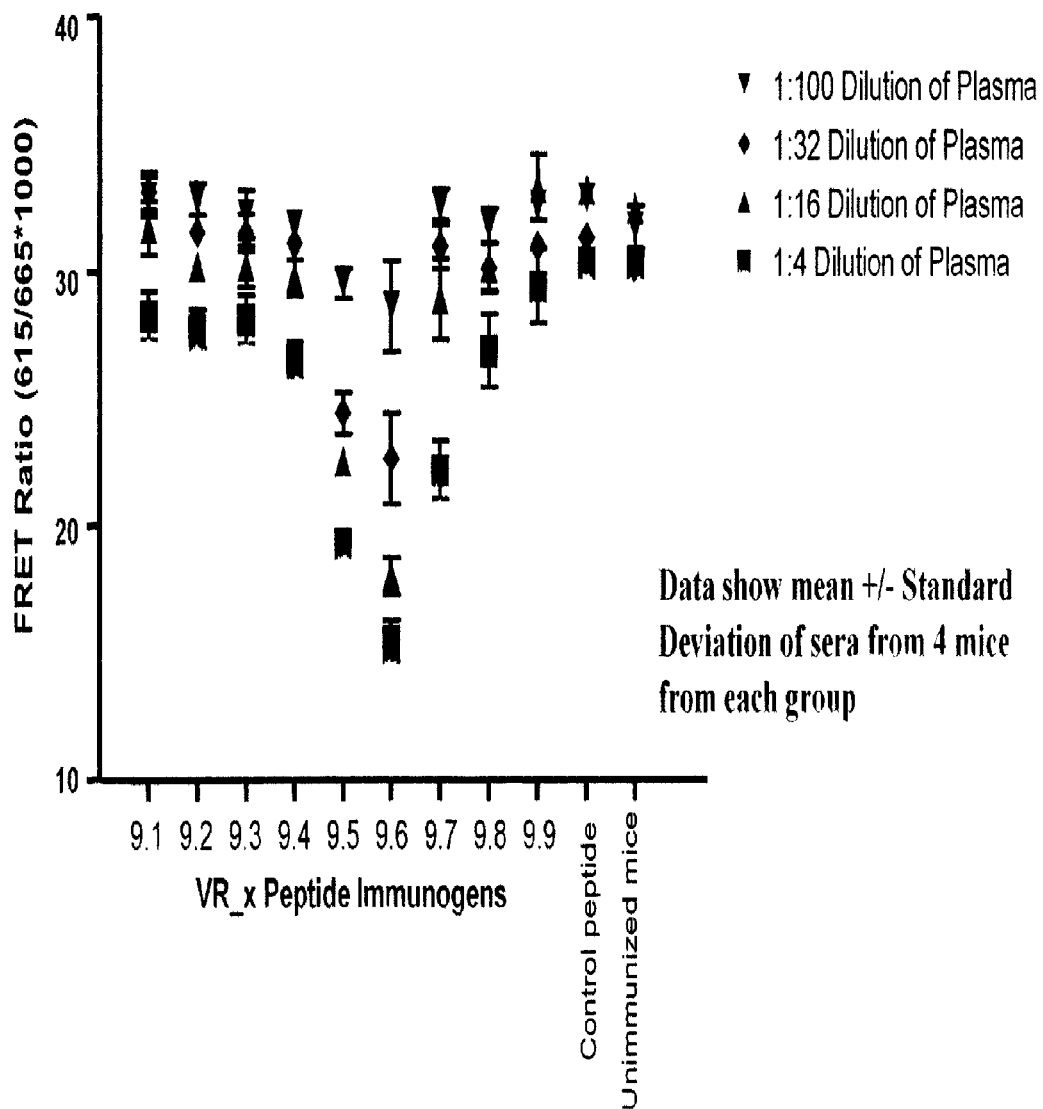
FIG. 5: Plasma samples used in FIGS. 2 to 4 were tested at different dilutions for their ability to inhibit the interaction between recombinant PCSK9 and the extracellular domain of the LDL receptor as measured by FRET assay.
Figure 6:
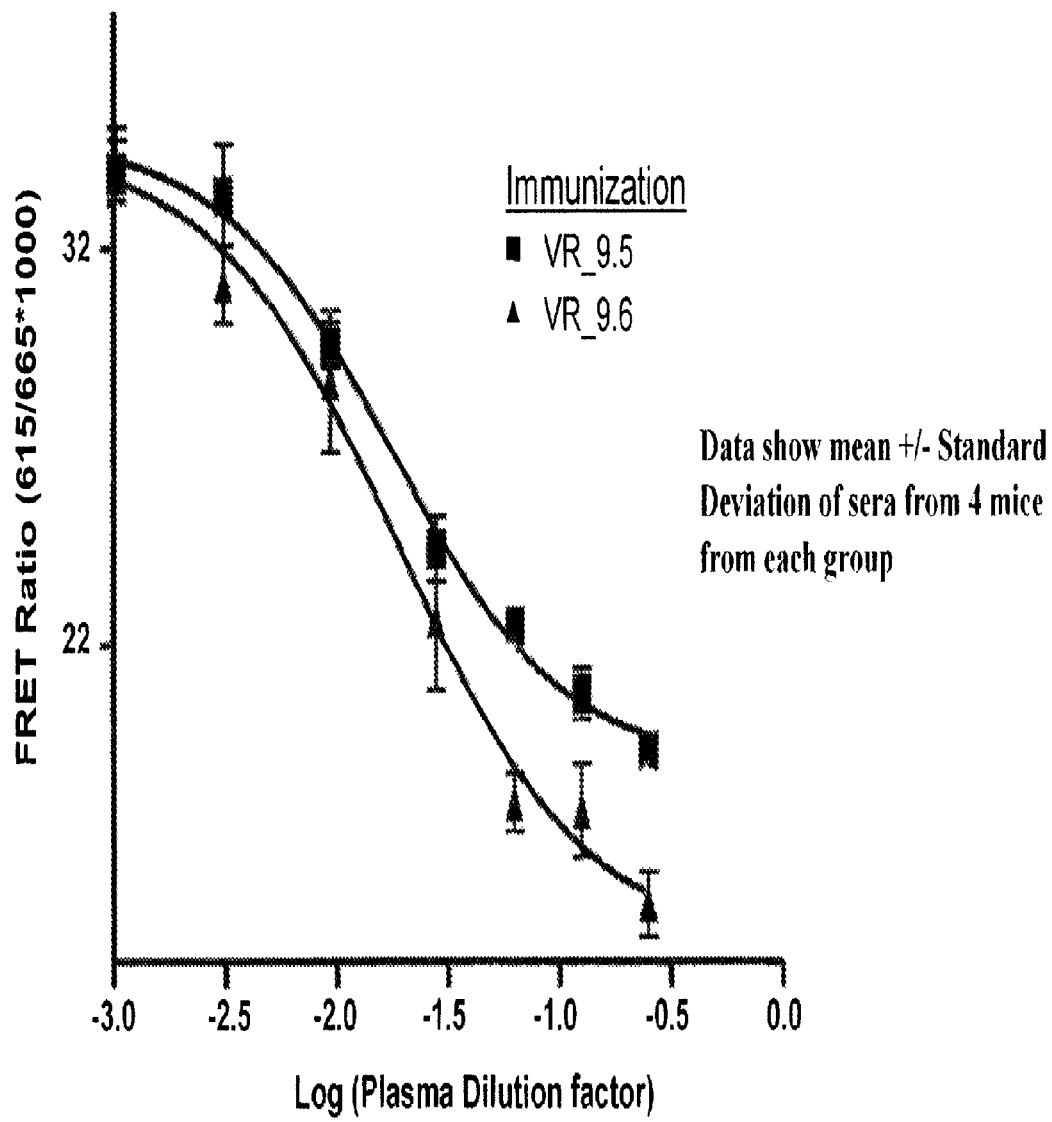
FIG. 6: Dilutions of plasma samples from peptides VR_9.5 and VR_9.6 vaccinations in FRET assay, showing dose-responsive inhibition of interaction between PCSK9 and the LDL receptor.

Results:

as shown in FIG. 2, all peptides used as immunogens were able to induce antibody responses to the intact full-length human PCSK9 protein, some inducing higher responses than others. In all cases these responses cross-reacted with mouse PCSK9 as shown in FIG. 3. FIG. 4 shows that peptide VR_9.5 immunization also led to a decrease in plasma cholesterol levels and FIGS. 5 and 6 show that VR_9.5 and VR_9.6 induced serum antibody responses that could inhibit the interaction between PCSK9 and LDL receptors using a fluorescence resonance energy transfer (FRET) assay.

Example 4

Design of Peptides Corresponding to Regions Distinct from Receptor EGF-A Domain Present in PDB: 3BPS The LDL receptor is a multidomain protein the extracellular domains of which consist of an N-terminal ligand binding domain, three EGF like repeats (of which EGF-A is one) a β-propeller domain and an "O linked sugar domain" (Kwon et al, PNAS 105, 1820-1825, 2008). The PDB file 3GCX details the structure of PCSK9 in complex with a soluble form of only the EGF-A domain of the LDL receptor, therefore we postulated that further non-obvious interactions may exist between PCSK9 and the LDL receptor that cannot be deduced from direct analysis of the molecules represented in PDB: 3GCX. Examples of these regions are detailed in FIG. 7 and specifically two sequences in PCSK9 were identified that could act as additional putative receptor interfaces (NAQDQPVTLGTL (SEQ ID NO:227) and INEAWFPEDQRVL (SEQ ID NO:263)—see FIG. 8).

```
SIPWNLERIIP (mouse)        (SEQ ID No 332)

NAQDQPVTLGTL               (SEQ ID No: 227)

INEAWFPEDQRVL              (SEQ ID No: 263)

INMAWFPEDQQVL (mouse)      (SEQ ID No 360)
```

Figure 8:
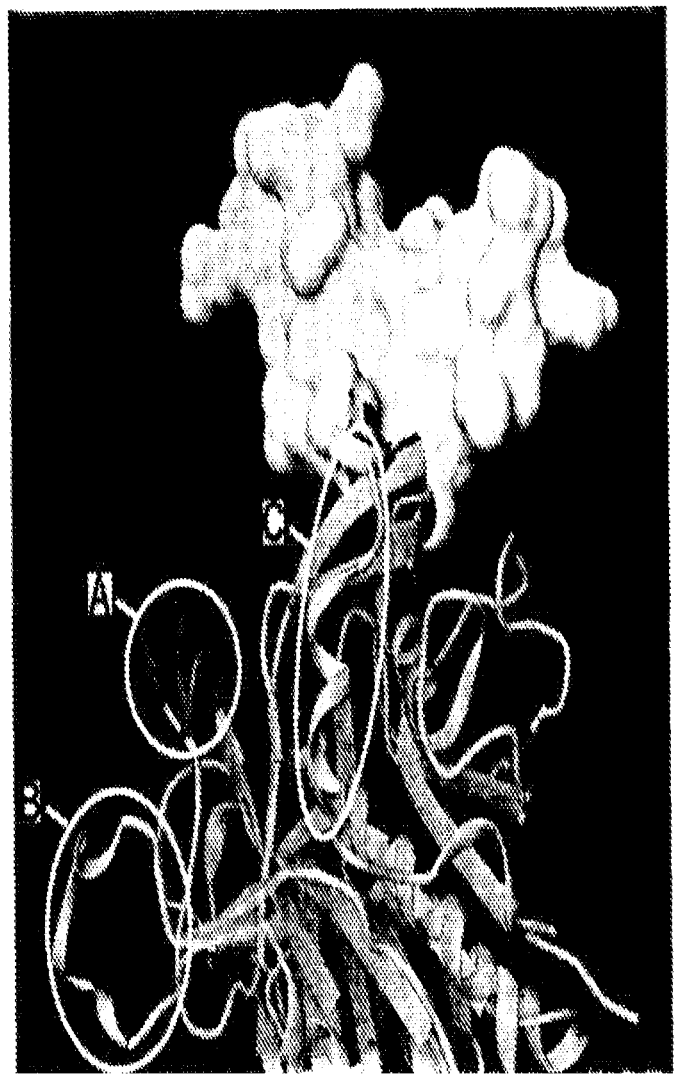
FIG. 8: Complex of PCSK9 (ribbons) and EGF-A (space fill), with the amino acids corresponding to peptides VR_13/14 (A) and VR_15/16 (B) and VR_9.5 (C) is displayed.

By using murine PCSK9 sequences as found in public databases the murine homologues were also identified (as displayed in table 3). We also postulated that part of the amino acid sequence contained within peptide VR_9.5 (described in Example 1) may also interact with parts of the LDL receptor not visible in the PDB: 3BPS (FIG. 8). This concept was probed by refining the sequence VR_9.5 by altering the amino acid linker and the orientation of conjugation. We also identified a peptide corresponding to the mouse homologue of VR_9.5 (peptide VR_9.10). The resultant series of peptide sequences from the approach described above were modified by the addition of amino acids to permit chemical conjugation and were evaluated as vaccine candidates (peptides detailed in table 3).

TABLE 3

Peptide sequences

| Peptide | Sequence | Species | SEQ ID No |
|---|---|---|---|
| VR_9.10 | SIPWNLERIIPC | Mouse | 322 |
| VR_9.11 | CGGSIPWNLERIIP | Mouse | 323 |
| VR_9.12 | SIPWNLERIIPGGC | Mouse | 324 |
| VR_9.13 | CGGNAQDQPVTLGTL | Mouse & Human | 325 |
| VR_9.14 | NAQDQPVTLGTLGGC | Mouse & Human | 326 |
| VR_9.15 | CGGINMAWFPEDQQVL | Mouse | 327 |
| VR_9.16 | INMAWFPEDQQVLGGC | Mouse | 328 |

Residues underlined indicate amino acids added for conjugation purposes.

Example 5

Figure 9:
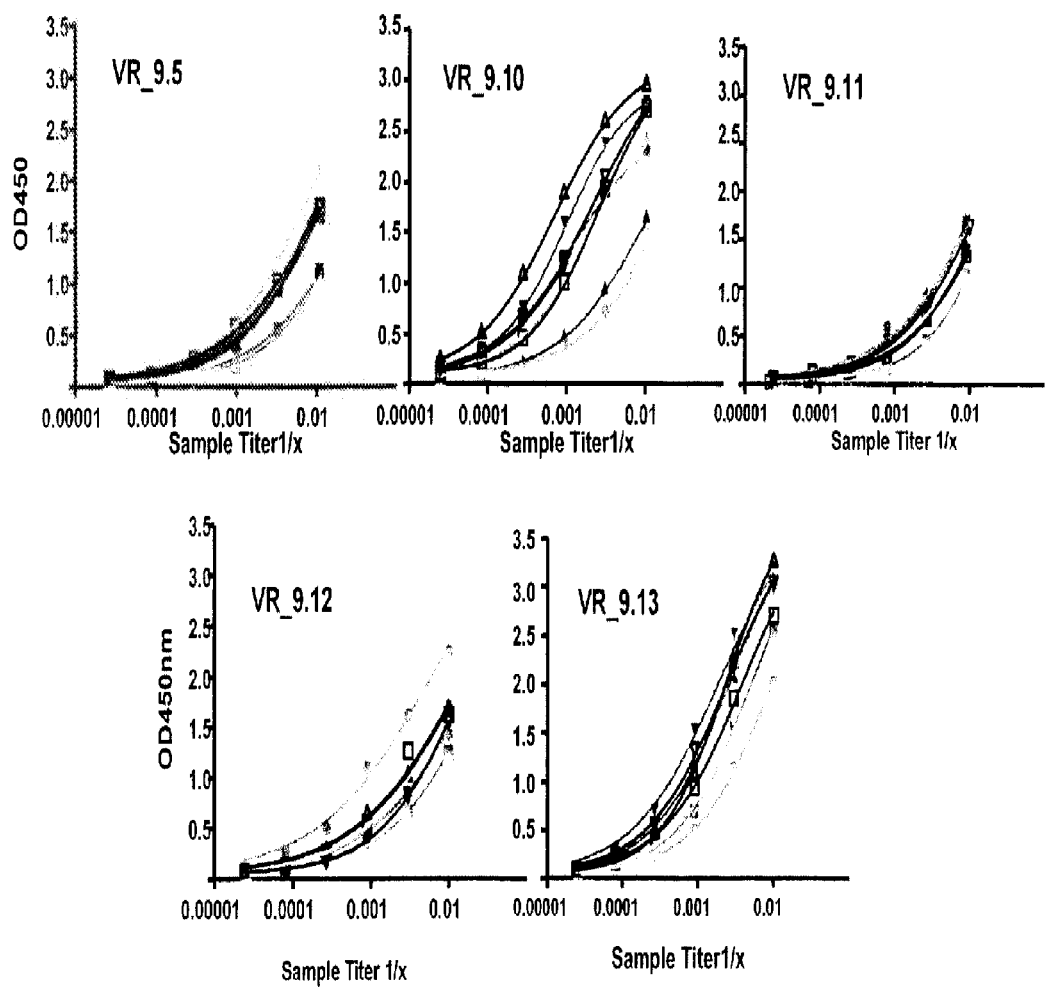
FIG. 9: Plasma antibody responses of mice vaccinated with peptides VR_9.5 (upper left panel), VR_9.10 (upper middle panel), VR_9.11 (upper right panel), VR_9.12 (lower left panel), and VR_9.13 (lower right panel). Antibodies to mouse PCSK9 were measured by ELISA assay of serial plasma dilutions using full-length mouse PCSK9 protein. Individual titration curves are shown for 8 mice per group, with ELISA responses of plasma from mice immunized with unconjugated VLP shown as a control.
Figure 10:
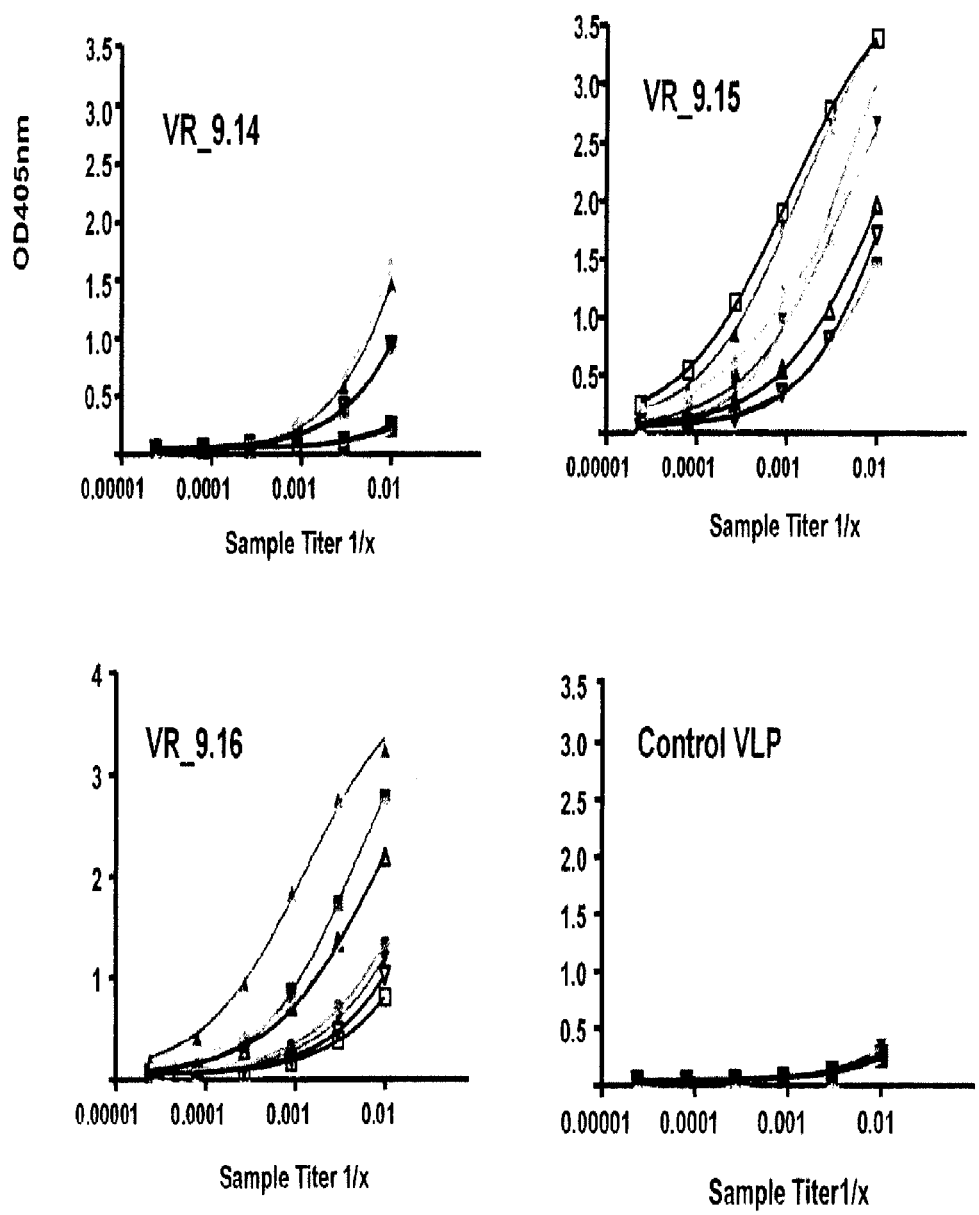
FIG. 10: Plasma antibody responses of mice vaccinated with peptides VR_9.14 (upper left panel), VR_9.15 (upper right panel), VR_9.16 (lower left panel), and Control VLP (lower right panel). Antibodies to mouse PCSK9 were measured by ELISA assay of serial plasma dilutions using full-length mouse PCSK9 protein. Individual titration curves are shown for 8 mice per group, with ELISA responses of plasma from mice immunized with unconjugated VLP shown as a control.

Peptides VR_9.10 to VR_9.16 (as well as VR_9.5 for comparison) were conjugated to Qβ VLP as described in example 2 and used to immunize mice and assess antibody responses to PCSK9 as described in example 3, with an unconjugated VLP used as a control immunogen. As shown in FIGS. 9 and 10, all peptides induced antibodies that could recognize intact full-length mouse PCSK9 in an ELISA assay.

Example 6

On the basis of our observation of cholesterol lowering being induced by immunization with peptide VR_9.5, representing the N-terminus of the mature processed form of human PCSK9 (SEQ ID No: 184), we hypothesize that, since the cleaved prodomain of immature PCSK9 is known to remain associated with the mature PCSK9 protein, regions of this prodomain (SEQ ID No. 329) are also candidate antibody targets for lowing cholesterol levels.

(SEQ ID No: 329)
MGTVSSRRSWWPLPLLLLLLLLLGPAGARAQEDEDGDYEELVLALRSEE

DGLAEAPEHGTTATFHRCAKDPWRLPGTYVVVLKEETHLSQSERTARRL

QAQAARRGYLTKILHVFHGLLPGFLVKMSGDLLELALKLPHVDYIEEDS

SVFAQ

Specific, non-restrictive, examples of peptides of interest are found within the C-terminal sequence of the prodomain region and surface exposed sequences and loops, including regions containing known loss-of-function or gain-of-function genetic mutations in humans:

| | |
|---|---|
| VDYIEEDSSVFAQ | (SEQ ID No: 308) |
| RCAKDPWRLPGT | (SEQ ID No: 309) |
| AQAARRGYLTKIL | (SEQ ID No: 310) |
| GDYEELVLALRSEEDG | (SEQ ID No: 311) |
| FLVKMSGDLLELALKLP | (SEQ ID No: 312) |

The above peptides and truncations thereof are synthesized with N- or C-terminally added linkers (e.g. CGG or GGC), or as cyclised or otherwise conformationally constrained molecules and coupled to Qβ VLPs as described in example 2 and used to immunize mice and assess antibody responses to PCSK9 as described in example 3.

Example 7

Peptides VR_9.5 and 9.10 were conjugated to Qβ VLP or to CRM197 as described in example 2 and used to immunize mice (BALB/c or C57BL/6) using TiterMax Gold, alum or alum-CpG as adjuvant. Hepatitis B virus derived peptide (amino acids 28-39 (IPQSLDSWWTSL)) was conjugated to Qβ VLP or to CRM197 and used as a control immunogen.

The ELISA method used was slightly different from the one disclosed in example 3: the ELISA method was performed as follows for Human and Mouse PCSK9 ELISA (Method 2): 384-well high bind assay plates (Greiner bio-one 781061) were coated with 25 μL/well of human or mouse PCSK9 protein stock diluted to 1 μg/mL with 1×PBS pH 7.4 and incubated at 4° C. over night. The following day, plates were blocked using 25 μL/well of 1×PBS/0.05% Tween-20/1% BSA, incubated on a shaker at RT for 1 hour. A 10 point ½ log serial dilution of each sample was prepared starting at 1:50 or 1:500 dilution (1×PBS/0.05% Tween-20 diluent), 25 μL/well of the serial dilution transferred in duplicate into the human or mouse PCSK9 coated plate then incubated shaking at RT for 1 hour. After washing ×3 with 1×PBS pH 7.4/0.05% Tween-20, 25 μL/well of Total IgG detection antibody (Goat Anti-Mouse IgG (γ), HRP, Invitrogen M30107) at a 1:3000 dilution with 1×PBS pH 7.4/0.05% Tween-20 was added then incubated shaking at RT for 1 hour. After washing ×5 with 1×PBS pH 7.4/0.05% Tween 20, 25 μL/well Bio-Rad TMB Peroxidase EIA Substrate Kit (Bio-Rad Cat #172-1067) were added and the plates incubated for 15 minutes. 12.5 μL/well of 1N sulfuric acid were added and the absorbance then read at Abs 450 nm.

Figure 11:
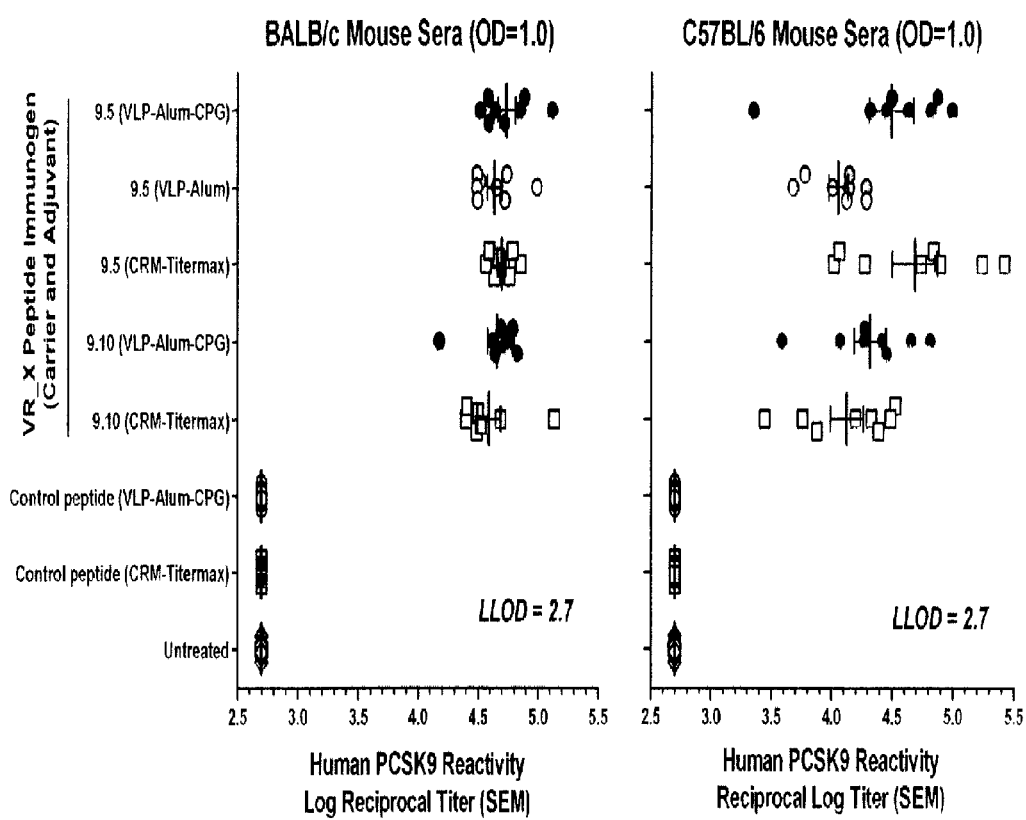
FIG. 11: Serum antibody responses to full-length human PCSK9 protein induced in BALB/c mice (left panel) and C57BL/6 mice (right panel) vaccinated with either peptide VR_9.5 or VR_9.10 conjugated to VLPs (using Alum+/−CpG as adjuvant) or CRM197 (using TiterMax as adjuvant). Antibodies to human PCSK9 were measured by titrating sera in an ELISA assay. Results are shown as log reciprocal titres determined at an optical density of 1.0 for each of 8 mice per group.
Figure 12:
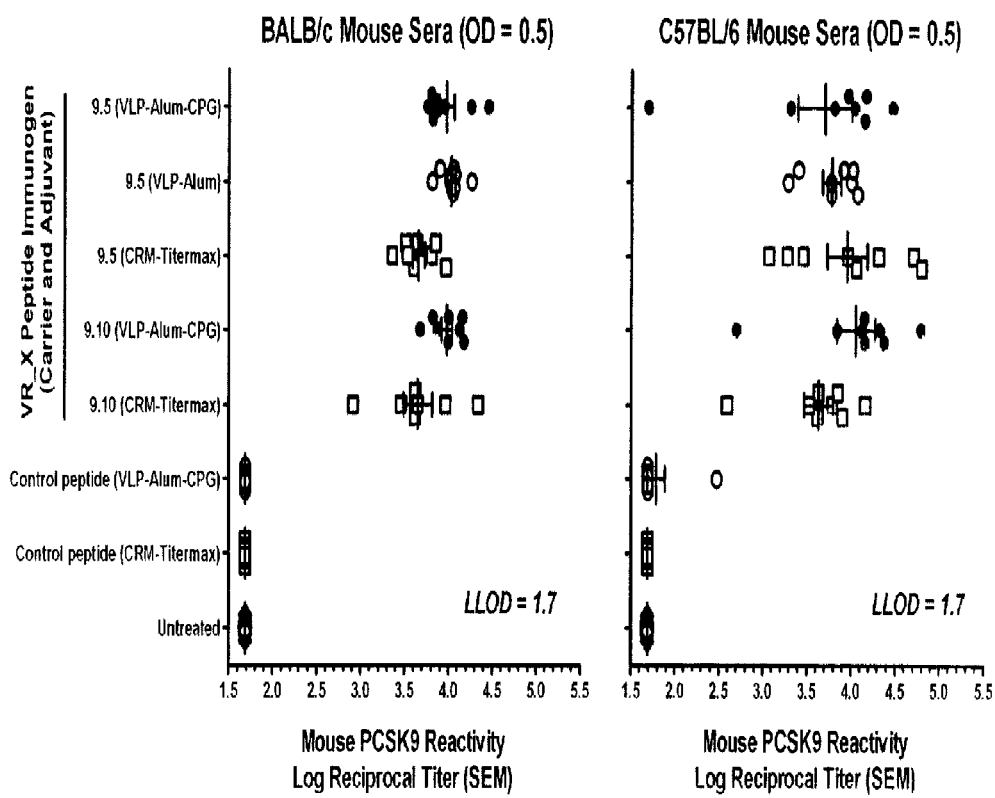
FIG. 12: Serum antibody responses to full-length mouse PCSK9 protein induced in BALB/c mice (left panel) and C57BL/6 mice (right panel) vaccinated as described for FIG. 11. Results are shown as log reciprocal titres determined at an optical density of 0.5 for each of 8 mice per group.
Figure 13:
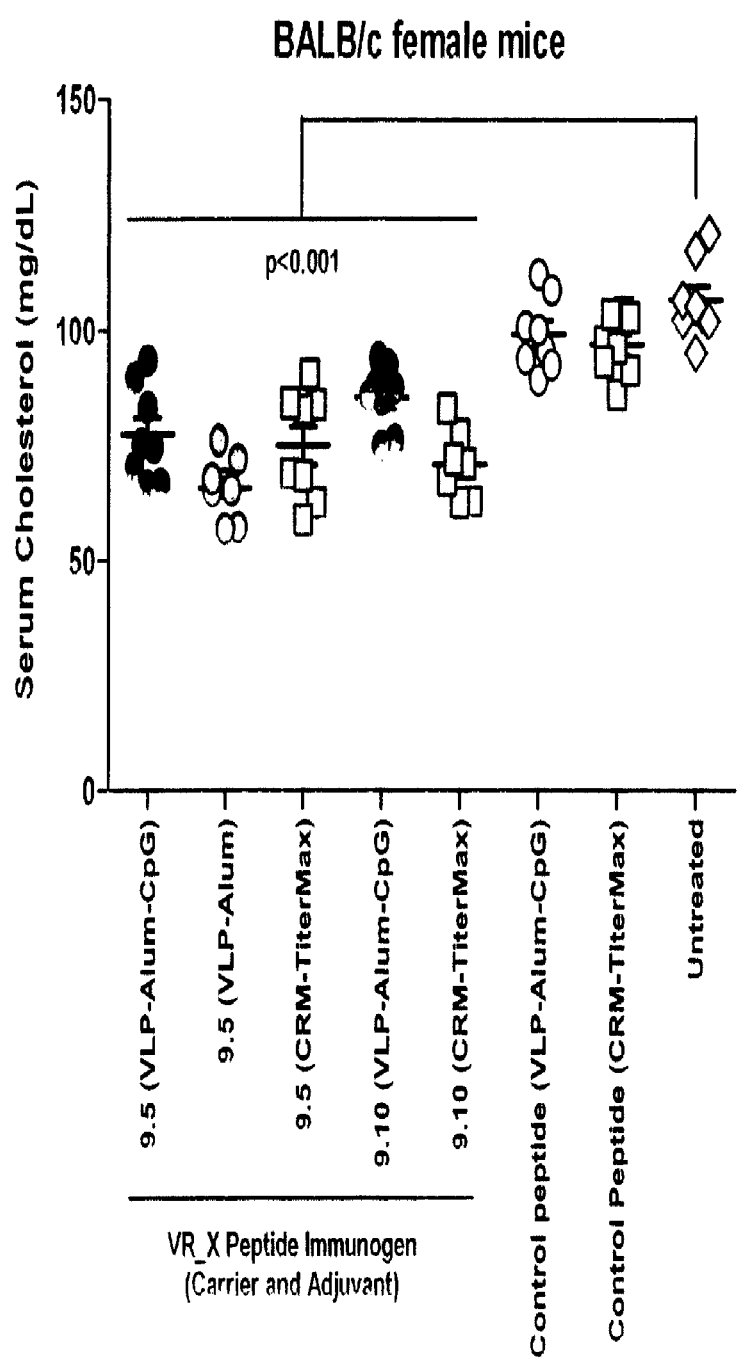
FIG. 13: Total cholesterol levels measured in the serum samples from BALB/c vaccinated mice (same samples used for antibody assays in FIGS. 11 and 12).
Figure 14:
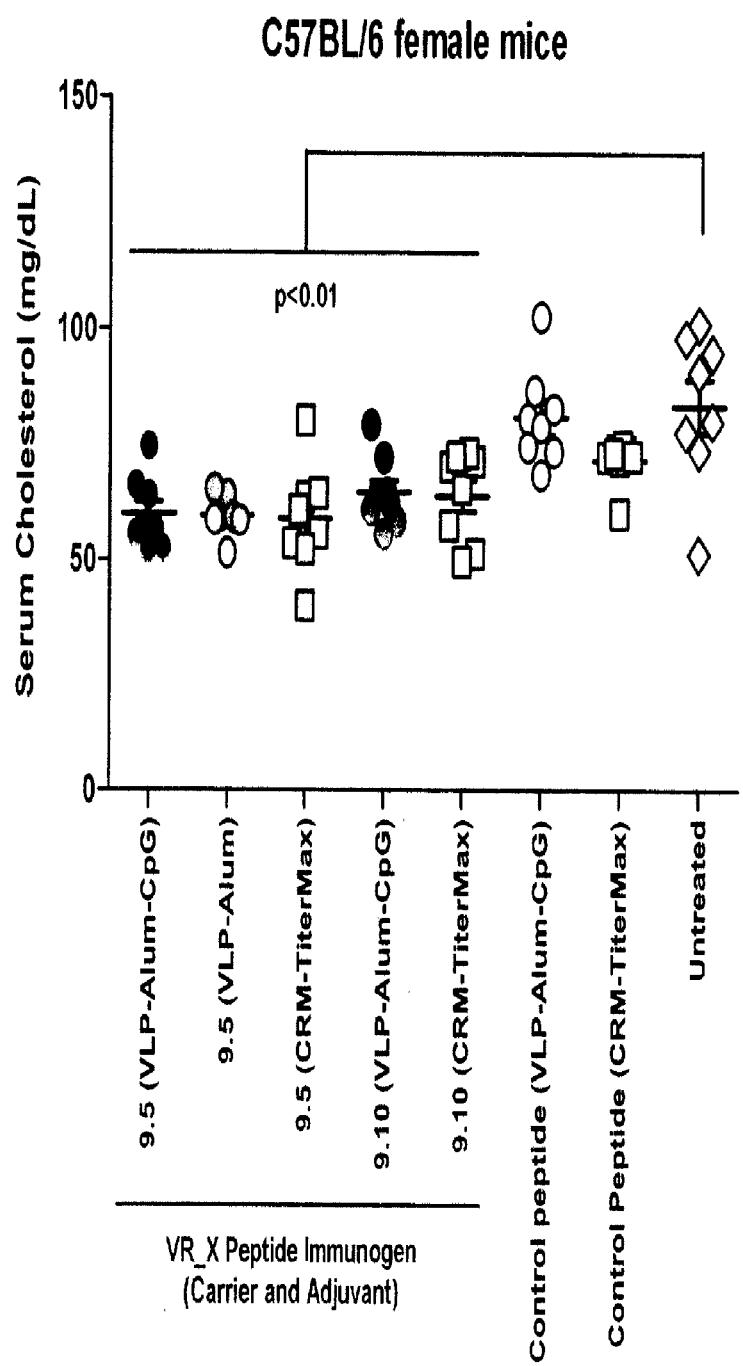
FIG. 14: Total cholesterol levels measured in the serum samples from C57BL/6 vaccinated mice (same samples used for antibody assays in FIGS. 11 and 12).

Results:

Peptides VR_9.5 and 9.10 conjugated to Qβ VLP or CRM197 were able to induce antibody responses to the intact full-length human and mouse PCSK9 protein (see FIGS. 11 and 12). FIGS. 13 and 14 and Table 4 also show that peptide VR_9.5 and 9.10 conjugated to different carriers and in the presence of different adjuvants led to a decrease in serum cholesterol levels.

TABLE 4

Total Cholesterol Levels in Immunized Mmice

| Mouse Strain | Immunogen | Carrier | Adjuvant(s) | N | Cholesterol (mg/dL) Mean | SEM | Stats[a] | Stats[b] |
|---|---|---|---|---|---|---|---|---|
| BALB/c | Untreated | — | — | 8 | 106.5 | 3.0 | — | — |
| | Control peptide | VLP | Alum + CpG | 8 | 99.0 | 2.8 | P > 0.05 | — |
| | VR_9.5 | VLP | Alum + CpG | 8 | 77.5 | 3.6 | P < 0.001 | P < 0.001 |

TABLE 4-continued

Total Cholesterol Levels in Immunized Mmice

| Mouse Strain | Immunogen | Carrier | Adjuvant(s) | N | Cholesterol (mg/dL) Mean | SEM | Stats[a] | Stats[b] |
|---|---|---|---|---|---|---|---|---|
| | VR_9.5 | VLP | Alum | 8 | 65.9 | 2.3 | P < 0.001 | P < 0.001 |
| | VR_9.10 | VLP | Alum + CpG | 8 | 85.3 | 2.4 | P < 0.001 | P < 0.05 |
| | Control peptide | CRM197 | TiterMax | 8 | 96.6 | 2.3 | P > 0.05 | — |
| | VR_9.5 | CRM197 | TiterMax | 8 | 75.0 | 4.1 | P < 0.001 | P < 0.001 |
| | VR_9.10 | CRM197 | TiterMax | 7 | 70.9 | 2.8 | P < 0.001 | P < 0.001 |
| C57BL/6 | Untreated | — | — | 8 | 83.4 | 5.8 | — | — |
| | Control peptide | VLP | Alum + CpG | 8 | 81.0 | 3.7 | P > 0.05 | — |
| | VR_9.5 | VLP | Alum + CpG | 8 | 59.7 | 2.8 | P < 0.001 | P < 0.01 |
| | VR_9.5 | VLP | Alum | 8 | 59.5 | 1.5 | P < 0.001 | P < 0.01 |
| | VR_9.10 | VLP | Alum + CpG | 8 | 64.5 | 2.7 | P < 0.01 | P < 0.05 |
| | Control peptide | CRM197 | TiterMax | 8 | 71.5 | 1.7 | P > 0.05 | — |
| | VR_9.5 | CRM197 | TiterMax | 8 | 58.7 | 4.1 | P < 0.001 | P > 0.05 |
| | VR_9.10 | CRM197 | TiterMax | 8 | 63.8 | 3.4 | P < 0.01 | P > 0.05 |

Stats[a]: 1-way ANOVA statistical comparison with Tukey post-hoc test displaying p values of test groups vs. untreated.
Stats[b]: 1-way ANOVA statistical comparison with Tukey post-hoc test displaying p values of test groups vs. matched control peptide-carrier.

Example 8

Additional peptides (SEQ ID No 312, 420, 421, 422, 423, 425, 426, 427, 428, 445, 482, 525 and 563) were chosen from both the prodomain and the C-terminal region of the catalytic domain of PCSK9 for surface exposure and association with gain of function or loss of function mutations identified in humans. The resultant series of peptide sequences from the approach described above were modified by the addition of amino acids to permit chemical conjugation and were evaluated as vaccine candidates (Table 5 peptides 9.23-9.35).

TABLE 5

Peptide sequences

| Peptide | Sequence | Species | SEQ ID No |
|---|---|---|---|
| VR_9.5 | SIPWNLERITPC | Human | 317 |
| VR_9.10 | SIPWNLERIIPC | Mouse | 322 |
| VR_9.17 | SIPWNLERIGGC | Human & Mouse | 401 |
| VR_9.18 | SIPWNLERGGC | Human & Mouse | 402 |
| VR_9.19 | SIPWNLEGGC | Human & Mouse | 403 |
| VR_9.20 | CGGSGRDAGVAKGA | Human | 404 |
| VR_9.21 | CGGSGRDAGVAKGT | Mouse | 405 |
| VR_9.22 | RDAGVAKGGC | Human | 406 |
| VR_9.23 | CSRHLAQASQELQ | Human | 407 |
| VR_9.24 | CRSRPSAKASWVQ | Mouse | 408 |
| VR_9.25 | CGGDYEELVLALR | Human | 409 |
| VR_9.26 | CGGDYEELMLALP | Mouse | 410 |
| VR_9.27 | LVLALRSEEDGGC | Human | 411 |
| VR_9.28 | LMLALPSQEDGGC | Mouse | 412 |
| VR_9.29 | AKDPWRLPGGC | Human | 413 |
| VR_9.30 | SKEAWRLPGGC | Mouse | 414 |
| VR_9.31 | CGGAARRGYLTK | Human | 415 |
| VR_9.32 | CGGAARRGYVIK | Mouse | 416 |
| VR_9.33 | FLVKMSGDLLELALKLPGGC | Human | 417 |
| VR_9.34 | FLVKMSSDLLGLALKLPGGC | Mouse | 418 |
| VR_9.35 | CGGEEDSSVFAQ | Human | 419 |

Residues underlined indicate amino acids added for conjugation purposes.

Example 9

Peptides VR_9.17 to VR_9.35 (as well as VR_9.5) were conjugated to Qβ VLP as described in example 2 and used to immunize mice to assess antibody responses to PCSK9 as described in example 3. Hepatitis B virus derived peptide (amino acids 28-39 (IPQSLDSWWTSL (SEQ ID NO:623)) was conjugated to Qβ VLP and used as a control immunogen. Method No 2 was used for the ELISA.

Figure 15:
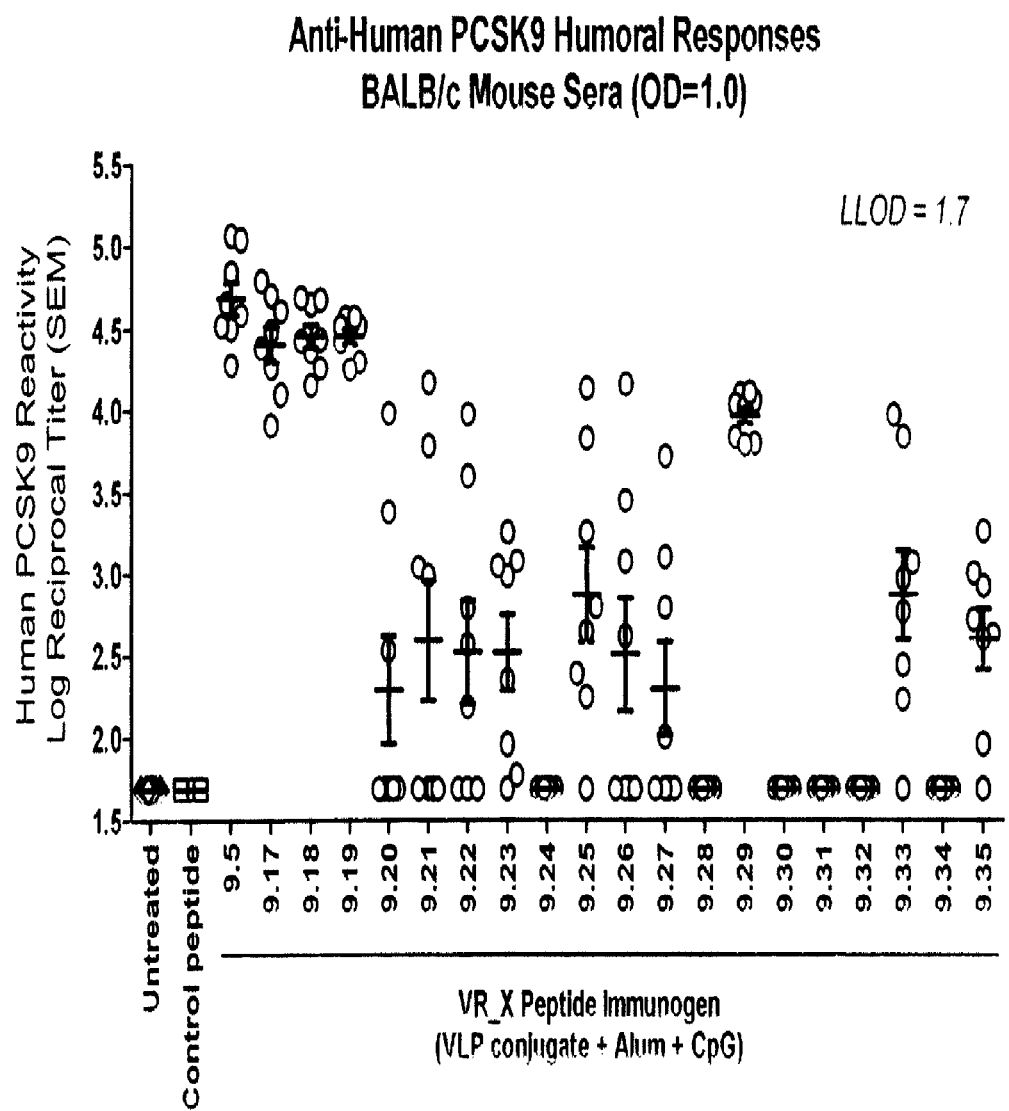
FIG. 15: Antibody responses to full-length human PCSK9 induced in BALB/c mice immunized with peptides VR_9.5 or VR_9.17 to VR_9.35 conjugated to VLPs using Alum plus CpG as adjuvant. Antibodies to human PCSK9 were measured by titrating sera in an ELISA assay. Results are shown as log reciprocal titres determined at an optical density of 1.0 for each of 8 mice per group.
Figure 16:
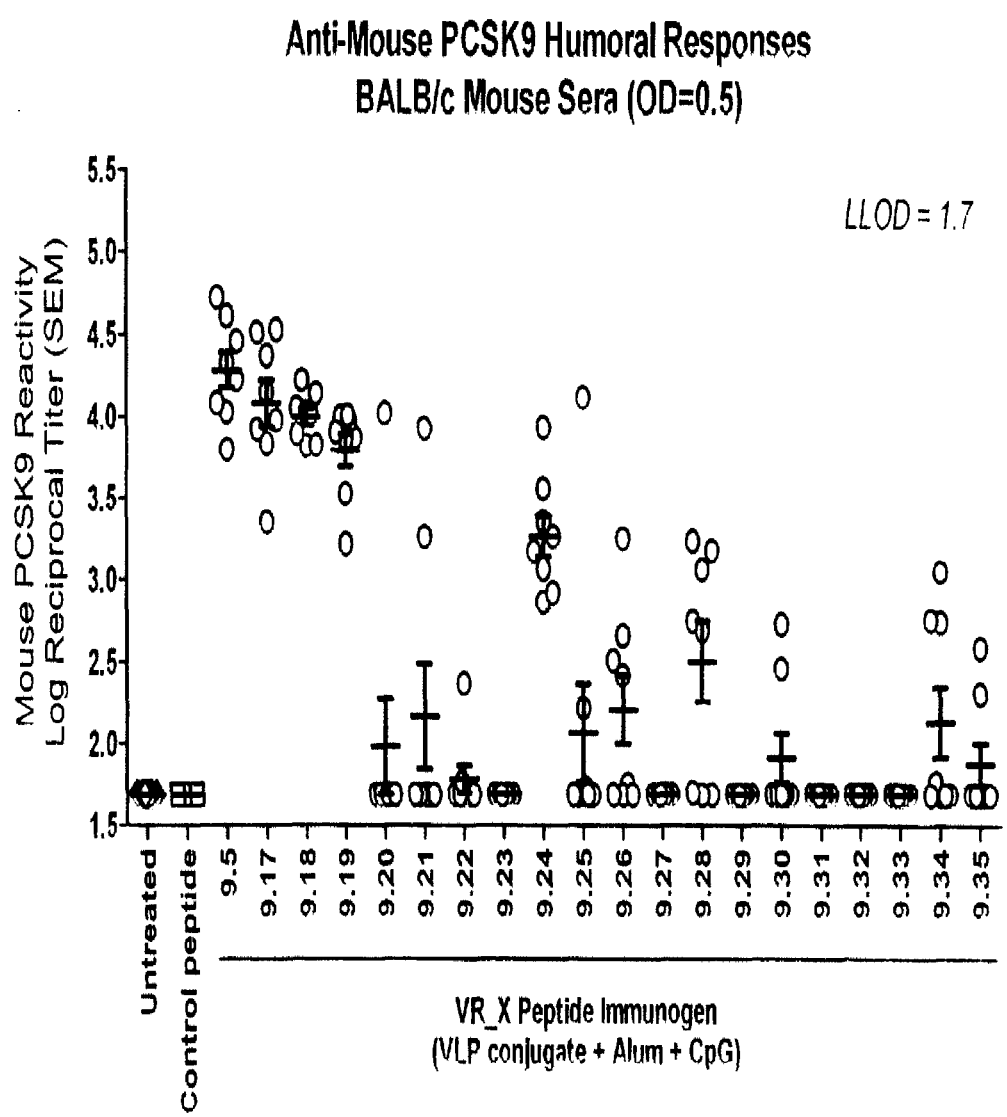
FIG. 16: Antibody responses to full-length mouse PCSK9 induced in BALB/c mice immunized as described for FIG. 15. Antibodies to mouse PCSK9 were measured by titrating sera in an ELISA assay. Results are shown as log reciprocal titres determined at an optical density of 0.5 for each of 8 mice per group.
Figure 17:
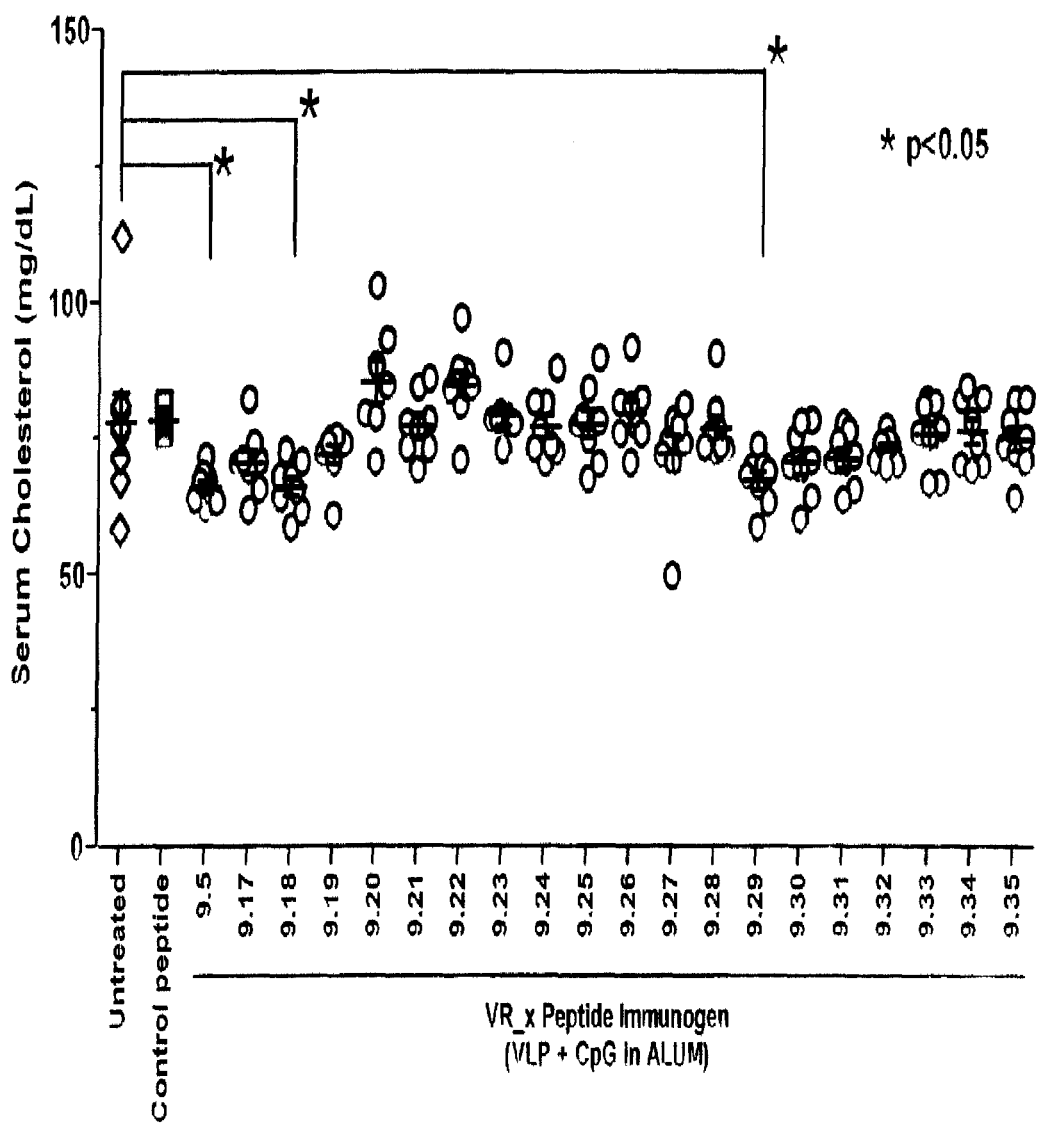
FIG. 17: Total cholesterol levels measured in the serum samples from BALB/c vaccinated mice (same samples used for antibody assays in FIGS. 15 and 16).
Figure 18:
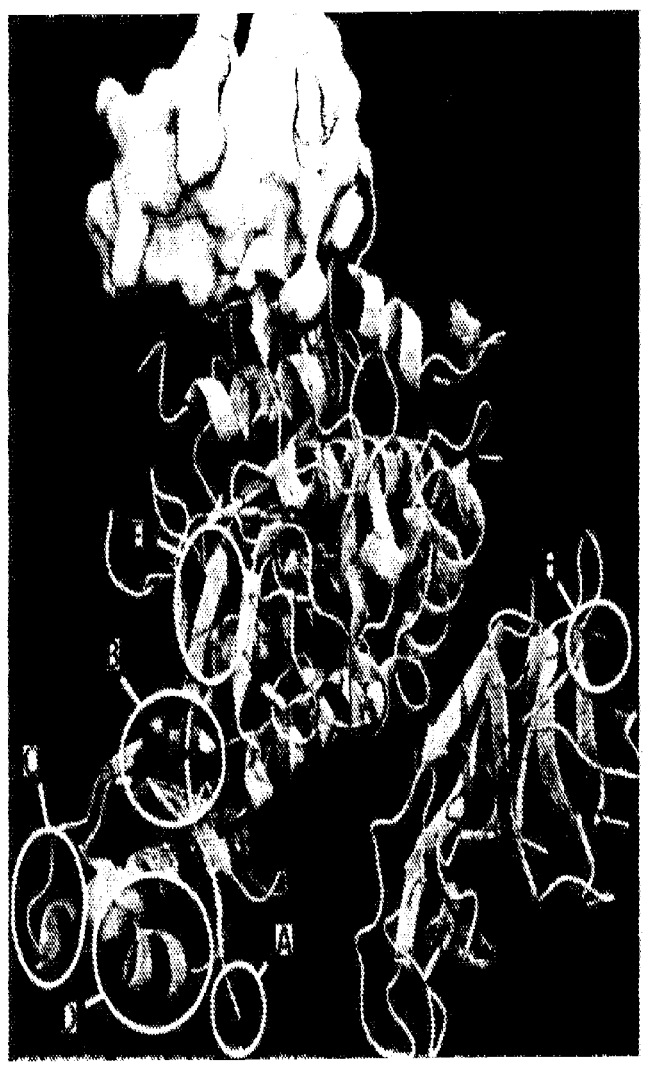
FIG. 18: Complex of PCSK9 (ribbons) and EGF-A (space fill) with regions of PCSK9 containing amino acids sequences linked to gain- or loss-of-function mutations and/or protein surface exposed epitopes indicated by ellipses.

Result:

As shown in FIGS. 15 and 16, most of the peptides conjugated to Qβ VLP were able to induce antibody responses to intact full length PCSK9. No antibody response was detected for peptides 9.31 and 9.32. In certain cases (peptides 9.23, 9.24, 9.27, 9.28, 9.29, 9.30, 9.33, and 9.34) the antibody responses were species specific. Immunization with peptides 9.5, 9.18, and 9.29 also resulted in decreased serum cholesterol, while immunization with peptides 9.17, 9.19, 9.30, 9.31, and 9.32 resulted in a trend to reduced cholesterol (Table 6, FIG. 17).

TABLE 6

Total Cholesterol Levels in Immunized Mice

| Mouse Strain | Immunogen | Carrier | Adjuvants | N | Cholesterol (mg/dL) Mean | SEM | Stats[a] | Stats[b] |
|---|---|---|---|---|---|---|---|---|
| BALB/c | Untreated | — | — | 8 | 77.7 | 5.5 | — | — |
| | Control peptide | VLP | Alum + CpG | 4 | 78.1 | 1.2 | P > 0.05 | — |
| | VR_9.5 | VLP | Alum + CpG | 8 | 65.8 | 1.1 | P < 0.05 | P > 0.05 |
| | VR_9.17 | VLP | Alum + CpG | 8 | 70.4 | 2.1 | P > 0.05 | P > 0.05 |
| | VR_9.18 | VLP | Alum + CpG | 8 | 65.9 | 1.6 | P < 0.05 | P > 0.05 |
| | VR_9.19 | VLP | Alum + CpG | 8 | 71.7 | 1.7 | P > 0.05 | P > 0.05 |
| | VR_9.20 | VLP | Alum + CpG | 7 | 85.2 | 4.0 | P > 0.05 | P > 0.05 |
| | VR_9.21 | VLP | Alum + CpG | 8 | 77.1 | 2.0 | P > 0.05 | P > 0.05 |
| | VR_9.22 | VLP | Alum + CpG | 8 | 84.5 | 2.6 | P > 0.05 | P > 0.05 |
| | VR_9.23 | VLP | Alum + CpG | 8 | 79.0 | 1.8 | P > 0.05 | P > 0.05 |
| | VR_9.24 | VLP | Alum + CpG | 8 | 76.9 | 2.1 | P > 0.05 | P > 0.05 |
| | VR_9.25 | VLP | Alum + CpG | 8 | 77.3 | 2.5 | P > 0.05 | P > 0.05 |
| | VR_9.26 | VLP | Alum + CpG | 8 | 79.2 | 2.2 | P > 0.05 | P > 0.05 |
| | VR_9.27 | VLP | Alum + CpG | 8 | 71.8 | 3.4 | P > 0.05 | P > 0.05 |
| | VR_9.28 | VLP | Alum + CpG | 8 | 76.6 | 2.2 | P > 0.05 | P > 0.05 |
| | VR_9.29 | VLP | Alum + CpG | 8 | 67.0 | 1.6 | P < 0.05 | P > 0.05 |
| | VR_9.30 | VLP | Alum + CpG | 8 | 70.4 | 2.3 | P > 0.05 | P > 0.05 |
| | VR_9.31 | VLP | Alum + CpG | 8 | 71.0 | 1.7 | P > 0.05 | P > 0.05 |
| | VR_9.32 | VLP | Alum + CpG | 8 | 72.8 | 1.0 | P > 0.05 | P > 0.05 |
| | VR_9.33 | VLP | Alum + CpG | 8 | 75.5 | 2.2 | P > 0.05 | P > 0.05 |
| | VR_9.34 | VLP | Alum + CpG | 8 | 76.0 | 2.3 | P > 0.05 | P > 0.05 |
| | VR_9.35 | VLP | Alum + CpG | 8 | 74.5 | 2.2 | P > 0.05 | P > 0.05 |

Stats[a]: 1-way ANOVA statistical comparison with Bonferroni post-hoc test displaying p values of test groups vs. untreated group.
Stats[b]: 1-way ANOVA statistical comparison with Bonferroni post-hoc test displaying p values of test groups vs. control peptide group.

Sequence listing:

| | |
|---|---|
| SEQ ID No 1 | IGASSDCSTCFVS |
| SEQ ID No 2 | IGASSDCSTCFV |
| SEQ ID No 3 | IGASSDCSTCF |
| SEQ ID No 4 | IGASSDCSTC |
| SEQ ID No 5 | IGASSDCST |
| SEQ ID No 6 | IGASSDCS |
| SEQ ID No 7 | IGASSDC |
| SEQ ID No 8 | IGASSD |
| SEQ ID No 9 | IGASS |
| SEQ ID No 10 | GASSDCSTCFVS |
| SEQ ID No 11 | GASSDCSTCFV |
| SEQ ID No 12 | GASSDCSTCF |
| SEQ ID No 13 | GASSDCSTC |
| SEQ ID No 14 | GASSDCST |
| SEQ ID No 15 | GASSDCS |
| SEQ ID No 16 | GASSDC |
| SEQ ID No 17 | GASSD |
| SEQ ID No 18 | ASSDCSTCFVS |
| SEQ ID No 19 | ASSDCSTCFV |
| SEQ ID No 20 | ASSDCSTCF |
| SEQ ID No 21 | ASSDCSTC |
| SEQ ID No 22 | ASSDCST |
| SEQ ID No 23 | ASSDCS |
| SEQ ID No 24 | ASSDC |
| SEQ ID No 25 | SSDCSTCFVS |
| SEQ ID No 26 | SSDCSTCFV |
| SEQ ID No 27 | SSDCSTCF |
| SEQ ID No 28 | SSDCSTC |
| SEQ ID No 29 | SSDCST |
| SEQ ID No 30 | SSDCS |
| SEQ ID No 31 | SDCSTCFVS |
| SEQ ID No 32 | SDCSTCFV |
| SEQ ID No 33 | SDCSTCF |
| SEQ ID No 34 | SDCSTC |
| SEQ ID No 35 | SDCST |
| SEQ ID No 36 | DCSTCFVS |
| SEQ ID No 37 | DCSTCFV |
| SEQ ID No 38 | DCSTCF |
| SEQ ID No 39 | DCSTC |
| SEQ ID No 40 | CSTCFVS |
| SEQ ID No 41 | CSTCFV |

| Sequence listing: | |
|---|---|
| SEQ ID No 42 | CSTCF |
| SEQ ID No 43 | STCFVS |
| SEQ ID No 44 | STCFV |
| SEQ ID No 45 | TCFVS |
| SEQ ID No 46 | EDGTRFHRQASKCDS |
| SEQ ID No 47 | EDGTRFHRQASKCD |
| SEQ ID No 48 | EDGTRFHRQASKC |
| SEQ ID No 49 | EDGTRFHRQASK |
| SEQ ID No 50 | EDGTRFHRQAS |
| SEQ ID No 51 | EDGTRFHRQA |
| SEQ ID No 52 | EDGTRFHRQ |
| SEQ ID No 53 | DGTRFHRQASKCDS |
| SEQ ID No 54 | DGTRFHRQASKCD |
| SEQ ID No 55 | DGTRFHRQASKC |
| SEQ ID No 56 | DGTRFHRQASK |
| SEQ ID No 57 | DGTRFHRQAS |
| SEQ ID No 58 | DGTRFHRQA |
| SEQ ID No 59 | DGTRFHRQ |
| SEQ ID No 60 | GTRFHRQASKCDS |
| SEQ ID No 61 | GTRFHRQASKCD |
| SEQ ID No 62 | GTRFHRQASKC |
| SEQ ID No 63 | GTRFHRQASK |
| SEQ ID No 64 | GTRFHRQAS |
| SEQ ID No 65 | GTRFHRQA |
| SEQ ID No 66 | GTRFHRQ |
| SEQ ID No 67 | TRFHRQASKCDS |
| SEQ ID No 68 | TRFHRQASKCD |
| SEQ ID No 69 | TRFHRQASKC |
| SEQ ID No 70 | TRFHRQASK |
| SEQ ID No 71 | TRFHRQAS |
| SEQ ID No 72 | TRFHRQA |
| SEQ ID No 73 | TRFHRQ |
| SEQ ID No 74 | RFHRQASKCDS |
| SEQ ID No 75 | RFHRQASKCD |
| SEQ ID No 76 | RFHRQASKC |
| SEQ ID No 77 | RFHRQASK |
| SEQ ID No 78 | RFHRQAS |
| SEQ ID No 79 | RFHRQA |
| SEQ ID No 80 | RFHRQ |
| SEQ ID No 81 | FHRQASKCDS |
| SEQ ID No 82 | FHRQASKCD |
| SEQ ID No 83 | FHRQASKC |
| SEQ ID No 84 | FHRQASK |
| SEQ ID No 85 | FHRQAS |
| SEQ ID No 86 | FHRQA |
| SEQ ID No 87 | HRQASKCDS |
| SEQ ID No 88 | HRQASKCD |
| SEQ ID No 89 | HRQASKC |
| SEQ ID No 90 | HRQASK |
| SEQ ID No 91 | HRQAS |
| SEQ ID No 92 | RQASKCDS |
| SEQ ID No 93 | RQASKCD |
| SEQ ID No 94 | RQASKC |
| SEQ ID No 95 | RQASK |
| SEQ ID No 96 | QASKCDS |
| SEQ ID No 97 | QASKCD |
| SEQ ID No 98 | QASKC |
| SEQ ID No 99 | ASKCDS |
| SEQ ID No 100 | ASKCD |
| SEQ ID No 101 | SKCDS |
| SEQ ID No 102 | SIQSDHREIEGRVM |
| SEQ ID No 103 | SIQSDHREIEGRV |
| SEQ ID No 104 | SIQSDHREIEGR |
| SEQ ID No 105 | SIQSDHREIEG |
| SEQ ID No 106 | SIQSDHREIE |
| SEQ ID No 107 | SIQSDHREI |
| SEQ ID No 108 | IQSDHREIEGRVM |
| SEQ ID No 109 | IQSDHREIEGRV |
| SEQ ID No 110 | IQSDHREIEGR |
| SEQ ID No 111 | IQSDHREIEG |
| SEQ ID No 112 | IQSDHREIE |
| SEQ ID No 113 | IQSDHREI |
| SEQ ID No 114 | QSDHREIEGRVM |
| SEQ ID No 115 | QSDHREIEGRV |
| SEQ ID No 116 | QSDHREIEGR |
| SEQ ID No 117 | QSDHREIEG |
| SEQ ID No 118 | QSDHREIE |

Sequence listing:

| SEQ ID No 119 | QSDHREI |
| SEQ ID No 120 | SDHREIEGRVM |
| SEQ ID No 121 | SDHREIEGRV |
| SEQ ID No 122 | SDHREIEGR |
| SEQ ID No 123 | SDHREIEG |
| SEQ ID No 124 | SDHREIE |
| SEQ ID No 125 | SDHREI |
| SEQ ID No 126 | DHREIEGRVM |
| SEQ ID No 127 | DHREIEGRV |
| SEQ ID No 128 | DHREIEGR |
| SEQ ID No 129 | DHREIEG |
| SEQ ID No 130 | DHREIE |
| SEQ ID No 131 | DHREI |
| SEQ ID No 132 | HREIEGRVM |
| SEQ ID No 133 | HREIEGRV |
| SEQ ID No 134 | HREIEGR |
| SEQ ID No 135 | HREIEG |
| SEQ ID No 136 | HREIE |
| SEQ ID No 137 | REIEGRVM |
| SEQ ID No 138 | REIEGRV |
| SEQ ID No 139 | REIEGR |
| SEQ ID No 140 | REIEG |
| SEQ ID No 141 | EIEGRVM |
| SEQ ID No 142 | EIEGRV |
| SEQ ID No 143 | EIEGR |
| SEQ ID No 144 | IEGRVM |
| SEQ ID No 145 | IEGRV |
| SEQ ID No 146 | EGRVM |
| SEQ ID No 147 | VSGRDAGVAKGAS |
| SEQ ID No 148 | VSGRDAGVAKGA |
| SEQ ID No 149 | VSGRDAGVAKG |
| SEQ ID No 150 | VSGRDAGVAK |
| SEQ ID No 151 | VSGRDAGVA |
| SEQ ID No 152 | SGRDAGVAKGAS |
| SEQ ID No 153 | SGRDAGVAKGA |
| SEQ ID No 154 | SGRDAGVAKG |
| SEQ ID No 155 | SGRDAGVAK |
| SEQ ID No 156 | SGRDAGVA |
| SEQ ID No 157 | GRDAGVAKGAS |
| SEQ ID No 158 | GRDAGVAKGA |
| SEQ ID No 159 | GRDAGVAKG |
| SEQ ID No 160 | GRDAGVAK |
| SEQ ID No 161 | GRDAGVA |
| SEQ ID No 162 | RDAGVAKGAS |
| SEQ ID No 163 | RDAGVAKGA |
| SEQ ID No 164 | RDAGVAKG |
| SEQ ID No 165 | RDAGVAK |
| SEQ ID No 166 | RDAGVA |
| SEQ ID No 167 | DAGVAKGAS |
| SEQ ID No 168 | DAGVAKGA |
| SEQ ID No 169 | DAGVAKG |
| SEQ ID No 170 | DAGVAK |
| SEQ ID No 171 | DAGVA |
| SEQ ID No 172 | AGVAKGAS |
| SEQ ID No 173 | AGVAKGA |
| SEQ ID No 174 | AGVAKG |
| SEQ ID No 175 | AGVAK |
| SEQ ID No 176 | GVAKGAS |
| SEQ ID No 177 | GVAKGA |
| SEQ ID No 178 | GVAKG |
| SEQ ID No 179 | VAKGAS |
| SEQ ID No 180 | VAKGA |
| SEQ ID No 181 | AKGAS |
| SEQ ID No 182 | SIPWNLERITPPR |
| SEQ ID No 183 | SIPWNLERITPP |
| SEQ ID No 184 | SIPWNLERITP |
| SEQ ID No 185 | SIPWNLERIT |
| SEQ ID No 186 | SIPWNLERI |
| SEQ ID No 187 | SIPWNLER |
| SEQ ID No 188 | SIPWNLE |
| SEQ ID No 189 | SIPWNL |
| SEQ ID No 190 | SIPWN |
| SEQ ID No 191 | IPWNLERITPPR |
| SEQ ID No 192 | IPWNLERITPP |
| SEQ ID No 193 | IPWNLERITP |
| SEQ ID No 194 | IPWNLERIT |
| SEQ ID No 195 | IPWNLERI |

-continued

| Sequence listing: | |
|---|---|
| SEQ ID No 196 | IPWNLER |
| SEQ ID No 197 | IPWNLE |
| SEQ ID No 198 | IPWNL |
| SEQ ID No 199 | PWNLERITPPR |
| SEQ ID No 200 | PWNLERITPP |
| SEQ ID No 201 | PWNLERITP |
| SEQ ID No 202 | PWNLERIT |
| SEQ ID No 203 | PWNLERI |
| SEQ ID No 204 | PWNLER |
| SEQ ID No 205 | PWNLE |
| SEQ ID No 206 | WNLERITPPR |
| SEQ ID No 207 | WNLERITPP |
| SEQ ID No 208 | WNLERITP |
| SEQ ID No 209 | WNLERIT |
| SEQ ID No 210 | WNLERI |
| SEQ ID No 211 | WNLER |
| SEQ ID No 212 | NLERITPPR |
| SEQ ID No 213 | NLERITPP |
| SEQ ID No 214 | NLERITP |
| SEQ ID No 215 | NLERIT |
| SEQ ID No 216 | NLERI |
| SEQ ID No 217 | LERITPPR |
| SEQ ID No 218 | LERITPP |
| SEQ ID No 219 | LERITP |
| SEQ ID No 220 | LERIT |
| SEQ ID No 221 | ERITPPR |
| SEQ ID No 222 | ERITPP |
| SEQ ID No 223 | ERITP |
| SEQ ID No 224 | RITPPR |
| SEQ ID No 225 | RITPP |
| SEQ ID No 226 | ITPPR |
| SEQ ID No 227 | NAQDQPVTLGTL |
| SEQ ID No 228 | NAQDQPVTLGT |
| SEQ ID No 229 | NAQDQPVTLG |
| SEQ ID No 230 | NAQDQPVTL |
| SEQ ID No 231 | NAQDQPVT |
| SEQ ID No 232 | NAQDQPV |
| SEQ ID No 233 | NAQDQP |

-continued

| Sequence listing: | |
|---|---|
| SEQ ID No 234 | NAQDQ |
| SEQ ID No 235 | AQDQPVTLGTL |
| SEQ ID No 236 | AQDQPVTLGT |
| SEQ ID No 237 | AQDQPVTLG |
| SEQ ID No 238 | AQDQPVTL |
| SEQ ID No 239 | AQDQPVT |
| SEQ ID No 240 | AQDQPV |
| SEQ ID No 241 | AQDQP |
| SEQ ID No 242 | QDQPVTLGTL |
| SEQ ID No 243 | QDQPVTLGT |
| SEQ ID No 244 | QDQPVTLG |
| SEQ ID No 245 | QDQPVTL |
| SEQ ID No 246 | QDQPVT |
| SEQ ID No 247 | QDQPV |
| SEQ ID No 248 | DQPVTLGTL |
| SEQ ID No 249 | DQPVTLGT |
| SEQ ID No 250 | DQPVTLG |
| SEQ ID No 251 | DQPVTL |
| SEQ ID No 252 | DQPVT |
| SEQ ID No 253 | QPVTLGTL |
| SEQ ID No 254 | QPVTLGT |
| SEQ ID No 255 | QPVTLG |
| SEQ ID No 256 | QPVTL |
| SEQ ID No 257 | PVTLGTL |
| SEQ ID No 258 | PVTLGT |
| SEQ ID No 259 | PVTLG |
| SEQ ID No 260 | VTLGTL |
| SEQ ID No 261 | VTLGT |
| SEQ ID No 262 | TLGTL |
| SEQ ID No 263 | INEAWFPEDQRVL |
| SEQ ID No 264 | INEAWFPEDQRV |
| SEQ ID No 265 | INEAWFPEDQR |
| SEQ ID No 266 | INEAWFPEDQ |
| SEQ ID No 267 | INEAWFPED |
| SEQ ID No 268 | INEAWFPE |
| SEQ ID No 269 | INEAWFP |
| SEQ ID No 270 | INEAWF |
| SEQ ID No 271 | INEAW |
| SEQ ID No 272 | NEAWFPEDQRVL |

| Sequence listing: | |
|---|---|
| SEQ ID No 273 | NEAWFPEDQRV |
| SEQ ID No 274 | NEAWFPEDQR |
| SEQ ID No 275 | NEAWFPEDQ |
| SEQ ID No 276 | NEAWFPED |
| SEQ ID No 277 | NEAWFPE |
| SEQ ID No 278 | NEAWFP |
| SEQ ID No 279 | NEAWF |
| SEQ ID No 280 | EAWFPEDQRVL |
| SEQ ID No 281 | EAWFPEDQRV |
| SEQ ID No 282 | EAWFPEDQR |
| SEQ ID No 283 | EAWFPEDQ |
| SEQ ID No 284 | EAWFPED |
| SEQ ID No 285 | EAWFPE |
| SEQ ID No 286 | EAWFP |
| SEQ ID No 287 | AWFPEDQRVL |
| SEQ ID No 288 | AWFPEDQRV |
| SEQ ID No 289 | AWFPEDQR |
| SEQ ID No 290 | AWFPEDQ |
| SEQ ID No 291 | AWFPED |
| SEQ ID No 292 | AWFPE |
| SEQ ID No 293 | WFPEDQRVL |
| SEQ ID No 294 | WFPEDQRV |
| SEQ ID No 295 | WFPEDQR |
| SEQ ID No 296 | WFPEDQ |
| SEQ ID No 297 | WFPED |
| SEQ ID No 298 | FPEDQRVL |
| SEQ ID No 299 | FPEDQRV |
| SEQ ID No 300 | FPEDQR |
| SEQ ID No 301 | FPEDQ |
| SEQ ID No 302 | PEDQRVL |
| SEQ ID No 303 | PEDQRV |
| SEQ ID No 304 | PEDQR |
| SEQ ID No 305 | EDQRVL |
| SEQ ID No 306 | EDQRV |
| SEQ ID No 307 | DQRVL |
| SEQ ID No 308 | VDYIEEDSSVFAQ |
| SEQ ID No 309 | RCAKDPWRLPGT |
| SEQ ID No 310 | AQAARRGYLTKIL |
| SEQ ID No 311 | GDYEELVLALRSEEDG |
| SEQ ID No 312 | FLVKMSGDLLELALKLP |
| SEQ ID No 313 | KGGASSDCSTCFV |
| SEQ ID No 314 | CGGTRFHRQASKC |
| SEQ ID No 315 | CGIQSDHREIEGRVC |
| SEQ ID No 316 | CSGRDAGVAKGAC |
| SEQ ID No 317 | SIPWNLERITPC |
| SEQ ID No 318 | ASKCGDGTRFHRQ |
| SEQ ID No 319 | AGCGTRFHRQ |
| SEQ ID No 320 | GRVCIQSDHREIE |
| SEQ ID No 321 | AGVAKGAGCSGRD |
| SEQ ID No 322 | SIPWNLERIIPC |
| SEQ ID No 323 | CGGSIPWNLERIIP |
| SEQ ID No 324 | SIPWNLERIIPGGC |
| SEQ ID No 325 | CGGNAQDQPVTLGTL |
| SEQ ID No 326 | NAQDQPVTLGTLGGC |
| SEQ ID No 327 | CGGINMAWFPEDQQVL |
| SEQ ID No 328 | NMAWFPEDQQVLGGC |
| SEQ ID No 329 | MGTVSSRRSWWPLPLLLLLLLLLGPAGARAQEDEDGDYEELVLALRSEEDGLAEAPEHGTTATFHRCAKDPWRLPGTYVVVLKEETHLSQSERTARRLQAQAARRGYLTKILHVFHGLLPGFLVKMSGDLLELALKLPHVDYIEEDSSVFAQ |
| SEQ ID No 330 | SIPWNLERIIPAW |
| SEQ ID No 331 | SIPWNLERIIPA |
| SEQ ID No 332 | SIPWNLERIIP |
| SEQ ID No 333 | SIPWNLERII |
| SEQ ID No 334 | IPWNLERIIPAW |
| SEQ ID No 335 | IPWNLERIIPAW |
| SEQ ID No 336 | IPWNLERIIP |
| SEQ ID No 337 | IPWNLERII |
| SEQ ID No 338 | PWNLERIIPAW |
| SEQ ID No 339 | PWNLERIIPA |
| SEQ ID No 340 | PWNLERIIP |
| SEQ ID No 341 | PWNLERII |
| SEQ ID No 342 | WNLERIIPAW |
| SEQ ID No 343 | WNLERIIPA |
| SEQ ID No 344 | WNLERIIP |
| SEQ ID No 345 | WNLERII |
| SEQ ID No 346 | NLERIIPAW |
| SEQ ID No 347 | NLERIIPA |

Sequence listing:

| | | |
|---|---|---|
| SEQ ID No 348 | NLERIIP | |
| SEQ ID No 349 | NLERII | |
| SEQ ID No 350 | LERIIPAW | |
| SEQ ID No 351 | LERIIPA | |
| SEQ ID No 352 | LERIIP | |
| SEQ ID No 353 | LERII | |
| SEQ ID No 354 | ERIIPAW | |
| SEQ ID No 355 | ERIIPA | |
| SEQ ID No 356 | ERIIP | |
| SEQ ID No 357 | RIIPAW | |
| SEQ ID No 358 | RIIPA | |
| SEQ ID No 359 | IIPAW | |
| SEQ ID No 360 | INMAWFPEDQQVL | |
| SEQ ID No 361 | INMAWFPEDQQV | |
| SEQ ID No 362 | INMAWFPEDQQ | |
| SEQ ID No 363 | INMAWFPEDQ | |
| SEQ ID No 364 | INMAWFPED | |
| SEQ ID No 365 | INMAWFPE | |
| SEQ ID No 366 | INMAWFP | |
| SEQ ID No 367 | INMAWF | |
| SEQ ID No 368 | INMAW | |
| SEQ ID No 369 | NMAWFPEDQQVL | |
| SEQ ID No 370 | NMAWFPEDQQV | |
| SEQ ID No 371 | NMAWFPEDQQ | |
| SEQ ID No 372 | NMAWFPEDQ | |
| SEQ ID No 373 | NMAWFPED | |
| SEQ ID No 374 | NMAWFPE | |
| SEQ ID No 375 | NMAWFP | |
| SEQ ID No 376 | NMAWF | |
| SEQ ID No 377 | MAWFPEDQQVL | |
| SEQ ID No 378 | MAWFPEDQQV | |
| SEQ ID No 379 | MAWFPEDQQ | |
| SEQ ID No 380 | MAWFPEDQ | |
| SEQ ID No 381 | MAWFPED | |
| SEQ ID No 382 | MAWFPE | |
| SEQ ID No 383 | MAWFP | |
| SEQ ID No 384 | AWFPEDQQVL | |
| SEQ ID No 385 | AWFPEDQQV | |
| SEQ ID No 386 | AWFPEDQQ | |
| SEQ ID No 387 | WFPEDQQVL | |
| SEQ ID No 388 | WFPEDQQV | |
| SEQ ID No 389 | WFPEDQQ | |
| SEQ ID No 390 | FPEDQQVL | |
| SEQ ID No 391 | FPEDQQV | |
| SEQ ID No 392 | FPEDQQ | |
| SEQ ID No 393 | PEDQQVL | |
| SEQ ID No 394 | PEDQQV | |
| SEQ ID No 395 | PEDQQ | |
| SEQ ID No 396 | EDQQVL | |
| SEQ ID No 397 | EDQQV | |
| SEQ ID No 398 | DQQVL | |
| SEQ ID No 399 | MGTVSSRRSWWPLPLLLLLLLLLGPAGARAQEDEDG DYEELVLALRSEEDGLAEAPEHGTTATFHRCAKDPW RLPGTYVVVLKEETHLSQSERTARRLQAQAARRGYL TKILHVFHGLLPGFLVKMSGDLLELALKLPHVDYIE EDSSVFAQSIPWNLERITPPRYRADEYQPPDGGSLV EVYLLDTSIQSDHREIEGRVMVTDFENVPEEDGTRF HRQASKCDSHGTHLAGVVSGRDAGVAKGASMRSLRV LNCQGKGTVSGTLIGLEFIRKSQLVQPVGPLVVLLP LAGGYSRVLNAACQRLARAGVVLVTAAGNFRDDACL YSPASAPEVITVGATNAQDQPVTLGTLGTNFGRCVD LFAPGEDIIGASSDCSTCFVSQSGTSQAAAHVAGIA AMMLSAEPELTLAELRQRLIHFSAKDVINEAWFPED QRVLTPNLVAALPPSTHGAGWQLFCRTVWSAHSGPT RMATAVARCAPDEELLSCSSFSRSGKRRGERMEAQG GKLVCRAHNAFGGEGVYAIARCCLLPQANCSVHTAP PAEASMGTRVHCHQQGHVLTGCSSHWEVEDLGTHKP PVLRPRGQPNQCVGHREASIHASCCHAPGLECKVKE HGIPAPQEQVTVACEEGWTLTGCSALPGTSHVLGAY AVDNTCVVRSRDVSTTGSTSEGAVTAVAICCRSRHL AQASQELQ | |
| SEQ ID No 400 | MGTHCSAWLRWPLLPLLPPLLLLLLLCPTGAGAQD EDGDYEELMLALPSQEDGLADEAAHVATATFRRCSK EAWRLPGTYIVVLMEETQRLQIEQTAHRLQTRAARR GYVIKVLHIFYDLFPGFLVKMSSDLLGLALKLPHVE YIEEDSFVFAQSIPWNLERIIPAWHQTEEDRSPDGS SQVEVYLLDTSIQGAHREIEGRVTITDFNSVPEEDG TRFHRQASKCDSHGTHLAGVVSGRDAGVAKGTSLHS LRVLNCQGKGTVSGTLIGLEFIRKSQLIQPSGPLVV LLPLAGGYSRILNAACRHLARTGVVLVAAAGNFRDD ACLYSPASAPEVITVGATNAQDQPVTLGTLGTNFGR CVDLFAPGKDIIGASSDCSTCFMSQSGTSQAAAHVA GIVARMLSREPTLTLAELRQRLIHFSTKDVINMAWF PEDQQVLTPNLVATLPPSTHETGGQLLCRTVWSAHS GPTRTATATARCAPEEELLSCSSFSRSGRRRGDWIE AIGGQQVCKALNAFGGEGVYAVARCCLVPRANCSIH NTPAARAGLETHVHCHQKDHVLTGCSFHWEVEDLSV RRQPALRSRRQPGQCVGHQAASVYASCCHAPGLECK IKEHGISGPSEQVTVACEAGWTLTGCNVLPGASLTL GAYSVDNLCVARVHDTARADRTSGEATVAAAICCRS RPSAKASWVQ | |
| SEQ ID No 401 | SIPWNLERIGGC | |
| SEQ ID No 402 | SIPWNLERGGC | |
| SEQ ID No 403 | SIPWNLEGGC | |
| SEQ ID No 404 | CGGSGRDAGVAKGA | |
| SEQ ID No 405 | CGGSGRDAGVAKGT | |

| Sequence listing: |  |
|---|---|
| SEQ ID No 406 | RDAGVAKGGC |
| SEQ ID No 407 | CSRHLAQASQELQ |
| SEQ ID No 408 | CRSRPSAKASWVQ |
| SEQ ID No 409 | CGGDYEELVLALR |
| SEQ ID No 410 | CGGDYEELMLALP |
| SEQ ID No 411 | LVLALRSEEDGGC |
| SEQ ID No 412 | LMLALPSQEDGGC |
| SEQ ID No 413 | AKDPWRLPGGC |
| SEQ ID No 414 | SKEAWRLPGGC |
| SEQ ID No 415 | CGGAARRGYLTK |
| SEQ ID No 416 | CGGAARRGYVIK |
| SEQ ID No 417 | FLVKMSGDLLELALKLPGGC |
| SEQ ID No 418 | FLVKMSSDLLGLALKLPGGC |
| SEQ ID No 419 | CGGEEDSSVFAQ |
| SEQ ID No 420 | SRHLAQASQELQ |
| SEQ ID No 421 | DYEELVLALR |
| SEQ ID No 422 | LVLALRSEEDG |
| SEQ ID No 423 | EEDSSVFAQ |
| SEQ ID No 424 | SGRDAGVAKGT |
| SEQ ID No 425 | RSRPSAKASWVQ |
| SEQ ID No 426 | GDYEELMLALP |
| SEQ ID No 427 | LMLALPSQED |
| SEQ ID No 428 | FLVKMSSDLLGLALKLP |
| SEQ ID No 429 | RCAKDPWRLPG |
| SEQ ID No 430 | RCAKDPWRLP |
| SEQ ID No 431 | RCAKDPWRL |
| SEQ ID No 432 | RCAKDPWR |
| SEQ ID No 433 | RCAKDPW |
| SEQ ID No 434 | RCAKDP |
| SEQ ID No 435 | RCAKD |
| SEQ ID No 436 | CAKDPWRLPGT |
| SEQ ID No 437 | CAKDPWRLPG |
| SEQ ID No 438 | CAKDPWRLP |
| SEQ ID No 439 | CAKDPWRL |
| SEQ ID No 440 | CAKDPWR |
| SEQ ID No 441 | CAKDPW |
| SEQ ID No 442 | CAKDP |
| SEQ ID No 443 | AKDPWRLPGT |
| SEQ ID No 444 | AKDPWRLPG |
| SEQ ID No 445 | AKDPWRLP |
| SEQ ID No 446 | AKDPWRL |
| SEQ ID No 447 | AKDPWR |
| SEQ ID No 448 | AKDPW |
| SEQ ID No 449 | KDPWRLPGT |
| SEQ ID No 450 | KDPWRLPG |
| SEQ ID No 451 | KDPWRLP |
| SEQ ID No 452 | KDPWRL |
| SEQ ID No 453 | KDPWR |
| SEQ ID No 454 | DPWRLPGT |
| SEQ ID No 455 | DPWRLPG |
| SEQ ID No 456 | DPWRLP |
| SEQ ID No 457 | DPWRL |
| SEQ ID No 458 | PWRLPGT |
| SEQ ID No 459 | PWRLPG |
| SEQ ID No 460 | PWRLP |
| SEQ ID No 461 | WRLPGT |
| SEQ ID No 462 | WRLPG |
| SEQ ID No 464 | AQAARRGYLTKI |
| SEQ ID No 465 | AQAARRGYLTK |
| SEQ ID No 466 | AQAARRGYLT |
| SEQ ID No 467 | AQAARRGYL |
| SEQ ID No 468 | AQAARRGY |
| SEQ ID No 469 | AQAARRG |
| SEQ ID No 470 | AQAARR |
| SEQ ID No 471 | AQAAR |
| SEQ ID No 472 | QAARRGYLTKIL |
| SEQ ID No 473 | QAARRGYLTKI |
| SEQ ID No 474 | QAARRGYLTK |
| SEQ ID No 475 | QAARRGYLT |
| SEQ ID No 476 | QAARRGYL |
| SEQ ID No 477 | QAARRGY |
| SEQ ID No 478 | QAARRG |
| SEQ ID No 479 | QAARR |
| SEQ ID No 480 | AARRGYLTKIL |
| SEQ ID No 481 | AARRGYLTKI |
| SEQ ID No 482 | AARRGYLTK |
| SEQ ID No 483 | AARRGYLT |

| Sequence listing: | |
|---|---|
| SEQ ID No 484 | AARRGYL |
| SEQ ID No 485 | AARRGY |
| SEQ ID No 486 | AARRG |
| SEQ ID No 487 | ARRGYLTKIL |
| SEQ ID No 488 | ARRGYLTKI |
| SEQ ID No 489 | ARRGYLTK |
| SEQ ID No 490 | ARRGYLT |
| SEQ ID No 491 | ARRGYL |
| SEQ ID No 492 | ARRGY |
| SEQ ID No 493 | RRGYLTKIL |
| SEQ ID No 494 | RRGYLTKI |
| SEQ ID No 495 | RRGYLTK |
| SEQ ID No 496 | RRGYLT |
| SEQ ID No 497 | RRGYL |
| SEQ ID No 498 | RGYLTKIL |
| SEQ ID No 499 | RGYLTKI |
| SEQ ID No 500 | RGYLTK |
| SEQ ID No 501 | RGYLT |
| SEQ ID No 502 | GYLTKIL |
| SEQ ID No 503 | GYLTKI |
| SEQ ID No 504 | GYLTK |
| SEQ ID No 505 | YLTKIL |
| SEQ ID No 506 | YLTKI |
| SEQ ID No 507 | LTKIL |
| SEQ ID No 508 | RCSKEAWRLPGT |
| SEQ ID No 509 | RCSKEAWRLPG |
| SEQ ID No 510 | RCSKEAWRLP |
| SEQ ID No 511 | RCSKEAWRL |
| SEQ ID No 512 | RCSKEAWR |
| SEQ ID No 513 | RCSKEAW |
| SEQ ID No 514 | RCSKEA |
| SEQ ID No 515 | RCSKE |
| SEQ ID No 516 | CSKEAWRLPGT |
| SEQ ID No 517 | CSKEAWRLPG |
| SEQ ID No 518 | CSKEAWRLP |
| SEQ ID No 519 | CSKEAWRL |
| SEQ ID No 520 | CSKEAWR |
| SEQ ID No 521 | CSKEAW |
| SEQ ID No 522 | CSKEA |
| SEQ ID No 523 | SKEAWRLPGT |
| SEQ ID No 524 | SKEAWRLPG |
| SEQ ID No 525 | SKEAWRLP |
| SEQ ID No 526 | SKEAWRL |
| SEQ ID No 527 | SKEAWR |
| SEQ ID No 528 | SKEAW |
| SEQ ID No 529 | KEAWRLPGT |
| SEQ ID No 530 | KEAWRLPG |
| SEQ ID No 531 | KEAWRLP |
| SEQ ID No 532 | KEAWRL |
| SEQ ID No 533 | KEAWR |
| SEQ ID No 534 | EAWRLPGT |
| SEQ ID No 535 | EAWRLPG |
| SEQ ID No 536 | EAWRLP |
| SEQ ID No 537 | EAWRL |
| SEQ ID No 538 | AWRLPGT |
| SEQ ID No 539 | AWRLPG |
| SEQ ID No 540 | AWRLP |
| SEQ ID No 541 | WRLPGT |
| SEQ ID No 542 | WRLPG |
| SEQ ID No 543 | RLPGT |
| SEQ ID No 544 | TRAARRGYVIKVL |
| SEQ ID No 545 | TRAARRGYVIKV |
| SEQ ID No 546 | TRAARRGYVIK |
| SEQ ID No 547 | TRAARRGYVI |
| SEQ ID No 548 | TRAARRGYV |
| SEQ ID No 549 | TRAARRGY |
| SEQ ID No 550 | TRAARRG |
| SEQ ID No 551 | TRAARR |
| SEQ ID No 552 | TRAAR |
| SEQ ID No 553 | RAARRGYVIKVL |
| SEQ ID No 554 | RAARRGYVIKV |
| SEQ ID No 555 | RAARRGYVIK |
| SEQ ID No 556 | RAARRGYVI |
| SEQ ID No 557 | RAARRGYV |
| SEQ ID No 558 | RAARRGY |
| SEQ ID No 559 | RAARRG |
| SEQ ID No 560 | RAARR |

| Sequence listing: | |
|---|---|
| SEQ ID No 561 | AARRGYVIKVL |
| SEQ ID No 562 | AARRGYVIKV |
| SEQ ID No 563 | AARRGYVIK |
| SEQ ID No 564 | AARRGYVI |
| SEQ ID No 565 | AARRGYV |
| SEQ ID No 566 | AARRGY |
| SEQ ID No 567 | AARRG |
| SEQ ID No 568 | ARRGYVIKVL |
| SEQ ID No 569 | ARRGYVIKV |
| SEQ ID No 570 | ARRGYVIK |
| SEQ ID No 571 | ARRGYVI |
| SEQ ID No 572 | ARRGYV |
| SEQ ID No 573 | ARRGY |
| SEQ ID No 574 | RRGYVIKVL |
| SEQ ID No 575 | RRGYVIKV |
| SEQ ID No 576 | RRGYVIK |
| SEQ ID No 577 | RRGYVI |
| SEQ ID No 578 | RRGYV |
| SEQ ID No 579 | RGYVIKVL |
| SEQ ID No 580 | RGYVIKV |
| SEQ ID No 581 | RGYVIK |
| SEQ ID No 582 | RGYVI |
| SEQ ID No 583 | GYVIKVL |
| SEQ ID No 584 | GYVIKV |
| SEQ ID No 585 | GYVIK |
| SEQ ID No 586 | YVIKVL |
| SEQ ID No 587 | YVIKV |
| SEQ ID No 588 | VIKVL |
| SEQ ID No 589 | TCGTCGTTTTTCGGTGCTTTT |
| SEQ ID No 590 | TCGTCGTTTTTCGGTCGTTTT |
| SEQ ID No 591 | TCGTCGTTTGTCGTTTTGTCGTT |
| SEQ ID No 592 | TCGTCGTTTCGTCGTTTTGTCGTT |
| SEQ ID No 593 | TCGTCGTTTGTCGTTTTTTTCGA |
| SEQ ID No 594 | TCGCGTCGTTCGGCGCGCGCCG |
| SEQ ID No 595 | TCGTCGACGTTCGGCGCGCGCCG |
| SEQ ID No 596 | TCGGACGTTCGGCGCGCGCCG |
| SEQ ID No 597 | TCGGACGTTCGGCGCGCCG |
| SEQ ID No 598 | TCGCGTCGTTCGGCGCGCCG |
| SEQ ID No 599 | TCGACGTTCGGCGCGCGCCG |
| SEQ ID No 600 | TCGACGTTCGGCGCGCCG |
| SEQ ID No 601 | TCGCGTCGTTCGGCGCCG |
| SEQ ID No 602 | TCGCGACGTTCGGCGCGCGCCG |
| SEQ ID No 603 | TCGTCGTTTTCGGCGCGCGCCG |
| SEQ ID No 604 | TCGTCGTTTTCGGCGGCCGCCG |
| SEQ ID No 605 | TCGTCGTTTTACGGCGCCGTGCCG |
| SEQ ID No 606 | TCGTCGTTTTCGGCGCGCGCCGT |
| SEQ ID No 607 | TCGTCGACGATCGGCGCGCGCCG |

The invention claimed is:

1. A method for alleviating a PCSK9-related disorder in an individual, comprising administering to the individual a therapeutically effective amount of an immunogen, wherein the immunogen comprises an antigenic PCSK9 peptide linked to an immunogenic carrier, wherein the antigenic PCSK9 peptide consists of an amino acid sequence selected from the group consisting of SEQ ID NOs:182, 183, 184, 185, 186, 187, and 188, wherein the immunogenic carrier is selected from the group consisting of CRM197 and a virus-like particle (VLP), and wherein the PCSK9-related disorder is selected from the group consisting of an aterio-sclerotic condition, a coronary artery disease, and a cardiovascular disease.

2. The method according to claim 1, wherein the antigenic PCSK9 peptide consists of an amino acid sequence selected from the group consisting of SEQ ID NOs:182, 183, 184, and 185.

3. The method according to claim 1, wherein the immunogenic carrier is CRM197.

4. The method according to claim 1, wherein the immunogenic carrier is a VLP.

5. The method according to claim 1 wherein the individual is a human.

6. The method according to claim 5, wherein the PCSK9-related disorder is a coronary artery disease.

7. The method according to claim 5, wherein the PCSK9-related disorder is an ateriosclerotic condition.

8. The method according to claim 5, wherein the PCSK9-related disorder is a cardiovascular disease.

9. The method according to claim 1, wherein the antigenic PCSK9 peptide consists of an amino acid sequence selected from the group consisting of SEQ ID NOs:186, 187, and 188.

10. The method according to claim 9, wherein the antigenic PCSK9 peptide consists of SEQ ID NO: 187.

11. The method according to claim 9, wherein the antigenic PCSK9 peptide consists of an amino acid sequence of SEQ ID NO: 188.

12. The method according claim 1, wherein the immunogen further comprises an amino acid linker, and wherein: (i) the amino acid linker is joined to the C-terminus of the antigenic PCSK9 peptide and is selected from the group consisting of GGC, GC, and a cysteine residue (C); and (ii) the antigenic PCSK9 peptide is linked to the immunogenic carrier through the cysteine residue of the amino acid linker.

13. The method according to claim 12, wherein the amino acid linker is a cysteine residue.

14. The method according to claim 12, wherein the amino acid linker is a GC.

15. The method according to claim 12, wherein the amino acid linker is a GGC.

16. The method according to claim 12, further comprising administering to the individual an adjuvant.

17. The method according to claim 16, wherein the adjuvant is selected from alum, CpG oligodeoxynucleotide, and QS21.

18. A method for alleviating a PCSK9-related disorder in an individual, comprising administering to the individual a therapeutically effective amount of an antigenic PCSK9 peptide consisting of an amino acid sequence selected from the group consisting of SEQ ID NOs: 317, 401, 402, and 403, wherein the PCSK9-related disorder is selected from the group consisting of an ateriosclerotic condition, a coronary artery disease, and a cardiovascular disease.

19. The method according to claim 18, wherein the antigenic PCSK9 peptide is linked to an immunogenic carrier selected from the group consisting of a VLP and CRM197.

20. The method according to claim 19, wherein the an immunogenic carrier is CRM197.

21. A method for reducing plasma cholesterol levels in an individual, comprising administering to the individual a therapeutically effective amount of an antigenic PCSK9 peptide consisting of an amino acid sequence selected from the group consisting of SEQ ID NOs: 317, 401, 402, and 403.

22. The method according to claim 21, wherein the antigenic PCSK9 peptide is linked to an immunogenic carrier selected from the group consisting of a VLP and CRM197.

23. The method according to claim 22, wherein the immunogenic carrier is CRM197.

24. A method for reducing plasma cholesterol levels in an individual, comprising administering to the individual a therapeutically effective amount of an immunogen, wherein the immunogen comprises an antigenic PCSK9 peptide linked to an immunogenic carrier, wherein the antigenic PCSK9 peptide consists of an amino acid sequence selected from the group consisting of SEQ ID NOs:182, 183, 184, 185, 186, 187, and 188, and wherein the immunogenic carrier is selected form the group consisting of CRM197 and a virus-like particle (VLP).

25. The method according to claim 24, wherein the immunogenic carrier is CRM197.

26. The method according claim 24, wherein the immunogen further comprises an amino acid linker, and wherein: (i) the amino acid linker is joined to the C-terminus of the antigenic PCSK9 peptide and is selected from the group consisting of GGC, GC, and a cysteine residue (C); and (ii) the antigenic PCSK9 peptide is linked to the immunogenic carrier through the cysteine residue of the amino acid linker.

27. The method according to claim 26, wherein the amino acid linker is a GGC.

28. The method according to claim 24, wherein the individual is a human.

29. The method according to claim 28, wherein the antigenic PCSK9 peptide consists of an amino acid sequence selected from the group consisting of SEQ ID NOs:182, 183, 184, and 185.

30. The method according to claim 28, wherein the antigenic PCSK9 peptide consists of an amino acid sequence of SEQ ID NO: 188.

* * * * *

SEQUENCE LISTING

<160> NUMBER OF SEQ ID NOS: 644

<210> SEQ ID NO 1
<211> LENGTH: 13
<212> TYPE: PRT
<213> ORGANISM: Artificial
<220> FEATURE:
<223> OTHER INFORMATION: Synthesized

<400> SEQUENCE: 1

Ile Gly Ala Ser Ser Asp Cys Ser Thr Cys Phe Val Ser
1               5                   10

<210> SEQ ID NO 2
<211> LENGTH: 12
<212> TYPE: PRT
<213> ORGANISM: Artificial
<220> FEATURE:
<223> OTHER INFORMATION: Synthesized

<400> SEQUENCE: 2

Ile Gly Ala Ser Ser Asp Cys Ser Thr Cys Phe Val
1               5                   10

<210> SEQ ID NO 3
<211> LENGTH: 11
<212> TYPE: PRT
<213> ORGANISM: Artificial
<220> FEATURE:
<223> OTHER INFORMATION: Synthesized

<400> SEQUENCE: 3

Ile Gly Ala Ser Ser Asp Cys Ser Thr Cys Phe
1               5                   10

<210> SEQ ID NO 4
<211> LENGTH: 10
<212> TYPE: PRT
<213> ORGANISM: Artificial
<220> FEATURE:
<223> OTHER INFORMATION: Synthesized

<400> SEQUENCE: 4

Ile Gly Ala Ser Ser Asp Cys Ser Thr Cys
1               5                   10

<210> SEQ ID NO 5
<211> LENGTH: 9
<212> TYPE: PRT
<213> ORGANISM: Artificial
<220> FEATURE:
<223> OTHER INFORMATION: Synthesized

<400> SEQUENCE: 5

Ile Gly Ala Ser Ser Asp Cys Ser Thr
1               5

<210> SEQ ID NO 6
<211> LENGTH: 8
<212> TYPE: PRT
<213> ORGANISM: Artificial
<220> FEATURE:
<223> OTHER INFORMATION: Synthesized

<400> SEQUENCE: 6

Ile Gly Ala Ser Ser Asp Cys Ser
1               5

<210> SEQ ID NO 7
<211> LENGTH: 7
<212> TYPE: PRT
<213> ORGANISM: Artificial
<220> FEATURE:
<223> OTHER INFORMATION: Synthesized

<400> SEQUENCE: 7

Ile Gly Ala Ser Ser Asp Cys
1               5

<210> SEQ ID NO 8
<211> LENGTH: 6
<212> TYPE: PRT
<213> ORGANISM: Artificial
<220> FEATURE:
<223> OTHER INFORMATION: Synthesized

<400> SEQUENCE: 8

Ile Gly Ala Ser Ser Asp
1               5

<210> SEQ ID NO 9
<211> LENGTH: 5
<212> TYPE: PRT
<213> ORGANISM: Artificial
<220> FEATURE:
<223> OTHER INFORMATION: Synthesized

<400> SEQUENCE: 9

Ile Gly Ala Ser Ser
1               5

<210> SEQ ID NO 10
<211> LENGTH: 12
<212> TYPE: PRT
<213> ORGANISM: Artificial
<220> FEATURE:
<223> OTHER INFORMATION: Synthesized

<400> SEQUENCE: 10

Gly Ala Ser Ser Asp Cys Ser Thr Cys Phe Val Ser
1               5                   10

<210> SEQ ID NO 11
<211> LENGTH: 11
<212> TYPE: PRT
<213> ORGANISM: Artificial
<220> FEATURE:
<223> OTHER INFORMATION: Synthesized

<400> SEQUENCE: 11

Gly Ala Ser Ser Asp Cys Ser Thr Cys Phe Val
1               5                   10

<210> SEQ ID NO 12
<211> LENGTH: 10
<212> TYPE: PRT
<213> ORGANISM: Artificial
<220> FEATURE:
<223> OTHER INFORMATION: Synthesized

<400> SEQUENCE: 12

Gly Ala Ser Ser Asp Cys Ser Thr Cys Phe
1               5                   10

<210> SEQ ID NO 13
<211> LENGTH: 9
<212> TYPE: PRT
<213> ORGANISM: Artificial
<220> FEATURE:
<223> OTHER INFORMATION: Synthesized

<400> SEQUENCE: 13

Gly Ala Ser Ser Asp Cys Ser Thr Cys
1               5

<210> SEQ ID NO 14
<211> LENGTH: 8
<212> TYPE: PRT
<213> ORGANISM: Artificial
<220> FEATURE:
<223> OTHER INFORMATION: Synthesized

<400> SEQUENCE: 14

Gly Ala Ser Ser Asp Cys Ser Thr

```
1               5

<210> SEQ ID NO 15
<211> LENGTH: 7
<212> TYPE: PRT
<213> ORGANISM: Artificial
<220> FEATURE:
<223> OTHER INFORMATION: Synthesized

<400> SEQUENCE: 15

Gly Ala Ser Ser Asp Cys Ser
1               5

<210> SEQ ID NO 16
<211> LENGTH: 6
<212> TYPE: PRT
<213> ORGANISM: Artificial
<220> FEATURE:
<223> OTHER INFORMATION: Synthesized

<400> SEQUENCE: 16

Gly Ala Ser Ser Asp Cys
1               5

<210> SEQ ID NO 17
<211> LENGTH: 5
<212> TYPE: PRT
<213> ORGANISM: Artificial
<220> FEATURE:
<223> OTHER INFORMATION: Synthesized

<400> SEQUENCE: 17

Gly Ala Ser Ser Asp
1               5

<210> SEQ ID NO 18
<211> LENGTH: 11
<212> TYPE: PRT
<213> ORGANISM: Artificial
<220> FEATURE:
<223> OTHER INFORMATION: Synthesized

<400> SEQUENCE: 18

Ala Ser Ser Asp Cys Ser Thr Cys Phe Val Ser
1               5                   10

<210> SEQ ID NO 19
<211> LENGTH: 10
<212> TYPE: PRT
<213> ORGANISM: Artificial
<220> FEATURE:
<223> OTHER INFORMATION: Synthesized

<400> SEQUENCE: 19

Ala Ser Ser Asp Cys Ser Thr Cys Phe Val
1               5                   10

<210> SEQ ID NO 20
<211> LENGTH: 9
<212> TYPE: PRT
<213> ORGANISM: Artificial
<220> FEATURE:
<223> OTHER INFORMATION: Synthesized

<400> SEQUENCE: 20

Ala Ser Ser Asp Cys Ser Thr Cys Phe
1               5
```

```
<210> SEQ ID NO 21
<211> LENGTH: 8
<212> TYPE: PRT
<213> ORGANISM: Artificial
<220> FEATURE:
<223> OTHER INFORMATION: Synthesized

<400> SEQUENCE: 21

Ala Ser Ser Asp Cys Ser Thr Cys
1               5

<210> SEQ ID NO 22
<211> LENGTH: 7
<212> TYPE: PRT
<213> ORGANISM: Artificial
<220> FEATURE:
<223> OTHER INFORMATION: Synthesized

<400> SEQUENCE: 22

Ala Ser Ser Asp Cys Ser Thr
1               5

<210> SEQ ID NO 23
<211> LENGTH: 6
<212> TYPE: PRT
<213> ORGANISM: Artificial
<220> FEATURE:
<223> OTHER INFORMATION: Synthesized

<400> SEQUENCE: 23

Ala Ser Ser Asp Cys Ser
1               5

<210> SEQ ID NO 24
<211> LENGTH: 5
<212> TYPE: PRT
<213> ORGANISM: Artificial
<220> FEATURE:
<223> OTHER INFORMATION: Synthesized

<400> SEQUENCE: 24

Ala Ser Ser Asp Cys
1               5

<210> SEQ ID NO 25
<211> LENGTH: 10
<212> TYPE: PRT
<213> ORGANISM: Artificial
<220> FEATURE:
<223> OTHER INFORMATION: Synthesized

<400> SEQUENCE: 25

Ser Ser Asp Cys Ser Thr Cys Phe Val Ser
1               5                   10

<210> SEQ ID NO 26
<211> LENGTH: 9
<212> TYPE: PRT
<213> ORGANISM: Artificial
<220> FEATURE:
<223> OTHER INFORMATION: Synthesized

<400> SEQUENCE: 26

Ser Ser Asp Cys Ser Thr Cys Phe Val
1               5
```

```
<210> SEQ ID NO 27
<211> LENGTH: 8
<212> TYPE: PRT
<213> ORGANISM: Artificial
<220> FEATURE:
<223> OTHER INFORMATION: Synthesized

<400> SEQUENCE: 27

Ser Ser Asp Cys Ser Thr Cys Phe
1               5

<210> SEQ ID NO 28
<211> LENGTH: 7
<212> TYPE: PRT
<213> ORGANISM: Artificial
<220> FEATURE:
<223> OTHER INFORMATION: Synthesized

<400> SEQUENCE: 28

Ser Ser Asp Cys Ser Thr Cys
1               5

<210> SEQ ID NO 29
<211> LENGTH: 6
<212> TYPE: PRT
<213> ORGANISM: Artificial
<220> FEATURE:
<223> OTHER INFORMATION: Synthesized

<400> SEQUENCE: 29

Ser Ser Asp Cys Ser Thr
1               5

<210> SEQ ID NO 30
<211> LENGTH: 5
<212> TYPE: PRT
<213> ORGANISM: Artificial
<220> FEATURE:
<223> OTHER INFORMATION: Synthesized

<400> SEQUENCE: 30

Ser Ser Asp Cys Ser
1               5

<210> SEQ ID NO 31
<211> LENGTH: 9
<212> TYPE: PRT
<213> ORGANISM: Artificial
<220> FEATURE:
<223> OTHER INFORMATION: Synthesized

<400> SEQUENCE: 31

Ser Asp Cys Ser Thr Cys Phe Val Ser
1               5

<210> SEQ ID NO 32
<211> LENGTH: 8
<212> TYPE: PRT
<213> ORGANISM: Artificial
<220> FEATURE:
<223> OTHER INFORMATION: Synthesized

<400> SEQUENCE: 32

Ser Asp Cys Ser Thr Cys Phe Val
1               5
```

```
<210> SEQ ID NO 33
<211> LENGTH: 7
<212> TYPE: PRT
<213> ORGANISM: Artificial
<220> FEATURE:
<223> OTHER INFORMATION: Synthesized

<400> SEQUENCE: 33

Ser Asp Cys Ser Thr Cys Phe
1               5

<210> SEQ ID NO 34
<211> LENGTH: 6
<212> TYPE: PRT
<213> ORGANISM: Artificial
<220> FEATURE:
<223> OTHER INFORMATION: Synthesized

<400> SEQUENCE: 34

Ser Asp Cys Ser Thr Cys
1               5

<210> SEQ ID NO 35
<211> LENGTH: 5
<212> TYPE: PRT
<213> ORGANISM: Artificial
<220> FEATURE:
<223> OTHER INFORMATION: Synthesized

<400> SEQUENCE: 35

Ser Asp Cys Ser Thr
1               5

<210> SEQ ID NO 36
<211> LENGTH: 8
<212> TYPE: PRT
<213> ORGANISM: Artificial
<220> FEATURE:
<223> OTHER INFORMATION: Synthesized

<400> SEQUENCE: 36

Asp Cys Ser Thr Cys Phe Val Ser
1               5

<210> SEQ ID NO 37
<211> LENGTH: 7
<212> TYPE: PRT
<213> ORGANISM: Artificial
<220> FEATURE:
<223> OTHER INFORMATION: Synthesized

<400> SEQUENCE: 37

Asp Cys Ser Thr Cys Phe Val
1               5

<210> SEQ ID NO 38
<211> LENGTH: 6
<212> TYPE: PRT
<213> ORGANISM: Artificial
<220> FEATURE:
<223> OTHER INFORMATION: Synthesized

<400> SEQUENCE: 38

Asp Cys Ser Thr Cys Phe
1               5

<210> SEQ ID NO 39
```

```
<211> LENGTH: 5
<212> TYPE: PRT
<213> ORGANISM: Artificial
<220> FEATURE:
<223> OTHER INFORMATION: Synthesized

<400> SEQUENCE: 39

Asp Cys Ser Thr Cys
1               5

<210> SEQ ID NO 40
<211> LENGTH: 7
<212> TYPE: PRT
<213> ORGANISM: Artificial
<220> FEATURE:
<223> OTHER INFORMATION: Synthesized

<400> SEQUENCE: 40

Cys Ser Thr Cys Phe Val Ser
1               5

<210> SEQ ID NO 41
<211> LENGTH: 6
<212> TYPE: PRT
<213> ORGANISM: Artificial
<220> FEATURE:
<223> OTHER INFORMATION: Synthesized

<400> SEQUENCE: 41

Cys Ser Thr Cys Phe Val
1               5

<210> SEQ ID NO 42
<211> LENGTH: 5
<212> TYPE: PRT
<213> ORGANISM: Artificial
<220> FEATURE:
<223> OTHER INFORMATION: Synthesized

<400> SEQUENCE: 42

Cys Ser Thr Cys Phe
1               5

<210> SEQ ID NO 43
<211> LENGTH: 6
<212> TYPE: PRT
<213> ORGANISM: Artificial
<220> FEATURE:
<223> OTHER INFORMATION: Synthesized

<400> SEQUENCE: 43

Ser Thr Cys Phe Val Ser
1               5

<210> SEQ ID NO 44
<211> LENGTH: 5
<212> TYPE: PRT
<213> ORGANISM: Artificial
<220> FEATURE:
<223> OTHER INFORMATION: Synthesized

<400> SEQUENCE: 44

Ser Thr Cys Phe Val
1               5

<210> SEQ ID NO 45
<211> LENGTH: 5
```

```
<212> TYPE: PRT
<213> ORGANISM: Artificial
<220> FEATURE:
<223> OTHER INFORMATION: Synthesized

<400> SEQUENCE: 45

Thr Cys Phe Val Ser
1               5

<210> SEQ ID NO 46
<211> LENGTH: 15
<212> TYPE: PRT
<213> ORGANISM: Artificial
<220> FEATURE:
<223> OTHER INFORMATION: Synthesized

<400> SEQUENCE: 46

Glu Asp Gly Thr Arg Phe His Arg Gln Ala Ser Lys Cys Asp Ser
1               5                   10                  15

<210> SEQ ID NO 47
<211> LENGTH: 14
<212> TYPE: PRT
<213> ORGANISM: Artificial
<220> FEATURE:
<223> OTHER INFORMATION: Synthesized

<400> SEQUENCE: 47

Glu Asp Gly Thr Arg Phe His Arg Gln Ala Ser Lys Cys Asp
1               5                   10

<210> SEQ ID NO 48
<211> LENGTH: 13
<212> TYPE: PRT
<213> ORGANISM: Artificial
<220> FEATURE:
<223> OTHER INFORMATION: Synthesized

<400> SEQUENCE: 48

Glu Asp Gly Thr Arg Phe His Arg Gln Ala Ser Lys Cys
1               5                   10

<210> SEQ ID NO 49
<211> LENGTH: 12
<212> TYPE: PRT
<213> ORGANISM: Artificial
<220> FEATURE:
<223> OTHER INFORMATION: Synthesized

<400> SEQUENCE: 49

Glu Asp Gly Thr Arg Phe His Arg Gln Ala Ser Lys
1               5                   10

<210> SEQ ID NO 50
<211> LENGTH: 11
<212> TYPE: PRT
<213> ORGANISM: Artificial
<220> FEATURE:
<223> OTHER INFORMATION: Synthesized

<400> SEQUENCE: 50

Glu Asp Gly Thr Arg Phe His Arg Gln Ala Ser
1               5                   10

<210> SEQ ID NO 51
<211> LENGTH: 10
<212> TYPE: PRT
```

```
<213> ORGANISM: Artificial
<220> FEATURE:
<223> OTHER INFORMATION: Synthesized

<400> SEQUENCE: 51

Glu Asp Gly Thr Arg Phe His Arg Gln Ala
1               5                   10

<210> SEQ ID NO 52
<211> LENGTH: 9
<212> TYPE: PRT
<213> ORGANISM: Artificial
<220> FEATURE:
<223> OTHER INFORMATION: Synthesized

<400> SEQUENCE: 52

Glu Asp Gly Thr Arg Phe His Arg Gln
1               5

<210> SEQ ID NO 53
<211> LENGTH: 14
<212> TYPE: PRT
<213> ORGANISM: Artificial
<220> FEATURE:
<223> OTHER INFORMATION: Synthesized

<400> SEQUENCE: 53

Asp Gly Thr Arg Phe His Arg Gln Ala Ser Lys Cys Asp Ser
1               5                   10

<210> SEQ ID NO 54
<211> LENGTH: 13
<212> TYPE: PRT
<213> ORGANISM: Artificial
<220> FEATURE:
<223> OTHER INFORMATION: Synthesized

<400> SEQUENCE: 54

Asp Gly Thr Arg Phe His Arg Gln Ala Ser Lys Cys Asp
1               5                   10

<210> SEQ ID NO 55
<211> LENGTH: 12
<212> TYPE: PRT
<213> ORGANISM: Artificial
<220> FEATURE:
<223> OTHER INFORMATION: Synthesized

<400> SEQUENCE: 55

Asp Gly Thr Arg Phe His Arg Gln Ala Ser Lys Cys
1               5                   10

<210> SEQ ID NO 56
<211> LENGTH: 11
<212> TYPE: PRT
<213> ORGANISM: Artificial
<220> FEATURE:
<223> OTHER INFORMATION: Synthesized

<400> SEQUENCE: 56

Asp Gly Thr Arg Phe His Arg Gln Ala Ser Lys
1               5                   10

<210> SEQ ID NO 57
<211> LENGTH: 10
<212> TYPE: PRT
<213> ORGANISM: Artificial
```

<220> FEATURE:
<223> OTHER INFORMATION: Synthesized

<400> SEQUENCE: 57

Asp Gly Thr Arg Phe His Arg Gln Ala Ser
1               5                   10

<210> SEQ ID NO 58
<211> LENGTH: 9
<212> TYPE: PRT
<213> ORGANISM: Artificial
<220> FEATURE:
<223> OTHER INFORMATION: Synthesized

<400> SEQUENCE: 58

Asp Gly Thr Arg Phe His Arg Gln Ala
1               5

<210> SEQ ID NO 59
<211> LENGTH: 8
<212> TYPE: PRT
<213> ORGANISM: Artificial
<220> FEATURE:
<223> OTHER INFORMATION: Synthesized

<400> SEQUENCE: 59

Asp Gly Thr Arg Phe His Arg Gln
1               5

<210> SEQ ID NO 60
<211> LENGTH: 13
<212> TYPE: PRT
<213> ORGANISM: Artificial
<220> FEATURE:
<223> OTHER INFORMATION: Synthesized

<400> SEQUENCE: 60

Gly Thr Arg Phe His Arg Gln Ala Ser Lys Cys Asp Ser
1               5                   10

<210> SEQ ID NO 61
<211> LENGTH: 12
<212> TYPE: PRT
<213> ORGANISM: Artificial
<220> FEATURE:
<223> OTHER INFORMATION: Synthesized

<400> SEQUENCE: 61

Gly Thr Arg Phe His Arg Gln Ala Ser Lys Cys Asp
1               5                   10

<210> SEQ ID NO 62
<211> LENGTH: 11
<212> TYPE: PRT
<213> ORGANISM: Artificial
<220> FEATURE:
<223> OTHER INFORMATION: Synthesized

<400> SEQUENCE: 62

Gly Thr Arg Phe His Arg Gln Ala Ser Lys Cys
1               5                   10

<210> SEQ ID NO 63
<211> LENGTH: 10
<212> TYPE: PRT
<213> ORGANISM: Artificial
<220> FEATURE:

<223> OTHER INFORMATION: Synthesized

<400> SEQUENCE: 63

Gly Thr Arg Phe His Arg Gln Ala Ser Lys
1               5                   10

<210> SEQ ID NO 64
<211> LENGTH: 9
<212> TYPE: PRT
<213> ORGANISM: Artificial
<220> FEATURE:
<223> OTHER INFORMATION: Synthesized

<400> SEQUENCE: 64

Gly Thr Arg Phe His Arg Gln Ala Ser
1               5

<210> SEQ ID NO 65
<211> LENGTH: 8
<212> TYPE: PRT
<213> ORGANISM: Artificial
<220> FEATURE:
<223> OTHER INFORMATION: Synthesized

<400> SEQUENCE: 65

Gly Thr Arg Phe His Arg Gln Ala
1               5

<210> SEQ ID NO 66
<211> LENGTH: 7
<212> TYPE: PRT
<213> ORGANISM: Artificial
<220> FEATURE:
<223> OTHER INFORMATION: Synthesized

<400> SEQUENCE: 66

Gly Thr Arg Phe His Arg Gln
1               5

<210> SEQ ID NO 67
<211> LENGTH: 12
<212> TYPE: PRT
<213> ORGANISM: Artificial
<220> FEATURE:
<223> OTHER INFORMATION: Synthesized

<400> SEQUENCE: 67

Thr Arg Phe His Arg Gln Ala Ser Lys Cys Asp Ser
1               5                   10

<210> SEQ ID NO 68
<211> LENGTH: 11
<212> TYPE: PRT
<213> ORGANISM: Artificial
<220> FEATURE:
<223> OTHER INFORMATION: Synthesized

<400> SEQUENCE: 68

Thr Arg Phe His Arg Gln Ala Ser Lys Cys Asp
1               5                   10

<210> SEQ ID NO 69
<211> LENGTH: 10
<212> TYPE: PRT
<213> ORGANISM: Artificial
<220> FEATURE:
<223> OTHER INFORMATION: Synthesized

```
<400> SEQUENCE: 69

Thr Arg Phe His Arg Gln Ala Ser Lys Cys
1               5                   10

<210> SEQ ID NO 70
<211> LENGTH: 9
<212> TYPE: PRT
<213> ORGANISM: Artificial
<220> FEATURE:
<223> OTHER INFORMATION: Synthesized

<400> SEQUENCE: 70

Thr Arg Phe His Arg Gln Ala Ser Lys
1               5

<210> SEQ ID NO 71
<211> LENGTH: 8
<212> TYPE: PRT
<213> ORGANISM: Artificial
<220> FEATURE:
<223> OTHER INFORMATION: Synthesized

<400> SEQUENCE: 71

Thr Arg Phe His Arg Gln Ala Ser
1               5

<210> SEQ ID NO 72
<211> LENGTH: 7
<212> TYPE: PRT
<213> ORGANISM: Artificial
<220> FEATURE:
<223> OTHER INFORMATION: Synthesized

<400> SEQUENCE: 72

Thr Arg Phe His Arg Gln Ala
1               5

<210> SEQ ID NO 73
<211> LENGTH: 6
<212> TYPE: PRT
<213> ORGANISM: Artificial
<220> FEATURE:
<223> OTHER INFORMATION: Synthesized

<400> SEQUENCE: 73

Thr Arg Phe His Arg Gln
1               5

<210> SEQ ID NO 74
<211> LENGTH: 11
<212> TYPE: PRT
<213> ORGANISM: Artificial
<220> FEATURE:
<223> OTHER INFORMATION: Synthesized

<400> SEQUENCE: 74

Arg Phe His Arg Gln Ala Ser Lys Cys Asp Ser
1               5                   10

<210> SEQ ID NO 75
<211> LENGTH: 10
<212> TYPE: PRT
<213> ORGANISM: Artificial
<220> FEATURE:
<223> OTHER INFORMATION: Synthesized
```

```
<400> SEQUENCE: 75

Arg Phe His Arg Gln Ala Ser Lys Cys Asp
1               5                   10

<210> SEQ ID NO 76
<211> LENGTH: 9
<212> TYPE: PRT
<213> ORGANISM: Artificial
<220> FEATURE:
<223> OTHER INFORMATION: Synthesized

<400> SEQUENCE: 76

Arg Phe His Arg Gln Ala Ser Lys Cys
1               5

<210> SEQ ID NO 77
<211> LENGTH: 8
<212> TYPE: PRT
<213> ORGANISM: Artificial
<220> FEATURE:
<223> OTHER INFORMATION: Synthesized

<400> SEQUENCE: 77

Arg Phe His Arg Gln Ala Ser Lys
1               5

<210> SEQ ID NO 78
<211> LENGTH: 7
<212> TYPE: PRT
<213> ORGANISM: Artificial
<220> FEATURE:
<223> OTHER INFORMATION: Synthesized

<400> SEQUENCE: 78

Arg Phe His Arg Gln Ala Ser
1               5

<210> SEQ ID NO 79
<211> LENGTH: 6
<212> TYPE: PRT
<213> ORGANISM: Artificial
<220> FEATURE:
<223> OTHER INFORMATION: Synthesized

<400> SEQUENCE: 79

Arg Phe His Arg Gln Ala
1               5

<210> SEQ ID NO 80
<211> LENGTH: 5
<212> TYPE: PRT
<213> ORGANISM: Artificial
<220> FEATURE:
<223> OTHER INFORMATION: Synthesized

<400> SEQUENCE: 80

Arg Phe His Arg Gln
1               5

<210> SEQ ID NO 81
<211> LENGTH: 10
<212> TYPE: PRT
<213> ORGANISM: Artificial
<220> FEATURE:
<223> OTHER INFORMATION: Synthesized

<400> SEQUENCE: 81
```

Phe His Arg Gln Ala Ser Lys Cys Asp Ser
1               5                   10

<210> SEQ ID NO 82
<211> LENGTH: 9
<212> TYPE: PRT
<213> ORGANISM: Artificial
<220> FEATURE:
<223> OTHER INFORMATION: Synthesized

<400> SEQUENCE: 82

Phe His Arg Gln Ala Ser Lys Cys Asp
1               5

<210> SEQ ID NO 83
<211> LENGTH: 8
<212> TYPE: PRT
<213> ORGANISM: Artificial
<220> FEATURE:
<223> OTHER INFORMATION: Synthesized

<400> SEQUENCE: 83

Phe His Arg Gln Ala Ser Lys Cys
1               5

<210> SEQ ID NO 84
<211> LENGTH: 7
<212> TYPE: PRT
<213> ORGANISM: Artificial
<220> FEATURE:
<223> OTHER INFORMATION: Synthesized

<400> SEQUENCE: 84

Phe His Arg Gln Ala Ser Lys
1               5

<210> SEQ ID NO 85
<211> LENGTH: 6
<212> TYPE: PRT
<213> ORGANISM: Artificial
<220> FEATURE:
<223> OTHER INFORMATION: Synthesized

<400> SEQUENCE: 85

Phe His Arg Gln Ala Ser
1               5

<210> SEQ ID NO 86
<211> LENGTH: 5
<212> TYPE: PRT
<213> ORGANISM: Artificial
<220> FEATURE:
<223> OTHER INFORMATION: Synthesized

<400> SEQUENCE: 86

Phe His Arg Gln Ala
1               5

<210> SEQ ID NO 87
<211> LENGTH: 9
<212> TYPE: PRT
<213> ORGANISM: Artificial
<220> FEATURE:
<223> OTHER INFORMATION: Synthesized

<400> SEQUENCE: 87

His Arg Gln Ala Ser Lys Cys Asp Ser
1               5

<210> SEQ ID NO 88
<211> LENGTH: 8
<212> TYPE: PRT
<213> ORGANISM: Artificial
<220> FEATURE:
<223> OTHER INFORMATION: Synthesized

<400> SEQUENCE: 88

His Arg Gln Ala Ser Lys Cys Asp
1               5

<210> SEQ ID NO 89
<211> LENGTH: 7
<212> TYPE: PRT
<213> ORGANISM: Artificial
<220> FEATURE:
<223> OTHER INFORMATION: Synthesized

<400> SEQUENCE: 89

His Arg Gln Ala Ser Lys Cys
1               5

<210> SEQ ID NO 90
<211> LENGTH: 6
<212> TYPE: PRT
<213> ORGANISM: Artificial
<220> FEATURE:
<223> OTHER INFORMATION: Synthesized

<400> SEQUENCE: 90

His Arg Gln Ala Ser Lys
1               5

<210> SEQ ID NO 91
<211> LENGTH: 5
<212> TYPE: PRT
<213> ORGANISM: Artificial
<220> FEATURE:
<223> OTHER INFORMATION: Synthesized

<400> SEQUENCE: 91

His Arg Gln Ala Ser
1               5

<210> SEQ ID NO 92
<211> LENGTH: 8
<212> TYPE: PRT
<213> ORGANISM: Artificial
<220> FEATURE:
<223> OTHER INFORMATION: Synthesized

<400> SEQUENCE: 92

Arg Gln Ala Ser Lys Cys Asp Ser
1               5

<210> SEQ ID NO 93
<211> LENGTH: 7
<212> TYPE: PRT
<213> ORGANISM: Artificial
<220> FEATURE:
<223> OTHER INFORMATION: Synthesized

<400> SEQUENCE: 93

Arg Gln Ala Ser Lys Cys Asp 1               5

<210> SEQ ID NO 94
<211> LENGTH: 6
<212> TYPE: PRT
<213> ORGANISM: Artificial
<220> FEATURE:
<223> OTHER INFORMATION: Synthesized

<400> SEQUENCE: 94

Arg Gln Ala Ser Lys Cys
1               5

<210> SEQ ID NO 95
<211> LENGTH: 5
<212> TYPE: PRT
<213> ORGANISM: Artificial
<220> FEATURE:
<223> OTHER INFORMATION: Synthesized

<400> SEQUENCE: 95

Arg Gln Ala Ser Lys
1               5

<210> SEQ ID NO 96
<211> LENGTH: 7
<212> TYPE: PRT
<213> ORGANISM: Artificial
<220> FEATURE:
<223> OTHER INFORMATION: Synthesized

<400> SEQUENCE: 96

Gln Ala Ser Lys Cys Asp Ser
1               5

<210> SEQ ID NO 97
<211> LENGTH: 6
<212> TYPE: PRT
<213> ORGANISM: Artificial
<220> FEATURE:
<223> OTHER INFORMATION: Synthesized

<400> SEQUENCE: 97

Gln Ala Ser Lys Cys Asp
1               5

<210> SEQ ID NO 98
<211> LENGTH: 5
<212> TYPE: PRT
<213> ORGANISM: Artificial
<220> FEATURE:
<223> OTHER INFORMATION: Synthesized

<400> SEQUENCE: 98

Gln Ala Ser Lys Cys
1               5

<210> SEQ ID NO 99
<211> LENGTH: 6
<212> TYPE: PRT
<213> ORGANISM: Artificial
<220> FEATURE:
<223> OTHER INFORMATION: Synthesized

<400> SEQUENCE: 99

Ala Ser Lys Cys Asp Ser
1               5

```
<210> SEQ ID NO 100
<211> LENGTH: 5
<212> TYPE: PRT
<213> ORGANISM: Artificial
<220> FEATURE:
<223> OTHER INFORMATION: Synthesized

<400> SEQUENCE: 100

Ala Ser Lys Cys Asp
1               5

<210> SEQ ID NO 101
<211> LENGTH: 5
<212> TYPE: PRT
<213> ORGANISM: Artificial
<220> FEATURE:
<223> OTHER INFORMATION: Synthesized

<400> SEQUENCE: 101

Ser Lys Cys Asp Ser
1               5

<210> SEQ ID NO 102
<211> LENGTH: 14
<212> TYPE: PRT
<213> ORGANISM: Artificial
<220> FEATURE:
<223> OTHER INFORMATION: Synthesized

<400> SEQUENCE: 102

Ser Ile Gln Ser Asp His Arg Glu Ile Glu Gly Arg Val Met
1               5                   10

<210> SEQ ID NO 103
<211> LENGTH: 13
<212> TYPE: PRT
<213> ORGANISM: Artificial
<220> FEATURE:
<223> OTHER INFORMATION: Synthesized

<400> SEQUENCE: 103

Ser Ile Gln Ser Asp His Arg Glu Ile Glu Gly Arg Val
1               5                   10

<210> SEQ ID NO 104
<211> LENGTH: 12
<212> TYPE: PRT
<213> ORGANISM: Artificial
<220> FEATURE:
<223> OTHER INFORMATION: Synthesized

<400> SEQUENCE: 104

Ser Ile Gln Ser Asp His Arg Glu Ile Glu Gly Arg
1               5                   10

<210> SEQ ID NO 105
<211> LENGTH: 11
<212> TYPE: PRT
<213> ORGANISM: Artificial
<220> FEATURE:
<223> OTHER INFORMATION: Synthesized

<400> SEQUENCE: 105

Ser Ile Gln Ser Asp His Arg Glu Ile Glu Gly
1               5                   10
```

<210> SEQ ID NO 106
<211> LENGTH: 10
<212> TYPE: PRT
<213> ORGANISM: Artificial
<220> FEATURE:
<223> OTHER INFORMATION: Synthesized

<400> SEQUENCE: 106

Ser Ile Gln Ser Asp His Arg Glu Ile Glu
1               5                   10

<210> SEQ ID NO 107
<211> LENGTH: 9
<212> TYPE: PRT
<213> ORGANISM: Artificial
<220> FEATURE:
<223> OTHER INFORMATION: Synthesized

<400> SEQUENCE: 107

Ser Ile Gln Ser Asp His Arg Glu Ile
1               5

<210> SEQ ID NO 108
<211> LENGTH: 13
<212> TYPE: PRT
<213> ORGANISM: Artificial
<220> FEATURE:
<223> OTHER INFORMATION: Synthesized

<400> SEQUENCE: 108

Ile Gln Ser Asp His Arg Glu Ile Glu Gly Arg Val Met
1               5                   10

<210> SEQ ID NO 109
<211> LENGTH: 12
<212> TYPE: PRT
<213> ORGANISM: Artificial
<220> FEATURE:
<223> OTHER INFORMATION: Synthesized

<400> SEQUENCE: 109

Ile Gln Ser Asp His Arg Glu Ile Glu Gly Arg Val
1               5                   10

<210> SEQ ID NO 110
<211> LENGTH: 11
<212> TYPE: PRT
<213> ORGANISM: Artificial
<220> FEATURE:
<223> OTHER INFORMATION: Synthesized

<400> SEQUENCE: 110

Ile Gln Ser Asp His Arg Glu Ile Glu Gly Arg
1               5                   10

<210> SEQ ID NO 111
<211> LENGTH: 10
<212> TYPE: PRT
<213> ORGANISM: Artificial
<220> FEATURE:
<223> OTHER INFORMATION: Synthesized

<400> SEQUENCE: 111

Ile Gln Ser Asp His Arg Glu Ile Glu Gly
1               5                   10

```
<210> SEQ ID NO 112
<211> LENGTH: 9
<212> TYPE: PRT
<213> ORGANISM: Artificial
<220> FEATURE:
<223> OTHER INFORMATION: Synthesized

<400> SEQUENCE: 112

Ile Gln Ser Asp His Arg Glu Ile Glu
1               5

<210> SEQ ID NO 113
<211> LENGTH: 8
<212> TYPE: PRT
<213> ORGANISM: Artificial
<220> FEATURE:
<223> OTHER INFORMATION: Synthesized

<400> SEQUENCE: 113

Ile Gln Ser Asp His Arg Glu Ile
1               5

<210> SEQ ID NO 114
<211> LENGTH: 12
<212> TYPE: PRT
<213> ORGANISM: Artificial
<220> FEATURE:
<223> OTHER INFORMATION: Synthesized

<400> SEQUENCE: 114

Gln Ser Asp His Arg Glu Ile Glu Gly Arg Val Met
1               5                   10

<210> SEQ ID NO 115
<211> LENGTH: 11
<212> TYPE: PRT
<213> ORGANISM: Artificial
<220> FEATURE:
<223> OTHER INFORMATION: Synthesized

<400> SEQUENCE: 115

Gln Ser Asp His Arg Glu Ile Glu Gly Arg Val
1               5                   10

<210> SEQ ID NO 116
<211> LENGTH: 10
<212> TYPE: PRT
<213> ORGANISM: Artificial
<220> FEATURE:
<223> OTHER INFORMATION: Synthesized

<400> SEQUENCE: 116

Gln Ser Asp His Arg Glu Ile Glu Gly Arg
1               5                   10

<210> SEQ ID NO 117
<211> LENGTH: 9
<212> TYPE: PRT
<213> ORGANISM: Artificial
<220> FEATURE:
<223> OTHER INFORMATION: Synthesized

<400> SEQUENCE: 117

Gln Ser Asp His Arg Glu Ile Glu Gly
1               5

<210> SEQ ID NO 118
```

```
<211> LENGTH: 8
<212> TYPE: PRT
<213> ORGANISM: Artificial
<220> FEATURE:
<223> OTHER INFORMATION: Synthesized

<400> SEQUENCE: 118

Gln Ser Asp His Arg Glu Ile Glu
1               5

<210> SEQ ID NO 119
<211> LENGTH: 7
<212> TYPE: PRT
<213> ORGANISM: Artificial
<220> FEATURE:
<223> OTHER INFORMATION: Synthesized

<400> SEQUENCE: 119

Gln Ser Asp His Arg Glu Ile
1               5

<210> SEQ ID NO 120
<211> LENGTH: 11
<212> TYPE: PRT
<213> ORGANISM: Artificial
<220> FEATURE:
<223> OTHER INFORMATION: Synthesized

<400> SEQUENCE: 120

Ser Asp His Arg Glu Ile Glu Gly Arg Val Met
1               5                   10

<210> SEQ ID NO 121
<211> LENGTH: 10
<212> TYPE: PRT
<213> ORGANISM: Artificial
<220> FEATURE:
<223> OTHER INFORMATION: Synthesized

<400> SEQUENCE: 121

Ser Asp His Arg Glu Ile Glu Gly Arg Val
1               5                   10

<210> SEQ ID NO 122
<211> LENGTH: 9
<212> TYPE: PRT
<213> ORGANISM: Artificial
<220> FEATURE:
<223> OTHER INFORMATION: Synthesized

<400> SEQUENCE: 122

Ser Asp His Arg Glu Ile Glu Gly Arg
1               5

<210> SEQ ID NO 123
<211> LENGTH: 8
<212> TYPE: PRT
<213> ORGANISM: Artificial
<220> FEATURE:
<223> OTHER INFORMATION: Synthesized

<400> SEQUENCE: 123

Ser Asp His Arg Glu Ile Glu Gly
1               5

<210> SEQ ID NO 124
<211> LENGTH: 7
```

```
<212> TYPE: PRT
<213> ORGANISM: Artificial
<220> FEATURE:
<223> OTHER INFORMATION: Synthesized

<400> SEQUENCE: 124

Ser Asp His Arg Glu Ile Glu
1               5

<210> SEQ ID NO 125
<211> LENGTH: 6
<212> TYPE: PRT
<213> ORGANISM: Artificial
<220> FEATURE:
<223> OTHER INFORMATION: Synthesized

<400> SEQUENCE: 125

Ser Asp His Arg Glu Ile
1               5

<210> SEQ ID NO 126
<211> LENGTH: 10
<212> TYPE: PRT
<213> ORGANISM: Artificial
<220> FEATURE:
<223> OTHER INFORMATION: Synthesized

<400> SEQUENCE: 126

Asp His Arg Glu Ile Glu Gly Arg Val Met
1               5                   10

<210> SEQ ID NO 127
<211> LENGTH: 9
<212> TYPE: PRT
<213> ORGANISM: Artificial
<220> FEATURE:
<223> OTHER INFORMATION: Synthesized

<400> SEQUENCE: 127

Asp His Arg Glu Ile Glu Gly Arg Val
1               5

<210> SEQ ID NO 128
<211> LENGTH: 8
<212> TYPE: PRT
<213> ORGANISM: Artificial
<220> FEATURE:
<223> OTHER INFORMATION: Synthesized

<400> SEQUENCE: 128

Asp His Arg Glu Ile Glu Gly Arg
1               5

<210> SEQ ID NO 129
<211> LENGTH: 7
<212> TYPE: PRT
<213> ORGANISM: Artificial
<220> FEATURE:
<223> OTHER INFORMATION: Synthesized

<400> SEQUENCE: 129

Asp His Arg Glu Ile Glu Gly
1               5

<210> SEQ ID NO 130
<211> LENGTH: 6
<212> TYPE: PRT
```

```
<213> ORGANISM: Artificial
<220> FEATURE:
<223> OTHER INFORMATION: Synthesized

<400> SEQUENCE: 130

Asp His Arg Glu Ile Glu
1               5

<210> SEQ ID NO 131
<211> LENGTH: 5
<212> TYPE: PRT
<213> ORGANISM: Artificial
<220> FEATURE:
<223> OTHER INFORMATION: Synthesized

<400> SEQUENCE: 131

Asp His Arg Glu Ile
1               5

<210> SEQ ID NO 132
<211> LENGTH: 9
<212> TYPE: PRT
<213> ORGANISM: Artificial
<220> FEATURE:
<223> OTHER INFORMATION: Synthesized

<400> SEQUENCE: 132

His Arg Glu Ile Glu Gly Arg Val Met
1               5

<210> SEQ ID NO 133
<211> LENGTH: 8
<212> TYPE: PRT
<213> ORGANISM: Artificial
<220> FEATURE:
<223> OTHER INFORMATION: Synthesized

<400> SEQUENCE: 133

His Arg Glu Ile Glu Gly Arg Val
1               5

<210> SEQ ID NO 134
<211> LENGTH: 7
<212> TYPE: PRT
<213> ORGANISM: Artificial
<220> FEATURE:
<223> OTHER INFORMATION: Synthesized

<400> SEQUENCE: 134

His Arg Glu Ile Glu Gly Arg
1               5

<210> SEQ ID NO 135
<211> LENGTH: 6
<212> TYPE: PRT
<213> ORGANISM: Artificial
<220> FEATURE:
<223> OTHER INFORMATION: Synthesized

<400> SEQUENCE: 135

His Arg Glu Ile Glu Gly
1               5

<210> SEQ ID NO 136
<211> LENGTH: 5
<212> TYPE: PRT
<213> ORGANISM: Artificial
```

```
<220> FEATURE:
<223> OTHER INFORMATION: Synthesized

<400> SEQUENCE: 136

His Arg Glu Ile Glu
1               5

<210> SEQ ID NO 137
<211> LENGTH: 8
<212> TYPE: PRT
<213> ORGANISM: Artificial
<220> FEATURE:
<223> OTHER INFORMATION: Synthesized

<400> SEQUENCE: 137

Arg Glu Ile Glu Gly Arg Val Met
1               5

<210> SEQ ID NO 138
<211> LENGTH: 7
<212> TYPE: PRT
<213> ORGANISM: Artificial
<220> FEATURE:
<223> OTHER INFORMATION: Synthesized

<400> SEQUENCE: 138

Arg Glu Ile Glu Gly Arg Val
1               5

<210> SEQ ID NO 139
<211> LENGTH: 6
<212> TYPE: PRT
<213> ORGANISM: Artificial
<220> FEATURE:
<223> OTHER INFORMATION: Synthesized

<400> SEQUENCE: 139

Arg Glu Ile Glu Gly Arg
1               5

<210> SEQ ID NO 140
<211> LENGTH: 5
<212> TYPE: PRT
<213> ORGANISM: Artificial
<220> FEATURE:
<223> OTHER INFORMATION: Synthesized

<400> SEQUENCE: 140

Arg Glu Ile Glu Gly
1               5

<210> SEQ ID NO 141
<211> LENGTH: 7
<212> TYPE: PRT
<213> ORGANISM: Artificial
<220> FEATURE:
<223> OTHER INFORMATION: Synthesized

<400> SEQUENCE: 141

Glu Ile Glu Gly Arg Val Met
1               5

<210> SEQ ID NO 142
<211> LENGTH: 6
<212> TYPE: PRT
<213> ORGANISM: Artificial
<220> FEATURE:
```

<223> OTHER INFORMATION: Synthesized

<400> SEQUENCE: 142

Glu Ile Glu Gly Arg Val
1               5

<210> SEQ ID NO 143
<211> LENGTH: 5
<212> TYPE: PRT
<213> ORGANISM: Artificial
<220> FEATURE:
<223> OTHER INFORMATION: Synthesized

<400> SEQUENCE: 143

Glu Ile Glu Gly Arg
1               5

<210> SEQ ID NO 144
<211> LENGTH: 6
<212> TYPE: PRT
<213> ORGANISM: Artificial
<220> FEATURE:
<223> OTHER INFORMATION: Synthesized

<400> SEQUENCE: 144

Ile Glu Gly Arg Val Met
1               5

<210> SEQ ID NO 145
<211> LENGTH: 5
<212> TYPE: PRT
<213> ORGANISM: Artificial
<220> FEATURE:
<223> OTHER INFORMATION: Synthesized

<400> SEQUENCE: 145

Ile Glu Gly Arg Val
1               5

<210> SEQ ID NO 146
<211> LENGTH: 5
<212> TYPE: PRT
<213> ORGANISM: Artificial
<220> FEATURE:
<223> OTHER INFORMATION: Synthesized

<400> SEQUENCE: 146

Glu Gly Arg Val Met
1               5

<210> SEQ ID NO 147
<211> LENGTH: 13
<212> TYPE: PRT
<213> ORGANISM: Artificial
<220> FEATURE:
<223> OTHER INFORMATION: Synthesized

<400> SEQUENCE: 147

Val Ser Gly Arg Asp Ala Gly Val Ala Lys Gly Ala Ser
1               5                   10

<210> SEQ ID NO 148
<211> LENGTH: 12
<212> TYPE: PRT
<213> ORGANISM: Artificial
<220> FEATURE:
<223> OTHER INFORMATION: Synthesized -continued

<400> SEQUENCE: 148

Val Ser Gly Arg Asp Ala Gly Val Ala Lys Gly Ala
1               5                   10

<210> SEQ ID NO 149
<211> LENGTH: 11
<212> TYPE: PRT
<213> ORGANISM: Artificial
<220> FEATURE:
<223> OTHER INFORMATION: Synthesized

<400> SEQUENCE: 149

Val Ser Gly Arg Asp Ala Gly Val Ala Lys Gly
1               5                   10

<210> SEQ ID NO 150
<211> LENGTH: 10
<212> TYPE: PRT
<213> ORGANISM: Artificial
<220> FEATURE:
<223> OTHER INFORMATION: Synthesized

<400> SEQUENCE: 150

Val Ser Gly Arg Asp Ala Gly Val Ala Lys
1               5                   10

<210> SEQ ID NO 151
<211> LENGTH: 9
<212> TYPE: PRT
<213> ORGANISM: Artificial
<220> FEATURE:
<223> OTHER INFORMATION: Synthesized

<400> SEQUENCE: 151

Val Ser Gly Arg Asp Ala Gly Val Ala
1               5

<210> SEQ ID NO 152
<211> LENGTH: 12
<212> TYPE: PRT
<213> ORGANISM: Artificial
<220> FEATURE:
<223> OTHER INFORMATION: Synthesized

<400> SEQUENCE: 152

Ser Gly Arg Asp Ala Gly Val Ala Lys Gly Ala Ser
1               5                   10

<210> SEQ ID NO 153
<211> LENGTH: 11
<212> TYPE: PRT
<213> ORGANISM: Artificial
<220> FEATURE:
<223> OTHER INFORMATION: Synthesized

<400> SEQUENCE: 153

Ser Gly Arg Asp Ala Gly Val Ala Lys Gly Ala
1               5                   10

<210> SEQ ID NO 154
<211> LENGTH: 10
<212> TYPE: PRT
<213> ORGANISM: Artificial
<220> FEATURE:
<223> OTHER INFORMATION: Synthesized

```
<400> SEQUENCE: 154

Ser Gly Arg Asp Ala Gly Val Ala Lys Gly
1               5                   10

<210> SEQ ID NO 155
<211> LENGTH: 9
<212> TYPE: PRT
<213> ORGANISM: Artificial
<220> FEATURE:
<223> OTHER INFORMATION: Synthesized

<400> SEQUENCE: 155

Ser Gly Arg Asp Ala Gly Val Ala Lys
1               5

<210> SEQ ID NO 156
<211> LENGTH: 8
<212> TYPE: PRT
<213> ORGANISM: Artificial
<220> FEATURE:
<223> OTHER INFORMATION: Synthesized

<400> SEQUENCE: 156

Ser Gly Arg Asp Ala Gly Val Ala
1               5

<210> SEQ ID NO 157
<211> LENGTH: 11
<212> TYPE: PRT
<213> ORGANISM: Artificial
<220> FEATURE:
<223> OTHER INFORMATION: Synthesized

<400> SEQUENCE: 157

Gly Arg Asp Ala Gly Val Ala Lys Gly Ala Ser
1               5                   10

<210> SEQ ID NO 158
<211> LENGTH: 10
<212> TYPE: PRT
<213> ORGANISM: Artificial
<220> FEATURE:
<223> OTHER INFORMATION: Synthesized

<400> SEQUENCE: 158

Gly Arg Asp Ala Gly Val Ala Lys Gly Ala
1               5                   10

<210> SEQ ID NO 159
<211> LENGTH: 9
<212> TYPE: PRT
<213> ORGANISM: Artificial
<220> FEATURE:
<223> OTHER INFORMATION: Synthesized

<400> SEQUENCE: 159

Gly Arg Asp Ala Gly Val Ala Lys Gly
1               5

<210> SEQ ID NO 160
<211> LENGTH: 8
<212> TYPE: PRT
<213> ORGANISM: Artificial
<220> FEATURE:
<223> OTHER INFORMATION: Synthesized

<400> SEQUENCE: 160
```

Gly Arg Asp Ala Gly Val Ala Lys
1               5

<210> SEQ ID NO 161
<211> LENGTH: 7
<212> TYPE: PRT
<213> ORGANISM: Artificial
<220> FEATURE:
<223> OTHER INFORMATION: Synthesized

<400> SEQUENCE: 161

Gly Arg Asp Ala Gly Val Ala
1               5

<210> SEQ ID NO 162
<211> LENGTH: 10
<212> TYPE: PRT
<213> ORGANISM: Artificial
<220> FEATURE:
<223> OTHER INFORMATION: Synthesized

<400> SEQUENCE: 162

Arg Asp Ala Gly Val Ala Lys Gly Ala Ser
1               5                   10

<210> SEQ ID NO 163
<211> LENGTH: 9
<212> TYPE: PRT
<213> ORGANISM: Artificial
<220> FEATURE:
<223> OTHER INFORMATION: Synthesized

<400> SEQUENCE: 163

Arg Asp Ala Gly Val Ala Lys Gly Ala
1               5

<210> SEQ ID NO 164
<211> LENGTH: 8
<212> TYPE: PRT
<213> ORGANISM: Artificial
<220> FEATURE:
<223> OTHER INFORMATION: Synthesized

<400> SEQUENCE: 164

Arg Asp Ala Gly Val Ala Lys Gly
1               5

<210> SEQ ID NO 165
<211> LENGTH: 7
<212> TYPE: PRT
<213> ORGANISM: Artificial
<220> FEATURE:
<223> OTHER INFORMATION: Synthesized

<400> SEQUENCE: 165

Arg Asp Ala Gly Val Ala Lys
1               5

<210> SEQ ID NO 166
<211> LENGTH: 6
<212> TYPE: PRT
<213> ORGANISM: Artificial
<220> FEATURE:
<223> OTHER INFORMATION: Synthesized

<400> SEQUENCE: 166

Arg Asp Ala Gly Val Ala
1               5

<210> SEQ ID NO 167
<211> LENGTH: 9
<212> TYPE: PRT
<213> ORGANISM: Artificial
<220> FEATURE:
<223> OTHER INFORMATION: Synthesized

<400> SEQUENCE: 167

Asp Ala Gly Val Ala Lys Gly Ala Ser
1               5

<210> SEQ ID NO 168
<211> LENGTH: 8
<212> TYPE: PRT
<213> ORGANISM: Artificial
<220> FEATURE:
<223> OTHER INFORMATION: Synthesized

<400> SEQUENCE: 168

Asp Ala Gly Val Ala Lys Gly Ala
1               5

<210> SEQ ID NO 169
<211> LENGTH: 7
<212> TYPE: PRT
<213> ORGANISM: Artificial
<220> FEATURE:
<223> OTHER INFORMATION: Synthesized

<400> SEQUENCE: 169

Asp Ala Gly Val Ala Lys Gly
1               5

<210> SEQ ID NO 170
<211> LENGTH: 6
<212> TYPE: PRT
<213> ORGANISM: Artificial
<220> FEATURE:
<223> OTHER INFORMATION: Synthesized

<400> SEQUENCE: 170

Asp Ala Gly Val Ala Lys
1               5

<210> SEQ ID NO 171
<211> LENGTH: 5
<212> TYPE: PRT
<213> ORGANISM: Artificial
<220> FEATURE:
<223> OTHER INFORMATION: Synthesized

<400> SEQUENCE: 171

Asp Ala Gly Val Ala
1               5

<210> SEQ ID NO 172
<211> LENGTH: 8
<212> TYPE: PRT
<213> ORGANISM: Artificial
<220> FEATURE:
<223> OTHER INFORMATION: Synthesized

<400> SEQUENCE: 172

Ala Gly Val Ala Lys Gly Ala Ser

```
1               5

<210> SEQ ID NO 173
<211> LENGTH: 7
<212> TYPE: PRT
<213> ORGANISM: Artificial
<220> FEATURE:
<223> OTHER INFORMATION: Synthesized

<400> SEQUENCE: 173

Ala Gly Val Ala Lys Gly Ala
1               5

<210> SEQ ID NO 174
<211> LENGTH: 6
<212> TYPE: PRT
<213> ORGANISM: Artificial
<220> FEATURE:
<223> OTHER INFORMATION: Synthesized

<400> SEQUENCE: 174

Ala Gly Val Ala Lys Gly
1               5

<210> SEQ ID NO 175
<211> LENGTH: 5
<212> TYPE: PRT
<213> ORGANISM: Artificial
<220> FEATURE:
<223> OTHER INFORMATION: Synthesized

<400> SEQUENCE: 175

Ala Gly Val Ala Lys
1               5

<210> SEQ ID NO 176
<211> LENGTH: 7
<212> TYPE: PRT
<213> ORGANISM: Artificial
<220> FEATURE:
<223> OTHER INFORMATION: Synthesized

<400> SEQUENCE: 176

Gly Val Ala Lys Gly Ala Ser
1               5

<210> SEQ ID NO 177
<211> LENGTH: 6
<212> TYPE: PRT
<213> ORGANISM: Artificial
<220> FEATURE:
<223> OTHER INFORMATION: Synthesized

<400> SEQUENCE: 177

Gly Val Ala Lys Gly Ala
1               5

<210> SEQ ID NO 178
<211> LENGTH: 5
<212> TYPE: PRT
<213> ORGANISM: Artificial
<220> FEATURE:
<223> OTHER INFORMATION: Synthesized

<400> SEQUENCE: 178

Gly Val Ala Lys Gly
1               5
```

<210> SEQ ID NO 179
<211> LENGTH: 6
<212> TYPE: PRT
<213> ORGANISM: Artificial
<220> FEATURE:
<223> OTHER INFORMATION: Synthesized

<400> SEQUENCE: 179

Val Ala Lys Gly Ala Ser
1               5

<210> SEQ ID NO 180
<211> LENGTH: 5
<212> TYPE: PRT
<213> ORGANISM: Artificial
<220> FEATURE:
<223> OTHER INFORMATION: Synthesized

<400> SEQUENCE: 180

Val Ala Lys Gly Ala
1               5

<210> SEQ ID NO 181
<211> LENGTH: 5
<212> TYPE: PRT
<213> ORGANISM: Artificial
<220> FEATURE:
<223> OTHER INFORMATION: Synthesized

<400> SEQUENCE: 181

Ala Lys Gly Ala Ser
1               5

<210> SEQ ID NO 182
<211> LENGTH: 13
<212> TYPE: PRT
<213> ORGANISM: Artificial
<220> FEATURE:
<223> OTHER INFORMATION: Synthesized

<400> SEQUENCE: 182

Ser Ile Pro Trp Asn Leu Glu Arg Ile Thr Pro Pro Arg
1               5                   10

<210> SEQ ID NO 183
<211> LENGTH: 12
<212> TYPE: PRT
<213> ORGANISM: Artificial
<220> FEATURE:
<223> OTHER INFORMATION: Synthesized

<400> SEQUENCE: 183

Ser Ile Pro Trp Asn Leu Glu Arg Ile Thr Pro Pro
1               5                   10

<210> SEQ ID NO 184
<211> LENGTH: 11
<212> TYPE: PRT
<213> ORGANISM: Artificial
<220> FEATURE:
<223> OTHER INFORMATION: Synthesized

<400> SEQUENCE: 184

Ser Ile Pro Trp Asn Leu Glu Arg Ile Thr Pro
1               5                   10

<210> SEQ ID NO 185
<211> LENGTH: 10
<212> TYPE: PRT
<213> ORGANISM: Artificial
<220> FEATURE:
<223> OTHER INFORMATION: Synthesized

<400> SEQUENCE: 185

Ser Ile Pro Trp Asn Leu Glu Arg Ile Thr
1               5                   10

<210> SEQ ID NO 186
<211> LENGTH: 9
<212> TYPE: PRT
<213> ORGANISM: Artificial
<220> FEATURE:
<223> OTHER INFORMATION: Synthesized

<400> SEQUENCE: 186

Ser Ile Pro Trp Asn Leu Glu Arg Ile
1               5

<210> SEQ ID NO 187
<211> LENGTH: 8
<212> TYPE: PRT
<213> ORGANISM: Artificial
<220> FEATURE:
<223> OTHER INFORMATION: Synthesized

<400> SEQUENCE: 187

Ser Ile Pro Trp Asn Leu Glu Arg
1               5

<210> SEQ ID NO 188
<211> LENGTH: 7
<212> TYPE: PRT
<213> ORGANISM: Artificial
<220> FEATURE:
<223> OTHER INFORMATION: Synthesized

<400> SEQUENCE: 188

Ser Ile Pro Trp Asn Leu Glu
1               5

<210> SEQ ID NO 189
<211> LENGTH: 6
<212> TYPE: PRT
<213> ORGANISM: Artificial
<220> FEATURE:
<223> OTHER INFORMATION: Synthesized

<400> SEQUENCE: 189

Ser Ile Pro Trp Asn Leu
1               5

<210> SEQ ID NO 190
<211> LENGTH: 5
<212> TYPE: PRT
<213> ORGANISM: Artificial
<220> FEATURE:
<223> OTHER INFORMATION: Synthesized

<400> SEQUENCE: 190

Ser Ile Pro Trp Asn
1               5

```
<210> SEQ ID NO 191
<211> LENGTH: 12
<212> TYPE: PRT
<213> ORGANISM: Artificial
<220> FEATURE:
<223> OTHER INFORMATION: Synthesized

<400> SEQUENCE: 191

Ile Pro Trp Asn Leu Glu Arg Ile Thr Pro Pro Arg
1               5                   10

<210> SEQ ID NO 192
<211> LENGTH: 11
<212> TYPE: PRT
<213> ORGANISM: Artificial
<220> FEATURE:
<223> OTHER INFORMATION: Synthesized

<400> SEQUENCE: 192

Ile Pro Trp Asn Leu Glu Arg Ile Thr Pro Pro
1               5                   10

<210> SEQ ID NO 193
<211> LENGTH: 10
<212> TYPE: PRT
<213> ORGANISM: Artificial
<220> FEATURE:
<223> OTHER INFORMATION: Synthesized

<400> SEQUENCE: 193

Ile Pro Trp Asn Leu Glu Arg Ile Thr Pro
1               5                   10

<210> SEQ ID NO 194
<211> LENGTH: 9
<212> TYPE: PRT
<213> ORGANISM: Artificial
<220> FEATURE:
<223> OTHER INFORMATION: Synthesized

<400> SEQUENCE: 194

Ile Pro Trp Asn Leu Glu Arg Ile Thr
1               5

<210> SEQ ID NO 195
<211> LENGTH: 8
<212> TYPE: PRT
<213> ORGANISM: Artificial
<220> FEATURE:
<223> OTHER INFORMATION: Synthesized

<400> SEQUENCE: 195

Ile Pro Trp Asn Leu Glu Arg Ile
1               5

<210> SEQ ID NO 196
<211> LENGTH: 7
<212> TYPE: PRT
<213> ORGANISM: Artificial
<220> FEATURE:
<223> OTHER INFORMATION: Synthesized

<400> SEQUENCE: 196

Ile Pro Trp Asn Leu Glu Arg
1               5

<210> SEQ ID NO 197
```

```
<211> LENGTH: 6
<212> TYPE: PRT
<213> ORGANISM: Artificial
<220> FEATURE:
<223> OTHER INFORMATION: Synthesized

<400> SEQUENCE: 197

Ile Pro Trp Asn Leu Glu
1               5

<210> SEQ ID NO 198
<211> LENGTH: 5
<212> TYPE: PRT
<213> ORGANISM: Artificial
<220> FEATURE:
<223> OTHER INFORMATION: Synthesized

<400> SEQUENCE: 198

Ile Pro Trp Asn Leu
1               5

<210> SEQ ID NO 199
<211> LENGTH: 11
<212> TYPE: PRT
<213> ORGANISM: Artificial
<220> FEATURE:
<223> OTHER INFORMATION: Synthesized

<400> SEQUENCE: 199

Pro Trp Asn Leu Glu Arg Ile Thr Pro Pro Arg
1               5                   10

<210> SEQ ID NO 200
<211> LENGTH: 10
<212> TYPE: PRT
<213> ORGANISM: Artificial
<220> FEATURE:
<223> OTHER INFORMATION: Synthesized

<400> SEQUENCE: 200

Pro Trp Asn Leu Glu Arg Ile Thr Pro Pro
1               5                   10

<210> SEQ ID NO 201
<211> LENGTH: 9
<212> TYPE: PRT
<213> ORGANISM: Artificial
<220> FEATURE:
<223> OTHER INFORMATION: Synthesized

<400> SEQUENCE: 201

Pro Trp Asn Leu Glu Arg Ile Thr Pro
1               5

<210> SEQ ID NO 202
<211> LENGTH: 8
<212> TYPE: PRT
<213> ORGANISM: Artificial
<220> FEATURE:
<223> OTHER INFORMATION: Synthesized

<400> SEQUENCE: 202

Pro Trp Asn Leu Glu Arg Ile Thr
1               5

<210> SEQ ID NO 203
<211> LENGTH: 7
```

```
<212> TYPE: PRT
<213> ORGANISM: Artificial
<220> FEATURE:
<223> OTHER INFORMATION: Synthesized

<400> SEQUENCE: 203

Pro Trp Asn Leu Glu Arg Ile
1               5

<210> SEQ ID NO 204
<211> LENGTH: 6
<212> TYPE: PRT
<213> ORGANISM: Artificial
<220> FEATURE:
<223> OTHER INFORMATION: Synthesized

<400> SEQUENCE: 204

Pro Trp Asn Leu Glu Arg
1               5

<210> SEQ ID NO 205
<211> LENGTH: 5
<212> TYPE: PRT
<213> ORGANISM: Artificial
<220> FEATURE:
<223> OTHER INFORMATION: Synthesized

<400> SEQUENCE: 205

Pro Trp Asn Leu Glu
1               5

<210> SEQ ID NO 206
<211> LENGTH: 10
<212> TYPE: PRT
<213> ORGANISM: Artificial
<220> FEATURE:
<223> OTHER INFORMATION: Synthesized

<400> SEQUENCE: 206

Trp Asn Leu Glu Arg Ile Thr Pro Pro Arg
1               5                   10

<210> SEQ ID NO 207
<211> LENGTH: 9
<212> TYPE: PRT
<213> ORGANISM: Artificial
<220> FEATURE:
<223> OTHER INFORMATION: Synthesized

<400> SEQUENCE: 207

Trp Asn Leu Glu Arg Ile Thr Pro Pro
1               5

<210> SEQ ID NO 208
<211> LENGTH: 8
<212> TYPE: PRT
<213> ORGANISM: Artificial
<220> FEATURE:
<223> OTHER INFORMATION: Synthesized

<400> SEQUENCE: 208

Trp Asn Leu Glu Arg Ile Thr Pro
1               5

<210> SEQ ID NO 209
<211> LENGTH: 7
<212> TYPE: PRT
```

```
<213> ORGANISM: Artificial
<220> FEATURE:
<223> OTHER INFORMATION: Synthesized

<400> SEQUENCE: 209

Trp Asn Leu Glu Arg Ile Thr
1               5

<210> SEQ ID NO 210
<211> LENGTH: 6
<212> TYPE: PRT
<213> ORGANISM: Artificial
<220> FEATURE:
<223> OTHER INFORMATION: Synthesized

<400> SEQUENCE: 210

Trp Asn Leu Glu Arg Ile
1               5

<210> SEQ ID NO 211
<211> LENGTH: 5
<212> TYPE: PRT
<213> ORGANISM: Artificial
<220> FEATURE:
<223> OTHER INFORMATION: Synthesized

<400> SEQUENCE: 211

Trp Asn Leu Glu Arg
1               5

<210> SEQ ID NO 212
<211> LENGTH: 9
<212> TYPE: PRT
<213> ORGANISM: Artificial
<220> FEATURE:
<223> OTHER INFORMATION: Synthesized

<400> SEQUENCE: 212

Asn Leu Glu Arg Ile Thr Pro Pro Arg
1               5

<210> SEQ ID NO 213
<211> LENGTH: 8
<212> TYPE: PRT
<213> ORGANISM: Artificial
<220> FEATURE:
<223> OTHER INFORMATION: Synthesized

<400> SEQUENCE: 213

Asn Leu Glu Arg Ile Thr Pro Pro
1               5

<210> SEQ ID NO 214
<211> LENGTH: 7
<212> TYPE: PRT
<213> ORGANISM: Artificial
<220> FEATURE:
<223> OTHER INFORMATION: Synthesized

<400> SEQUENCE: 214

Asn Leu Glu Arg Ile Thr Pro
1               5

<210> SEQ ID NO 215
<211> LENGTH: 6
<212> TYPE: PRT
<213> ORGANISM: Artificial
```

```
<220> FEATURE:
<223> OTHER INFORMATION: Synthesized

<400> SEQUENCE: 215

Asn Leu Glu Arg Ile Thr
1               5

<210> SEQ ID NO 216
<211> LENGTH: 5
<212> TYPE: PRT
<213> ORGANISM: Artificial
<220> FEATURE:
<223> OTHER INFORMATION: Synthesized

<400> SEQUENCE: 216

Asn Leu Glu Arg Ile
1               5

<210> SEQ ID NO 217
<211> LENGTH: 8
<212> TYPE: PRT
<213> ORGANISM: Artificial
<220> FEATURE:
<223> OTHER INFORMATION: Synthesized

<400> SEQUENCE: 217

Leu Glu Arg Ile Thr Pro Pro Arg
1               5

<210> SEQ ID NO 218
<211> LENGTH: 7
<212> TYPE: PRT
<213> ORGANISM: Artificial
<220> FEATURE:
<223> OTHER INFORMATION: Synthesized

<400> SEQUENCE: 218

Leu Glu Arg Ile Thr Pro Pro
1               5

<210> SEQ ID NO 219
<211> LENGTH: 6
<212> TYPE: PRT
<213> ORGANISM: Artificial
<220> FEATURE:
<223> OTHER INFORMATION: Synthesized

<400> SEQUENCE: 219

Leu Glu Arg Ile Thr Pro
1               5

<210> SEQ ID NO 220
<211> LENGTH: 5
<212> TYPE: PRT
<213> ORGANISM: Artificial
<220> FEATURE:
<223> OTHER INFORMATION: Synthesized

<400> SEQUENCE: 220

Leu Glu Arg Ile Thr
1               5

<210> SEQ ID NO 221
<211> LENGTH: 7
<212> TYPE: PRT
<213> ORGANISM: Artificial
<220> FEATURE:
```

<223> OTHER INFORMATION: Synthesized

<400> SEQUENCE: 221

Glu Arg Ile Thr Pro Pro Arg
1               5

<210> SEQ ID NO 222
<211> LENGTH: 6
<212> TYPE: PRT
<213> ORGANISM: Artificial
<220> FEATURE:
<223> OTHER INFORMATION: Synthesized

<400> SEQUENCE: 222

Glu Arg Ile Thr Pro Pro
1               5

<210> SEQ ID NO 223
<211> LENGTH: 5
<212> TYPE: PRT
<213> ORGANISM: Artificial
<220> FEATURE:
<223> OTHER INFORMATION: Synthesized

<400> SEQUENCE: 223

Glu Arg Ile Thr Pro
1               5

<210> SEQ ID NO 224
<211> LENGTH: 6
<212> TYPE: PRT
<213> ORGANISM: Artificial
<220> FEATURE:
<223> OTHER INFORMATION: Synthesized

<400> SEQUENCE: 224

Arg Ile Thr Pro Pro Arg
1               5

<210> SEQ ID NO 225
<211> LENGTH: 5
<212> TYPE: PRT
<213> ORGANISM: Artificial
<220> FEATURE:
<223> OTHER INFORMATION: Synthesized

<400> SEQUENCE: 225

Arg Ile Thr Pro Pro
1               5

<210> SEQ ID NO 226
<211> LENGTH: 5
<212> TYPE: PRT
<213> ORGANISM: Artificial
<220> FEATURE:
<223> OTHER INFORMATION: Synthesized

<400> SEQUENCE: 226

Ile Thr Pro Pro Arg
1               5

<210> SEQ ID NO 227
<211> LENGTH: 12
<212> TYPE: PRT
<213> ORGANISM: Artificial
<220> FEATURE:
<223> OTHER INFORMATION: Synthesized

<400> SEQUENCE: 227

Asn Ala Gln Asp Gln Pro Val Thr Leu Gly Thr Leu
1               5                   10

<210> SEQ ID NO 228
<211> LENGTH: 11
<212> TYPE: PRT
<213> ORGANISM: Artificial
<220> FEATURE:
<223> OTHER INFORMATION: Synthesized

<400> SEQUENCE: 228

Asn Ala Gln Asp Gln Pro Val Thr Leu Gly Thr
1               5                   10

<210> SEQ ID NO 229
<211> LENGTH: 10
<212> TYPE: PRT
<213> ORGANISM: Artificial
<220> FEATURE:
<223> OTHER INFORMATION: Synthesized

<400> SEQUENCE: 229

Asn Ala Gln Asp Gln Pro Val Thr Leu Gly
1               5                   10

<210> SEQ ID NO 230
<211> LENGTH: 9
<212> TYPE: PRT
<213> ORGANISM: Artificial
<220> FEATURE:
<223> OTHER INFORMATION: Synthesized

<400> SEQUENCE: 230

Asn Ala Gln Asp Gln Pro Val Thr Leu
1               5

<210> SEQ ID NO 231
<211> LENGTH: 8
<212> TYPE: PRT
<213> ORGANISM: Artificial
<220> FEATURE:
<223> OTHER INFORMATION: Synthesized

<400> SEQUENCE: 231

Asn Ala Gln Asp Gln Pro Val Thr
1               5

<210> SEQ ID NO 232
<211> LENGTH: 7
<212> TYPE: PRT
<213> ORGANISM: Artificial
<220> FEATURE:
<223> OTHER INFORMATION: Synthesized

<400> SEQUENCE: 232

Asn Ala Gln Asp Gln Pro Val
1               5

<210> SEQ ID NO 233
<211> LENGTH: 6
<212> TYPE: PRT
<213> ORGANISM: Artificial
<220> FEATURE:
<223> OTHER INFORMATION: Synthesized

```
<400> SEQUENCE: 233

Asn Ala Gln Asp Gln Pro
1               5

<210> SEQ ID NO 234
<211> LENGTH: 5
<212> TYPE: PRT
<213> ORGANISM: Artificial
<220> FEATURE:
<223> OTHER INFORMATION: Synthesized

<400> SEQUENCE: 234

Asn Ala Gln Asp Gln
1               5

<210> SEQ ID NO 235
<211> LENGTH: 11
<212> TYPE: PRT
<213> ORGANISM: Artificial
<220> FEATURE:
<223> OTHER INFORMATION: Synthesized

<400> SEQUENCE: 235

Ala Gln Asp Gln Pro Val Thr Leu Gly Thr Leu
1               5                   10

<210> SEQ ID NO 236
<211> LENGTH: 10
<212> TYPE: PRT
<213> ORGANISM: Artificial
<220> FEATURE:
<223> OTHER INFORMATION: Synthesized

<400> SEQUENCE: 236

Ala Gln Asp Gln Pro Val Thr Leu Gly Thr
1               5                   10

<210> SEQ ID NO 237
<211> LENGTH: 9
<212> TYPE: PRT
<213> ORGANISM: Artificial
<220> FEATURE:
<223> OTHER INFORMATION: Synthesized

<400> SEQUENCE: 237

Ala Gln Asp Gln Pro Val Thr Leu Gly
1               5

<210> SEQ ID NO 238
<211> LENGTH: 8
<212> TYPE: PRT
<213> ORGANISM: Artificial
<220> FEATURE:
<223> OTHER INFORMATION: Synthesized

<400> SEQUENCE: 238

Ala Gln Asp Gln Pro Val Thr Leu
1               5

<210> SEQ ID NO 239
<211> LENGTH: 7
<212> TYPE: PRT
<213> ORGANISM: Artificial
<220> FEATURE:
<223> OTHER INFORMATION: Synthesized

<400> SEQUENCE: 239
```

```
Ala Gln Asp Gln Pro Val Thr
1               5

<210> SEQ ID NO 240
<211> LENGTH: 6
<212> TYPE: PRT
<213> ORGANISM: Artificial
<220> FEATURE:
<223> OTHER INFORMATION: Synthesized

<400> SEQUENCE: 240

Ala Gln Asp Gln Pro Val
1               5

<210> SEQ ID NO 241
<211> LENGTH: 5
<212> TYPE: PRT
<213> ORGANISM: Artificial
<220> FEATURE:
<223> OTHER INFORMATION: Synthesized

<400> SEQUENCE: 241

Ala Gln Asp Gln Pro
1               5

<210> SEQ ID NO 242
<211> LENGTH: 10
<212> TYPE: PRT
<213> ORGANISM: Artificial
<220> FEATURE:
<223> OTHER INFORMATION: Synthesized

<400> SEQUENCE: 242

Gln Asp Gln Pro Val Thr Leu Gly Thr Leu
1               5                   10

<210> SEQ ID NO 243
<211> LENGTH: 9
<212> TYPE: PRT
<213> ORGANISM: Artificial
<220> FEATURE:
<223> OTHER INFORMATION: Synthesized

<400> SEQUENCE: 243

Gln Asp Gln Pro Val Thr Leu Gly Thr
1               5

<210> SEQ ID NO 244
<211> LENGTH: 8
<212> TYPE: PRT
<213> ORGANISM: Artificial
<220> FEATURE:
<223> OTHER INFORMATION: Synthesized

<400> SEQUENCE: 244

Gln Asp Gln Pro Val Thr Leu Gly
1               5

<210> SEQ ID NO 245
<211> LENGTH: 7
<212> TYPE: PRT
<213> ORGANISM: Artificial
<220> FEATURE:
<223> OTHER INFORMATION: Synthesized

<400> SEQUENCE: 245
```

```
Gln Asp Gln Pro Val Thr Leu
1               5

<210> SEQ ID NO 246
<211> LENGTH: 6
<212> TYPE: PRT
<213> ORGANISM: Artificial
<220> FEATURE:
<223> OTHER INFORMATION: Synthesized

<400> SEQUENCE: 246

Gln Asp Gln Pro Val Thr
1               5

<210> SEQ ID NO 247
<211> LENGTH: 5
<212> TYPE: PRT
<213> ORGANISM: Artificial
<220> FEATURE:
<223> OTHER INFORMATION: Synthesized

<400> SEQUENCE: 247

Gln Asp Gln Pro Val
1               5

<210> SEQ ID NO 248
<211> LENGTH: 9
<212> TYPE: PRT
<213> ORGANISM: Artificial
<220> FEATURE:
<223> OTHER INFORMATION: Synthesized

<400> SEQUENCE: 248

Asp Gln Pro Val Thr Leu Gly Thr Leu
1               5

<210> SEQ ID NO 249
<211> LENGTH: 8
<212> TYPE: PRT
<213> ORGANISM: Artificial
<220> FEATURE:
<223> OTHER INFORMATION: Synthesized

<400> SEQUENCE: 249

Asp Gln Pro Val Thr Leu Gly Thr
1               5

<210> SEQ ID NO 250
<211> LENGTH: 7
<212> TYPE: PRT
<213> ORGANISM: Artificial
<220> FEATURE:
<223> OTHER INFORMATION: Synthesized

<400> SEQUENCE: 250

Asp Gln Pro Val Thr Leu Gly
1               5

<210> SEQ ID NO 251
<211> LENGTH: 6
<212> TYPE: PRT
<213> ORGANISM: Artificial
<220> FEATURE:
<223> OTHER INFORMATION: Synthesized

<400> SEQUENCE: 251

Asp Gln Pro Val Thr Leu
```

```
<210> SEQ ID NO 252
<211> LENGTH: 5
<212> TYPE: PRT
<213> ORGANISM: Artificial
<220> FEATURE:
<223> OTHER INFORMATION: Synthesized

<400> SEQUENCE: 252

Asp Gln Pro Val Thr
1               5

<210> SEQ ID NO 253
<211> LENGTH: 8
<212> TYPE: PRT
<213> ORGANISM: Artificial
<220> FEATURE:
<223> OTHER INFORMATION: Synthesized

<400> SEQUENCE: 253

Gln Pro Val Thr Leu Gly Thr Leu
1               5

<210> SEQ ID NO 254
<211> LENGTH: 7
<212> TYPE: PRT
<213> ORGANISM: Artificial
<220> FEATURE:
<223> OTHER INFORMATION: Synthesized

<400> SEQUENCE: 254

Gln Pro Val Thr Leu Gly Thr
1               5

<210> SEQ ID NO 255
<211> LENGTH: 6
<212> TYPE: PRT
<213> ORGANISM: Artificial
<220> FEATURE:
<223> OTHER INFORMATION: Synthesized

<400> SEQUENCE: 255

Gln Pro Val Thr Leu Gly
1               5

<210> SEQ ID NO 256
<211> LENGTH: 5
<212> TYPE: PRT
<213> ORGANISM: Artificial
<220> FEATURE:
<223> OTHER INFORMATION: Synthesized

<400> SEQUENCE: 256

Gln Pro Val Thr Leu
1               5

<210> SEQ ID NO 257
<211> LENGTH: 7
<212> TYPE: PRT
<213> ORGANISM: Artificial
<220> FEATURE:
<223> OTHER INFORMATION: Synthesized

<400> SEQUENCE: 257

Pro Val Thr Leu Gly Thr Leu
1               5
```

```
<210> SEQ ID NO 258
<211> LENGTH: 6
<212> TYPE: PRT
<213> ORGANISM: Artificial
<220> FEATURE:
<223> OTHER INFORMATION: Synthesized

<400> SEQUENCE: 258

Pro Val Thr Leu Gly Thr
1               5

<210> SEQ ID NO 259
<211> LENGTH: 5
<212> TYPE: PRT
<213> ORGANISM: Artificial
<220> FEATURE:
<223> OTHER INFORMATION: Synthesized

<400> SEQUENCE: 259

Pro Val Thr Leu Gly
1               5

<210> SEQ ID NO 260
<211> LENGTH: 6
<212> TYPE: PRT
<213> ORGANISM: Artificial
<220> FEATURE:
<223> OTHER INFORMATION: Synthesized

<400> SEQUENCE: 260

Val Thr Leu Gly Thr Leu
1               5

<210> SEQ ID NO 261
<211> LENGTH: 5
<212> TYPE: PRT
<213> ORGANISM: Artificial
<220> FEATURE:
<223> OTHER INFORMATION: Synthesized

<400> SEQUENCE: 261

Val Thr Leu Gly Thr
1               5

<210> SEQ ID NO 262
<211> LENGTH: 5
<212> TYPE: PRT
<213> ORGANISM: Artificial
<220> FEATURE:
<223> OTHER INFORMATION: Synthesized

<400> SEQUENCE: 262

Thr Leu Gly Thr Leu
1               5

<210> SEQ ID NO 263
<211> LENGTH: 13
<212> TYPE: PRT
<213> ORGANISM: Artificial
<220> FEATURE:
<223> OTHER INFORMATION: Synthesized

<400> SEQUENCE: 263

Ile Asn Glu Ala Trp Phe Pro Glu Asp Gln Arg Val Leu
1               5                   10
```

```
<210> SEQ ID NO 264
<211> LENGTH: 12
<212> TYPE: PRT
<213> ORGANISM: Artificial
<220> FEATURE:
<223> OTHER INFORMATION: Synthesized

<400> SEQUENCE: 264

Ile Asn Glu Ala Trp Phe Pro Glu Asp Gln Arg Val
1               5                   10

<210> SEQ ID NO 265
<211> LENGTH: 11
<212> TYPE: PRT
<213> ORGANISM: Artificial
<220> FEATURE:
<223> OTHER INFORMATION: Synthesized

<400> SEQUENCE: 265

Ile Asn Glu Ala Trp Phe Pro Glu Asp Gln Arg
1               5                   10

<210> SEQ ID NO 266
<211> LENGTH: 10
<212> TYPE: PRT
<213> ORGANISM: Artificial
<220> FEATURE:
<223> OTHER INFORMATION: Synthesized

<400> SEQUENCE: 266

Ile Asn Glu Ala Trp Phe Pro Glu Asp Gln
1               5                   10

<210> SEQ ID NO 267
<211> LENGTH: 9
<212> TYPE: PRT
<213> ORGANISM: Artificial
<220> FEATURE:
<223> OTHER INFORMATION: Synthesized

<400> SEQUENCE: 267

Ile Asn Glu Ala Trp Phe Pro Glu Asp
1               5

<210> SEQ ID NO 268
<211> LENGTH: 8
<212> TYPE: PRT
<213> ORGANISM: Artificial
<220> FEATURE:
<223> OTHER INFORMATION: Synthesized

<400> SEQUENCE: 268

Ile Asn Glu Ala Trp Phe Pro Glu
1               5

<210> SEQ ID NO 269
<211> LENGTH: 7
<212> TYPE: PRT
<213> ORGANISM: Artificial
<220> FEATURE:
<223> OTHER INFORMATION: Synthesized

<400> SEQUENCE: 269

Ile Asn Glu Ala Trp Phe Pro
1               5
```

```
<210> SEQ ID NO 270
<211> LENGTH: 6
<212> TYPE: PRT
<213> ORGANISM: Artificial
<220> FEATURE:
<223> OTHER INFORMATION: Synthesized

<400> SEQUENCE: 270

Ile Asn Glu Ala Trp Phe
1               5

<210> SEQ ID NO 271
<211> LENGTH: 5
<212> TYPE: PRT
<213> ORGANISM: Artificial
<220> FEATURE:
<223> OTHER INFORMATION: Synthesized

<400> SEQUENCE: 271

Ile Asn Glu Ala Trp
1               5

<210> SEQ ID NO 272
<211> LENGTH: 12
<212> TYPE: PRT
<213> ORGANISM: Artificial
<220> FEATURE:
<223> OTHER INFORMATION: Synthesized

<400> SEQUENCE: 272

Asn Glu Ala Trp Phe Pro Glu Asp Gln Arg Val Leu
1               5                   10

<210> SEQ ID NO 273
<211> LENGTH: 11
<212> TYPE: PRT
<213> ORGANISM: Artificial
<220> FEATURE:
<223> OTHER INFORMATION: Synthesized

<400> SEQUENCE: 273

Asn Glu Ala Trp Phe Pro Glu Asp Gln Arg Val
1               5                   10

<210> SEQ ID NO 274
<211> LENGTH: 10
<212> TYPE: PRT
<213> ORGANISM: Artificial
<220> FEATURE:
<223> OTHER INFORMATION: Synthesized

<400> SEQUENCE: 274

Asn Glu Ala Trp Phe Pro Glu Asp Gln Arg
1               5                   10

<210> SEQ ID NO 275
<211> LENGTH: 9
<212> TYPE: PRT
<213> ORGANISM: Artificial
<220> FEATURE:
<223> OTHER INFORMATION: Synthesized

<400> SEQUENCE: 275

Asn Glu Ala Trp Phe Pro Glu Asp Gln
1               5

<210> SEQ ID NO 276
```

```
<211> LENGTH: 8
<212> TYPE: PRT
<213> ORGANISM: Artificial
<220> FEATURE:
<223> OTHER INFORMATION: Synthesized

<400> SEQUENCE: 276

Asn Glu Ala Trp Phe Pro Glu Asp
1               5

<210> SEQ ID NO 277
<211> LENGTH: 7
<212> TYPE: PRT
<213> ORGANISM: Artificial
<220> FEATURE:
<223> OTHER INFORMATION: Synthesized

<400> SEQUENCE: 277

Asn Glu Ala Trp Phe Pro Glu
1               5

<210> SEQ ID NO 278
<211> LENGTH: 6
<212> TYPE: PRT
<213> ORGANISM: Artificial
<220> FEATURE:
<223> OTHER INFORMATION: Synthesized

<400> SEQUENCE: 278

Asn Glu Ala Trp Phe Pro
1               5

<210> SEQ ID NO 279
<211> LENGTH: 5
<212> TYPE: PRT
<213> ORGANISM: Artificial
<220> FEATURE:
<223> OTHER INFORMATION: Synthesized

<400> SEQUENCE: 279

Asn Glu Ala Trp Phe
1               5

<210> SEQ ID NO 280
<211> LENGTH: 11
<212> TYPE: PRT
<213> ORGANISM: Artificial
<220> FEATURE:
<223> OTHER INFORMATION: Synthesized

<400> SEQUENCE: 280

Glu Ala Trp Phe Pro Glu Asp Gln Arg Val Leu
1               5                   10

<210> SEQ ID NO 281
<211> LENGTH: 10
<212> TYPE: PRT
<213> ORGANISM: Artificial
<220> FEATURE:
<223> OTHER INFORMATION: Synthesized

<400> SEQUENCE: 281

Glu Ala Trp Phe Pro Glu Asp Gln Arg Val
1               5                   10

<210> SEQ ID NO 282
<211> LENGTH: 9
```

```
<212> TYPE: PRT
<213> ORGANISM: Artificial
<220> FEATURE:
<223> OTHER INFORMATION: Synthesized

<400> SEQUENCE: 282

Glu Ala Trp Phe Pro Glu Asp Gln Arg
1               5

<210> SEQ ID NO 283
<211> LENGTH: 8
<212> TYPE: PRT
<213> ORGANISM: Artificial
<220> FEATURE:
<223> OTHER INFORMATION: Synthesized

<400> SEQUENCE: 283

Glu Ala Trp Phe Pro Glu Asp Gln
1               5

<210> SEQ ID NO 284
<211> LENGTH: 7
<212> TYPE: PRT
<213> ORGANISM: Artificial
<220> FEATURE:
<223> OTHER INFORMATION: Synthesized

<400> SEQUENCE: 284

Glu Ala Trp Phe Pro Glu Asp
1               5

<210> SEQ ID NO 285
<211> LENGTH: 6
<212> TYPE: PRT
<213> ORGANISM: Artificial
<220> FEATURE:
<223> OTHER INFORMATION: Synthesized

<400> SEQUENCE: 285

Glu Ala Trp Phe Pro Glu
1               5

<210> SEQ ID NO 286
<211> LENGTH: 5
<212> TYPE: PRT
<213> ORGANISM: Artificial
<220> FEATURE:
<223> OTHER INFORMATION: Synthesized

<400> SEQUENCE: 286

Glu Ala Trp Phe Pro
1               5

<210> SEQ ID NO 287
<211> LENGTH: 10
<212> TYPE: PRT
<213> ORGANISM: Artificial
<220> FEATURE:
<223> OTHER INFORMATION: Synthesized

<400> SEQUENCE: 287

Ala Trp Phe Pro Glu Asp Gln Arg Val Leu
1               5                   10

<210> SEQ ID NO 288
<211> LENGTH: 9
<212> TYPE: PRT
```

```
<213> ORGANISM: Artificial
<220> FEATURE:
<223> OTHER INFORMATION: Synthesized

<400> SEQUENCE: 288

Ala Trp Phe Pro Glu Asp Gln Arg Val
1               5

<210> SEQ ID NO 289
<211> LENGTH: 8
<212> TYPE: PRT
<213> ORGANISM: Artificial
<220> FEATURE:
<223> OTHER INFORMATION: Synthesized

<400> SEQUENCE: 289

Ala Trp Phe Pro Glu Asp Gln Arg
1               5

<210> SEQ ID NO 290
<211> LENGTH: 7
<212> TYPE: PRT
<213> ORGANISM: Artificial
<220> FEATURE:
<223> OTHER INFORMATION: Synthesized

<400> SEQUENCE: 290

Ala Trp Phe Pro Glu Asp Gln
1               5

<210> SEQ ID NO 291
<211> LENGTH: 6
<212> TYPE: PRT
<213> ORGANISM: Artificial
<220> FEATURE:
<223> OTHER INFORMATION: Synthesized

<400> SEQUENCE: 291

Ala Trp Phe Pro Glu Asp
1               5

<210> SEQ ID NO 292
<211> LENGTH: 5
<212> TYPE: PRT
<213> ORGANISM: Artificial
<220> FEATURE:
<223> OTHER INFORMATION: Synthesized

<400> SEQUENCE: 292

Ala Trp Phe Pro Glu
1               5

<210> SEQ ID NO 293
<211> LENGTH: 9
<212> TYPE: PRT
<213> ORGANISM: Artificial
<220> FEATURE:
<223> OTHER INFORMATION: Synthesized

<400> SEQUENCE: 293

Trp Phe Pro Glu Asp Gln Arg Val Leu
1               5

<210> SEQ ID NO 294
<211> LENGTH: 8
<212> TYPE: PRT
<213> ORGANISM: Artificial
```

<220> FEATURE:
<223> OTHER INFORMATION: Synthesized

<400> SEQUENCE: 294

Trp Phe Pro Glu Asp Gln Arg Val
1               5

<210> SEQ ID NO 295
<211> LENGTH: 7
<212> TYPE: PRT
<213> ORGANISM: Artificial
<220> FEATURE:
<223> OTHER INFORMATION: Synthesized

<400> SEQUENCE: 295

Trp Phe Pro Glu Asp Gln Arg
1               5

<210> SEQ ID NO 296
<211> LENGTH: 6
<212> TYPE: PRT
<213> ORGANISM: Artificial
<220> FEATURE:
<223> OTHER INFORMATION: Synthesized

<400> SEQUENCE: 296

Trp Phe Pro Glu Asp Gln
1               5

<210> SEQ ID NO 297
<211> LENGTH: 5
<212> TYPE: PRT
<213> ORGANISM: Artificial
<220> FEATURE:
<223> OTHER INFORMATION: Synthesized

<400> SEQUENCE: 297

Trp Phe Pro Glu Asp
1               5

<210> SEQ ID NO 298
<211> LENGTH: 8
<212> TYPE: PRT
<213> ORGANISM: Artificial
<220> FEATURE:
<223> OTHER INFORMATION: Synthesized

<400> SEQUENCE: 298

Phe Pro Glu Asp Gln Arg Val Leu
1               5

<210> SEQ ID NO 299
<211> LENGTH: 7
<212> TYPE: PRT
<213> ORGANISM: Artificial
<220> FEATURE:
<223> OTHER INFORMATION: Synthesized

<400> SEQUENCE: 299

Phe Pro Glu Asp Gln Arg Val
1               5

<210> SEQ ID NO 300
<211> LENGTH: 6
<212> TYPE: PRT
<213> ORGANISM: Artificial
<220> FEATURE:

```
<223> OTHER INFORMATION: Synthesized

<400> SEQUENCE: 300

Phe Pro Glu Asp Gln Arg
1               5

<210> SEQ ID NO 301
<211> LENGTH: 5
<212> TYPE: PRT
<213> ORGANISM: Artificial
<220> FEATURE:
<223> OTHER INFORMATION: Synthesized

<400> SEQUENCE: 301

Phe Pro Glu Asp Gln
1               5

<210> SEQ ID NO 302
<211> LENGTH: 7
<212> TYPE: PRT
<213> ORGANISM: Artificial
<220> FEATURE:
<223> OTHER INFORMATION: Synthesized

<400> SEQUENCE: 302

Pro Glu Asp Gln Arg Val Leu
1               5

<210> SEQ ID NO 303
<211> LENGTH: 6
<212> TYPE: PRT
<213> ORGANISM: Artificial
<220> FEATURE:
<223> OTHER INFORMATION: Synthesized

<400> SEQUENCE: 303

Pro Glu Asp Gln Arg Val
1               5

<210> SEQ ID NO 304
<211> LENGTH: 5
<212> TYPE: PRT
<213> ORGANISM: Artificial
<220> FEATURE:
<223> OTHER INFORMATION: Synthesized

<400> SEQUENCE: 304

Pro Glu Asp Gln Arg
1               5

<210> SEQ ID NO 305
<211> LENGTH: 6
<212> TYPE: PRT
<213> ORGANISM: Artificial
<220> FEATURE:
<223> OTHER INFORMATION: Synthesized

<400> SEQUENCE: 305

Glu Asp Gln Arg Val Leu
1               5

<210> SEQ ID NO 306
<211> LENGTH: 5
<212> TYPE: PRT
<213> ORGANISM: Artificial
<220> FEATURE:
<223> OTHER INFORMATION: Synthesized
```

```
<400> SEQUENCE: 306

Glu Asp Gln Arg Val
1               5

<210> SEQ ID NO 307
<211> LENGTH: 5
<212> TYPE: PRT
<213> ORGANISM: Artificial
<220> FEATURE:
<223> OTHER INFORMATION: Synthesized

<400> SEQUENCE: 307

Asp Gln Arg Val Leu
1               5

<210> SEQ ID NO 308
<211> LENGTH: 13
<212> TYPE: PRT
<213> ORGANISM: Artificial
<220> FEATURE:
<223> OTHER INFORMATION: Synthesized

<400> SEQUENCE: 308

Val Asp Tyr Ile Glu Glu Asp Ser Ser Val Phe Ala Gln
1               5                  10

<210> SEQ ID NO 309
<211> LENGTH: 12
<212> TYPE: PRT
<213> ORGANISM: Artificial
<220> FEATURE:
<223> OTHER INFORMATION: Synthesized

<400> SEQUENCE: 309

Arg Cys Ala Lys Asp Pro Trp Arg Leu Pro Gly Thr
1               5                  10

<210> SEQ ID NO 310
<211> LENGTH: 13
<212> TYPE: PRT
<213> ORGANISM: Artificial
<220> FEATURE:
<223> OTHER INFORMATION: Synthesized

<400> SEQUENCE: 310

Ala Gln Ala Ala Arg Arg Gly Tyr Leu Thr Lys Ile Leu
1               5                  10

<210> SEQ ID NO 311
<211> LENGTH: 16
<212> TYPE: PRT
<213> ORGANISM: Artificial
<220> FEATURE:
<223> OTHER INFORMATION: Synthesized

<400> SEQUENCE: 311

Gly Asp Tyr Glu Glu Leu Val Leu Ala Leu Arg Ser Glu Glu Asp Gly
1               5                  10                  15

<210> SEQ ID NO 312
<211> LENGTH: 17
<212> TYPE: PRT
<213> ORGANISM: Artificial
<220> FEATURE:
<223> OTHER INFORMATION: Synthesized
```

```
<400> SEQUENCE: 312

Phe Leu Val Lys Met Ser Gly Asp Leu Leu Glu Leu Ala Leu Lys Leu
1               5                   10                  15

Pro

<210> SEQ ID NO 313
<211> LENGTH: 13
<212> TYPE: PRT
<213> ORGANISM: Artificial
<220> FEATURE:
<223> OTHER INFORMATION: Synthesized

<400> SEQUENCE: 313

Lys Gly Gly Ala Ser Ser Asp Cys Ser Thr Cys Phe Val
1               5                   10

<210> SEQ ID NO 314
<211> LENGTH: 13
<212> TYPE: PRT
<213> ORGANISM: Artificial
<220> FEATURE:
<223> OTHER INFORMATION: Synthesized

<400> SEQUENCE: 314

Cys Gly Gly Thr Arg Phe His Arg Gln Ala Ser Lys Cys
1               5                   10

<210> SEQ ID NO 315
<211> LENGTH: 15
<212> TYPE: PRT
<213> ORGANISM: Artificial
<220> FEATURE:
<223> OTHER INFORMATION: Synthesized

<400> SEQUENCE: 315

Cys Gly Ile Gln Ser Asp His Arg Glu Ile Glu Gly Arg Val Cys
1               5                   10                  15

<210> SEQ ID NO 316
<211> LENGTH: 13
<212> TYPE: PRT
<213> ORGANISM: Artificial
<220> FEATURE:
<223> OTHER INFORMATION: Synthesized

<400> SEQUENCE: 316

Cys Ser Gly Arg Asp Ala Gly Val Ala Lys Gly Ala Cys
1               5                   10

<210> SEQ ID NO 317
<211> LENGTH: 12
<212> TYPE: PRT
<213> ORGANISM: Artificial
<220> FEATURE:
<223> OTHER INFORMATION: Synthesized

<400> SEQUENCE: 317

Ser Ile Pro Trp Asn Leu Glu Arg Ile Thr Pro Cys
1               5                   10

<210> SEQ ID NO 318
<211> LENGTH: 13
<212> TYPE: PRT
<213> ORGANISM: Artificial
<220> FEATURE:
<223> OTHER INFORMATION: Synthesized
```

```
<400> SEQUENCE: 318

Ala Ser Lys Cys Gly Asp Gly Thr Arg Phe His Arg Gln
1               5                   10

<210> SEQ ID NO 319
<211> LENGTH: 10
<212> TYPE: PRT
<213> ORGANISM: Artificial
<220> FEATURE:
<223> OTHER INFORMATION: Synthesized

<400> SEQUENCE: 319

Ala Gly Cys Gly Thr Arg Phe His Arg Gln
1               5                   10

<210> SEQ ID NO 320
<211> LENGTH: 13
<212> TYPE: PRT
<213> ORGANISM: Artificial
<220> FEATURE:
<223> OTHER INFORMATION: Synthesized

<400> SEQUENCE: 320

Gly Arg Val Cys Ile Gln Ser Asp His Arg Glu Ile Glu
1               5                   10

<210> SEQ ID NO 321
<211> LENGTH: 13
<212> TYPE: PRT
<213> ORGANISM: Artificial
<220> FEATURE:
<223> OTHER INFORMATION: Synthesized

<400> SEQUENCE: 321

Ala Gly Val Ala Lys Gly Ala Gly Cys Ser Gly Arg Asp
1               5                   10

<210> SEQ ID NO 322
<211> LENGTH: 12
<212> TYPE: PRT
<213> ORGANISM: Artificial
<220> FEATURE:
<223> OTHER INFORMATION: Synthesized

<400> SEQUENCE: 322

Ser Ile Pro Trp Asn Leu Glu Arg Ile Ile Pro Cys
1               5                   10

<210> SEQ ID NO 323
<211> LENGTH: 14
<212> TYPE: PRT
<213> ORGANISM: Artificial
<220> FEATURE:
<223> OTHER INFORMATION: Synthesized

<400> SEQUENCE: 323

Cys Gly Gly Ser Ile Pro Trp Asn Leu Glu Arg Ile Ile Pro
1               5                   10

<210> SEQ ID NO 324
<211> LENGTH: 14
<212> TYPE: PRT
<213> ORGANISM: Artificial
<220> FEATURE:
<223> OTHER INFORMATION: Synthesized
```

```
<400> SEQUENCE: 324

Ser Ile Pro Trp Asn Leu Glu Arg Ile Ile Pro Gly Gly Cys
1               5                   10

<210> SEQ ID NO 325
<211> LENGTH: 15
<212> TYPE: PRT
<213> ORGANISM: Artificial
<220> FEATURE:
<223> OTHER INFORMATION: Synthesized

<400> SEQUENCE: 325

Cys Gly Gly Asn Ala Gln Asp Gln Pro Val Thr Leu Gly Thr Leu
1               5                   10                  15

<210> SEQ ID NO 326
<211> LENGTH: 15
<212> TYPE: PRT
<213> ORGANISM: Artificial
<220> FEATURE:
<223> OTHER INFORMATION: Synthesized

<400> SEQUENCE: 326

Asn Ala Gln Asp Gln Pro Val Thr Leu Gly Thr Leu Gly Gly Cys
1               5                   10                  15

<210> SEQ ID NO 327
<211> LENGTH: 16
<212> TYPE: PRT
<213> ORGANISM: Artificial
<220> FEATURE:
<223> OTHER INFORMATION: Synthesized

<400> SEQUENCE: 327

Cys Gly Gly Ile Asn Met Ala Trp Phe Pro Glu Asp Gln Gln Val Leu
1               5                   10                  15

<210> SEQ ID NO 328
<211> LENGTH: 15
<212> TYPE: PRT
<213> ORGANISM: Artificial
<220> FEATURE:
<223> OTHER INFORMATION: Synthesized

<400> SEQUENCE: 328

Asn Met Ala Trp Phe Pro Glu Asp Gln Gln Val Leu Gly Gly Cys
1               5                   10                  15

<210> SEQ ID NO 329
<211> LENGTH: 152
<212> TYPE: PRT
<213> ORGANISM: Artificial
<220> FEATURE:
<223> OTHER INFORMATION: Synthesized

<400> SEQUENCE: 329

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
        50                  55                  60
```

```
His Arg Cys Ala Lys Asp Pro Trp Arg Leu Pro Gly Thr Tyr Val Val
 65                  70                  75                  80

Val Leu Lys Glu Glu Thr His Leu Ser Gln Ser Glu Arg Thr Ala Arg
                 85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
130                 135                 140

Glu Asp Ser Ser Val Phe Ala Gln
145                 150

<210> SEQ ID NO 330
<211> LENGTH: 13
<212> TYPE: PRT
<213> ORGANISM: Artificial
<220> FEATURE:
<223> OTHER INFORMATION: Synthesized

<400> SEQUENCE: 330

Ser Ile Pro Trp Asn Leu Glu Arg Ile Ile Pro Ala Trp
1               5                   10

<210> SEQ ID NO 331
<211> LENGTH: 12
<212> TYPE: PRT
<213> ORGANISM: Artificial
<220> FEATURE:
<223> OTHER INFORMATION: Synthesized

<400> SEQUENCE: 331

Ser Ile Pro Trp Asn Leu Glu Arg Ile Ile Pro Ala
1               5                   10

<210> SEQ ID NO 332
<211> LENGTH: 11
<212> TYPE: PRT
<213> ORGANISM: Artificial
<220> FEATURE:
<223> OTHER INFORMATION: Synthesized

<400> SEQUENCE: 332

Ser Ile Pro Trp Asn Leu Glu Arg Ile Ile Pro
1               5                   10

<210> SEQ ID NO 333
<211> LENGTH: 10
<212> TYPE: PRT
<213> ORGANISM: Artificial
<220> FEATURE:
<223> OTHER INFORMATION: Synthesized

<400> SEQUENCE: 333

Ser Ile Pro Trp Asn Leu Glu Arg Ile Ile
1               5                   10

<210> SEQ ID NO 334
<211> LENGTH: 12
<212> TYPE: PRT
<213> ORGANISM: Artificial
<220> FEATURE:
<223> OTHER INFORMATION: Synthesized

<400> SEQUENCE: 334
```

```
Ile Pro Trp Asn Leu Glu Arg Ile Ile Pro Ala Trp
1               5                   10

<210> SEQ ID NO 335
<211> LENGTH: 12
<212> TYPE: PRT
<213> ORGANISM: Artificial
<220> FEATURE:
<223> OTHER INFORMATION: Synthesized

<400> SEQUENCE: 335

Ile Pro Trp Asn Leu Glu Arg Ile Ile Pro Ala Trp
1               5                   10

<210> SEQ ID NO 336
<211> LENGTH: 10
<212> TYPE: PRT
<213> ORGANISM: Artificial
<220> FEATURE:
<223> OTHER INFORMATION: Synthesized

<400> SEQUENCE: 336

Ile Pro Trp Asn Leu Glu Arg Ile Ile Pro
1               5                   10

<210> SEQ ID NO 337
<211> LENGTH: 9
<212> TYPE: PRT
<213> ORGANISM: Artificial
<220> FEATURE:
<223> OTHER INFORMATION: Synthesized

<400> SEQUENCE: 337

Ile Pro Trp Asn Leu Glu Arg Ile Ile
1               5

<210> SEQ ID NO 338
<211> LENGTH: 11
<212> TYPE: PRT
<213> ORGANISM: Artificial
<220> FEATURE:
<223> OTHER INFORMATION: Synthesized

<400> SEQUENCE: 338

Pro Trp Asn Leu Glu Arg Ile Ile Pro Ala Trp
1               5                   10

<210> SEQ ID NO 339
<211> LENGTH: 10
<212> TYPE: PRT
<213> ORGANISM: Artificial
<220> FEATURE:
<223> OTHER INFORMATION: Synthesized

<400> SEQUENCE: 339

Pro Trp Asn Leu Glu Arg Ile Ile Pro Ala
1               5                   10

<210> SEQ ID NO 340
<211> LENGTH: 9
<212> TYPE: PRT
<213> ORGANISM: Artificial
<220> FEATURE:
<223> OTHER INFORMATION: Synthesized

<400> SEQUENCE: 340
```

```
Pro Trp Asn Leu Glu Arg Ile Ile Pro
1               5
```

<210> SEQ ID NO 341
<211> LENGTH: 8
<212> TYPE: PRT
<213> ORGANISM: Artificial
<220> FEATURE:
<223> OTHER INFORMATION: Synthesized

<400> SEQUENCE: 341

```
Pro Trp Asn Leu Glu Arg Ile Ile
1               5
```

<210> SEQ ID NO 342
<211> LENGTH: 10
<212> TYPE: PRT
<213> ORGANISM: Artificial
<220> FEATURE:
<223> OTHER INFORMATION: Synthesized

<400> SEQUENCE: 342

```
Trp Asn Leu Glu Arg Ile Ile Pro Ala Trp
1               5                   10
```

<210> SEQ ID NO 343
<211> LENGTH: 9
<212> TYPE: PRT
<213> ORGANISM: Artificial
<220> FEATURE:
<223> OTHER INFORMATION: Synthesized

<400> SEQUENCE: 343

```
Trp Asn Leu Glu Arg Ile Ile Pro Ala
1               5
```

<210> SEQ ID NO 344
<211> LENGTH: 8
<212> TYPE: PRT
<213> ORGANISM: Artificial
<220> FEATURE:
<223> OTHER INFORMATION: Synthesized

<400> SEQUENCE: 344

```
Trp Asn Leu Glu Arg Ile Ile Pro
1               5
```

<210> SEQ ID NO 345
<211> LENGTH: 7
<212> TYPE: PRT
<213> ORGANISM: Artificial
<220> FEATURE:
<223> OTHER INFORMATION: Synthesized

<400> SEQUENCE: 345

```
Trp Asn Leu Glu Arg Ile Ile
1               5
```

<210> SEQ ID NO 346
<211> LENGTH: 9
<212> TYPE: PRT
<213> ORGANISM: Artificial
<220> FEATURE:
<223> OTHER INFORMATION: Synthesized

<400> SEQUENCE: 346

```
Asn Leu Glu Arg Ile Ile Pro Ala Trp
```

```
1               5

<210> SEQ ID NO 347
<211> LENGTH: 8
<212> TYPE: PRT
<213> ORGANISM: Artificial
<220> FEATURE:
<223> OTHER INFORMATION: Synthesized

<400> SEQUENCE: 347

Asn Leu Glu Arg Ile Ile Pro Ala
1               5

<210> SEQ ID NO 348
<211> LENGTH: 7
<212> TYPE: PRT
<213> ORGANISM: Artificial
<220> FEATURE:
<223> OTHER INFORMATION: Synthesized

<400> SEQUENCE: 348

Asn Leu Glu Arg Ile Ile Pro
1               5

<210> SEQ ID NO 349
<211> LENGTH: 6
<212> TYPE: PRT
<213> ORGANISM: Artificial
<220> FEATURE:
<223> OTHER INFORMATION: Synthesized

<400> SEQUENCE: 349

Asn Leu Glu Arg Ile Ile
1               5

<210> SEQ ID NO 350
<211> LENGTH: 8
<212> TYPE: PRT
<213> ORGANISM: Artificial
<220> FEATURE:
<223> OTHER INFORMATION: Synthesized

<400> SEQUENCE: 350

Leu Glu Arg Ile Ile Pro Ala Trp
1               5

<210> SEQ ID NO 351
<211> LENGTH: 7
<212> TYPE: PRT
<213> ORGANISM: Artificial
<220> FEATURE:
<223> OTHER INFORMATION: Synthesized

<400> SEQUENCE: 351

Leu Glu Arg Ile Ile Pro Ala
1               5

<210> SEQ ID NO 352
<211> LENGTH: 6
<212> TYPE: PRT
<213> ORGANISM: Artificial
<220> FEATURE:
<223> OTHER INFORMATION: Synthesized

<400> SEQUENCE: 352

Leu Glu Arg Ile Ile Pro
1               5
```

```
<210> SEQ ID NO 353
<211> LENGTH: 5
<212> TYPE: PRT
<213> ORGANISM: Artificial
<220> FEATURE:
<223> OTHER INFORMATION: Synthesized

<400> SEQUENCE: 353

Leu Glu Arg Ile Ile
1               5

<210> SEQ ID NO 354
<211> LENGTH: 7
<212> TYPE: PRT
<213> ORGANISM: Artificial
<220> FEATURE:
<223> OTHER INFORMATION: Synthesized

<400> SEQUENCE: 354

Glu Arg Ile Ile Pro Ala Trp
1               5

<210> SEQ ID NO 355
<211> LENGTH: 6
<212> TYPE: PRT
<213> ORGANISM: Artificial
<220> FEATURE:
<223> OTHER INFORMATION: Synthesized

<400> SEQUENCE: 355

Glu Arg Ile Ile Pro Ala
1               5

<210> SEQ ID NO 356
<211> LENGTH: 5
<212> TYPE: PRT
<213> ORGANISM: Artificial
<220> FEATURE:
<223> OTHER INFORMATION: Synthesized

<400> SEQUENCE: 356

Glu Arg Ile Ile Pro
1               5

<210> SEQ ID NO 357
<211> LENGTH: 6
<212> TYPE: PRT
<213> ORGANISM: Artificial
<220> FEATURE:
<223> OTHER INFORMATION: Synthesized

<400> SEQUENCE: 357

Arg Ile Ile Pro Ala Trp
1               5

<210> SEQ ID NO 358
<211> LENGTH: 5
<212> TYPE: PRT
<213> ORGANISM: Artificial
<220> FEATURE:
<223> OTHER INFORMATION: Synthesized

<400> SEQUENCE: 358

Arg Ile Ile Pro Ala
1               5
```

<210> SEQ ID NO 359
<211> LENGTH: 5
<212> TYPE: PRT
<213> ORGANISM: Artificial
<220> FEATURE:
<223> OTHER INFORMATION: Synthesized

<400> SEQUENCE: 359

Ile Ile Pro Ala Trp
1               5

<210> SEQ ID NO 360
<211> LENGTH: 13
<212> TYPE: PRT
<213> ORGANISM: Artificial
<220> FEATURE:
<223> OTHER INFORMATION: Synthesized

<400> SEQUENCE: 360

Ile Asn Met Ala Trp Phe Pro Glu Asp Gln Gln Val Leu
1               5                   10

<210> SEQ ID NO 361
<211> LENGTH: 12
<212> TYPE: PRT
<213> ORGANISM: Artificial
<220> FEATURE:
<223> OTHER INFORMATION: Synthesized

<400> SEQUENCE: 361

Ile Asn Met Ala Trp Phe Pro Glu Asp Gln Gln Val
1               5                   10

<210> SEQ ID NO 362
<211> LENGTH: 11
<212> TYPE: PRT
<213> ORGANISM: Artificial
<220> FEATURE:
<223> OTHER INFORMATION: Synthesized

<400> SEQUENCE: 362

Ile Asn Met Ala Trp Phe Pro Glu Asp Gln Gln
1               5                   10

<210> SEQ ID NO 363
<211> LENGTH: 10
<212> TYPE: PRT
<213> ORGANISM: Artificial
<220> FEATURE:
<223> OTHER INFORMATION: Synthesized

<400> SEQUENCE: 363

Ile Asn Met Ala Trp Phe Pro Glu Asp Gln
1               5                   10

<210> SEQ ID NO 364
<211> LENGTH: 9
<212> TYPE: PRT
<213> ORGANISM: Artificial
<220> FEATURE:
<223> OTHER INFORMATION: Synthesized

<400> SEQUENCE: 364

Ile Asn Met Ala Trp Phe Pro Glu Asp
1               5

```
<210> SEQ ID NO 365
<211> LENGTH: 8
<212> TYPE: PRT
<213> ORGANISM: Artificial
<220> FEATURE:
<223> OTHER INFORMATION: Synthesized

<400> SEQUENCE: 365

Ile Asn Met Ala Trp Phe Pro Glu
1               5

<210> SEQ ID NO 366
<211> LENGTH: 7
<212> TYPE: PRT
<213> ORGANISM: Artificial
<220> FEATURE:
<223> OTHER INFORMATION: Synthesized

<400> SEQUENCE: 366

Ile Asn Met Ala Trp Phe Pro
1               5

<210> SEQ ID NO 367
<211> LENGTH: 6
<212> TYPE: PRT
<213> ORGANISM: Artificial
<220> FEATURE:
<223> OTHER INFORMATION: Synthesized

<400> SEQUENCE: 367

Ile Asn Met Ala Trp Phe
1               5

<210> SEQ ID NO 368
<211> LENGTH: 5
<212> TYPE: PRT
<213> ORGANISM: Artificial
<220> FEATURE:
<223> OTHER INFORMATION: Synthesized

<400> SEQUENCE: 368

Ile Asn Met Ala Trp
1               5

<210> SEQ ID NO 369
<211> LENGTH: 12
<212> TYPE: PRT
<213> ORGANISM: Artificial
<220> FEATURE:
<223> OTHER INFORMATION: Synthesized

<400> SEQUENCE: 369

Asn Met Ala Trp Phe Pro Glu Asp Gln Gln Val Leu
1               5                   10

<210> SEQ ID NO 370
<211> LENGTH: 11
<212> TYPE: PRT
<213> ORGANISM: Artificial
<220> FEATURE:
<223> OTHER INFORMATION: Synthesized

<400> SEQUENCE: 370

Asn Met Ala Trp Phe Pro Glu Asp Gln Gln Val
1               5                   10

<210> SEQ ID NO 371
```

<211> LENGTH: 10
<212> TYPE: PRT
<213> ORGANISM: Artificial
<220> FEATURE:
<223> OTHER INFORMATION: Synthesized

<400> SEQUENCE: 371

Asn Met Ala Trp Phe Pro Glu Asp Gln Gln
1               5                   10

<210> SEQ ID NO 372
<211> LENGTH: 9
<212> TYPE: PRT
<213> ORGANISM: Artificial
<220> FEATURE:
<223> OTHER INFORMATION: Synthesized

<400> SEQUENCE: 372

Asn Met Ala Trp Phe Pro Glu Asp Gln
1               5

<210> SEQ ID NO 373
<211> LENGTH: 8
<212> TYPE: PRT
<213> ORGANISM: Artificial
<220> FEATURE:
<223> OTHER INFORMATION: Synthesized

<400> SEQUENCE: 373

Asn Met Ala Trp Phe Pro Glu Asp
1               5

<210> SEQ ID NO 374
<211> LENGTH: 7
<212> TYPE: PRT
<213> ORGANISM: Artificial
<220> FEATURE:
<223> OTHER INFORMATION: Synthesized

<400> SEQUENCE: 374

Asn Met Ala Trp Phe Pro Glu
1               5

<210> SEQ ID NO 375
<211> LENGTH: 6
<212> TYPE: PRT
<213> ORGANISM: Artificial
<220> FEATURE:
<223> OTHER INFORMATION: Synthesized

<400> SEQUENCE: 375

Asn Met Ala Trp Phe Pro
1               5

<210> SEQ ID NO 376
<211> LENGTH: 5
<212> TYPE: PRT
<213> ORGANISM: Artificial
<220> FEATURE:
<223> OTHER INFORMATION: Synthesized

<400> SEQUENCE: 376

Asn Met Ala Trp Phe
1               5

<210> SEQ ID NO 377
<211> LENGTH: 11

```
<212> TYPE: PRT
<213> ORGANISM: Artificial
<220> FEATURE:
<223> OTHER INFORMATION: Synthesized

<400> SEQUENCE: 377

Met Ala Trp Phe Pro Glu Asp Gln Gln Val Leu
1               5                   10

<210> SEQ ID NO 378
<211> LENGTH: 10
<212> TYPE: PRT
<213> ORGANISM: Artificial
<220> FEATURE:
<223> OTHER INFORMATION: Synthesized

<400> SEQUENCE: 378

Met Ala Trp Phe Pro Glu Asp Gln Gln Val
1               5                   10

<210> SEQ ID NO 379
<211> LENGTH: 9
<212> TYPE: PRT
<213> ORGANISM: Artificial
<220> FEATURE:
<223> OTHER INFORMATION: Synthesized

<400> SEQUENCE: 379

Met Ala Trp Phe Pro Glu Asp Gln Gln
1               5

<210> SEQ ID NO 380
<211> LENGTH: 8
<212> TYPE: PRT
<213> ORGANISM: Artificial
<220> FEATURE:
<223> OTHER INFORMATION: Synthesized

<400> SEQUENCE: 380

Met Ala Trp Phe Pro Glu Asp Gln
1               5

<210> SEQ ID NO 381
<211> LENGTH: 7
<212> TYPE: PRT
<213> ORGANISM: Artificial
<220> FEATURE:
<223> OTHER INFORMATION: Synthesized

<400> SEQUENCE: 381

Met Ala Trp Phe Pro Glu Asp
1               5

<210> SEQ ID NO 382
<211> LENGTH: 6
<212> TYPE: PRT
<213> ORGANISM: Artificial
<220> FEATURE:
<223> OTHER INFORMATION: Synthesized

<400> SEQUENCE: 382

Met Ala Trp Phe Pro Glu
1               5

<210> SEQ ID NO 383
<211> LENGTH: 5
<212> TYPE: PRT
```

```
<213> ORGANISM: Artificial
<220> FEATURE:
<223> OTHER INFORMATION: Synthesized

<400> SEQUENCE: 383

Met Ala Trp Phe Pro
1               5

<210> SEQ ID NO 384
<211> LENGTH: 10
<212> TYPE: PRT
<213> ORGANISM: Artificial
<220> FEATURE:
<223> OTHER INFORMATION: Synthesized

<400> SEQUENCE: 384

Ala Trp Phe Pro Glu Asp Gln Gln Val Leu
1               5                   10

<210> SEQ ID NO 385
<211> LENGTH: 9
<212> TYPE: PRT
<213> ORGANISM: Artificial
<220> FEATURE:
<223> OTHER INFORMATION: Synthesized

<400> SEQUENCE: 385

Ala Trp Phe Pro Glu Asp Gln Gln Val
1               5

<210> SEQ ID NO 386
<211> LENGTH: 8
<212> TYPE: PRT
<213> ORGANISM: Artificial
<220> FEATURE:
<223> OTHER INFORMATION: Synthesized

<400> SEQUENCE: 386

Ala Trp Phe Pro Glu Asp Gln Gln
1               5

<210> SEQ ID NO 387
<211> LENGTH: 9
<212> TYPE: PRT
<213> ORGANISM: Artificial
<220> FEATURE:
<223> OTHER INFORMATION: Synthesized

<400> SEQUENCE: 387

Trp Phe Pro Glu Asp Gln Gln Val Leu
1               5

<210> SEQ ID NO 388
<211> LENGTH: 8
<212> TYPE: PRT
<213> ORGANISM: Artificial
<220> FEATURE:
<223> OTHER INFORMATION: Synthesized

<400> SEQUENCE: 388

Trp Phe Pro Glu Asp Gln Gln Val
1               5

<210> SEQ ID NO 389
<211> LENGTH: 7
<212> TYPE: PRT
<213> ORGANISM: Artificial
```

<220> FEATURE:
<223> OTHER INFORMATION: Synthesized

<400> SEQUENCE: 389

Trp Phe Pro Glu Asp Gln Gln
1               5

<210> SEQ ID NO 390
<211> LENGTH: 8
<212> TYPE: PRT
<213> ORGANISM: Artificial
<220> FEATURE:
<223> OTHER INFORMATION: Synthesized

<400> SEQUENCE: 390

Phe Pro Glu Asp Gln Gln Val Leu
1               5

<210> SEQ ID NO 391
<211> LENGTH: 7
<212> TYPE: PRT
<213> ORGANISM: Artificial
<220> FEATURE:
<223> OTHER INFORMATION: Synthesized

<400> SEQUENCE: 391

Phe Pro Glu Asp Gln Gln Val
1               5

<210> SEQ ID NO 392
<211> LENGTH: 6
<212> TYPE: PRT
<213> ORGANISM: Artificial
<220> FEATURE:
<223> OTHER INFORMATION: Synthesized

<400> SEQUENCE: 392

Phe Pro Glu Asp Gln Gln
1               5

<210> SEQ ID NO 393
<211> LENGTH: 7
<212> TYPE: PRT
<213> ORGANISM: Artificial
<220> FEATURE:
<223> OTHER INFORMATION: Synthesized

<400> SEQUENCE: 393

Pro Glu Asp Gln Gln Val Leu
1               5

<210> SEQ ID NO 394
<211> LENGTH: 6
<212> TYPE: PRT
<213> ORGANISM: Artificial
<220> FEATURE:
<223> OTHER INFORMATION: Synthesized

<400> SEQUENCE: 394

Pro Glu Asp Gln Gln Val
1               5

<210> SEQ ID NO 395
<211> LENGTH: 5
<212> TYPE: PRT
<213> ORGANISM: Artificial
<220> FEATURE:

```
<223> OTHER INFORMATION: Synthesized

<400> SEQUENCE: 395

Pro Glu Asp Gln Gln
1               5

<210> SEQ ID NO 396
<211> LENGTH: 6
<212> TYPE: PRT
<213> ORGANISM: Artificial
<220> FEATURE:
<223> OTHER INFORMATION: Synthesized

<400> SEQUENCE: 396

Glu Asp Gln Gln Val Leu
1               5

<210> SEQ ID NO 397
<211> LENGTH: 5
<212> TYPE: PRT
<213> ORGANISM: Artificial
<220> FEATURE:
<223> OTHER INFORMATION: Synthesized

<400> SEQUENCE: 397

Glu Asp Gln Gln Val
1               5

<210> SEQ ID NO 398
<211> LENGTH: 5
<212> TYPE: PRT
<213> ORGANISM: Artificial
<220> FEATURE:
<223> OTHER INFORMATION: Synthesized

<400> SEQUENCE: 398

Asp Gln Gln Val Leu
1               5

<210> SEQ ID NO 399
<211> LENGTH: 692
<212> TYPE: PRT
<213> ORGANISM: Artificial
<220> FEATURE:
<223> OTHER INFORMATION: Synthesized

<400> SEQUENCE: 399

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
                35                  40                  45

Glu Asp Gly Leu Ala Glu Ala Pro Glu His Gly Thr Thr Ala Thr Phe
            50                  55                  60

His Arg Cys Ala Lys Asp Pro Trp Arg Leu Pro Gly Thr Tyr Val Val
65              70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
                100                 105                 110

His Val Phe His Gly Leu Leu Pro Gly Phe Leu Val Lys Met Ser Gly
            115                 120                 125
```

```
Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
                180                 185                 190

His Arg Glu Ile Glu Gly Arg Val Met Val Thr Asp Phe Glu Asn Val
                195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Val Leu Leu Pro
    275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
                355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
                435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
                500                 505                 510

Asn Ala Phe Gly Gly Glu Gly Val Tyr Ala Ile Ala Arg Cys Cys Leu
                515                 520                 525

Leu Pro Gln Ala Asn Cys Ser Val His Thr Ala Pro Pro Ala Glu Ala
    530                 535                 540
```

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys His Ala Pro Gly Leu Glu Cys
        595                 600                 605

Lys Val Lys Glu His Gly Ile Pro Ala Pro Gln Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 400
<211> LENGTH: 694
<212> TYPE: PRT
<213> ORGANISM: Artificial
<220> FEATURE:
<223> OTHER INFORMATION: Synthesized

<400> SEQUENCE: 400

Met Gly Thr His Cys Ser Ala Trp Leu Arg Trp Pro Leu Pro Leu
1               5                   10                  15

Leu Pro Pro Leu Leu Leu Leu Leu Leu Cys Pro Thr Gly Ala
            20                  25                  30

Gly Ala Gln Asp Glu Asp Gly Asp Tyr Glu Glu Leu Met Leu Ala Leu
            35                  40                  45

Pro Ser Gln Glu Asp Gly Leu Ala Asp Glu Ala Ala His Val Ala Thr
    50                  55                  60

Ala Thr Phe Arg Arg Cys Ser Lys Glu Ala Trp Arg Leu Pro Gly Thr
65                  70                  75                  80

Tyr Ile Val Val Leu Met Glu Glu Thr Gln Arg Leu Gln Ile Glu Gln
                85                  90                  95

Thr Ala His Arg Leu Gln Thr Arg Ala Ala Arg Arg Gly Tyr Val Ile
            100                 105                 110

Lys Val Leu His Ile Phe Tyr Asp Leu Phe Pro Gly Phe Leu Val Lys
        115                 120                 125

Met Ser Ser Asp Leu Leu Gly Leu Ala Leu Lys Leu Pro His Val Glu
    130                 135                 140

Tyr Ile Glu Glu Asp Ser Phe Val Phe Ala Gln Ser Ile Pro Trp Asn
145                 150                 155                 160

Leu Glu Arg Ile Ile Pro Ala Trp His Gln Thr Glu Glu Asp Arg Ser
                165                 170                 175

Pro Asp Gly Ser Ser Gln Val Glu Val Tyr Leu Leu Asp Thr Ser Ile
            180                 185                 190

Gln Gly Ala His Arg Glu Ile Glu Gly Arg Val Thr Ile Thr Asp Phe
        195                 200                 205

```
Asn Ser Val Pro Glu Glu Asp Gly Thr Arg Phe His Arg Gln Ala Ser
    210                 215                 220
Lys Cys Asp Ser His Gly Thr His Leu Ala Gly Val Val Ser Gly Arg
225                 230                 235                 240
Asp Ala Gly Val Ala Lys Gly Thr Ser Leu His Ser Leu Arg Val Leu
                245                 250                 255
Asn Cys Gln Gly Lys Gly Thr Val Ser Gly Thr Leu Ile Gly Leu Glu
                260                 265                 270
Phe Ile Arg Lys Ser Gln Leu Ile Gln Pro Ser Gly Pro Leu Val Val
            275                 280                 285
Leu Leu Pro Leu Ala Gly Gly Tyr Ser Arg Ile Leu Asn Ala Ala Cys
290                 295                 300
Arg His Leu Ala Arg Thr Gly Val Val Leu Val Ala Ala Ala Gly Asn
305                 310                 315                 320
Phe Arg Asp Asp Ala Cys Leu Tyr Ser Pro Ala Ser Ala Pro Glu Val
                325                 330                 335
Ile Thr Val Gly Ala Thr Asn Ala Gln Asp Gln Pro Val Thr Leu Gly
                340                 345                 350
Thr Leu Gly Thr Asn Phe Gly Arg Cys Val Asp Leu Phe Ala Pro Gly
            355                 360                 365
Lys Asp Ile Ile Gly Ala Ser Ser Asp Cys Ser Thr Cys Phe Met Ser
370                 375                 380
Gln Ser Gly Thr Ser Gln Ala Ala Ala His Val Ala Gly Ile Val Ala
385                 390                 395                 400
Arg Met Leu Ser Arg Glu Pro Thr Leu Thr Leu Ala Glu Leu Arg Gln
                405                 410                 415
Arg Leu Ile His Phe Ser Thr Lys Asp Val Ile Asn Met Ala Trp Phe
                420                 425                 430
Pro Glu Asp Gln Gln Val Leu Thr Pro Asn Leu Val Ala Thr Leu Pro
            435                 440                 445
Pro Ser Thr His Glu Thr Gly Gly Gln Leu Leu Cys Arg Thr Val Trp
450                 455                 460
Ser Ala His Ser Gly Pro Thr Arg Thr Ala Thr Ala Thr Ala Arg Cys
465                 470                 475                 480
Ala Pro Glu Glu Glu Leu Leu Ser Cys Ser Ser Phe Ser Arg Ser Gly
                485                 490                 495
Arg Arg Arg Gly Asp Trp Ile Glu Ala Ile Gly Gly Gln Gln Val Cys
                500                 505                 510
Lys Ala Leu Asn Ala Phe Gly Gly Glu Gly Val Tyr Ala Val Ala Arg
            515                 520                 525
Cys Cys Leu Val Pro Arg Ala Asn Cys Ser Ile His Asn Thr Pro Ala
530                 535                 540
Ala Arg Ala Gly Leu Glu Thr His Val His Cys His Gln Lys Asp His
545                 550                 555                 560
Val Leu Thr Gly Cys Ser Phe His Trp Glu Val Glu Asp Leu Ser Val
                565                 570                 575
Arg Arg Gln Pro Ala Leu Arg Ser Arg Arg Gln Pro Gly Gln Cys Val
                580                 585                 590
Gly His Gln Ala Ala Ser Val Tyr Ala Ser Cys Cys His Ala Pro Gly
            595                 600                 605
Leu Glu Cys Lys Ile Lys Glu His Gly Ile Ser Gly Pro Ser Glu Gln
610                 615                 620
Val Thr Val Ala Cys Glu Ala Gly Trp Thr Leu Thr Gly Cys Asn Val
```

```
                625                 630                 635                 640
Leu Pro Gly Ala Ser Leu Thr Leu Gly Ala Tyr Ser Val Asp Asn Leu
                    645                 650                 655

Cys Val Ala Arg Val His Asp Thr Ala Arg Ala Asp Arg Thr Ser Gly
                660                 665                 670

Glu Ala Thr Val Ala Ala Ala Ile Cys Cys Arg Ser Arg Pro Ser Ala
            675                 680                 685

Lys Ala Ser Trp Val Gln
    690
```

<210> SEQ ID NO 401
<211> LENGTH: 12
<212> TYPE: PRT
<213> ORGANISM: Artificial
<220> FEATURE:
<223> OTHER INFORMATION: Synthesized

<400> SEQUENCE: 401

```
Ser Ile Pro Trp Asn Leu Glu Arg Ile Gly Gly Cys
1               5                   10
```

<210> SEQ ID NO 402
<211> LENGTH: 11
<212> TYPE: PRT
<213> ORGANISM: Artificial
<220> FEATURE:
<223> OTHER INFORMATION: Synthesized

<400> SEQUENCE: 402

```
Ser Ile Pro Trp Asn Leu Glu Arg Gly Gly Cys
1               5                   10
```

<210> SEQ ID NO 403
<211> LENGTH: 10
<212> TYPE: PRT
<213> ORGANISM: Artificial
<220> FEATURE:
<223> OTHER INFORMATION: Synthesized

<400> SEQUENCE: 403

```
Ser Ile Pro Trp Asn Leu Glu Gly Gly Cys
1               5                   10
```

<210> SEQ ID NO 404
<211> LENGTH: 14
<212> TYPE: PRT
<213> ORGANISM: Artificial
<220> FEATURE:
<223> OTHER INFORMATION: Synthesized

<400> SEQUENCE: 404

```
Cys Gly Gly Ser Gly Arg Asp Ala Gly Val Ala Lys Gly Ala
1               5                   10
```

<210> SEQ ID NO 405
<211> LENGTH: 14
<212> TYPE: PRT
<213> ORGANISM: Artificial
<220> FEATURE:
<223> OTHER INFORMATION: Synthesized

<400> SEQUENCE: 405

```
Cys Gly Gly Ser Gly Arg Asp Ala Gly Val Ala Lys Gly Thr
1               5                   10
```

<210> SEQ ID NO 406
<211> LENGTH: 10
<212> TYPE: PRT
<213> ORGANISM: Artificial
<220> FEATURE:
<223> OTHER INFORMATION: Synthesized

<400> SEQUENCE: 406

Arg Asp Ala Gly Val Ala Lys Gly Gly Cys
1               5                   10

<210> SEQ ID NO 407
<211> LENGTH: 13
<212> TYPE: PRT
<213> ORGANISM: Artificial
<220> FEATURE:
<223> OTHER INFORMATION: Synthesized

<400> SEQUENCE: 407

Cys Ser Arg His Leu Ala Gln Ala Ser Gln Glu Leu Gln
1               5                   10

<210> SEQ ID NO 408
<211> LENGTH: 13
<212> TYPE: PRT
<213> ORGANISM: Artificial
<220> FEATURE:
<223> OTHER INFORMATION: Synthesized

<400> SEQUENCE: 408

Cys Arg Ser Arg Pro Ser Ala Lys Ala Ser Trp Val Gln
1               5                   10

<210> SEQ ID NO 409
<211> LENGTH: 13
<212> TYPE: PRT
<213> ORGANISM: Artificial
<220> FEATURE:
<223> OTHER INFORMATION: Synthesized

<400> SEQUENCE: 409

Cys Gly Gly Asp Tyr Glu Glu Leu Val Leu Ala Leu Arg
1               5                   10

<210> SEQ ID NO 410
<211> LENGTH: 13
<212> TYPE: PRT
<213> ORGANISM: Artificial
<220> FEATURE:
<223> OTHER INFORMATION: Synthesized

<400> SEQUENCE: 410

Cys Gly Gly Asp Tyr Glu Glu Leu Met Leu Ala Leu Pro
1               5                   10

<210> SEQ ID NO 411
<211> LENGTH: 13
<212> TYPE: PRT
<213> ORGANISM: Artificial
<220> FEATURE:
<223> OTHER INFORMATION: Synthesized

<400> SEQUENCE: 411

Leu Val Leu Ala Leu Arg Ser Glu Glu Asp Gly Gly Cys
1               5                   10

```
<210> SEQ ID NO 412
<211> LENGTH: 13
<212> TYPE: PRT
<213> ORGANISM: Artificial
<220> FEATURE:
<223> OTHER INFORMATION: Synthesized

<400> SEQUENCE: 412

Leu Met Leu Ala Leu Pro Ser Gln Glu Asp Gly Gly Cys
1               5                   10

<210> SEQ ID NO 413
<211> LENGTH: 11
<212> TYPE: PRT
<213> ORGANISM: Artificial
<220> FEATURE:
<223> OTHER INFORMATION: Synthesized

<400> SEQUENCE: 413

Ala Lys Asp Pro Trp Arg Leu Pro Gly Gly Cys
1               5                   10

<210> SEQ ID NO 414
<211> LENGTH: 11
<212> TYPE: PRT
<213> ORGANISM: Artificial
<220> FEATURE:
<223> OTHER INFORMATION: Synthesized

<400> SEQUENCE: 414

Ser Lys Glu Ala Trp Arg Leu Pro Gly Gly Cys
1               5                   10

<210> SEQ ID NO 415
<211> LENGTH: 12
<212> TYPE: PRT
<213> ORGANISM: Artificial
<220> FEATURE:
<223> OTHER INFORMATION: Synthesized

<400> SEQUENCE: 415

Cys Gly Gly Ala Ala Arg Arg Gly Tyr Leu Thr Lys
1               5                   10

<210> SEQ ID NO 416
<211> LENGTH: 12
<212> TYPE: PRT
<213> ORGANISM: Artificial
<220> FEATURE:
<223> OTHER INFORMATION: Synthesized

<400> SEQUENCE: 416

Cys Gly Gly Ala Ala Arg Arg Gly Tyr Val Ile Lys
1               5                   10

<210> SEQ ID NO 417
<211> LENGTH: 20
<212> TYPE: PRT
<213> ORGANISM: Artificial
<220> FEATURE:
<223> OTHER INFORMATION: Synthesized

<400> SEQUENCE: 417

Phe Leu Val Lys Met Ser Gly Asp Leu Leu Glu Leu Ala Leu Lys Leu
1               5                   10                  15

Pro Gly Gly Cys
            20
```

<210> SEQ ID NO 418
<211> LENGTH: 20
<212> TYPE: PRT
<213> ORGANISM: Artificial
<220> FEATURE:
<223> OTHER INFORMATION: Synthesized

<400> SEQUENCE: 418

Phe Leu Val Lys Met Ser Ser Asp Leu Leu Gly Leu Ala Leu Lys Leu
1               5                   10                  15

Pro Gly Gly Cys
            20

<210> SEQ ID NO 419
<211> LENGTH: 12
<212> TYPE: PRT
<213> ORGANISM: Artificial
<220> FEATURE:
<223> OTHER INFORMATION: Synthesized

<400> SEQUENCE: 419

Cys Gly Gly Glu Glu Asp Ser Ser Val Phe Ala Gln
1               5                   10

<210> SEQ ID NO 420
<211> LENGTH: 12
<212> TYPE: PRT
<213> ORGANISM: Artificial
<220> FEATURE:
<223> OTHER INFORMATION: Synthesized

<400> SEQUENCE: 420

Ser Arg His Leu Ala Gln Ala Ser Gln Glu Leu Gln
1               5                   10

<210> SEQ ID NO 421
<211> LENGTH: 10
<212> TYPE: PRT
<213> ORGANISM: Artificial
<220> FEATURE:
<223> OTHER INFORMATION: Synthesized

<400> SEQUENCE: 421

Asp Tyr Glu Glu Leu Val Leu Ala Leu Arg
1               5                   10

<210> SEQ ID NO 422
<211> LENGTH: 11
<212> TYPE: PRT
<213> ORGANISM: Artificial
<220> FEATURE:
<223> OTHER INFORMATION: Synthesized

<400> SEQUENCE: 422

Leu Val Leu Ala Leu Arg Ser Glu Glu Asp Gly
1               5                   10

<210> SEQ ID NO 423
<211> LENGTH: 9
<212> TYPE: PRT
<213> ORGANISM: Artificial
<220> FEATURE:
<223> OTHER INFORMATION: Synthesized

<400> SEQUENCE: 423

```
Glu Glu Asp Ser Ser Val Phe Ala Gln
1               5

<210> SEQ ID NO 424
<211> LENGTH: 11
<212> TYPE: PRT
<213> ORGANISM: Artificial
<220> FEATURE:
<223> OTHER INFORMATION: Synthesized

<400> SEQUENCE: 424

Ser Gly Arg Asp Ala Gly Val Ala Lys Gly Thr
1               5                   10

<210> SEQ ID NO 425
<211> LENGTH: 12
<212> TYPE: PRT
<213> ORGANISM: Artificial
<220> FEATURE:
<223> OTHER INFORMATION: Synthesized

<400> SEQUENCE: 425

Arg Ser Arg Pro Ser Ala Lys Ala Ser Trp Val Gln
1               5                   10

<210> SEQ ID NO 426
<211> LENGTH: 11
<212> TYPE: PRT
<213> ORGANISM: Artificial
<220> FEATURE:
<223> OTHER INFORMATION: Synthesized

<400> SEQUENCE: 426

Gly Asp Tyr Glu Glu Leu Met Leu Ala Leu Pro
1               5                   10

<210> SEQ ID NO 427
<211> LENGTH: 10
<212> TYPE: PRT
<213> ORGANISM: Artificial
<220> FEATURE:
<223> OTHER INFORMATION: Synthesized

<400> SEQUENCE: 427

Leu Met Leu Ala Leu Pro Ser Gln Glu Asp
1               5                   10

<210> SEQ ID NO 428
<211> LENGTH: 17
<212> TYPE: PRT
<213> ORGANISM: Artificial
<220> FEATURE:
<223> OTHER INFORMATION: Synthesized

<400> SEQUENCE: 428

Phe Leu Val Lys Met Ser Ser Asp Leu Leu Gly Leu Ala Leu Lys Leu
1               5                   10                  15

Pro

<210> SEQ ID NO 429
<211> LENGTH: 11
<212> TYPE: PRT
<213> ORGANISM: Artificial
<220> FEATURE:
<223> OTHER INFORMATION: Synthesized

<400> SEQUENCE: 429
```

```
Arg Cys Ala Lys Asp Pro Trp Arg Leu Pro Gly
1               5                   10

<210> SEQ ID NO 430
<211> LENGTH: 10
<212> TYPE: PRT
<213> ORGANISM: Artificial
<220> FEATURE:
<223> OTHER INFORMATION: Synthesized

<400> SEQUENCE: 430

Arg Cys Ala Lys Asp Pro Trp Arg Leu Pro
1               5                   10

<210> SEQ ID NO 431
<211> LENGTH: 9
<212> TYPE: PRT
<213> ORGANISM: Artificial
<220> FEATURE:
<223> OTHER INFORMATION: Synthesized

<400> SEQUENCE: 431

Arg Cys Ala Lys Asp Pro Trp Arg Leu
1               5

<210> SEQ ID NO 432
<211> LENGTH: 8
<212> TYPE: PRT
<213> ORGANISM: Artificial
<220> FEATURE:
<223> OTHER INFORMATION: Synthesized

<400> SEQUENCE: 432

Arg Cys Ala Lys Asp Pro Trp Arg
1               5

<210> SEQ ID NO 433
<211> LENGTH: 7
<212> TYPE: PRT
<213> ORGANISM: Artificial
<220> FEATURE:
<223> OTHER INFORMATION: Synthesized

<400> SEQUENCE: 433

Arg Cys Ala Lys Asp Pro Trp
1               5

<210> SEQ ID NO 434
<211> LENGTH: 6
<212> TYPE: PRT
<213> ORGANISM: Artificial
<220> FEATURE:
<223> OTHER INFORMATION: Synthesized

<400> SEQUENCE: 434

Arg Cys Ala Lys Asp Pro
1               5

<210> SEQ ID NO 435
<211> LENGTH: 5
<212> TYPE: PRT
<213> ORGANISM: Artificial
<220> FEATURE:
<223> OTHER INFORMATION: Synthesized

<400> SEQUENCE: 435
```

Arg Cys Ala Lys Asp
1               5

<210> SEQ ID NO 436
<211> LENGTH: 11
<212> TYPE: PRT
<213> ORGANISM: Artificial
<220> FEATURE:
<223> OTHER INFORMATION: Synthesized

<400> SEQUENCE: 436

Cys Ala Lys Asp Pro Trp Arg Leu Pro Gly Thr
1               5                   10

<210> SEQ ID NO 437
<211> LENGTH: 10
<212> TYPE: PRT
<213> ORGANISM: Artificial
<220> FEATURE:
<223> OTHER INFORMATION: Synthesized

<400> SEQUENCE: 437

Cys Ala Lys Asp Pro Trp Arg Leu Pro Gly
1               5                   10

<210> SEQ ID NO 438
<211> LENGTH: 9
<212> TYPE: PRT
<213> ORGANISM: Artificial
<220> FEATURE:
<223> OTHER INFORMATION: Synthesized

<400> SEQUENCE: 438

Cys Ala Lys Asp Pro Trp Arg Leu Pro
1               5

<210> SEQ ID NO 439
<211> LENGTH: 8
<212> TYPE: PRT
<213> ORGANISM: Artificial
<220> FEATURE:
<223> OTHER INFORMATION: Synthesized

<400> SEQUENCE: 439

Cys Ala Lys Asp Pro Trp Arg Leu
1               5

<210> SEQ ID NO 440
<211> LENGTH: 7
<212> TYPE: PRT
<213> ORGANISM: Artificial
<220> FEATURE:
<223> OTHER INFORMATION: Synthesized

<400> SEQUENCE: 440

Cys Ala Lys Asp Pro Trp Arg
1               5

<210> SEQ ID NO 441
<211> LENGTH: 6
<212> TYPE: PRT
<213> ORGANISM: Artificial
<220> FEATURE:
<223> OTHER INFORMATION: Synthesized

<400> SEQUENCE: 441

Cys Ala Lys Asp Pro Trp

```
1               5

<210> SEQ ID NO 442
<211> LENGTH: 5
<212> TYPE: PRT
<213> ORGANISM: Artificial
<220> FEATURE:
<223> OTHER INFORMATION: Synthesized

<400> SEQUENCE: 442

Cys Ala Lys Asp Pro
1               5

<210> SEQ ID NO 443
<211> LENGTH: 10
<212> TYPE: PRT
<213> ORGANISM: Artificial
<220> FEATURE:
<223> OTHER INFORMATION: Synthesized

<400> SEQUENCE: 443

Ala Lys Asp Pro Trp Arg Leu Pro Gly Thr
1               5                   10

<210> SEQ ID NO 444
<211> LENGTH: 9
<212> TYPE: PRT
<213> ORGANISM: Artificial
<220> FEATURE:
<223> OTHER INFORMATION: Synthesized

<400> SEQUENCE: 444

Ala Lys Asp Pro Trp Arg Leu Pro Gly
1               5

<210> SEQ ID NO 445
<211> LENGTH: 8
<212> TYPE: PRT
<213> ORGANISM: Artificial
<220> FEATURE:
<223> OTHER INFORMATION: Synthesized

<400> SEQUENCE: 445

Ala Lys Asp Pro Trp Arg Leu Pro
1               5

<210> SEQ ID NO 446
<211> LENGTH: 7
<212> TYPE: PRT
<213> ORGANISM: Artificial
<220> FEATURE:
<223> OTHER INFORMATION: Synthesized

<400> SEQUENCE: 446

Ala Lys Asp Pro Trp Arg Leu
1               5

<210> SEQ ID NO 447
<211> LENGTH: 6
<212> TYPE: PRT
<213> ORGANISM: Artificial
<220> FEATURE:
<223> OTHER INFORMATION: Synthesized

<400> SEQUENCE: 447

Ala Lys Asp Pro Trp Arg
1               5
```

```
<210> SEQ ID NO 448
<211> LENGTH: 5
<212> TYPE: PRT
<213> ORGANISM: Artificial
<220> FEATURE:
<223> OTHER INFORMATION: Synthesized

<400> SEQUENCE: 448

Ala Lys Asp Pro Trp
1               5

<210> SEQ ID NO 449
<211> LENGTH: 9
<212> TYPE: PRT
<213> ORGANISM: Artificial
<220> FEATURE:
<223> OTHER INFORMATION: Synthesized

<400> SEQUENCE: 449

Lys Asp Pro Trp Arg Leu Pro Gly Thr
1               5

<210> SEQ ID NO 450
<211> LENGTH: 8
<212> TYPE: PRT
<213> ORGANISM: Artificial
<220> FEATURE:
<223> OTHER INFORMATION: Synthesized

<400> SEQUENCE: 450

Lys Asp Pro Trp Arg Leu Pro Gly
1               5

<210> SEQ ID NO 451
<211> LENGTH: 7
<212> TYPE: PRT
<213> ORGANISM: Artificial
<220> FEATURE:
<223> OTHER INFORMATION: Synthesized

<400> SEQUENCE: 451

Lys Asp Pro Trp Arg Leu Pro
1               5

<210> SEQ ID NO 452
<211> LENGTH: 6
<212> TYPE: PRT
<213> ORGANISM: Artificial
<220> FEATURE:
<223> OTHER INFORMATION: Synthesized

<400> SEQUENCE: 452

Lys Asp Pro Trp Arg Leu
1               5

<210> SEQ ID NO 453
<211> LENGTH: 5
<212> TYPE: PRT
<213> ORGANISM: Artificial
<220> FEATURE:
<223> OTHER INFORMATION: Synthesized

<400> SEQUENCE: 453

Lys Asp Pro Trp Arg
1               5
```

```
<210> SEQ ID NO 454
<211> LENGTH: 8
<212> TYPE: PRT
<213> ORGANISM: Artificial
<220> FEATURE:
<223> OTHER INFORMATION: Synthesized

<400> SEQUENCE: 454

Asp Pro Trp Arg Leu Pro Gly Thr
1               5

<210> SEQ ID NO 455
<211> LENGTH: 7
<212> TYPE: PRT
<213> ORGANISM: Artificial
<220> FEATURE:
<223> OTHER INFORMATION: Synthesized

<400> SEQUENCE: 455

Asp Pro Trp Arg Leu Pro Gly
1               5

<210> SEQ ID NO 456
<211> LENGTH: 6
<212> TYPE: PRT
<213> ORGANISM: Artificial
<220> FEATURE:
<223> OTHER INFORMATION: Synthesized

<400> SEQUENCE: 456

Asp Pro Trp Arg Leu Pro
1               5

<210> SEQ ID NO 457
<211> LENGTH: 5
<212> TYPE: PRT
<213> ORGANISM: Artificial
<220> FEATURE:
<223> OTHER INFORMATION: Synthesized

<400> SEQUENCE: 457

Asp Pro Trp Arg Leu
1               5

<210> SEQ ID NO 458
<211> LENGTH: 7
<212> TYPE: PRT
<213> ORGANISM: Artificial
<220> FEATURE:
<223> OTHER INFORMATION: Synthesized

<400> SEQUENCE: 458

Pro Trp Arg Leu Pro Gly Thr
1               5

<210> SEQ ID NO 459
<211> LENGTH: 6
<212> TYPE: PRT
<213> ORGANISM: Artificial
<220> FEATURE:
<223> OTHER INFORMATION: Synthesized

<400> SEQUENCE: 459

Pro Trp Arg Leu Pro Gly
1               5
```

```
<210> SEQ ID NO 460
<211> LENGTH: 5
<212> TYPE: PRT
<213> ORGANISM: Artificial
<220> FEATURE:
<223> OTHER INFORMATION: Synthesized

<400> SEQUENCE: 460

Pro Trp Arg Leu Pro
1               5

<210> SEQ ID NO 461
<211> LENGTH: 6
<212> TYPE: PRT
<213> ORGANISM: Artificial
<220> FEATURE:
<223> OTHER INFORMATION: Synthesized

<400> SEQUENCE: 461

Trp Arg Leu Pro Gly Thr
1               5

<210> SEQ ID NO 462
<211> LENGTH: 5
<212> TYPE: PRT
<213> ORGANISM: Artificial
<220> FEATURE:
<223> OTHER INFORMATION: Synthesized

<400> SEQUENCE: 462

Trp Arg Leu Pro Gly
1               5

<210> SEQ ID NO 463
<211> LENGTH: 5
<212> TYPE: PRT
<213> ORGANISM: Artificial
<220> FEATURE:
<223> OTHER INFORMATION: Synthesized

<400> SEQUENCE: 463

Arg Leu Pro Gly Thr
1               5

<210> SEQ ID NO 464
<211> LENGTH: 12
<212> TYPE: PRT
<213> ORGANISM: Artificial
<220> FEATURE:
<223> OTHER INFORMATION: Synthesized

<400> SEQUENCE: 464

Ala Gln Ala Ala Arg Arg Gly Tyr Leu Thr Lys Ile
1               5                   10

<210> SEQ ID NO 465
<211> LENGTH: 11
<212> TYPE: PRT
<213> ORGANISM: Artificial
<220> FEATURE:
<223> OTHER INFORMATION: Synthesized

<400> SEQUENCE: 465

Ala Gln Ala Ala Arg Arg Gly Tyr Leu Thr Lys
1               5                   10

<210> SEQ ID NO 466
```

```
<211> LENGTH: 10
<212> TYPE: PRT
<213> ORGANISM: Artificial
<220> FEATURE:
<223> OTHER INFORMATION: Synthesized

<400> SEQUENCE: 466

Ala Gln Ala Ala Arg Arg Gly Tyr Leu Thr
1               5                   10

<210> SEQ ID NO 467
<211> LENGTH: 9
<212> TYPE: PRT
<213> ORGANISM: Artificial
<220> FEATURE:
<223> OTHER INFORMATION: Synthesized

<400> SEQUENCE: 467

Ala Gln Ala Ala Arg Arg Gly Tyr Leu
1               5

<210> SEQ ID NO 468
<211> LENGTH: 8
<212> TYPE: PRT
<213> ORGANISM: Artificial
<220> FEATURE:
<223> OTHER INFORMATION: Synthesized

<400> SEQUENCE: 468

Ala Gln Ala Ala Arg Arg Gly Tyr
1               5

<210> SEQ ID NO 469
<211> LENGTH: 7
<212> TYPE: PRT
<213> ORGANISM: Artificial
<220> FEATURE:
<223> OTHER INFORMATION: Synthesized

<400> SEQUENCE: 469

Ala Gln Ala Ala Arg Arg Gly
1               5

<210> SEQ ID NO 470
<211> LENGTH: 6
<212> TYPE: PRT
<213> ORGANISM: Artificial
<220> FEATURE:
<223> OTHER INFORMATION: Synthesized

<400> SEQUENCE: 470

Ala Gln Ala Ala Arg Arg
1               5

<210> SEQ ID NO 471
<211> LENGTH: 5
<212> TYPE: PRT
<213> ORGANISM: Artificial
<220> FEATURE:
<223> OTHER INFORMATION: Synthesized

<400> SEQUENCE: 471

Ala Gln Ala Ala Arg
1               5

<210> SEQ ID NO 472
<211> LENGTH: 12
```

```
<212> TYPE: PRT
<213> ORGANISM: Artificial
<220> FEATURE:
<223> OTHER INFORMATION: Synthesized

<400> SEQUENCE: 472

Gln Ala Ala Arg Arg Gly Tyr Leu Thr Lys Ile Leu
1               5                   10

<210> SEQ ID NO 473
<211> LENGTH: 11
<212> TYPE: PRT
<213> ORGANISM: Artificial
<220> FEATURE:
<223> OTHER INFORMATION: Synthesized

<400> SEQUENCE: 473

Gln Ala Ala Arg Arg Gly Tyr Leu Thr Lys Ile
1               5                   10

<210> SEQ ID NO 474
<211> LENGTH: 10
<212> TYPE: PRT
<213> ORGANISM: Artificial
<220> FEATURE:
<223> OTHER INFORMATION: Synthesized

<400> SEQUENCE: 474

Gln Ala Ala Arg Arg Gly Tyr Leu Thr Lys
1               5                   10

<210> SEQ ID NO 475
<211> LENGTH: 9
<212> TYPE: PRT
<213> ORGANISM: Artificial
<220> FEATURE:
<223> OTHER INFORMATION: Synthesized

<400> SEQUENCE: 475

Gln Ala Ala Arg Arg Gly Tyr Leu Thr
1               5

<210> SEQ ID NO 476
<211> LENGTH: 8
<212> TYPE: PRT
<213> ORGANISM: Artificial
<220> FEATURE:
<223> OTHER INFORMATION: Synthesized

<400> SEQUENCE: 476

Gln Ala Ala Arg Arg Gly Tyr Leu
1               5

<210> SEQ ID NO 477
<211> LENGTH: 7
<212> TYPE: PRT
<213> ORGANISM: Artificial
<220> FEATURE:
<223> OTHER INFORMATION: Synthesized

<400> SEQUENCE: 477

Gln Ala Ala Arg Arg Gly Tyr
1               5

<210> SEQ ID NO 478
<211> LENGTH: 6
<212> TYPE: PRT
```

<213> ORGANISM: Artificial
<220> FEATURE:
<223> OTHER INFORMATION: Synthesized

<400> SEQUENCE: 478

Gln Ala Ala Arg Arg Gly
1               5

<210> SEQ ID NO 479
<211> LENGTH: 5
<212> TYPE: PRT
<213> ORGANISM: Artificial
<220> FEATURE:
<223> OTHER INFORMATION: Synthesized

<400> SEQUENCE: 479

Gln Ala Ala Arg Arg
1               5

<210> SEQ ID NO 480
<211> LENGTH: 11
<212> TYPE: PRT
<213> ORGANISM: Artificial
<220> FEATURE:
<223> OTHER INFORMATION: Synthesized

<400> SEQUENCE: 480

Ala Ala Arg Arg Gly Tyr Leu Thr Lys Ile Leu
1               5                   10

<210> SEQ ID NO 481
<211> LENGTH: 10
<212> TYPE: PRT
<213> ORGANISM: Artificial
<220> FEATURE:
<223> OTHER INFORMATION: Synthesized

<400> SEQUENCE: 481

Ala Ala Arg Arg Gly Tyr Leu Thr Lys Ile
1               5                   10

<210> SEQ ID NO 482
<211> LENGTH: 9
<212> TYPE: PRT
<213> ORGANISM: Artificial
<220> FEATURE:
<223> OTHER INFORMATION: Synthesized

<400> SEQUENCE: 482

Ala Ala Arg Arg Gly Tyr Leu Thr Lys
1               5

<210> SEQ ID NO 483
<211> LENGTH: 8
<212> TYPE: PRT
<213> ORGANISM: Artificial
<220> FEATURE:
<223> OTHER INFORMATION: Synthesized

<400> SEQUENCE: 483

Ala Ala Arg Arg Gly Tyr Leu Thr
1               5

<210> SEQ ID NO 484
<211> LENGTH: 7
<212> TYPE: PRT
<213> ORGANISM: Artificial

```
<220> FEATURE:
<223> OTHER INFORMATION: Synthesized

<400> SEQUENCE: 484

Ala Ala Arg Arg Gly Tyr Leu
1               5

<210> SEQ ID NO 485
<211> LENGTH: 6
<212> TYPE: PRT
<213> ORGANISM: Artificial
<220> FEATURE:
<223> OTHER INFORMATION: Synthesized

<400> SEQUENCE: 485

Ala Ala Arg Arg Gly Tyr
1               5

<210> SEQ ID NO 486
<211> LENGTH: 5
<212> TYPE: PRT
<213> ORGANISM: Artificial
<220> FEATURE:
<223> OTHER INFORMATION: Synthesized

<400> SEQUENCE: 486

Ala Ala Arg Arg Gly
1               5

<210> SEQ ID NO 487
<211> LENGTH: 10
<212> TYPE: PRT
<213> ORGANISM: Artificial
<220> FEATURE:
<223> OTHER INFORMATION: Synthesized

<400> SEQUENCE: 487

Ala Arg Arg Gly Tyr Leu Thr Lys Ile Leu
1               5                   10

<210> SEQ ID NO 488
<211> LENGTH: 9
<212> TYPE: PRT
<213> ORGANISM: Artificial
<220> FEATURE:
<223> OTHER INFORMATION: Synthesized

<400> SEQUENCE: 488

Ala Arg Arg Gly Tyr Leu Thr Lys Ile
1               5

<210> SEQ ID NO 489
<211> LENGTH: 8
<212> TYPE: PRT
<213> ORGANISM: Artificial
<220> FEATURE:
<223> OTHER INFORMATION: Synthesized

<400> SEQUENCE: 489

Ala Arg Arg Gly Tyr Leu Thr Lys
1               5

<210> SEQ ID NO 490
<211> LENGTH: 7
<212> TYPE: PRT
<213> ORGANISM: Artificial
<220> FEATURE:
```

<223> OTHER INFORMATION: Synthesized

<400> SEQUENCE: 490

Ala Arg Arg Gly Tyr Leu Thr
1               5

<210> SEQ ID NO 491
<211> LENGTH: 6
<212> TYPE: PRT
<213> ORGANISM: Artificial
<220> FEATURE:
<223> OTHER INFORMATION: Synthesized

<400> SEQUENCE: 491

Ala Arg Arg Gly Tyr Leu
1               5

<210> SEQ ID NO 492
<211> LENGTH: 5
<212> TYPE: PRT
<213> ORGANISM: Artificial
<220> FEATURE:
<223> OTHER INFORMATION: Synthesized

<400> SEQUENCE: 492

Ala Arg Arg Gly Tyr
1               5

<210> SEQ ID NO 493
<211> LENGTH: 9
<212> TYPE: PRT
<213> ORGANISM: Artificial
<220> FEATURE:
<223> OTHER INFORMATION: Synthesized

<400> SEQUENCE: 493

Arg Arg Gly Tyr Leu Thr Lys Ile Leu
1               5

<210> SEQ ID NO 494
<211> LENGTH: 8
<212> TYPE: PRT
<213> ORGANISM: Artificial
<220> FEATURE:
<223> OTHER INFORMATION: Synthesized

<400> SEQUENCE: 494

Arg Arg Gly Tyr Leu Thr Lys Ile
1               5

<210> SEQ ID NO 495
<211> LENGTH: 7
<212> TYPE: PRT
<213> ORGANISM: Artificial
<220> FEATURE:
<223> OTHER INFORMATION: Synthesized

<400> SEQUENCE: 495

Arg Arg Gly Tyr Leu Thr Lys
1               5

<210> SEQ ID NO 496
<211> LENGTH: 6
<212> TYPE: PRT
<213> ORGANISM: Artificial
<220> FEATURE:
<223> OTHER INFORMATION: Synthesized

<400> SEQUENCE: 496

Arg Arg Gly Tyr Leu Thr
1               5

<210> SEQ ID NO 497
<211> LENGTH: 5
<212> TYPE: PRT
<213> ORGANISM: Artificial
<220> FEATURE:
<223> OTHER INFORMATION: Synthesized

<400> SEQUENCE: 497

Arg Arg Gly Tyr Leu
1               5

<210> SEQ ID NO 498
<211> LENGTH: 8
<212> TYPE: PRT
<213> ORGANISM: Artificial
<220> FEATURE:
<223> OTHER INFORMATION: Synthesized

<400> SEQUENCE: 498

Arg Gly Tyr Leu Thr Lys Ile Leu
1               5

<210> SEQ ID NO 499
<211> LENGTH: 7
<212> TYPE: PRT
<213> ORGANISM: Artificial
<220> FEATURE:
<223> OTHER INFORMATION: Synthesized

<400> SEQUENCE: 499

Arg Gly Tyr Leu Thr Lys Ile
1               5

<210> SEQ ID NO 500
<211> LENGTH: 6
<212> TYPE: PRT
<213> ORGANISM: Artificial
<220> FEATURE:
<223> OTHER INFORMATION: Synthesized

<400> SEQUENCE: 500

Arg Gly Tyr Leu Thr Lys
1               5

<210> SEQ ID NO 501
<211> LENGTH: 5
<212> TYPE: PRT
<213> ORGANISM: Artificial
<220> FEATURE:
<223> OTHER INFORMATION: Synthesized

<400> SEQUENCE: 501

Arg Gly Tyr Leu Thr
1               5

<210> SEQ ID NO 502
<211> LENGTH: 7
<212> TYPE: PRT
<213> ORGANISM: Artificial
<220> FEATURE:
<223> OTHER INFORMATION: Synthesized

```
<400> SEQUENCE: 502

Gly Tyr Leu Thr Lys Ile Leu
1               5

<210> SEQ ID NO 503
<211> LENGTH: 6
<212> TYPE: PRT
<213> ORGANISM: Artificial
<220> FEATURE:
<223> OTHER INFORMATION: Synthesized

<400> SEQUENCE: 503

Gly Tyr Leu Thr Lys Ile
1               5

<210> SEQ ID NO 504
<211> LENGTH: 5
<212> TYPE: PRT
<213> ORGANISM: Artificial
<220> FEATURE:
<223> OTHER INFORMATION: Synthesized

<400> SEQUENCE: 504

Gly Tyr Leu Thr Lys
1               5

<210> SEQ ID NO 505
<211> LENGTH: 6
<212> TYPE: PRT
<213> ORGANISM: Artificial
<220> FEATURE:
<223> OTHER INFORMATION: Synthesized

<400> SEQUENCE: 505

Tyr Leu Thr Lys Ile Leu
1               5

<210> SEQ ID NO 506
<211> LENGTH: 5
<212> TYPE: PRT
<213> ORGANISM: Artificial
<220> FEATURE:
<223> OTHER INFORMATION: Synthesized

<400> SEQUENCE: 506

Tyr Leu Thr Lys Ile
1               5

<210> SEQ ID NO 507
<211> LENGTH: 5
<212> TYPE: PRT
<213> ORGANISM: Artificial
<220> FEATURE:
<223> OTHER INFORMATION: Synthesized

<400> SEQUENCE: 507

Leu Thr Lys Ile Leu
1               5

<210> SEQ ID NO 508
<211> LENGTH: 12
<212> TYPE: PRT
<213> ORGANISM: Artificial
<220> FEATURE:
<223> OTHER INFORMATION: Synthesized

<400> SEQUENCE: 508
```

Arg Cys Ser Lys Glu Ala Trp Arg Leu Pro Gly Thr
1               5                   10

<210> SEQ ID NO 509
<211> LENGTH: 11
<212> TYPE: PRT
<213> ORGANISM: Artificial
<220> FEATURE:
<223> OTHER INFORMATION: Synthesized

<400> SEQUENCE: 509

Arg Cys Ser Lys Glu Ala Trp Arg Leu Pro Gly
1               5                   10

<210> SEQ ID NO 510
<211> LENGTH: 10
<212> TYPE: PRT
<213> ORGANISM: Artificial
<220> FEATURE:
<223> OTHER INFORMATION: Synthesized

<400> SEQUENCE: 510

Arg Cys Ser Lys Glu Ala Trp Arg Leu Pro
1               5                   10

<210> SEQ ID NO 511
<211> LENGTH: 9
<212> TYPE: PRT
<213> ORGANISM: Artificial
<220> FEATURE:
<223> OTHER INFORMATION: Synthesized

<400> SEQUENCE: 511

Arg Cys Ser Lys Glu Ala Trp Arg Leu
1               5

<210> SEQ ID NO 512
<211> LENGTH: 8
<212> TYPE: PRT
<213> ORGANISM: Artificial
<220> FEATURE:
<223> OTHER INFORMATION: Synthesized

<400> SEQUENCE: 512

Arg Cys Ser Lys Glu Ala Trp Arg
1               5

<210> SEQ ID NO 513
<211> LENGTH: 7
<212> TYPE: PRT
<213> ORGANISM: Artificial
<220> FEATURE:
<223> OTHER INFORMATION: Synthesized

<400> SEQUENCE: 513

Arg Cys Ser Lys Glu Ala Trp
1               5

<210> SEQ ID NO 514
<211> LENGTH: 6
<212> TYPE: PRT
<213> ORGANISM: Artificial
<220> FEATURE:
<223> OTHER INFORMATION: Synthesized

<400> SEQUENCE: 514

```
Arg Cys Ser Lys Glu Ala
1               5

<210> SEQ ID NO 515
<211> LENGTH: 5
<212> TYPE: PRT
<213> ORGANISM: Artificial
<220> FEATURE:
<223> OTHER INFORMATION: Synthesized

<400> SEQUENCE: 515

Arg Cys Ser Lys Glu
1               5

<210> SEQ ID NO 516
<211> LENGTH: 11
<212> TYPE: PRT
<213> ORGANISM: Artificial
<220> FEATURE:
<223> OTHER INFORMATION: Synthesized

<400> SEQUENCE: 516

Cys Ser Lys Glu Ala Trp Arg Leu Pro Gly Thr
1               5                   10

<210> SEQ ID NO 517
<211> LENGTH: 10
<212> TYPE: PRT
<213> ORGANISM: Artificial
<220> FEATURE:
<223> OTHER INFORMATION: Synthesized

<400> SEQUENCE: 517

Cys Ser Lys Glu Ala Trp Arg Leu Pro Gly
1               5                   10

<210> SEQ ID NO 518
<211> LENGTH: 9
<212> TYPE: PRT
<213> ORGANISM: Artificial
<220> FEATURE:
<223> OTHER INFORMATION: Synthesized

<400> SEQUENCE: 518

Cys Ser Lys Glu Ala Trp Arg Leu Pro
1               5

<210> SEQ ID NO 519
<211> LENGTH: 8
<212> TYPE: PRT
<213> ORGANISM: Artificial
<220> FEATURE:
<223> OTHER INFORMATION: Synthesized

<400> SEQUENCE: 519

Cys Ser Lys Glu Ala Trp Arg Leu
1               5

<210> SEQ ID NO 520
<211> LENGTH: 7
<212> TYPE: PRT
<213> ORGANISM: Artificial
<220> FEATURE:
<223> OTHER INFORMATION: Synthesized

<400> SEQUENCE: 520

Cys Ser Lys Glu Ala Trp Arg
```

```
1               5

<210> SEQ ID NO 521
<211> LENGTH: 6
<212> TYPE: PRT
<213> ORGANISM: Artificial
<220> FEATURE:
<223> OTHER INFORMATION: Synthesized

<400> SEQUENCE: 521

Cys Ser Lys Glu Ala Trp
1               5

<210> SEQ ID NO 522
<211> LENGTH: 5
<212> TYPE: PRT
<213> ORGANISM: Artificial
<220> FEATURE:
<223> OTHER INFORMATION: Synthesized

<400> SEQUENCE: 522

Cys Ser Lys Glu Ala
1               5

<210> SEQ ID NO 523
<211> LENGTH: 10
<212> TYPE: PRT
<213> ORGANISM: Artificial
<220> FEATURE:
<223> OTHER INFORMATION: Synthesized

<400> SEQUENCE: 523

Ser Lys Glu Ala Trp Arg Leu Pro Gly Thr
1               5                   10

<210> SEQ ID NO 524
<211> LENGTH: 9
<212> TYPE: PRT
<213> ORGANISM: Artificial
<220> FEATURE:
<223> OTHER INFORMATION: Synthesized

<400> SEQUENCE: 524

Ser Lys Glu Ala Trp Arg Leu Pro Gly
1               5

<210> SEQ ID NO 525
<211> LENGTH: 8
<212> TYPE: PRT
<213> ORGANISM: Artificial
<220> FEATURE:
<223> OTHER INFORMATION: Synthesized

<400> SEQUENCE: 525

Ser Lys Glu Ala Trp Arg Leu Pro
1               5

<210> SEQ ID NO 526
<211> LENGTH: 7
<212> TYPE: PRT
<213> ORGANISM: Artificial
<220> FEATURE:
<223> OTHER INFORMATION: Synthesized

<400> SEQUENCE: 526

Ser Lys Glu Ala Trp Arg Leu
1               5
```

```
<210> SEQ ID NO 527
<211> LENGTH: 6
<212> TYPE: PRT
<213> ORGANISM: Artificial
<220> FEATURE:
<223> OTHER INFORMATION: Synthesized

<400> SEQUENCE: 527

Ser Lys Glu Ala Trp Arg
1               5

<210> SEQ ID NO 528
<211> LENGTH: 5
<212> TYPE: PRT
<213> ORGANISM: Artificial
<220> FEATURE:
<223> OTHER INFORMATION: Synthesized

<400> SEQUENCE: 528

Ser Lys Glu Ala Trp
1               5

<210> SEQ ID NO 529
<211> LENGTH: 9
<212> TYPE: PRT
<213> ORGANISM: Artificial
<220> FEATURE:
<223> OTHER INFORMATION: Synthesized

<400> SEQUENCE: 529

Lys Glu Ala Trp Arg Leu Pro Gly Thr
1               5

<210> SEQ ID NO 530
<211> LENGTH: 8
<212> TYPE: PRT
<213> ORGANISM: Artificial
<220> FEATURE:
<223> OTHER INFORMATION: Synthesized

<400> SEQUENCE: 530

Lys Glu Ala Trp Arg Leu Pro Gly
1               5

<210> SEQ ID NO 531
<211> LENGTH: 7
<212> TYPE: PRT
<213> ORGANISM: Artificial
<220> FEATURE:
<223> OTHER INFORMATION: Synthesized

<400> SEQUENCE: 531

Lys Glu Ala Trp Arg Leu Pro
1               5

<210> SEQ ID NO 532
<211> LENGTH: 6
<212> TYPE: PRT
<213> ORGANISM: Artificial
<220> FEATURE:
<223> OTHER INFORMATION: Synthesized

<400> SEQUENCE: 532

Lys Glu Ala Trp Arg Leu
1               5
```

<210> SEQ ID NO 533
<211> LENGTH: 5
<212> TYPE: PRT
<213> ORGANISM: Artificial
<220> FEATURE:
<223> OTHER INFORMATION: Synthesized

<400> SEQUENCE: 533

Lys Glu Ala Trp Arg
1               5

<210> SEQ ID NO 534
<211> LENGTH: 8
<212> TYPE: PRT
<213> ORGANISM: Artificial
<220> FEATURE:
<223> OTHER INFORMATION: Synthesized

<400> SEQUENCE: 534

Glu Ala Trp Arg Leu Pro Gly Thr
1               5

<210> SEQ ID NO 535
<211> LENGTH: 7
<212> TYPE: PRT
<213> ORGANISM: Artificial
<220> FEATURE:
<223> OTHER INFORMATION: Synthesized

<400> SEQUENCE: 535

Glu Ala Trp Arg Leu Pro Gly
1               5

<210> SEQ ID NO 536
<211> LENGTH: 6
<212> TYPE: PRT
<213> ORGANISM: Artificial
<220> FEATURE:
<223> OTHER INFORMATION: Synthesized

<400> SEQUENCE: 536

Glu Ala Trp Arg Leu Pro
1               5

<210> SEQ ID NO 537
<211> LENGTH: 5
<212> TYPE: PRT
<213> ORGANISM: Artificial
<220> FEATURE:
<223> OTHER INFORMATION: Synthesized

<400> SEQUENCE: 537

Glu Ala Trp Arg Leu
1               5

<210> SEQ ID NO 538
<211> LENGTH: 7
<212> TYPE: PRT
<213> ORGANISM: Artificial
<220> FEATURE:
<223> OTHER INFORMATION: Synthesized

<400> SEQUENCE: 538

Ala Trp Arg Leu Pro Gly Thr
1               5

```
<210> SEQ ID NO 539
<211> LENGTH: 6
<212> TYPE: PRT
<213> ORGANISM: Artificial
<220> FEATURE:
<223> OTHER INFORMATION: Synthesized

<400> SEQUENCE: 539

Ala Trp Arg Leu Pro Gly
1               5

<210> SEQ ID NO 540
<211> LENGTH: 5
<212> TYPE: PRT
<213> ORGANISM: Artificial
<220> FEATURE:
<223> OTHER INFORMATION: Synthesized

<400> SEQUENCE: 540

Ala Trp Arg Leu Pro
1               5

<210> SEQ ID NO 541
<211> LENGTH: 6
<212> TYPE: PRT
<213> ORGANISM: Artificial
<220> FEATURE:
<223> OTHER INFORMATION: Synthesized

<400> SEQUENCE: 541

Trp Arg Leu Pro Gly Thr
1               5

<210> SEQ ID NO 542
<211> LENGTH: 5
<212> TYPE: PRT
<213> ORGANISM: Artificial
<220> FEATURE:
<223> OTHER INFORMATION: Synthesized

<400> SEQUENCE: 542

Trp Arg Leu Pro Gly
1               5

<210> SEQ ID NO 543
<211> LENGTH: 5
<212> TYPE: PRT
<213> ORGANISM: Artificial
<220> FEATURE:
<223> OTHER INFORMATION: Synthesized

<400> SEQUENCE: 543

Arg Leu Pro Gly Thr
1               5

<210> SEQ ID NO 544
<211> LENGTH: 13
<212> TYPE: PRT
<213> ORGANISM: Artificial
<220> FEATURE:
<223> OTHER INFORMATION: Synthesized

<400> SEQUENCE: 544

Thr Arg Ala Ala Arg Arg Gly Tyr Val Ile Lys Val Leu
1               5                   10

<210> SEQ ID NO 545
```

<211> LENGTH: 12
<212> TYPE: PRT
<213> ORGANISM: Artificial
<220> FEATURE:
<223> OTHER INFORMATION: Synthesized

<400> SEQUENCE: 545

Thr Arg Ala Ala Arg Arg Gly Tyr Val Ile Lys Val
1               5                   10

<210> SEQ ID NO 546
<211> LENGTH: 11
<212> TYPE: PRT
<213> ORGANISM: Artificial
<220> FEATURE:
<223> OTHER INFORMATION: Synthesized

<400> SEQUENCE: 546

Thr Arg Ala Ala Arg Arg Gly Tyr Val Ile Lys
1               5                   10

<210> SEQ ID NO 547
<211> LENGTH: 10
<212> TYPE: PRT
<213> ORGANISM: Artificial
<220> FEATURE:
<223> OTHER INFORMATION: Synthesized

<400> SEQUENCE: 547

Thr Arg Ala Ala Arg Arg Gly Tyr Val Ile
1               5                   10

<210> SEQ ID NO 548
<211> LENGTH: 9
<212> TYPE: PRT
<213> ORGANISM: Artificial
<220> FEATURE:
<223> OTHER INFORMATION: Synthesized

<400> SEQUENCE: 548

Thr Arg Ala Ala Arg Arg Gly Tyr Val
1               5

<210> SEQ ID NO 549
<211> LENGTH: 8
<212> TYPE: PRT
<213> ORGANISM: Artificial
<220> FEATURE:
<223> OTHER INFORMATION: Synthesized

<400> SEQUENCE: 549

Thr Arg Ala Ala Arg Arg Gly Tyr
1               5

<210> SEQ ID NO 550
<211> LENGTH: 7
<212> TYPE: PRT
<213> ORGANISM: Artificial
<220> FEATURE:
<223> OTHER INFORMATION: Synthesized

<400> SEQUENCE: 550

Thr Arg Ala Ala Arg Arg Gly
1               5

<210> SEQ ID NO 551
<211> LENGTH: 6

```
<212> TYPE: PRT
<213> ORGANISM: Artificial
<220> FEATURE:
<223> OTHER INFORMATION: Synthesized

<400> SEQUENCE: 551

Thr Arg Ala Ala Arg Arg
1               5

<210> SEQ ID NO 552
<211> LENGTH: 5
<212> TYPE: PRT
<213> ORGANISM: Artificial
<220> FEATURE:
<223> OTHER INFORMATION: Synthesized

<400> SEQUENCE: 552

Thr Arg Ala Ala Arg
1               5

<210> SEQ ID NO 553
<211> LENGTH: 12
<212> TYPE: PRT
<213> ORGANISM: Artificial
<220> FEATURE:
<223> OTHER INFORMATION: Synthesized

<400> SEQUENCE: 553

Arg Ala Ala Arg Arg Gly Tyr Val Ile Lys Val Leu
1               5                   10

<210> SEQ ID NO 554
<211> LENGTH: 11
<212> TYPE: PRT
<213> ORGANISM: Artificial
<220> FEATURE:
<223> OTHER INFORMATION: Synthesized

<400> SEQUENCE: 554

Arg Ala Ala Arg Arg Gly Tyr Val Ile Lys Val
1               5                   10

<210> SEQ ID NO 555
<211> LENGTH: 10
<212> TYPE: PRT
<213> ORGANISM: Artificial
<220> FEATURE:
<223> OTHER INFORMATION: Synthesized

<400> SEQUENCE: 555

Arg Ala Ala Arg Arg Gly Tyr Val Ile Lys
1               5                   10

<210> SEQ ID NO 556
<211> LENGTH: 9
<212> TYPE: PRT
<213> ORGANISM: Artificial
<220> FEATURE:
<223> OTHER INFORMATION: Synthesized

<400> SEQUENCE: 556

Arg Ala Ala Arg Arg Gly Tyr Val Ile
1               5

<210> SEQ ID NO 557
<211> LENGTH: 8
<212> TYPE: PRT
```

<213> ORGANISM: Artificial
<220> FEATURE:
<223> OTHER INFORMATION: Synthesized

<400> SEQUENCE: 557

Arg Ala Ala Arg Arg Gly Tyr Val
1               5

<210> SEQ ID NO 558
<211> LENGTH: 7
<212> TYPE: PRT
<213> ORGANISM: Artificial
<220> FEATURE:
<223> OTHER INFORMATION: Synthesized

<400> SEQUENCE: 558

Arg Ala Ala Arg Arg Gly Tyr
1               5

<210> SEQ ID NO 559
<211> LENGTH: 6
<212> TYPE: PRT
<213> ORGANISM: Artificial
<220> FEATURE:
<223> OTHER INFORMATION: Synthesized

<400> SEQUENCE: 559

Arg Ala Ala Arg Arg Gly
1               5

<210> SEQ ID NO 560
<211> LENGTH: 5
<212> TYPE: PRT
<213> ORGANISM: Artificial
<220> FEATURE:
<223> OTHER INFORMATION: Synthesized

<400> SEQUENCE: 560

Arg Ala Ala Arg Arg
1               5

<210> SEQ ID NO 561
<211> LENGTH: 11
<212> TYPE: PRT
<213> ORGANISM: Artificial
<220> FEATURE:
<223> OTHER INFORMATION: Synthesized

<400> SEQUENCE: 561

Ala Ala Arg Arg Gly Tyr Val Ile Lys Val Leu
1               5                   10

<210> SEQ ID NO 562
<211> LENGTH: 10
<212> TYPE: PRT
<213> ORGANISM: Artificial
<220> FEATURE:
<223> OTHER INFORMATION: Synthesized

<400> SEQUENCE: 562

Ala Ala Arg Arg Gly Tyr Val Ile Lys Val
1               5                   10

<210> SEQ ID NO 563
<211> LENGTH: 9
<212> TYPE: PRT
<213> ORGANISM: Artificial

```
<220> FEATURE:
<223> OTHER INFORMATION: Synthesized

<400> SEQUENCE: 563

Ala Ala Arg Arg Gly Tyr Val Ile Lys
1               5

<210> SEQ ID NO 564
<211> LENGTH: 8
<212> TYPE: PRT
<213> ORGANISM: Artificial
<220> FEATURE:
<223> OTHER INFORMATION: Synthesized

<400> SEQUENCE: 564

Ala Ala Arg Arg Gly Tyr Val Ile
1               5

<210> SEQ ID NO 565
<211> LENGTH: 7
<212> TYPE: PRT
<213> ORGANISM: Artificial
<220> FEATURE:
<223> OTHER INFORMATION: Synthesized

<400> SEQUENCE: 565

Ala Ala Arg Arg Gly Tyr Val
1               5

<210> SEQ ID NO 566
<211> LENGTH: 6
<212> TYPE: PRT
<213> ORGANISM: Artificial
<220> FEATURE:
<223> OTHER INFORMATION: Synthesized

<400> SEQUENCE: 566

Ala Ala Arg Arg Gly Tyr
1               5

<210> SEQ ID NO 567
<211> LENGTH: 5
<212> TYPE: PRT
<213> ORGANISM: Artificial
<220> FEATURE:
<223> OTHER INFORMATION: Synthesized

<400> SEQUENCE: 567

Ala Ala Arg Arg Gly
1               5

<210> SEQ ID NO 568
<211> LENGTH: 10
<212> TYPE: PRT
<213> ORGANISM: Artificial
<220> FEATURE:
<223> OTHER INFORMATION: Synthesized

<400> SEQUENCE: 568

Ala Arg Arg Gly Tyr Val Ile Lys Val Leu
1               5                   10

<210> SEQ ID NO 569
<211> LENGTH: 9
<212> TYPE: PRT
<213> ORGANISM: Artificial
<220> FEATURE:
```

<223> OTHER INFORMATION: Synthesized

<400> SEQUENCE: 569

Ala Arg Arg Gly Tyr Val Ile Lys Val
1               5

<210> SEQ ID NO 570
<211> LENGTH: 8
<212> TYPE: PRT
<213> ORGANISM: Artificial
<220> FEATURE:
<223> OTHER INFORMATION: Synthesized

<400> SEQUENCE: 570

Ala Arg Arg Gly Tyr Val Ile Lys
1               5

<210> SEQ ID NO 571
<211> LENGTH: 7
<212> TYPE: PRT
<213> ORGANISM: Artificial
<220> FEATURE:
<223> OTHER INFORMATION: Synthesized

<400> SEQUENCE: 571

Ala Arg Arg Gly Tyr Val Ile
1               5

<210> SEQ ID NO 572
<211> LENGTH: 6
<212> TYPE: PRT
<213> ORGANISM: Artificial
<220> FEATURE:
<223> OTHER INFORMATION: Synthesized

<400> SEQUENCE: 572

Ala Arg Arg Gly Tyr Val
1               5

<210> SEQ ID NO 573
<211> LENGTH: 5
<212> TYPE: PRT
<213> ORGANISM: Artificial
<220> FEATURE:
<223> OTHER INFORMATION: Synthesized

<400> SEQUENCE: 573

Ala Arg Arg Gly Tyr
1               5

<210> SEQ ID NO 574
<211> LENGTH: 9
<212> TYPE: PRT
<213> ORGANISM: Artificial
<220> FEATURE:
<223> OTHER INFORMATION: Synthesized

<400> SEQUENCE: 574

Arg Arg Gly Tyr Val Ile Lys Val Leu
1               5

<210> SEQ ID NO 575
<211> LENGTH: 8
<212> TYPE: PRT
<213> ORGANISM: Artificial
<220> FEATURE:
<223> OTHER INFORMATION: Synthesized

<400> SEQUENCE: 575

Arg Arg Gly Tyr Val Ile Lys Val
1               5

<210> SEQ ID NO 576
<211> LENGTH: 7
<212> TYPE: PRT
<213> ORGANISM: Artificial
<220> FEATURE:
<223> OTHER INFORMATION: Synthesized

<400> SEQUENCE: 576

Arg Arg Gly Tyr Val Ile Lys
1               5

<210> SEQ ID NO 577
<211> LENGTH: 6
<212> TYPE: PRT
<213> ORGANISM: Artificial
<220> FEATURE:
<223> OTHER INFORMATION: Synthesized

<400> SEQUENCE: 577

Arg Arg Gly Tyr Val Ile
1               5

<210> SEQ ID NO 578
<211> LENGTH: 5
<212> TYPE: PRT
<213> ORGANISM: Artificial
<220> FEATURE:
<223> OTHER INFORMATION: Synthesized

<400> SEQUENCE: 578

Arg Arg Gly Tyr Val
1               5

<210> SEQ ID NO 579
<211> LENGTH: 8
<212> TYPE: PRT
<213> ORGANISM: Artificial
<220> FEATURE:
<223> OTHER INFORMATION: Synthesized

<400> SEQUENCE: 579

Arg Gly Tyr Val Ile Lys Val Leu
1               5

<210> SEQ ID NO 580
<211> LENGTH: 7
<212> TYPE: PRT
<213> ORGANISM: Artificial
<220> FEATURE:
<223> OTHER INFORMATION: Synthesized

<400> SEQUENCE: 580

Arg Gly Tyr Val Ile Lys Val
1               5

<210> SEQ ID NO 581
<211> LENGTH: 6
<212> TYPE: PRT
<213> ORGANISM: Artificial
<220> FEATURE:
<223> OTHER INFORMATION: Synthesized

```
<400> SEQUENCE: 581

Arg Gly Tyr Val Ile Lys
1               5

<210> SEQ ID NO 582
<211> LENGTH: 5
<212> TYPE: PRT
<213> ORGANISM: Artificial
<220> FEATURE:
<223> OTHER INFORMATION: Synthesized

<400> SEQUENCE: 582

Arg Gly Tyr Val Ile
1               5

<210> SEQ ID NO 583
<211> LENGTH: 7
<212> TYPE: PRT
<213> ORGANISM: Artificial
<220> FEATURE:
<223> OTHER INFORMATION: Synthesized

<400> SEQUENCE: 583

Gly Tyr Val Ile Lys Val Leu
1               5

<210> SEQ ID NO 584
<211> LENGTH: 6
<212> TYPE: PRT
<213> ORGANISM: Artificial
<220> FEATURE:
<223> OTHER INFORMATION: Synthesized

<400> SEQUENCE: 584

Gly Tyr Val Ile Lys Val
1               5

<210> SEQ ID NO 585
<211> LENGTH: 5
<212> TYPE: PRT
<213> ORGANISM: Artificial
<220> FEATURE:
<223> OTHER INFORMATION: Synthesized

<400> SEQUENCE: 585

Gly Tyr Val Ile Lys
1               5

<210> SEQ ID NO 586
<211> LENGTH: 6
<212> TYPE: PRT
<213> ORGANISM: Artificial
<220> FEATURE:
<223> OTHER INFORMATION: Synthesized

<400> SEQUENCE: 586

Tyr Val Ile Lys Val Leu
1               5

<210> SEQ ID NO 587
<211> LENGTH: 5
<212> TYPE: PRT
<213> ORGANISM: Artificial
<220> FEATURE:
<223> OTHER INFORMATION: Synthesized

<400> SEQUENCE: 587
```

Tyr Val Ile Lys Val
1               5

<210> SEQ ID NO 588
<211> LENGTH: 5
<212> TYPE: PRT
<213> ORGANISM: Artificial
<220> FEATURE:
<223> OTHER INFORMATION: Synthesized

<400> SEQUENCE: 588

Val Ile Lys Val Leu
1               5

<210> SEQ ID NO 589
<211> LENGTH: 21
<212> TYPE: DNA
<213> ORGANISM: Artificial
<220> FEATURE:
<223> OTHER INFORMATION: Synthesized

<400> SEQUENCE: 589
tcgtcgtttt tcggtgcttt t                                             21

<210> SEQ ID NO 590
<211> LENGTH: 21
<212> TYPE: DNA
<213> ORGANISM: Artificial
<220> FEATURE:
<223> OTHER INFORMATION: Synthesized

<400> SEQUENCE: 590
tcgtcgtttt tcggtcgttt t                                             21

<210> SEQ ID NO 591
<211> LENGTH: 24
<212> TYPE: DNA
<213> ORGANISM: Artificial
<220> FEATURE:
<223> OTHER INFORMATION: Synthesized

<400> SEQUENCE: 591
tcgtcgtttt gtcgttttgt cgtt                                          24

<210> SEQ ID NO 592
<211> LENGTH: 24
<212> TYPE: DNA
<213> ORGANISM: Artificial
<220> FEATURE:
<223> OTHER INFORMATION: Synthesized

<400> SEQUENCE: 592
tcgtcgtttc gtcgttttgt cgtt                                          24

<210> SEQ ID NO 593
<211> LENGTH: 24
<212> TYPE: DNA
<213> ORGANISM: Artificial
<220> FEATURE:
<223> OTHER INFORMATION: Synthesized

<400> SEQUENCE: 593
tcgtcgtttt gtcgtttttt tcga                                          24

<210> SEQ ID NO 594

```
<211> LENGTH: 22
<212> TYPE: DNA
<213> ORGANISM: Artificial
<220> FEATURE:
<223> OTHER INFORMATION: Synthesized

<400> SEQUENCE: 594
tcgcgtcgtt cggcgcgcgc cg                                              22

<210> SEQ ID NO 595
<211> LENGTH: 23
<212> TYPE: DNA
<213> ORGANISM: Artificial
<220> FEATURE:
<223> OTHER INFORMATION: Synthesized

<400> SEQUENCE: 595
tcgtcgacgt tcggcgcgcg ccg                                             23

<210> SEQ ID NO 596
<211> LENGTH: 21
<212> TYPE: DNA
<213> ORGANISM: Artificial
<220> FEATURE:
<223> OTHER INFORMATION: Synthesized

<400> SEQUENCE: 596
tcggacgttc ggcgcgcgcc g                                               21

<210> SEQ ID NO 597
<211> LENGTH: 19
<212> TYPE: DNA
<213> ORGANISM: Artificial
<220> FEATURE:
<223> OTHER INFORMATION: Synthesized

<400> SEQUENCE: 597
tcggacgttc ggcgcgccg                                                  19

<210> SEQ ID NO 598
<211> LENGTH: 20
<212> TYPE: DNA
<213> ORGANISM: Artificial
<220> FEATURE:
<223> OTHER INFORMATION: Synthesized

<400> SEQUENCE: 598
tcgcgtcgtt cggcgcgccg                                                 20

<210> SEQ ID NO 599
<211> LENGTH: 20
<212> TYPE: DNA
<213> ORGANISM: Artificial
<220> FEATURE:
<223> OTHER INFORMATION: Synthesized

<400> SEQUENCE: 599
tcgacgttcg gcgcgcgccg                                                 20

<210> SEQ ID NO 600
<211> LENGTH: 18
<212> TYPE: DNA
<213> ORGANISM: Artificial
<220> FEATURE:
<223> OTHER INFORMATION: Synthesized

<400> SEQUENCE: 600
```
tcgacgttcg gcgcgccg                                    18

<210> SEQ ID NO 601
<211> LENGTH: 18
<212> TYPE: DNA
<213> ORGANISM: Artificial
<220> FEATURE:
<223> OTHER INFORMATION: Synthesized

<400> SEQUENCE: 601
tcgcgtcgtt cggcgccg                                    18

<210> SEQ ID NO 602
<211> LENGTH: 22
<212> TYPE: DNA
<213> ORGANISM: Artificial
<220> FEATURE:
<223> OTHER INFORMATION: Synthesized

<400> SEQUENCE: 602
tcgcgacgtt cggcgcgcgc cg                               22

<210> SEQ ID NO 603
<211> LENGTH: 22
<212> TYPE: DNA
<213> ORGANISM: Artificial
<220> FEATURE:
<223> OTHER INFORMATION: Synthesized

<400> SEQUENCE: 603
tcgtcgtttt cggcgcgcgc cg                               22

<210> SEQ ID NO 604
<211> LENGTH: 22
<212> TYPE: DNA
<213> ORGANISM: Artificial
<220> FEATURE:
<223> OTHER INFORMATION: Synthesized

<400> SEQUENCE: 604
tcgtcgtttt cggcggccgc cg                               22

<210> SEQ ID NO 605
<211> LENGTH: 24
<212> TYPE: DNA
<213> ORGANISM: Artificial
<220> FEATURE:
<223> OTHER INFORMATION: Synthesized

<400> SEQUENCE: 605
tcgtcgtttt acggcgccgt gccg                             24

<210> SEQ ID NO 606
<211> LENGTH: 23
<212> TYPE: DNA
<213> ORGANISM: Artificial
<220> FEATURE:
<223> OTHER INFORMATION: Synthesized

<400> SEQUENCE: 606
tcgtcgtttt cggcgcgcgc cgt                              23

<210> SEQ ID NO 607
<211> LENGTH: 23
<212> TYPE: DNA

```
<213> ORGANISM: Artificial
<220> FEATURE:
<223> OTHER INFORMATION: Synthesized

<400> SEQUENCE: 607
tcgtcgacga tcggcgcgcg ccg                                          23

<210> SEQ ID NO 608
<211> LENGTH: 10
<212> TYPE: PRT
<213> ORGANISM: Artificial
<220> FEATURE:
<223> OTHER INFORMATION: Synthesized

<400> SEQUENCE: 608

Cys Gly Asp Lys Thr His Thr Ser Pro Pro
1               5                   10

<210> SEQ ID NO 609
<211> LENGTH: 10
<212> TYPE: PRT
<213> ORGANISM: Artificial
<220> FEATURE:
<223> OTHER INFORMATION: Synthesized

<400> SEQUENCE: 609

Asp Lys Thr His Thr Ser Pro Pro Cys Gly
1               5                   10

<210> SEQ ID NO 610
<211> LENGTH: 17
<212> TYPE: PRT
<213> ORGANISM: Artificial
<220> FEATURE:
<223> OTHER INFORMATION: Synthesized

<400> SEQUENCE: 610

Cys Gly Gly Pro Lys Pro Ser Thr Pro Pro Gly Ser Ser Gly Gly Ala
1               5                   10                  15

Pro

<210> SEQ ID NO 611
<211> LENGTH: 18
<212> TYPE: PRT
<213> ORGANISM: Artificial
<220> FEATURE:
<223> OTHER INFORMATION: Synthesized

<400> SEQUENCE: 611

Pro Lys Pro Ser Thr Pro Pro Gly Ser Ser Gly Gly Ala Pro Gly Gly
1               5                   10                  15

Cys Gly

<210> SEQ ID NO 612
<211> LENGTH: 6
<212> TYPE: PRT
<213> ORGANISM: Artificial
<220> FEATURE:
<223> OTHER INFORMATION: Synthesized

<400> SEQUENCE: 612

Gly Cys Gly Gly Gly Gly
1               5

<210> SEQ ID NO 613
```

```
<211> LENGTH: 6
<212> TYPE: PRT
<213> ORGANISM: Artificial
<220> FEATURE:
<223> OTHER INFORMATION: Synthesized

<400> SEQUENCE: 613

Gly Gly Gly Gly Cys Gly
1               5

<210> SEQ ID NO 614
<211> LENGTH: 6
<212> TYPE: PRT
<213> ORGANISM: Artificial
<220> FEATURE:
<223> OTHER INFORMATION: Synthesized

<400> SEQUENCE: 614

Cys Gly Lys Lys Gly Gly
1               5

<210> SEQ ID NO 615
<211> LENGTH: 6
<212> TYPE: PRT
<213> ORGANISM: Artificial
<220> FEATURE:
<223> OTHER INFORMATION: Synthesized

<400> SEQUENCE: 615

Cys Gly Asp Glu Gly Gly
1               5

<210> SEQ ID NO 616
<211> LENGTH: 6
<212> TYPE: PRT
<213> ORGANISM: Artificial
<220> FEATURE:
<223> OTHER INFORMATION: Synthesized

<400> SEQUENCE: 616

Gly Gly Lys Lys Gly Cys
1               5

<210> SEQ ID NO 617
<211> LENGTH: 6
<212> TYPE: PRT
<213> ORGANISM: Artificial
<220> FEATURE:
<223> OTHER INFORMATION: Synthesized

<400> SEQUENCE: 617

Gly Gly Glu Asp Gly Cys
1               5

<210> SEQ ID NO 618
<211> LENGTH: 4
<212> TYPE: PRT
<213> ORGANISM: Artificial
<220> FEATURE:
<223> OTHER INFORMATION: Synthesized

<400> SEQUENCE: 618

Gly Gly Cys Gly
1

<210> SEQ ID NO 619
<211> LENGTH: 4
```

```
<212> TYPE: PRT
<213> ORGANISM: Artificial
<220> FEATURE:
<223> OTHER INFORMATION: Synthesized

<400> SEQUENCE: 619

Gly Gly Gly Cys
1

<210> SEQ ID NO 620
<211> LENGTH: 4
<212> TYPE: PRT
<213> ORGANISM: Artificial
<220> FEATURE:
<223> OTHER INFORMATION: Synthesized

<400> SEQUENCE: 620

Cys Gly Gly Gly
1

<210> SEQ ID NO 621
<211> LENGTH: 6
<212> TYPE: PRT
<213> ORGANISM: Artificial
<220> FEATURE:
<223> OTHER INFORMATION: Synthesized

<400> SEQUENCE: 621

Gly Gly Gly Gly Gly Cys
1               5

<210> SEQ ID NO 622
<211> LENGTH: 5
<212> TYPE: PRT
<213> ORGANISM: Artificial
<220> FEATURE:
<223> OTHER INFORMATION: Synthesized

<400> SEQUENCE: 622

Gly Gly Gly Gly Cys
1               5

<210> SEQ ID NO 623
<211> LENGTH: 12
<212> TYPE: PRT
<213> ORGANISM: Artificial
<220> FEATURE:
<223> OTHER INFORMATION: Synthesized

<400> SEQUENCE: 623

Ile Pro Gln Ser Leu Asp Ser Trp Trp Thr Ser Leu
1               5                   10

<210> SEQ ID NO 624
<211> LENGTH: 6
<212> TYPE: PRT
<213> ORGANISM: Artificial
<220> FEATURE:
<223> OTHER INFORMATION: Synthesized

<400> SEQUENCE: 624

Gly Gly Gly Gly Gly Lys
1               5

<210> SEQ ID NO 625
<211> LENGTH: 5
<212> TYPE: PRT
```

<213> ORGANISM: Artificial
<220> FEATURE:
<223> OTHER INFORMATION: Synthesized

<400> SEQUENCE: 625

Gly Gly Gly Gly Lys
1               5

<210> SEQ ID NO 626
<211> LENGTH: 4
<212> TYPE: PRT
<213> ORGANISM: Artificial
<220> FEATURE:
<223> OTHER INFORMATION: Synthesized

<400> SEQUENCE: 626

Gly Gly Gly Lys
1

<210> SEQ ID NO 627
<211> LENGTH: 6
<212> TYPE: PRT
<213> ORGANISM: Artificial
<220> FEATURE:
<223> OTHER INFORMATION: Synthesized

<400> SEQUENCE: 627

Gly Gly Gly Gly Ser Cys
1               5

<210> SEQ ID NO 628
<211> LENGTH: 5
<212> TYPE: PRT
<213> ORGANISM: Artificial
<220> FEATURE:
<223> OTHER INFORMATION: Synthesized

<400> SEQUENCE: 628

Gly Gly Gly Ser Cys
1               5

<210> SEQ ID NO 629
<211> LENGTH: 4
<212> TYPE: PRT
<213> ORGANISM: Artificial
<220> FEATURE:
<223> OTHER INFORMATION: Synthesized

<400> SEQUENCE: 629

Gly Gly Ser Cys
1

<210> SEQ ID NO 630
<211> LENGTH: 6
<212> TYPE: PRT
<213> ORGANISM: Artificial
<220> FEATURE:
<223> OTHER INFORMATION: Synthesized

<400> SEQUENCE: 630

Cys Ser Gly Gly Gly Gly
1               5

<210> SEQ ID NO 631
<211> LENGTH: 5
<212> TYPE: PRT
<213> ORGANISM: Artificial

```
<220> FEATURE:
<223> OTHER INFORMATION: Synthesized

<400> SEQUENCE: 631

Cys Ser Gly Gly Gly
1               5

<210> SEQ ID NO 632
<211> LENGTH: 4
<212> TYPE: PRT
<213> ORGANISM: Artificial
<220> FEATURE:
<223> OTHER INFORMATION: Synthesized

<400> SEQUENCE: 632

Cys Ser Gly Gly
1

<210> SEQ ID NO 633
<211> LENGTH: 5
<212> TYPE: PRT
<213> ORGANISM: Artificial
<220> FEATURE:
<223> OTHER INFORMATION: Synthesized

<400> SEQUENCE: 633

Lys Gly Gly Gly Gly
1               5

<210> SEQ ID NO 634
<211> LENGTH: 4
<212> TYPE: PRT
<213> ORGANISM: Artificial
<220> FEATURE:
<223> OTHER INFORMATION: Synthesized

<400> SEQUENCE: 634

Lys Gly Gly Gly
1

<210> SEQ ID NO 635
<211> LENGTH: 5
<212> TYPE: PRT
<213> ORGANISM: Artificial
<220> FEATURE:
<223> OTHER INFORMATION: Synthesized

<400> SEQUENCE: 635

Cys Gly Gly Gly Gly
1               5

<210> SEQ ID NO 636
<211> LENGTH: 5
<212> TYPE: PRT
<213> ORGANISM: Artificial
<220> FEATURE:
<223> OTHER INFORMATION: Synthesized

<400> SEQUENCE: 636

Cys Gly Gly Gly Gly
1               5

<210> SEQ ID NO 637
<211> LENGTH: 21
<212> TYPE: DNA
<213> ORGANISM: Artificial
<220> FEATURE:
```

<223> OTHER INFORMATION: Synthesized

<400> SEQUENCE: 637 gggacgacg tcgtgggggg g                                           21

<210> SEQ ID NO 638
<211> LENGTH: 133
<212> TYPE: PRT
<213> ORGANISM: Artificial
<220> FEATURE:
<223> OTHER INFORMATION: Synthesized

<400> SEQUENCE: 638

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
    130

<210> SEQ ID NO 639
<211> LENGTH: 12
<212> TYPE: DNA
<213> ORGANISM: Artificial
<220> FEATURE:
<223> OTHER INFORMATION: Synthesized

<400> SEQUENCE: 639
cgacgttcgt cg                                                    12

<210> SEQ ID NO 640
<211> LENGTH: 13
<212> TYPE: DNA
<213> ORGANISM: Artificial
<220> FEATURE:
<223> OTHER INFORMATION: Synthesized

<400> SEQUENCE: 640
cggcgccgtg ccg                                                   13

<210> SEQ ID NO 641
<211> LENGTH: 12
<212> TYPE: DNA
<213> ORGANISM: Artificial
<220> FEATURE:
<223> OTHER INFORMATION: Synthesized

<400> SEQUENCE: 641 cccccgggg gg                                                     12

```
<210> SEQ ID NO 642
<211> LENGTH: 12
<212> TYPE: DNA
<213> ORGANISM: Artificial
<220> FEATURE:
<223> OTHER INFORMATION: Synthesized

<400> SEQUENCE: 642 gggggggcccc cc                                                          12

<210> SEQ ID NO 643
<211> LENGTH: 10
<212> TYPE: DNA
<213> ORGANISM: Artificial
<220> FEATURE:
<223> OTHER INFORMATION: Synthesized

<400> SEQUENCE: 643
cccccggggg                                                              10

<210> SEQ ID NO 644
<211> LENGTH: 10
<212> TYPE: DNA
<213> ORGANISM: Artificial
<220> FEATURE:
<223> OTHER INFORMATION: Synthesized

<400> SEQUENCE: 644
gggggccccc                                                              10
```